United States Patent
Koizumi et al.

(10) Patent No.: US 11,958,878 B2
(45) Date of Patent: Apr. 16, 2024

(54) THERAPEUTIC AGENT FOR GLYCOGEN STORAGE DISEASE TYPE IA

(71) Applicants: DAIICHI SANKYO COMPANY, LIMITED, Tokyo (JP); KOBE GAKUIN EDUCATIONAL FOUNDATION, Hyogo (JP)

(72) Inventors: Makoto Koizumi, Tokyo (JP); Yoshiyuki Onishi, Tokyo (JP); Takeshi Masuda, Tokyo (JP); Mitsuhiro Iwamoto, Tokyo (JP); Yukiko Sekiguchi, Tokyo (JP); Kentaro Ito, Tokyo (JP); Shinnosuke Tsuji, Tokyo (JP); Masafumi Matsuo, Hyogo (JP)

(73) Assignees: Daiichi Sankyo Company, Limited, Tokyo (JP); Kobe Gakuin Educational Foundation, Hyogo (JP)

(*) Notice: Subject to any disclaimer, the term of this patent is extended or adjusted under 35 U.S.C. 154(b) by 0 days.

(21) Appl. No.: 16/966,132

(22) PCT Filed: Mar. 5, 2019

(86) PCT No.: PCT/JP2019/008713
§ 371 (c)(1),
(2) Date: Jul. 30, 2020

(87) PCT Pub. No.: WO2019/172286
PCT Pub. Date: Sep. 12, 2019

(65) Prior Publication Data
US 2020/0407394 A1  Dec. 31, 2020

(30) Foreign Application Priority Data

Mar. 9, 2018 (JP) .................. 2018-043524
Jul. 5, 2018 (JP) .................. 2018-128015

(51) Int. Cl.
C07H 21/02 (2006.01)
(52) U.S. Cl.
CPC .................. C07H 21/02 (2013.01)
(58) Field of Classification Search
CPC .................. C12N 15/113; C07H 21/02
See application file for complete search history.

(56) References Cited

U.S. PATENT DOCUMENTS

| | | | |
|---|---|---|---|
| 5,916,808 A | 6/1999 | Kole et al. | |
| 6,621,840 B2 | 9/2003 | Araki et al. | |
| 2005/0261233 A1 | 11/2005 | Bhanot et al. | |
| 2006/0051769 A1 | 3/2006 | Barts | |
| 2011/0178283 A1 | 7/2011 | Rigoutsos et al. | |
| 2013/0337447 A1* | 12/2013 | Porreca ................ | C12Q 1/6886 435/6.11 |
| 2014/0024698 A1 | 1/2014 | Kole et al. | |
| 2014/0179767 A1 | 6/2014 | Rozet et al. | |
| 2014/0343123 A1 | 11/2014 | Prakash et al. | |
| 2015/0273016 A1 | 10/2015 | Parenti et al. | |
| 2015/0368642 A1 | 12/2015 | Albaek et al. | |
| 2016/0376585 A1 | 12/2016 | Manoharan et al. | |
| 2019/0382798 A1* | 12/2019 | Cowan ........... | C12Y 301/03009 |
| 2020/0246369 A1 | 8/2020 | Tajima et al. | |

FOREIGN PATENT DOCUMENTS

| | | |
|---|---|---|
| CN | 105934515 | 9/2016 |
| EP | 1 568 769 | 8/2005 |
| EP | 3 594 346 | 1/2020 |
| JP | 7-87982 | 4/1995 |
| JP | 8-510130 | 10/1996 |
| JP | 2000-297097 | 10/2000 |
| JP | 2012-530715 | 12/2012 |
| JP | 2015-501817 | 1/2015 |
| JP | 2016-523515 | 8/2016 |
| JP | 2016-529230 | 9/2016 |
| JP | 2017-501684 | 1/2017 |
| WO | 99/14226 | 3/1999 |
| WO | 00/47599 | 8/2000 |
| WO | 2008/109366 | 9/2008 |

(Continued)

OTHER PUBLICATIONS

Rake et al., "Glycogen storage disease type I: diagnosis, management, clinical course and outcome. Results of the European Study on Glycogen Storage Disease Type I (ESGSD I)", Eur J Pediatr., 2002, vol. 161, Suppl 1, pp. / S20-34.
Chou et al., "Mutations in the Glucose-6-Phosphatase-α (G6PC) Gene That Cause Type Ia Glycogen Storage Disease", Human Mutation, 2008, vol. 29, No. 7, pp. 921-930.
Duff et al., "Intrabody Tissue-Specific Delivery of Antisense Conjugates in Animals: Ligand-Linker-Antisense Oligomer Conjugates", Methods in Enzymology, 1999, vol. 313, pp. 297-321.
Kinberger et al., "Conjugation of mono and di—GalNAc sugars enhances the potency of antisense oligonucleotides via ASGR mediated delivery to hepatocytes", Bioorganic & Medicinal Chemistry Letters, 2016, vol. 26, pp. 3690-3693.
International Search Report (ISR) dated May 28, 2019 in corresponding International (PCT) Application No. PCT/JP2019/008713.
Go Tajima et al., "Expression repair of G6PC frequent splicing mutation by antisense nucleic acid", The Journal of the Japan Pediatric Society, vol. 123, No. 2, p. 281 (2-O-248), ISSN 0001-6543, Feb. 2019, cited in CA.

(Continued)

*Primary Examiner* — Brian Whiteman
(74) *Attorney, Agent, or Firm* — Wenderoth, Lind & Ponack, L.L.P.

(57) ABSTRACT

The present invention establishes a molecular therapy for glycogen storage disease type Ia. The present invention provides an oligonucleotide of 15-30 bases comprising a nucleotide sequence complementary to die cDNA of G6PC gene with c.648G>T mutation, wherein the oligonucleotide comprises a sequence complementary to a region comprising any site between the $82^{nd}$ to the $92^{nd}$ nucleotide from the 5' end of exon 5 of the G6PC gene with c.648C>T mutation, a pharmacologically acceptable salt or solvate thereof. Also provided is a pharmaceutical drug comprising the oligonucleotide, a pharmacologically acceptable salt or solvate thereof (e.g., therapeutic drug for glycogen storage disease type Ia).

6 Claims, 26 Drawing Sheets
Specification includes a Sequence Listing.

(56) References Cited

FOREIGN PATENT DOCUMENTS

| WO | 2009/073809 | 6/2009 |
| WO | 2012/168435 | 12/2012 |
| WO | 2014/076196 | 5/2014 |
| WO | 2014/109384 | 7/2014 |
| WO | 2014/179620 | 11/2014 |
| WO | 2015/006740 | 1/2015 |
| WO | 2015/105083 | 7/2015 |
| WO | 2016/055601 | 4/2016 |
| WO | 2016/106303 | 6/2016 |
| WO | 2017/023817 | 2/2017 |
| WO | 2017/077386 | 5/2017 |
| WO | 2017/084987 | 5/2017 |
| WO | 2017/106210 | 6/2017 |
| WO | 2017/131236 | 8/2017 |
| WO | 2018/164275 | 9/2018 |

OTHER PUBLICATIONS

Susumu Kajihara et al., "Exon Redefinition by a Point Mutation within Exon 5 of the Glucose-6-Phosphatase Gene is the Major Cause of Glycogen Storage Disease Type Ia in Japan", Am. J. Hum. Genet., vol. 57, issue 3, pp. 549-555, ISSN 0002-9297, 1995, cited in CA.

English Translation of the International Preliminary Report of Patentability and Written Opinion of the International Search Authority dated Sep. 15, 2020 in International (PCT) Application No. PCT/JP2019/008713.

Extended European Search Report dated Nov. 11, 2021 in corresponding European Patent Application No. 19763548.5.

Chou, Janice Y. et al., "Glycogen storage disease type I and G6Pase-[beta] deficiency: etiology and therapy", Nature Reviews, Endocrinology, 2010, vol. 6, No. 12, pp. 676-688.

Chou, Janice Y. et al., "Mutations in the glucose-6-phosphatase-[alpha] (G6PC) gene that cause type Ia glycogen storage disease", Human Mutation, 2008, vol. 29, No. 7, pp. 921-930.

Shimo, Takenori et al., "Design and evaluation of locked nucleic acid-based splice-switching oligonucleotides in Vitro", Nucleic Acids Research, 2014, vol. 42, No. 12, pp. 8174-8187.

Li, Jing-yi et al., "A Novel Compound Heterozygous Mutation in Glucose-6-Phosphatase Gene in a Chinese Patient with Glycogen Storage Disease Ia", Medical Journal of Peking Union Medical College Hospital, 2016, vol. 7, No. 4, pp. 264-268.

Akanuma, Jun et al., "Glycogen Storage Disease Type Ia: Molecular Diagnosis of 51 Japanese Patients and Characterization of Splicing Mutations by Analysis of Ectopically Transcribed mRNA From Lymphoblastoid Cells", American Journal of Medical Genetics, 2000, vol. 91, pp. 107-112.

Havens, Mallory A. et al., "Targeting RNA splicing for disease therapy", WIREs RNA, 2013, vol. 4, pp. 247-266.

Chou, Janice Y. et al., "Type I glycogen storage diseases: disorders of the glucose-6-phosphatase/glucose-6-phosphate transporter complexes", J Inherit Metab Dis, 2015, vol. 38, pp. 511-519.

\* cited by examiner

Fig. 3

G6PC exon5

```
       1          10         20         30         40         50         60
       GCAUUGCUGU UACAGAAACU UUCAGCCACA UCCACAGCAU CUAUAAUGCC AGCCUCAAGA    G6PC mRNA
       CGUAACGACA AUGUCUUUGA AAGUCGGUGU AGGUGUCGUA GAUAUUACGG UCGGAGUUCU    G6PC AS cryptic site
                                                      G
                                                       ↓
       70         80         90         100        110        120
       AAUAUUUUCU CAUUACCUUC UUCCUUUUCA GCUUCGCCAU CGGAUUUUAU CUGCUGCUCA 3' G6PC mRNA
       UUAUAAAAGA GUAAUGGAAG AAGGAAAAGU CGAAGCGGUA GCCUAAAAUA GACGACGAGU 5' G6PC AS GcGguA     gcCuaAaaTa gAcgA          21e_001
                                       GaAgcGguA   gcCuaAaaTa gA 5'          21e_002
                                   Gu CgaAgcGguA   gcCuaAaaT 5'              21e_003
                                  AaAgu CgaAgcGguA gcC 5'                    21e_004
                               GgAaaAgu CgaAgcGguA 5'                        21e_005
                           aAggAaaAgu CgaAgcG 5'                             21e_006
                        G aAggAaaAgu CgaAgcG 5'                              21e_007
                       GaAg aAggAaaAgu CgaA 5'                               21e_008
                   AuGgaAg aAggAaaAgu C 5'                                   21e_009
               GtAauGgaAg aAggAaaAgu 5'                                      21e_010
        AgA gtAauGgaAg aAggA 5'                                              21e_011
   AaAagA gtAauGgaAg aAgga 5'                                                21e_012
 TaTaaAagA gtAauGgaAg aA 5'
```

Fig.8

```
                                                                        120
              80          G  90            100          110
         CAUUACCUUC UUCCUUUUCA GCUUCGCCAU CGGAUUUUAU CUGCUGCUCA 3'    G6PC mRNA
         GUAAUGGAAG AAGGAAAAGU CGAAGCGGUA GCCUAAAAUA GACGACGAGU 5'    G6PC AS
                                 cryptic site ↓
                                  GCGguA    gcCuaAaaTa  gAcgA 5'     21e_001
                                AgCggTa    gCcuAaaAua   GacG 5'      21e_013
                               AaGcgGta    GCcuAaaAauA  gaC 5'       21e_014
                              GaAgcGguA    gcCuaAaaTa   gA 5'        21e_002
                             CgAagCggTa    gCcuAaaAua   G 5'         21e_015
                            CgaAagCgguA    GcCuaaAauA   5'           21e_016
                           T cGaaAgCggTa   gcCuaAaaT 5'              21e_003
                          Gu  CgaAagCgguA  gcCcuAaaA 5'              21e_017
                         AgT  cgaAgcGgTa   GcCuaaA 5'                21e_018
                        AaGu  CgaAgCgguA   gcCuaA 5'                 21e_004
                       AaAagu cGaaAgCggTa  gCCuA 5'                  21e_019
                      AaAagT  CgaAgcCggTa  gCCT 5'                   21e_020
                     GaAaaGu  cGaaGcGguA   gcC 5'                    21e_005
                    CgAaaAagT CgAagCggTa   gC 5'                     21e_021
                   AgGaAaaAgu cBaaAgCgguA  G 5'                      21e_022
                  AaGgaAaaGu  CgAaAgCggua  5'                        21e_006
                 G aAggAaaAgu CgaAgcGguA   5'
```

Fig.12

```
                                       cryptic site
            80          90         100         110         120
    CAUUACCUUC UUCCUUUUCA GCUUCGCCAU CGGAUUUUAU CUGCUGCUCA 3'  G6PC mRNA
    GUAAUGGAAG AAGGAAAAGU CGAAGCGGUA GCCUAAAAUA GACGACGAGU 5'  G6PC AS
                             cggua gccuaaaaua gac 5'            18m_001
                            gcggua gccuaaaaua ga 5'             18m_002
                           agcggua gccuaaaaua g 5'              18m_003
                          aagcggua gccuaaaaau 5'                18m_004
                        u cgaagcggua gccuaaaaa 5'               18m_005
                       gu cgaagcggua gccuaaaa 5'                18m_006
                      agu cgaagcggua gccuaaa 5'                 18m_007
                     aagu cgaagcggua gccuaa 5'                  18m_008
                    aaagu cgaagcggua gccua 5'                   18m_009
                   aaaagu cgaagcggua gccu 5'                    18m_010
                  aaaaagu cgaagcggua gcc 5'                     18m_011
                 gaaaaagu cgaagcggua gc 5'                      18m_012
                ggaaaaagu cgaagcggua g 5'                       18m_013
               aggaaaaagu cgaagcggua 5'                         18m_014
              aaggaaaaagu cgaagcggu 5'                          18m_015
             aaaggaaaaagu cgaagcgg 5'                           18m_016
            g aaggaaaaagu cgaagcg 5'                            18m_017
```

Fig.15

```
                                                                                G
                 80              90             100             110             120
         CAUUACCUUC UUCCUUUUCA GCUUCGCCAU CGGAUUUUAU CUGCUGCUCA 3' G6PC mRNA
         GUAAUGGAAG AAGGAAAAGU CGAAGCGGUA GCCUAAAAUA GACGACGAGU 5' G6PC AS
                                cryptic site →
                                   CggTa     gCCuaaaaTa    gaC 5'  18e_018
                                  gCggTa     gCCuaaaaTa    ga  5'  18e_019
                                 agCggTa     gCCuaaaaTa    g   5'  18e_020
                                 aagCggTa    gCCuaaaaTa        5'  18e_021
                                 aaagCggTa   gCCuaaaaT         5'  18e_022
                                 CgaagCggTa  gCCuaaaa          5'  18e_023
                               T CgaagCggTa  gCCuaaa           5'  18e_024
                              gT CgaagCggTa  gCCua             5'  18e_025
                              agT CgaagCggTa gCCua             5'  18e_026
                                   cggTa     gCCuaaaAua   GaC  5'  18e_027
                                  gcgGgua    GCcuaaAauA    gA  5'  18e_028
                                 agcGGguA    gccuaaAaaTa   G   5'  18e_029
                                 aagCggTa    gccuaAaaAuA       5'  18e_030
                                 gaaGcgGua   gccTaaAaAT        5'  18e_031
```

THERAPEUTIC AGENT FOR GLYCOGEN STORAGE DISEASE TYPE IA

A sequence listing in electronic (ASCII text file) format is filed with this application and incorporated herein by reference. The name of the ASCII text file is "230517FP-251PCT-US_sequence_listing_ST25.txt"; the file was created on May 26, 2023; the size of the file is 148,989 bytes.

TECHNICAL FIELD

The present invention relates to a therapeutic agent for glycogen storage disease type Ia. More specifically, the present invention relates to an oligonucleotide which is capable of repairing G6PC gene with c.648G>T mutation in glycogen storage disease type Ia patients at the mRNA level and thereby allowing expression of normal G6PC protein, as well as a pharmaceutical drug comprising the oligonucleotide.

BACKGROUND ART

Glycogen storage disease type Ia is a metabolic abnormality of autosomal recessive inheritance caused by glucose-6-phosphatase (G6PC) gene, and has major symptoms including hypoglycemia, hepatomegaly and nephromegaly. Although prognosis of survival in this disease has been greatly improved by glycemic control with diet therapy, more than half of even well glycemic-controlled patients present hepatic adenoma and albuminuria (Non-Patent Document No. 1). Several common mutations in glycogen storage disease type Ia patients have been reported, and G6PC c.648G>T mutation causing splicing abnormality has been known as a common mutation in East Asia (Non-Patent Document No. 2).

As a method of delivering oligonucleotide to hepatic parenchymal cells, nucleic acid drug (antisense or siRNA, etc.) conjugates covalently bound to N-acetyl-D-galactosamine (GalNAc) or the like as a ligand capable of binding to asialoglycoprotein receptor (ASGPR) have been reported (Non-Patent Document No. 3 and Patent Documents Nos. 1 to 9). One to three GalNAc molecules are bound to one oligonucleotide molecule. An example of two GalNAc molecules bound to one oligonucleotide molecule is described in Non-Patent Document No. 4.

PRIOR ART LITERATURE

Non-Patent Documents

Non-Patent Document No. 1: Eur J Pediatr. 2002, Vol. 161 Suppl 1:S20-34
Non-Patent Document No. 2: Hum Mutat. 2008, Vol. 9, pp. 921-930.
Non-Patent Document No. 3: Methods in Enzymology, 1999, Vol. 313, pp. 297-321
Non-Patent Document No. 4: Bioorganic & Medicinal Chemistry Letters 26 (2016) 3690-3693

Patent Documents

Patent Document No. 1: WO 2009/073809
Patent Document No. 2: WO 2014/076196
Patent Document No. 3: WO 2014/179620
Patent Document No. 4: WO 2015/006740
Patent Document No. 5: WO 2015/105083
Patent Document No. 6: WO 2016/055601
Patent Document No. 7: WO 2017/023817
Patent Document No. 8: WO 2017/084987
Patent Document No. 9: WO 2017/131236

DISCLOSURE OF THE INVENTION

Problem for Solution by the Invention

It is an object of the present invention to establish a molecular therapy for glycogen storage disease type Ia.

Means to Solve the Problem

The present inventors have established a therapeutic method with administration of an antisense oligonucleotide (ASO) to glycogen storage disease type Ia patients with G6PC c.648G>T mutation by repairing abnormal splicing of mRNA to induce production of normal G6PC protein (FIG. 1). In G6PC c.648G>T mutation, abnormal splicing of mRNA occurs, which results in deletion of 91 nucleotides in the exon 5 portion of the intron 4/exon 5 junction, and resulted frame shift leads to deactivation of G6PC enzyme. When the abnormal splicing of mRNA has been corrected, it is expected that the resulting translated amino acid sequence would be the same as the corresponding normal amino acid sequence (CUG(Leu)→CUU(Leu)). Therefore, by this therapeutic method of repairing abnormal splicing of mRNA, normal G6PC protein having activity will be produced in patients with G6PC c.648G>T mutation, enabling reduction of the risk of hypoglycemic episode, reversal of organ swelling and reduction of the risk of hepatic adenoma in glycogen storage disease type Ia patients. The present study is a development research of the first molecular therapy for glycogen storage disease type Ia in the world.

A summary of the present invention is as described below.

(1) An oligonucleotide of 15-30 bases comprising a nucleotide sequence complementary to the cDNA of G6PC gene with c.648G>T mutation, wherein the oligonucleotide comprises a sequence complementary to a region comprising any site between the $82^{nd}$ to the $92^{nd}$ nucleotide from the 5' end of exon 5 of the G6PC gene with c.648G>T mutation, a pharmacologically acceptable salt or solvate thereof.

(2) The oligonucleotide, a pharmacologically acceptable salt or solvate thereof of (1), wherein the oligonucleotide has 15-21 bases and comprises a sequence complementary to a region comprising any site between the $86^{th}$ to the $92^{nd}$ nucleotide from the 5' end of exon 5 of the G6PC gene with c.648G>T mutation.

(3) The oligonucleotide, a pharmacologically acceptable salt or solvate thereof of (1), wherein the oligonucleotide has 15-21 bases and comprises a sequence complementary to a region comprising the site of the $92^{nd}$ nucleotide from the 5' end of exon 5 of the G6PC gene with c.648G>T mutation.

(4) The oligonucleotide, a pharmacologically acceptable salt or solvate thereof of (1), wherein the oligonucleotide has 15-18 bases and comprises a sequence complementary to a region comprising the site of the $92^{nd}$ nucleotide from the 5' end of exon 5 of the G6PC gene with c.648G>T mutation.

(5) The oligonucleotide, a pharmacologically acceptable salt or solvate thereof of (1), wherein the oligonucleotide has 18 bases and comprises a sequence complementary to a region comprising the site of the $92^{nd}$ nucleotide from the 5' end of exon 5 of the G6PC gene with c.648G>T mutation.

(6) The oligonucleotide, a pharmacologically acceptable salt or solvate thereof of (1), wherein the oligonucleotide has 17 bases and comprises a sequence complementary to a region comprising the site of the $92^{nd}$ nucleotide from the 5' end of exon 5 of the G6PC gene with c.648G>T mutation.

(7) The oligonucleotide, a pharmacologically acceptable salt or solvate thereof of (1), wherein the oligonucleotide has 16 bases and comprises a sequence complementary to a region comprising the site of the $92^{nd}$ nucleotide from the 5' end of exon 5 of the G6PC gene with c.648G>T mutation.

(8) The oligonucleotide, a pharmacologically acceptable salt or solvate thereof of (1), wherein the oligonucleotide has 15 bases and comprises a sequence complementary to a region comprising the site of the $92^{nd}$ nucleotide from the 5' end of exon 5 of the G6PC gene with c.648G>T mutation.

(9) The oligonucleotide, a pharmacologically acceptable salt or solvate thereof of (1), wherein the oligonucleotide comprises a sequence of at least 15 consecutive nucleotides in any of the sequences shown in SEQ ID NOS: 1 to 32, 40 to 42, 44 to 48, 98 to 147, and 161 to 179.

(10) The oligonucleotide, a pharmacologically acceptable salt or solvate thereof of any one of (1) to (9), wherein an oligonucleotide cleavable in a living body is further added to the 5' end and/or the 3' end.

(11) The oligonucleotide, a pharmacologically acceptable salt or solvate thereof of any one of (1) to (10), wherein at least one of the sugar and/or the phosphodiester bond constituting the oligonucleotide is modified.

(12) The oligonucleotide, a pharmacologically acceptable salt or solvate thereof of any one of (1) to (10), wherein the sugar constituting the oligonucleotide is D-ribofuranose and modification of the sugar is modification of the hydroxy group at 2'-position of D-ribofuranose.

(13) The oligonucleotide, a pharmacologically acceptable salt or solvate thereof of any one of (1) to (10), wherein the sugar constituting the oligonucleotide is D-ribofuranose and modification of the sugar is 2'-O-alkylation and/or 2'-, 4'-bridging of D-ribofuranose.

(14) The oligonucleotide, a pharmacologically acceptable salt or solvate thereof of any one of (1) to (10), wherein the sugar constituting the oligonucleotide is D-ribofuranose and modification of the sugar is 2'-O-alkylation and/or 2'-0, 4'-C-alkylenation of D-ribofuranose.

(15) The oligonucleotide, a pharmacologically acceptable salt or solvate thereof of any one of (1) to (14), wherein modification of the phosphodiester bond is phosphorothioate bond.

(16) The oligonucleotide, a pharmacologically acceptable salt or solvate thereof of any one of (1) to (15), wherein a GalNAc unit is bound to the 5' end and/or the 3' end.

(17) The oligonucleotide, a pharmacologically acceptable salt or solvate thereof of any one of (1) to (15), wherein a GalNAc unit is bound to the 5' end.

(18) The oligonucleotide, a pharmacologically acceptable salt or solvate thereof of (16) or (17), wherein the GalNAc unit is represented by the following Formula:

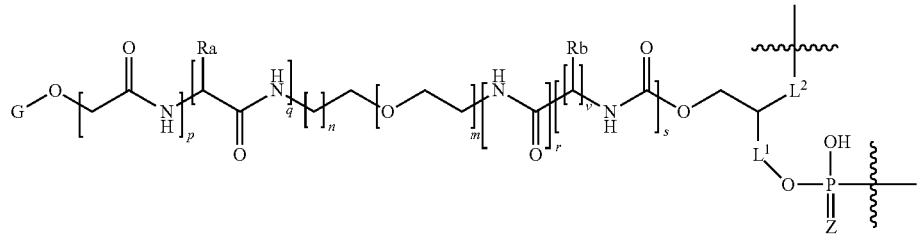

[Formula 1]

wherein Ra is a group represented by the following Formula;

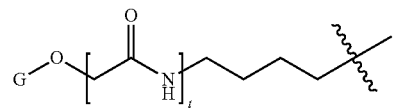

[Formula 2]

Rb is a group represented by the following Formula or a hydrogen atom;

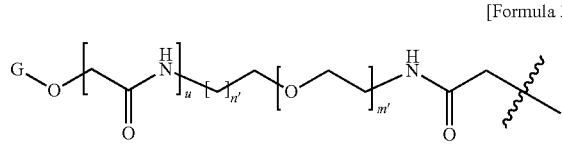

[Formula 3]

XX is a group represented by the following Formula;

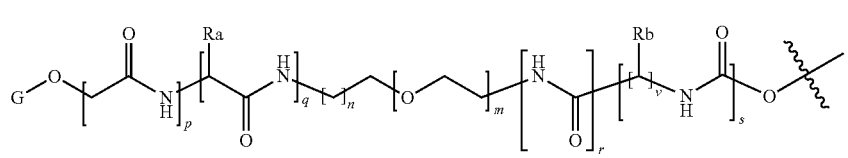

[Formula 4]

G is 5-acetamide-2-hydroxymethyl-3,4-dihydroxytetrahydropyran-6-yl group (GalNAc); Z is an oxygen atom or a sulfur atom; either of $L^1$ or $L^2$ is a methylene group ($CH_2$) and the other is no atom; p, q, r, s, t and u are each independently 0 or 1; n and n' are each independently an integer from 1 to 15; m and m' are each independently an integer from 0 to 5; when Rb is not a hydrogen atom, v is 1; when Rb is a hydrogen atom, v is an integer from 1 to 7; provided that when n is 1, m is an integer from 0 to 5; when n is an integer from 2 to 15, m is 0; when n' is 1, m' is an integer from 1 to 5; when n' is an integer from 2 to 15, m' is 0; a hydroxyl group, an XX group or an OG group may be attached to a binding moiety distant from the phosphorus atom.

(19) The oligonucleotide, a pharmacologically acceptable salt or solvate thereof of (16) or (17), wherein the GalNAc unit is a group represented by the following Formula:

[Formula 5]

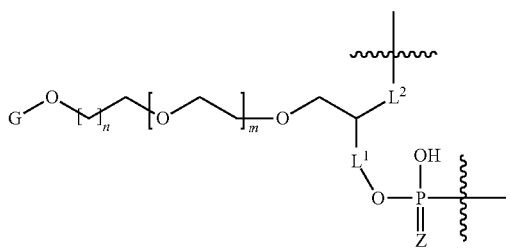

wherein G, Z, $L^1$, $L^2$, n and m are as defined above.

(20) The oligonucleotide, a pharmacologically acceptable salt or solvate thereof of (16) or (17), wherein the GalNAc unit is a group represented by the following Formula:

[Formula 6]

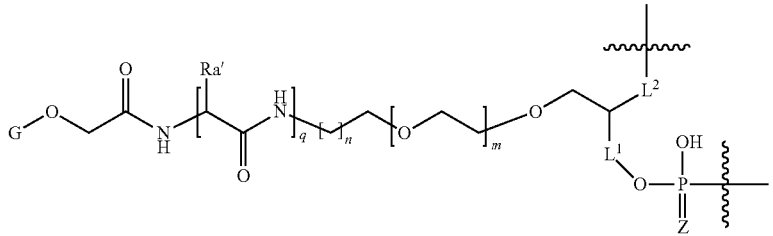

wherein G, Z, $L^1$, $L^2$, q, n and m are as defined above, and Ra' is a group represented by the following Formula:

[Formula 7]

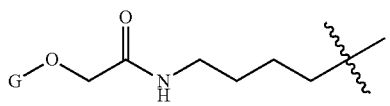

(21) The oligonucleotide, a pharmacologically acceptable salt or solvate thereof of (16) or (17), wherein the GalNAc unit is a group represented by the following Formula:

[Formula 8]

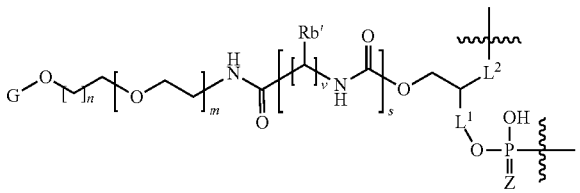

wherein G, Z, $L^1$, $L^2$, s, n, m and v are as defined above, and Rb' is a group represented by the following Formula or a hydrogen atom:

[Formula 9]

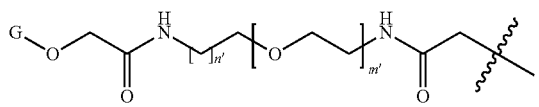

wherein n' and m' are as defined above.

(22) The oligonucleotide, a pharmacologically acceptable salt or solvate thereof of (16) or (17), wherein the GalNAc unit is a group represented by the following Formula:

[Formula 10]

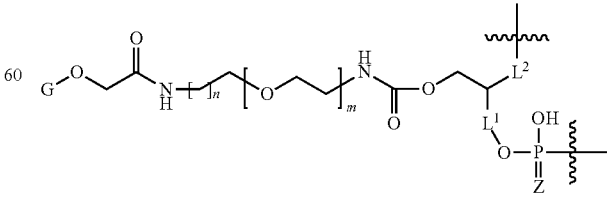

wherein G, Z, $L^1$, $L^2$, n and m are as defined above.

(23) The oligonucleotide, a pharmacologically acceptable salt or solvate thereof of (16) or (17), wherein the GalNAc unit is a group represented by the following Formula:

[Formula 11]

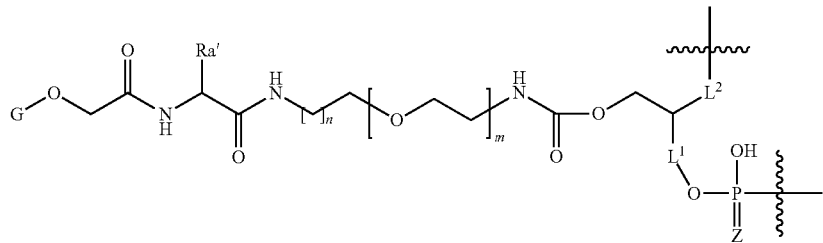

wherein G, Z, $L^1$, $L^2$, n, m and Ra' are as defined above.

(24) The oligonucleotide, a pharmacologically acceptable salt or solvate thereof of (1) represented by the following Formula:

RO-Xg-Xf-Xe-Xd-Xc-Xb-Xa-T    [Formula 12]

wherein R is a hydrogen atom, an XX group or a G group;
T is an oligonucleotide which does not have a hydroxyl group at the 5' end; Xg is a GalNAc unit selected from the group consisting of $X^1$ to $X^6$ and $X^9$ to $X^{17}$; or RO-Xg is a GalNAc unit selected from the group consisting of $X^7$, $X^8$, $X^{18}$, $X^{19}$, $X^{20}$, $X^{21}$ and $X^{22}$; Xa, Xb, Xc, Xd, Xe and Xf are each independently a GalNAc unit selected from the group consisting of $X^1$ to $X^6$ and $X^9$ to $X^{17}$ or optical isomers thereof, or a single bond.

[Formula 13]

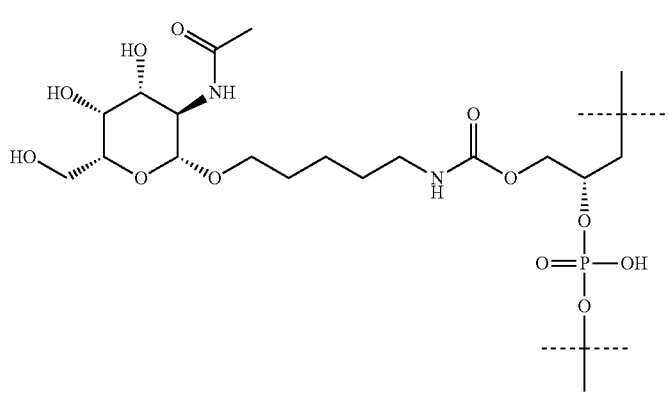

$X^1$

[Formula 14]

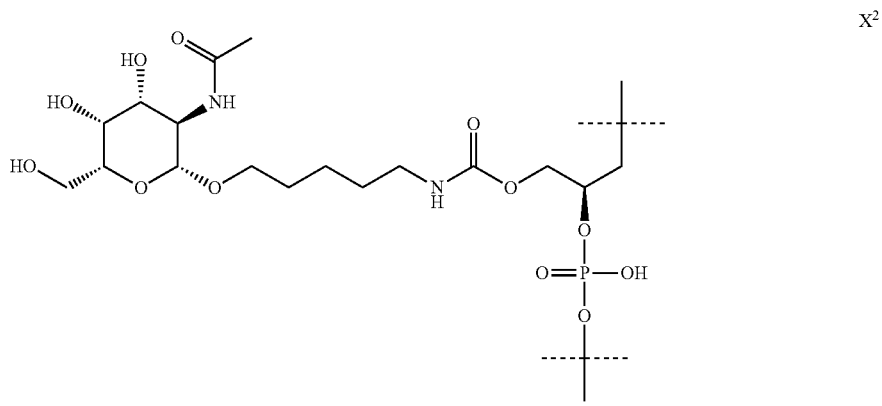

$X^2$

-continued
[Formula 15]
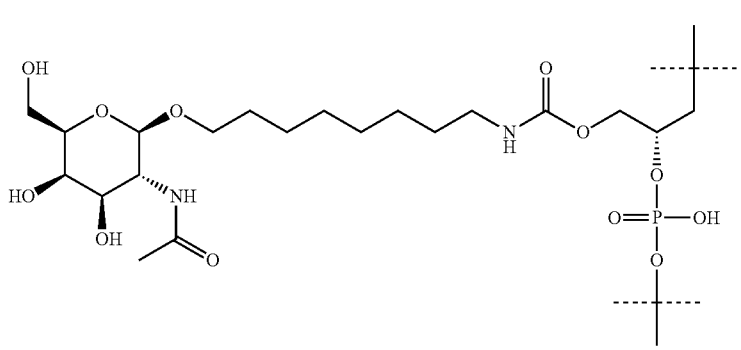
X³
[Formula 16]
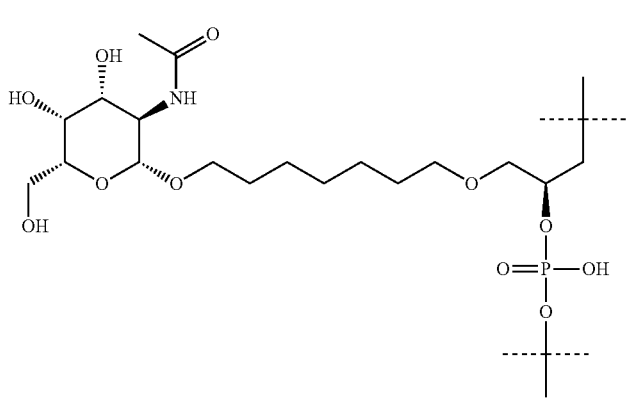
X⁴
[Formula 17]
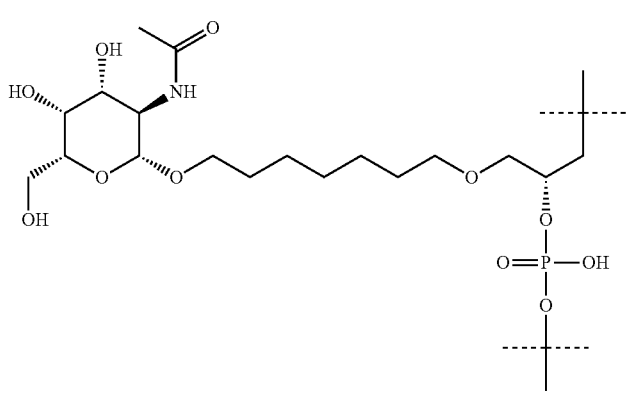
X⁵
[Formula 18]
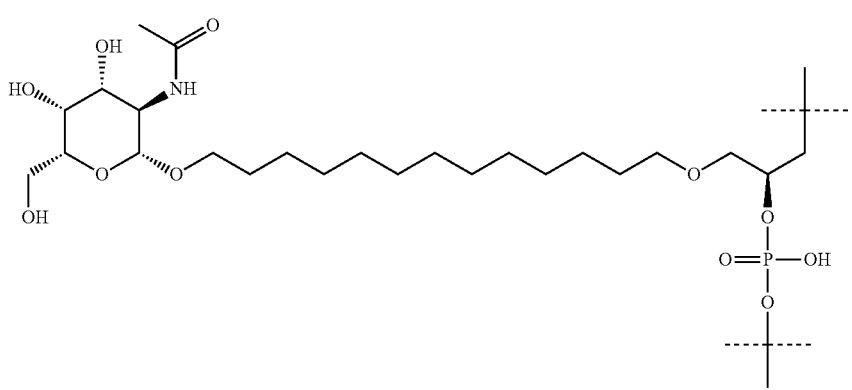
X⁶

[Formula 19]
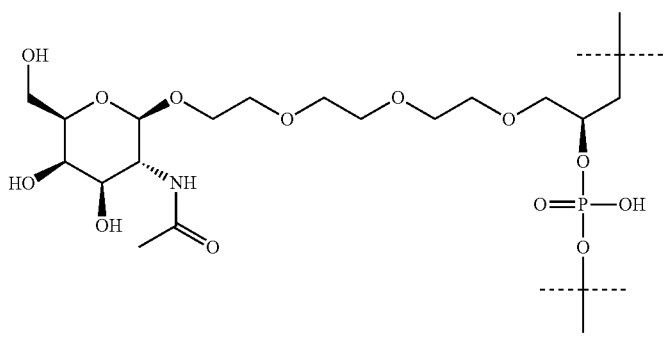
X⁹
[Formula 20]
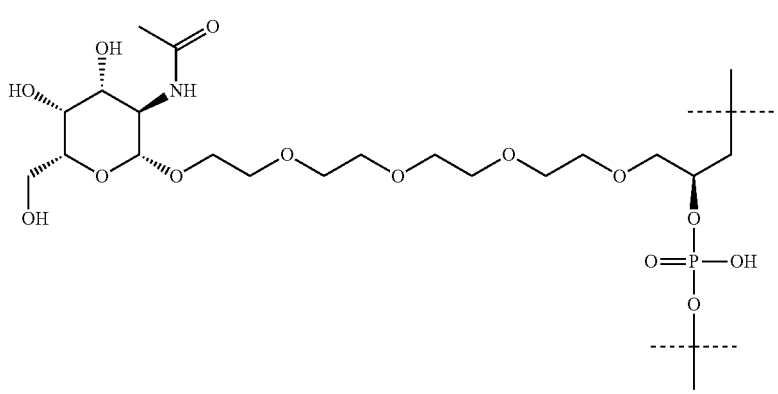
X¹⁰
[Formula 21]
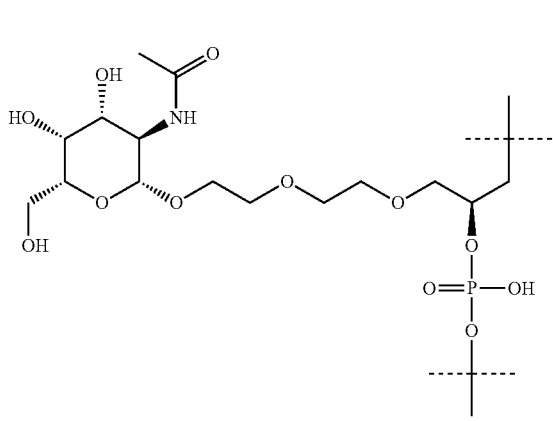
X¹¹
[Formula 22]
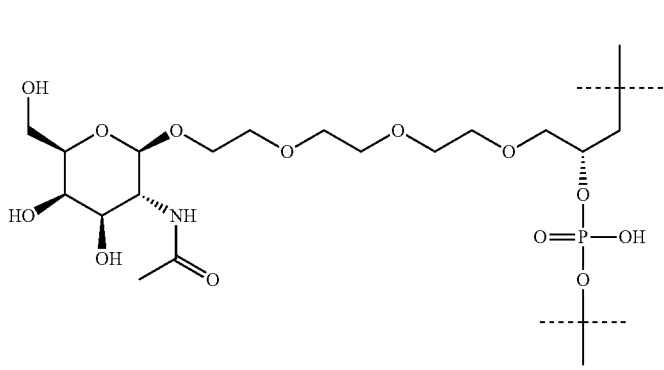
X¹²

[Formula 23]
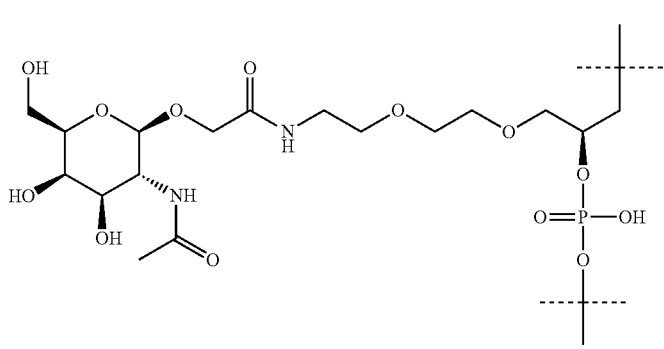
X¹³
[Formula 24]
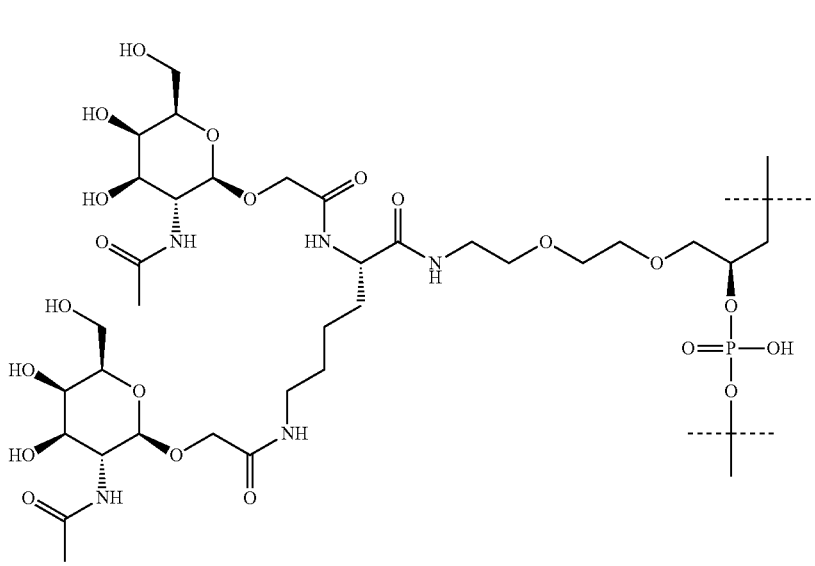
X¹⁴
[Formula 25]
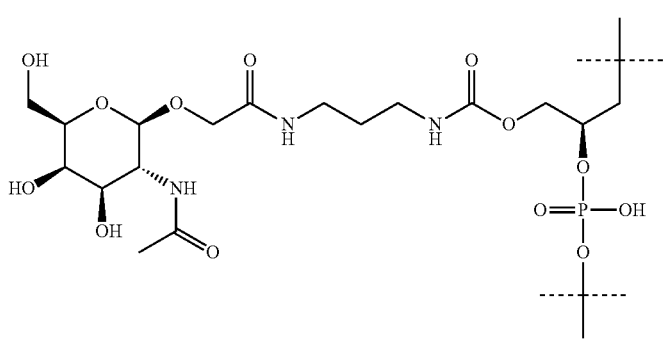
X¹⁵

[Formula 26]
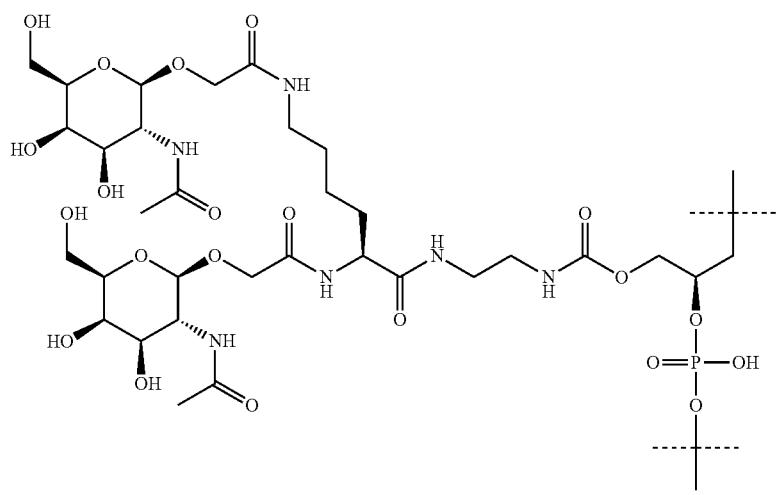
X^16
[Formula 27]
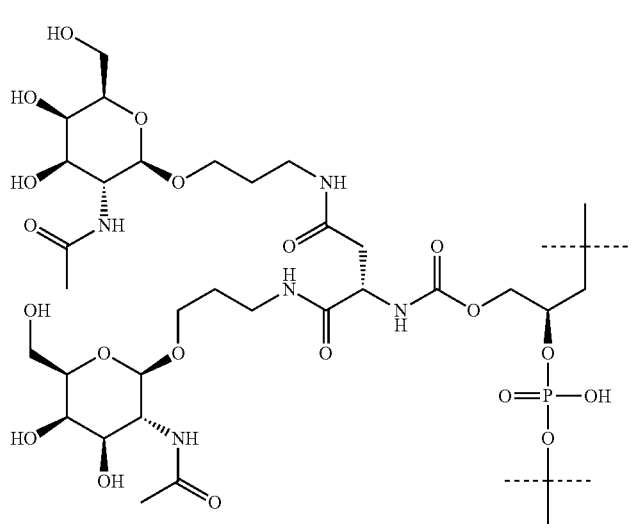
X^17
[Formula 28]
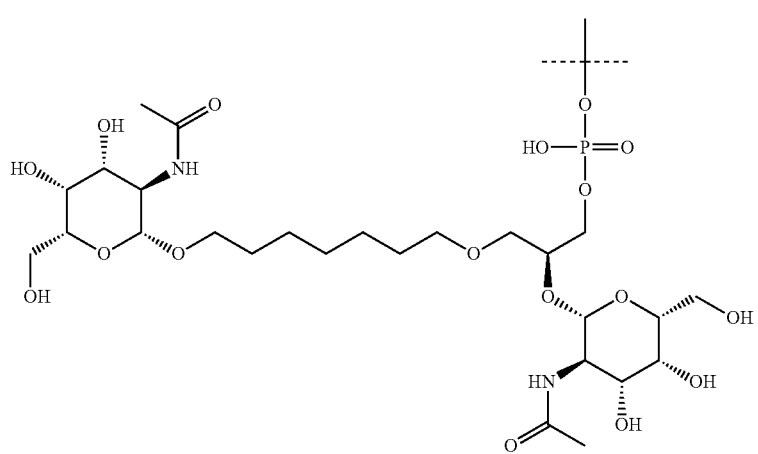
X^7

[Formula 29]
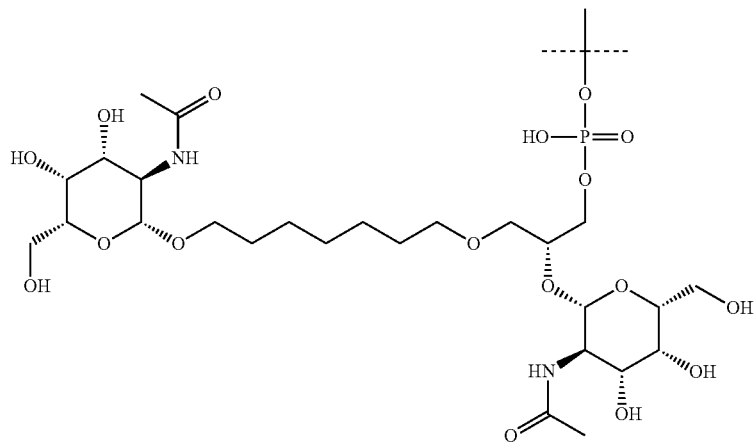
X⁸
[Formula 30]
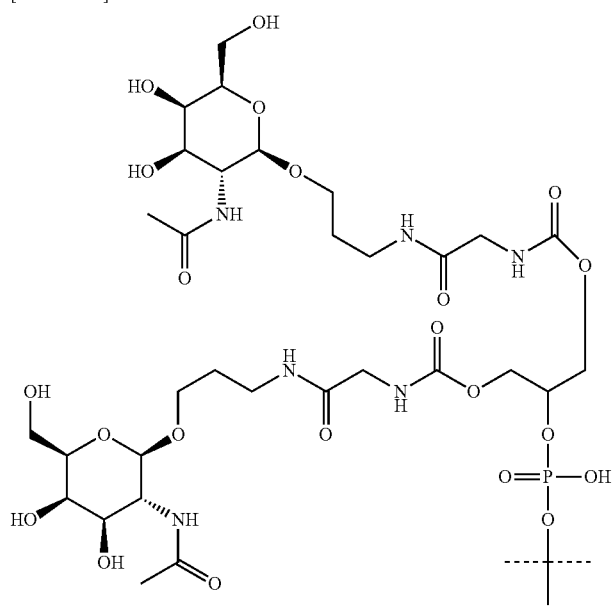
X¹⁸
[Formula 31]
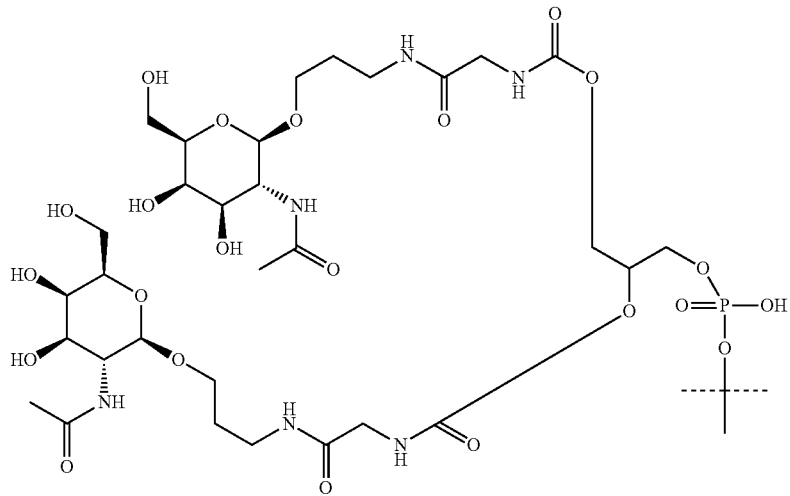
X¹⁹

[Formula 32]
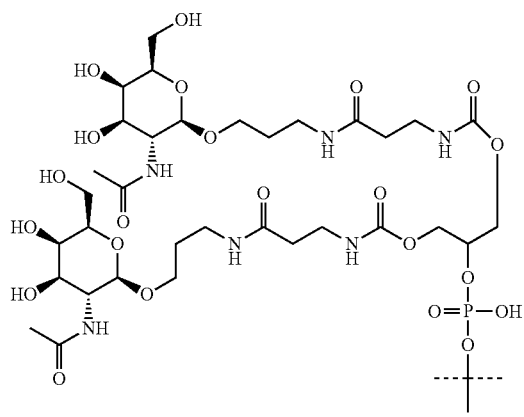
X²⁰
[Formula 33]
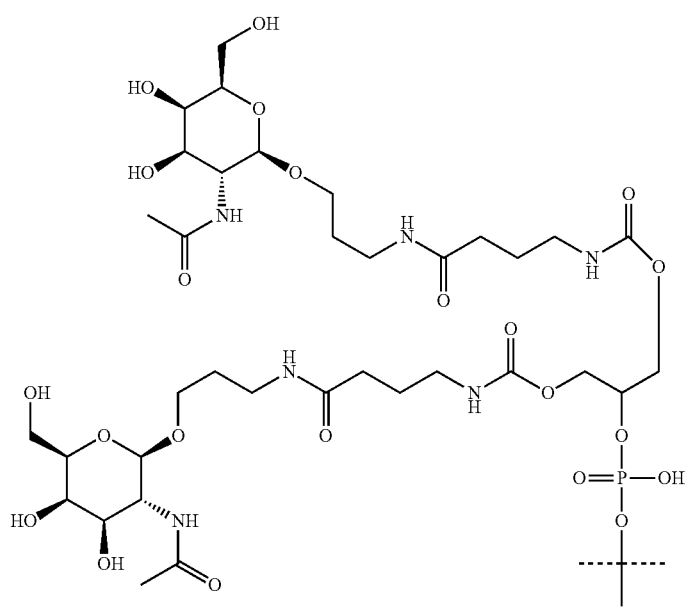
X²¹

[Formula 34]

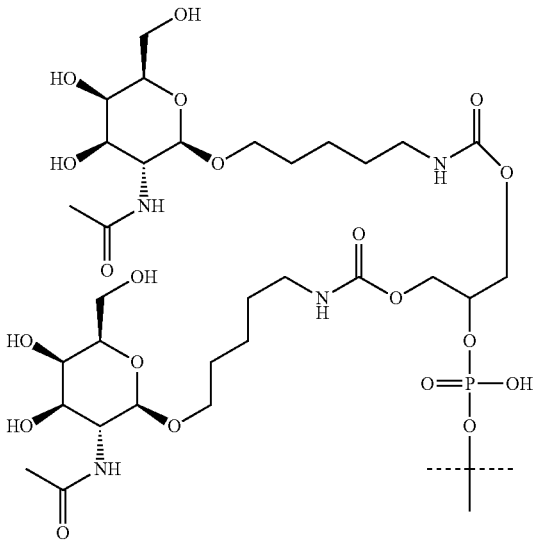

$X^{22}$

(25) A pharmaceutical drug comprising the oligonucleotide, a pharmacologically acceptable salt or solvate thereof of any one of (1) to (24).

(26) A therapeutic drug for glycogen storage disease type Ia, comprising the oligonucleotide of any one of (1) to (24), a pharmaceutically acceptable salt thereof, or a solvate thereof.

(27) A method of treating glycogen storage disease type Ia, comprising administering to a subject the oligonucleotide, a pharmacologically acceptable salt or solvate thereof of any one of (1) to (24) in a pharmaceutically effective amount.

(28) The oligonucleotide, a pharmacologically acceptable salt or solvate thereof of any one of (1) to (24) for use in a method of treating glycogen storage disease type Ia.

(29) A formulation for oral or parenteral administration, comprising the oligonucleotide, a pharmacologically acceptable salt or solvate thereof of any one of (1) to (24).

(30) The oligonucleotide of any one of (1) to (24), a pharmacologically acceptable salt or solvate thereof for use as a pharmaceutical drug.

Effect of the Invention

According to the present invention, it is possible to repair c.648G>T mutation-harboring G6PC gene at the mRNA level in glycogen storage disease type Ia patients. As a result, normal G6PC protein is produced, which enables normalization of hypoglycemia, normalization of liver swelling, and suppressed progression into hepatoma in glycogen storage disease type Ia patients.

The present specification encompasses the contents disclosed in the specifications and/or drawings of Japanese Patent Applications No. 2018-43524 and No. 2018-128015 based on which the present patent application claims priority.

BRIEF DESCRIPTION OF THE DRAWINGS

FIG. 3 A diagram showing sequences of ASOs (21e_001 to 21e_012) capable of binding to exon 5 of the mRNA of c.648G>T mutation-harboring G6PC gene. In FIG. 3, G6PC mRNA corresponds to SEQ ID NO: 96, G6PC AS corresponds to SEQ ID NO: 97, 21e_001 corresponds to SEQ ID NO: 33, 21e_002 corresponds to SEQ ID NO: 1, 21e_003 corresponds to SEQ ID NO: 2, 21e_004 corresponds to SEQ ID NO: 3, 21e_005 corresponds to SEQ ID NO: 4, 21e_006 corresponds to SEQ ID NO: 5, 21e_007 corresponds to SEQ ID NO: 6, 21e_008 corresponds to SEQ ID NO: 7, 21e_009 corresponds to SEQ ID NO: 8, 21e_010 corresponds to SEQ ID NO: 9, 21e_011 corresponds to SEQ ID NO: 10, and 21e_012 corresponds to SEQ ID NO: 11.

In FIG. 4, G6PC mRNA corresponds to SEQ ID NO: 96, G6PC AS corresponds to SEQ ID NO: 97, 21m_001 corresponds to SEQ ID NO: 160, 21m_002 corresponds to SEQ ID NO: 98, 21m_003 corresponds to SEQ ID NO: 99, 21m_004 corresponds to SEQ ID NO: 100, 21m_005 corresponds to SEQ ID NO: 101, 21m_006 corresponds to SEQ ID NO: 102, 21m_007 corresponds to SEQ ID NO: 103, 21m_008 corresponds to SEQ ID NO: 104, 21m_009 corresponds to SEQ ID NO: 105, 21m_010 corresponds to SEQ ID NO: 106, 21m_011 corresponds to SEQ ID NO: 107, and 21m_012 corresponds to SEQ ID NO: 108.

FIG. 8 A diagram showing sequences of ASOs (21e_001 to 21e_006 and 21e_013 to 21e_022) capable of binding to exon 5 of the mRNA of c.648G>T mutation-harboring G6PC gene. In FIG. 8, G6PC mRNA corresponds to bases 70-120 of SEQ ID NO: 96, G6PC AS corresponds to bases 1-50 of SEQ ID NO: 97, 21e_001 corresponds to SEQ ID NO: 33, 21e_013 corresponds to SEQ ID NO: 34, 21e_014 corresponds to SEQ ID NO: 35, 21e_002 corresponds to SEQ ID NO: 1, 21e_015 corresponds to SEQ ID NO: 12, 21e_016 corresponds to SEQ ID NO: 13, 21m_003 corresponds to SEQ ID NO: 2, 21e_017 corresponds to SEQ ID NO: 14, 21e_018 corresponds to SEQ ID NO: 15, 21e_004 corresponds to SEQ ID NO: 3, 21e_019 corresponds to SEQ ID NO: 16, 21e_020 corresponds to SEQ ID NO: 17, 21e_005 corresponds to SEQ ID NO: 4, 21e_021 corresponds to SEQ ID NO: 18, 21e_022 corresponds to SEQ ID NO: 19, and 21e_006 corresponds to SEQ ID NO: 5.

In FIG. 11, G6PC mRNA corresponds to bases 70-120 of SEQ ID NO: 96, G6PC AS corresponds to bases 1-50 of SEQ ID NO: 97, 18e_001 corresponds to SEQ ID NO: 36, 18e_002 corresponds to SEQ ID NO: 37, 18e_003 corresponds to SEQ ID NO: 38, 18e_004 corresponds to SEQ ID NO: 39, 18e_005 corresponds to SEQ ID NO: 20, 18e_006 corresponds to SEQ ID NO: 21, 18e_007 corresponds to SEQ ID NO: 22, 18e_008 corresponds to SEQ ID NO: 23, 18e_009 corresponds to SEQ ID NO: 24, 18e_010 corresponds to SEQ ID NO: 25, 18e_011 corresponds to SEQ ID NO: 26, 18e_012 corresponds to SEQ ID NO: 27, 18e_013 corresponds to SEQ ID NO: 28, 18e_014 corresponds to SEQ ID NO: 29, 18e_015 corresponds to SEQ ID NO: 30, 18e_016 corresponds to SEQ ID NO: 31, and 18e_017 corresponds to SEQ ID NO: 32.

FIG. 12 A diagram showing sequences of ASOs (18m_001 to 18m_017) capable of binding to exon 5 of the mRNA of c.648G>T mutation-harboring G6PC gene. In FIG. 12, G6PC mRNA corresponds to bases 70-120 of SEQ ID NO: 96, G6PC AS corresponds to bases 1-50 of SEQ ID NO: 97, 18m_001 corresponds to SEQ ID NO: 156, 18m_002 corresponds to SEQ ID NO: 157, 18m_003 corresponds to SEQ ID NO: 158, 18m_004 corresponds to SEQ ID NO: 159, 18m_005 corresponds to SEQ ID NO: 135, 18m_006 corresponds to SEQ ID NO: 136, 18m_007 corresponds to SEQ ID NO: 137, 18m_008 corresponds to SEQ ID NO: 138, 18m_009 corresponds to SEQ ID NO: 139, 18m_010 corresponds to SEQ ID NO: 140, 18m_011 corresponds to SEQ ID NO: 141, 18m_012 corresponds to SEQ ID NO: 142, 18m_013 corresponds to SEQ ID NO: 143, 18m_014 corresponds to SEQ ID NO: 144, 18m_015 corresponds to SEQ ID NO: 145, 18m_016 corresponds to SEQ ID NO: 146, and 18m_017 corresponds to SEQ ID NO: 147.

FIG. 15 A diagram showing sequences of ASOs (18e_018 to 18e_031) capable of binding to exon 5 of the mRNA of c.648G>T mutation-harboring G6PC gene. In FIG. 15, G6PC mRNA corresponds to bases 70-120 of SEQ ID NO: 96, G6PC AS corresponds to bases 1-50 of SEQ ID NO: 97, 18e_018 corresponds to SEQ ID NO: 148, 18e_019 corresponds to SEQ ID NO: 149, 18e_020 corresponds to SEQ ID NO: 150, 18e_021 corresponds to SEQ ID NO: 151, 18e_022 corresponds to SEQ ID NO: 129, 18e_023 corresponds to SEQ ID NO: 130, 18e_024 corresponds to SEQ ID NO: 131, 18e_025 corresponds to SEQ ID NO: 132, 18e_026 corresponds to SEQ ID NO: 133, 18e_027 corresponds to SEQ ID NO: 152, 18e_028 corresponds to SEQ ID NO: 153, 18e_029 corresponds to SEQ ID NO: 154, 18e_030 corresponds to SEQ ID NO: 155, and 18e_031 corresponds to SEQ ID NO: 134.

BEST MODES FOR CARRYING OUT THE INVENTION

Figure 1:
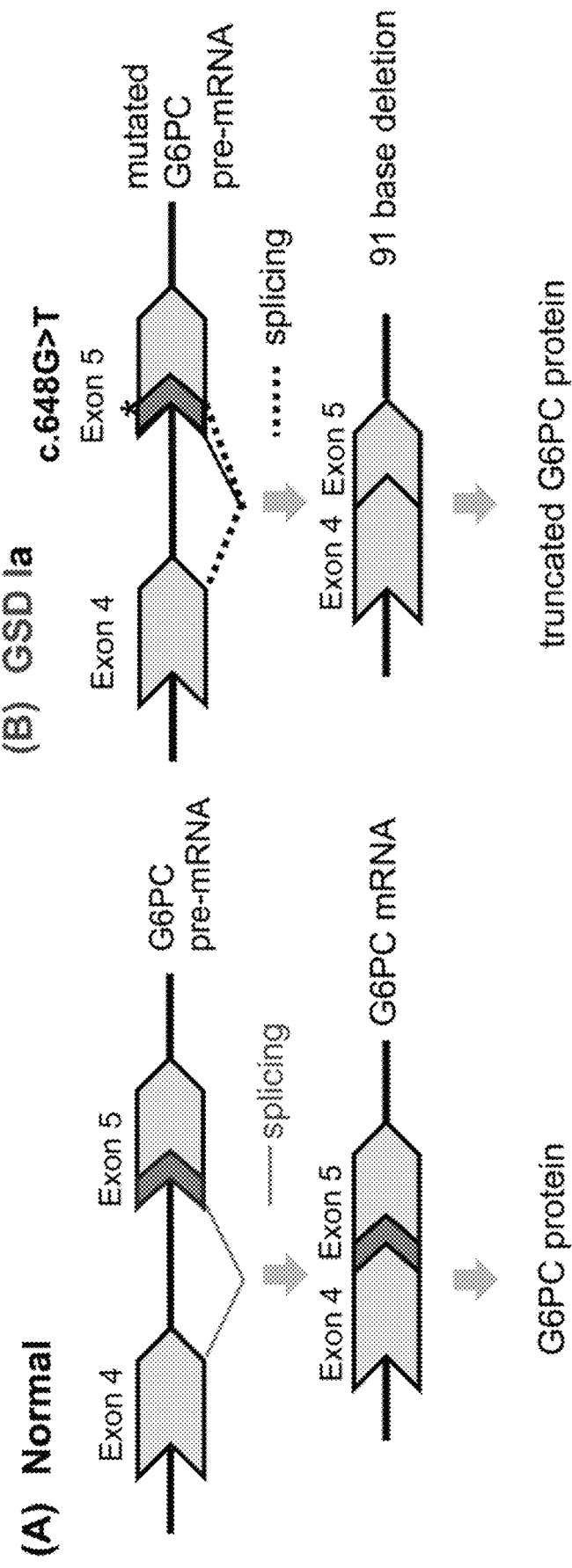
FIG. 1 (A) A diagram illustrating the process of generation of G6PC protein from G6PC gene. (B) A diagram showing the splicing pattern of mRNA of c.648G>T mutation-harboring G6PC gene in glycogen storage disease type Ia patients.
Figure 2:
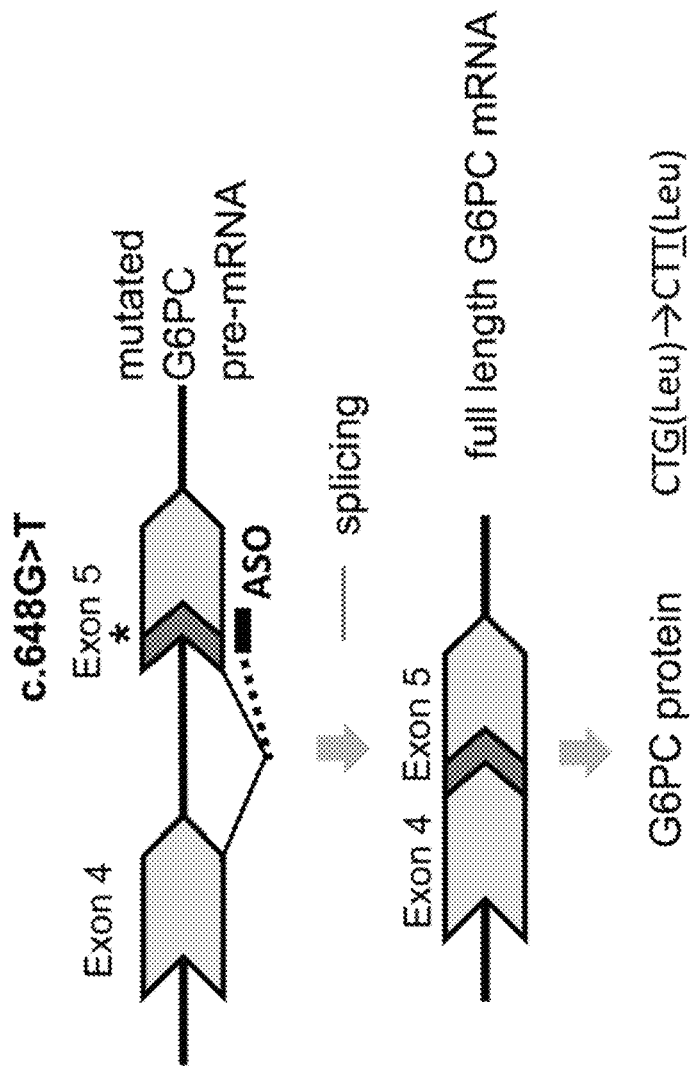
FIG. 2 A schematic diagram showing the therapeutic principle using the therapeutic drug for glycogen storage disease type Ia (ASO) of the present invention.
Figure 4:
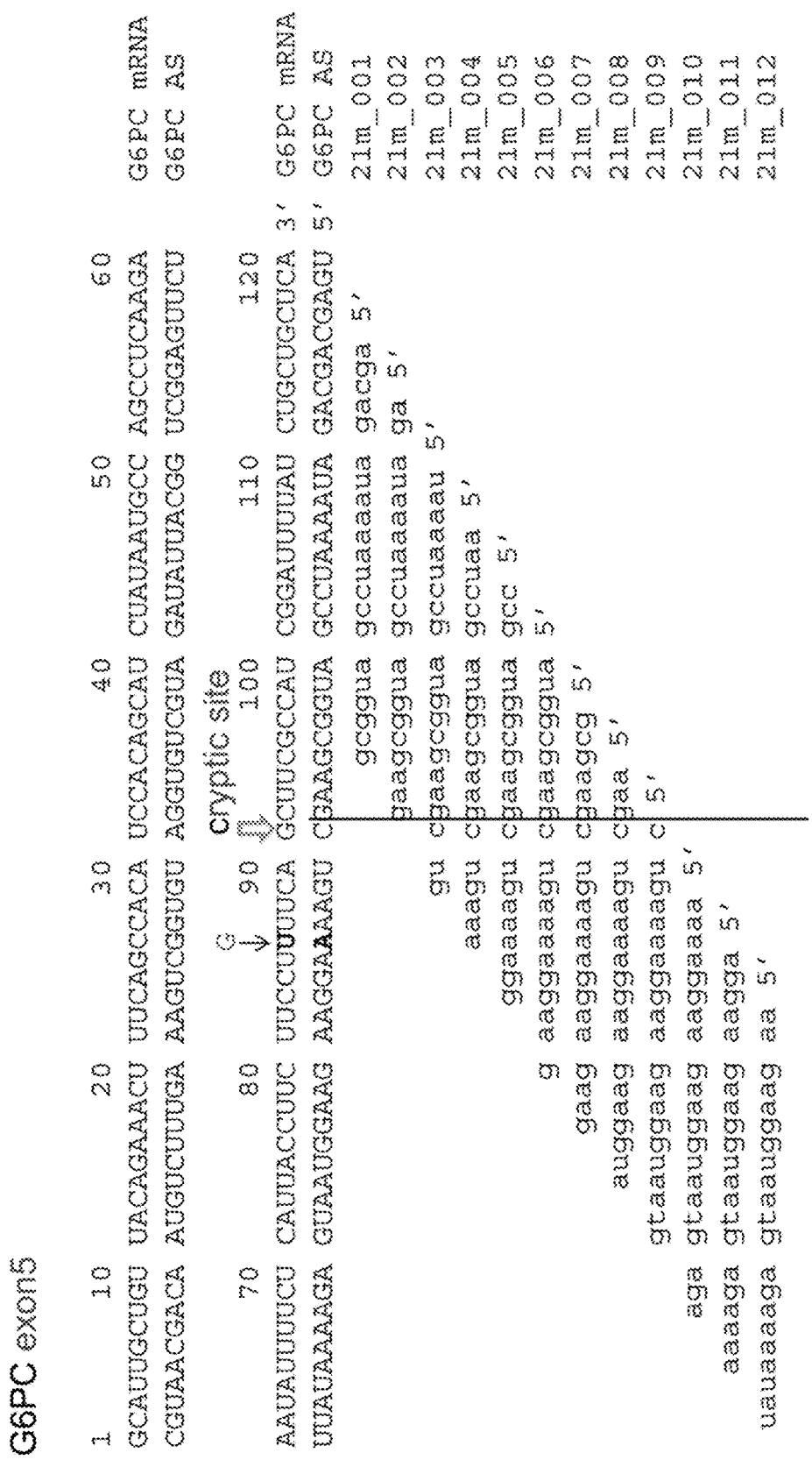
FIG. 4 A diagram showing sequences of ASOs (21m_001 to 21m_012) capable of binding to exon 5 of the mRNA of c.648G>T mutation-harboring G6PC gene.

Hereinbelow, embodiments of the present invention is described in detail.

The present invention provides an oligonucleotide capable of repairing G6PC gene with c.648G>T mutation at the mRNA level in glycogen storage disease type Ia patients and thereby allowing expression of normal G6PC protein, a pharmacologically acceptable salt or solvate thereof. The oligonucleotide of the present invention is an oligonucleotide of 15-30 bases comprising a nucleotide sequence complementary to the cDNA of G6PC gene with c.648G>T mutation, wherein the oligonucleotide comprises a sequence complementary to a region comprising any site between the $82^{nd}$ to the $92^{nd}$ nucleotide from the 5' end of exon 5 of the G6PC gene with c.648G>T mutation.

Among glycogen storage disease type Ia patients, those patients who have c.648G>T mutation may be targets of the present invention. Not only c.648G>T mutation-homozygous patients but also compound heterozygous patients with c.648G>T mutation and other mutation may be targets of the present invention.

The c.648G>T mutation in G6PC gene is a mutation of G to T at nucleotide No. 728 in *Homo sapiens* glucose-6-phosphatase catalytic subunit (G6PC), transcript variant 1, mRNA (NCBI-GenBank accession No. NM_000151.3). This mutation is positioned at the $86^{th}$ nucleotide from the 5' end of exon 5. The oligonucleotide of the present invention may consist of a nucleotide sequence complementary to a region comprising any site between the $86^{th}$ to the $92^{nd}$ nucleotide from the 5' end of exon 5 of the G6PC gene with c.648G>T mutation; preferably, the oligonucleotide of the present invention comprises a nucleotide sequence complementary to a region comprising the site of the $92^{nd}$ nucleotide.

As specific examples of the above-described oligonucleotide of 15-30 bases comprising a nucleotide sequence complementary to the cDNA of G6PC gene with c.648G>T mutation, wherein the oligonucleotide comprises a sequence complementary to a region comprising any site between the $82^{nd}$ to the $92^{nd}$ nucleotide from the 5' end of exon 5 of the G6PC gene with c.648G>T mutation, oligonucleotides comprising all or part of any sequence as shown in SEQ ID NOS: 1 to 32, 40 to 42, 44 to 48, 98 to 147 and 161 to 179 may be given. In the present invention, the expression "part of sequence" usually refers to 80% or more of the entire relevant sequence, preferably 85%, more preferably 90%, and most preferably 94%. The base number of the oligonucleotide of the present invention is appropriately 15 to 30, preferably 15 to 21, and more preferably 15 to 18.

Nucleotides constituting the oligonucleotide (antisense oligonucleotide) of the present invention may be either natural DNA, natural RNA, chimera DNA/RNA, or modified DNA, RNA or DNA/RNA. Preferably, at least one of the nucleotides is a modified nucleotide.

Examples of modified nucleotides include those in which sugar is modified (e.g., D-ribofuranose is 2'-O-alkylated, D-ribofuranose is 2'-O, 4'-C-alkylenated, or D-ribofuranose is 2'-,4'-bridged), those in which phosphodiester bond is modified (e.g., thioated), those in which base is modified, combinations of above-described nucleotides, and so forth. Antisense oligonucleotides in which at least one D-ribofuranose constituting the oligonucleotides is 2'-O-alkylated or 2'-O, 4'-C-alkylenated have high RNA binding affinity and high resistance to nuclease. Thus, they are expected to produce higher therapeutic effect than natural nucleotides (i.e. oligo DNA or oligo RNA). Further, oligonucleotides in which at least one phosphodiester bond constituting the oligonucleotides is thioated also have high resistance to nuclease and, thus, are expected to produce higher therapeutic effect than natural nucleotides (i.e. oligo DNA or oligo RNA). Oligonucleotides comprising both the modified sugar and the modified phosphate as described above have even higher resistance to nuclease and, thus, are expected to produce even higher therapeutic effect.

With respect to the oligonucleotide (antisense oligonucleotide), examples of modified sugars include, but are not limited to, D-ribofuranose as 2'-O-alkylated (e.g. 2'-O-methylated, 2'-O-aminoethylated, 2'-O-propylated, 2'-O-allylated, 2'-O-methoxyethylated, 2'-O-butylated, 2'-O-pentylated, or 2'-O-propargylated); D-ribofuranose as 2'-O,4'-C-alkylenated (e.g. 2'-O,4'-C-ethylenated, 2'-O,4'-C-methylenated, 2'-O,4'-C-propylenated, 2'-O,4'-C-tetramethylenated, or 2'-O,4'-C-pentamethylenated); D-ribofuranose as 2'-deoxy-2'-C,4'-C-methyleneoxymethylenated, S-cEt (2',4'-constrained ethyl), AmNA (Amide-bridged nucleic acid), 3'-deoxy-3'-amino-2'-deoxy-D-ribofuranose; and 3'-deoxy-3'-amino-2'-deoxy-2'-fluoro-D-ribofuranose.

With respect to the oligonucleotide (antisense oligonucleotide), examples of the 2'-,4'-bridging modification of sugars include, but are not limited to, D-ribofuranose as 2'-O,4'-C-alkylenated (e.g. 2'-O,4'-C-ethylenated, 2'-O,4'-C-methylenated, 2'-O,4'-C-propylenated, 2'-O,4'-C-tetramethylenated, or 2'-O,4'-C-pentamethylenated); D-ribofuranose as 2'-deoxy-2'-C,4'-C-methyleneoxymethylenated, S-cEt (2',4'-constrained ethyl) and AmNA.

With respect to the oligonucleotide (antisense oligonucleotide), examples of the modification of phosphodiester bond include, but are not limited to, phosphorothioate bond, methylphosphonate bond, methylthiophosphonate bond, phosphorodithioate bond and phosphoramidate bond.

Examples of modified bases include, but are not limited to, cytosine as 5-methylated, 5-fluorinated, 5-brominated, 5-iodinated or N4-methylated; thymine as 5-demethylated (uracil), 5-fluorinated, 5-brominated or 5-iodinated; adenine as N6-methylated or 8-brominated; and guanine as N2-methylated or 8-brominated.

The oligonucleotide (antisense oligonucleotide) may be synthesized with a commercially available DNA synthesizer (e.g., PerkinElmer Model 392 based on the phosphoramidite method) according to the method described in Nucleic Acids Research, 12, 4539 (1984) with necessary modifications. As phosphoramidite reagents to be used in the process, natural nucleosides and 2'-O-methylnucleosides (i.e., 2'-O-methylguanosine, 2'-O-methyladenosine, 2'-O-methylcytidine and 2'-O-methyluridine) are commercially available. As regards 2'-O-alkylguanosine, -alkyladenosine, -alkylcytidine and -alkyluridine in which the carbon number of the alkyl group is 2-6, the following methods may be employed.

2'-O-aminoethylguanosine, -aminoethyladenosine, -aminoethylcytidine and -aminoethyluridine may be synthesized as previously described (Blommers et al., Biochemistry (1998), 37, 17714-17725).

2'-O-propylguanosine, -propyladenosine, -propylcytidine and -propyluridine may be synthesized as previously described (Lesnik, E. A. et al., Biochemistry (1993), 32, 7832-7838).

For the synthesis of 2'-O-allylguanosine, -allyladenosine, -allylcytidine and -allyluridine, commercially available reagents may be used.

2'-O-methoxyethylguanosine, -methoxyethyladenosine, -methoxyethylcytidine and -methoxyethyluridine may be synthesized as previously described (U.S. Pat. No. 6,261,840 or Martin, P. Helv. Chim. Acta. (1995) 78, 486-504).

2'-O-butylguanosine, -butyladenosine, -butylcytidine and -butyluridine may be synthesized as previously described (Lesnik, E. A. et al., Biochemistry (1993), 32, 7832-7838).

2'-O-pentylguanosine, -pentyladenosine, -pentylcytidine and -pentyluridine may be synthesized as previously described (Lesnik, E. A. et al., Biochemistry (1993), 32, 7832-7838).

For the synthesis of 2'-O-propargylguanosine, -propargyladenosine, -propargylcytidine and -propargyluridine, commercially available reagents may be used.

2'-O,4'-C-methyleneguanosine, 2'-O,4'-C-methyleneadenosine, 2'-O,4'-C-methylenecytidine, 5-methylcytidine and 5-methylthymidine may be prepared according to the method described in WO99/14226; and 2'-O,4'-C-alkyleneguanosine, 2'-O,4'-C-alkyleneadenosine, 2'-O,4'-C-methylenecytidine, 5-methylcytidine and 5-methylthymidine in which the carbon number of the alkylene group is 2-5 may be prepared according to the method described in WO00/47599.

Nucleosides in which D-ribofuranose is 2'-deoxy-2'-C,4'-C-methyleneoxymethylenated may be synthesized as previously described (Wang, G. et al., Tetrahedron (1999), 55, 7707-774).

S-cEt (constrained ethyl) may be synthesized as previously described (Seth, P. P. et al. J. Org. Chem (2010), 75, 1569-1581).

AmNA may be synthesized as previously described (Yahara, A. et al. ChemBioChem (2012), 13, 2513-2516; or WO2014/109384).

In the present invention, nucleobase sequences may be described using the abbreviation "A" or "a" for adenine, "G" or "g" for guanine, "C" or "c" for cytosine and "U" or "u" for uracil. Instead of cytosine, 5-methylsytosine may be used. Among nucleobases, uracil (U or u) and thymine (T or t) are interchangeable. Either uracil (U or u) or thymine (T or t) may be used for base pairing with adenine (A or a) in the complementary strand.

An antisense oligonucleotide with phosphorothioate bonds can be synthesized by coupling phosphoramidite reagents and then reacting sulfur, tetraethylthiuram disulfide (TETD; Applied Biosystems), Beaucage reagent (Glen Research) or a reagent such as xanthan hydride (Tetrahedron Letters, 32, 3005 (1991); J. Am. Chem. Soc. 112, 1253 (1990); PCT/WO98/54198).

As controlled pore glass (CPG) to be used in a DNA synthesizer, 2'-O-methylnucleoside-bound CPG is commercially available. As regards 2'-O,4'-C-methyleneguanosine, 2'-O,4'-C-methyleneadenosine, 5-methylcytidine and 5-methylthymidine, they may be prepared according to the method described in WO99/14226; and as regards 2'-O,4'-C-alkyleneguanosine, 2'-O,4'-C-alkyleneadenosine, 5-methylcytidine and 5-methylthymidine in which the carbon number of the alkylene group is 2-5, they may be prepared according to the method described in WO00/47599. The thus prepared nucleosides may then be bound to CPG as previously described (Oligonucleotide Synthesis, Edited by M. J. Gait, Oxford University Press, 1984). By using the modified CPG (as disclosed in Example 12b of Japanese Unexamined Patent Publication No. Hei7-87982), an oligonucleotide in which a 2-hydroxyethylphosphate group is bound at the 3' end can be synthesized. If 3-amino-Modifier C3 CPG, 3-amino-Modifier C7 CPG or Glyceryl CPG (Glen Research) or 3'-spacer C3 SynBase CPG 1000 or 3'-spacer C9 SynBase CPG 1000 (Link Technologies) is used, an oligonucleotide in which a hydroxyalkylphosphate group or aminoalkylphosphate group is bound at the 3' end can be synthesized.

The oligonucleotide (antisense oligonucleotide) of the present invention may be an oligonucleotide in which GalNAc is bound via a linker and the phosphate portion.

The term "GalNAc unit" in the present invention refers to a unit containing a phosphate group to which a GalNAc-bound linker is bound, and this GalNAc unit may have another binding moiety The phosphate group in the GalNAc unit is capable of binding to the 5' end and/or the 3' end of oligonucleotides. Preferably, the GalNAc unit binds to the 5' end of oligonucleotides. When the GalNAc unit has a binding moiety other than the phosphate group, the binding moiety is capable of binding to hydroxyl group, GalNAc, GalNAc-bound linker, phosphate group of other GalNAc unit, or phosphate group of the 3' end of oligonucleotides. The number of GalNAc molecules binding to one GalNAc unit is preferably 1 to 7, more preferably 1 to 5, especially preferably 1 to 3, and optimally 2.

In the present invention, one GalNAc unit may be bound to the oligonucleotide. Alternatively, multiple GalNAc units as bound consecutively may be bound to the oligonucleotide. The number of GalNAc units binding to one oligonucleotide is preferably 1 to 7, more preferably 1 to 5, especially preferably 1 to 3, and optimally 1.

In the present invention, the oligonucleotide (antisense oligonucleotide) binding to the GalNAc unit may, at its 5' end and/or the 3' end, have an oligonucleotide sequence that is a nucleotide sequence different than the antisense oligonucleotide, which comprises a phosphate diester bond, and which is cleavable in a living body. The strand length of the cleavable oligonucleotide is preferably 1 to 6 nucleotides, and more preferably 1 to 3 nucleotides. The cleavable oligonucleotide is not particularly limited as long as it is cleavable. Examples of such cleavable oligonucleotide include, but are not limited to, natural oligodeoxynucleotides entirely consisting of DNA, or natural oligonucleotides entirely consisting of RNA. The applicable nucleotide sequence is not particularly limited as long as it is cleavable. Examples of the sequence include, but are not limited to, 5'-TCATCA-3', 5'-CATCA-3', 5'-ATCA-3', 5'-TCA-3', 5'-CA-3' and 5'-A-3'.

One example of the GalNAc unit is a group represented by the following general formula.

[Formula 35]

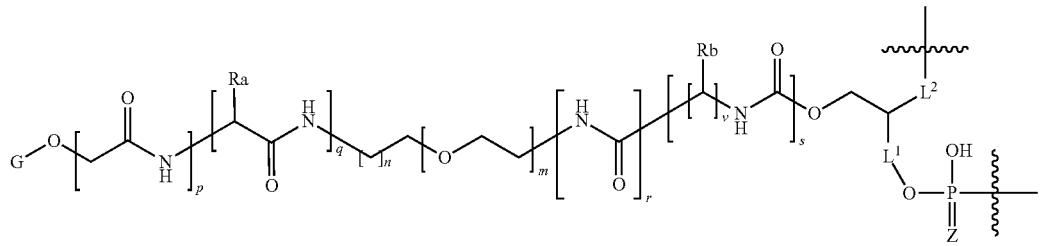

wherein Ra is a group represented by the following formula;

[Formula 36]

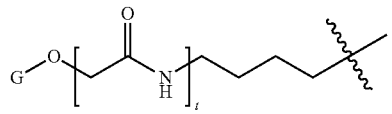

Rb is a group represented by the following formula or a hydrogen atom;

[Formula 37]

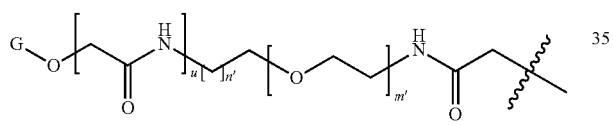

XX is a group represented by the following formula;

[Formula 38]

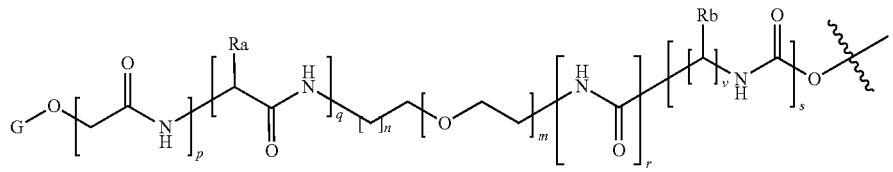

G is 5-acetamide-2-hydroxymethyl-3,4-dihydroxytetrahydropyran-6-yl group (GalNAc); z is an oxygen atom or a sulfur atom; either of $L^1$ or $L^2$ is a methylene group ($CH_2$) and the other is no atom; p, q, r, s, t and u are each independently 0 or 1; n and n' are each independently an integer from 1 to 15; m and m' are each independently an integer from 0 to 5; when Rb is not a hydrogen atom, v is 1; when Rb is a hydrogen atom, v is an integer from 1 to 7; provided that when n is 1, m is an integer from 0 to 5; when n is an integer from 2 to 15, m is 0; when n' is 1, m' is an integer from 1 to 5; when n' is an integer from 2 to 15, m' is 0; a hydroxyl group, an XX group or an OG group may be attached to a bining moiety distant from the phosphorus atom. Preferably, the GalNAc unit is a group represented by the following formula:

[Formula 39]

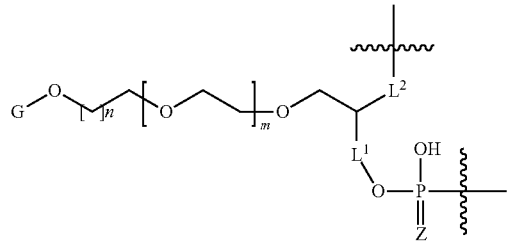

wherein G, Z, $L^1$, $L^2$, n and m are as defined above; a group represented by the following formula:

[Formula 40]

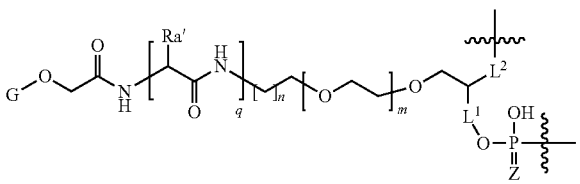

wherein G, Z, $L^1$, $L^2$, q, n and m are as defined above; and Ra' is a group represented by the following formula:

[Formula 41]

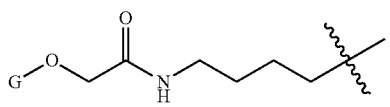

a group represented by the following formula:

[Formula 42]

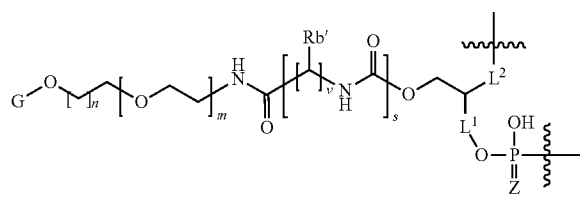

wherein G, Z, $L^1$, $L^2$, s, n, m and v are as defined above; and Rb' is a group represented by the following formula or a hydrogen atom:

[Formula 45]

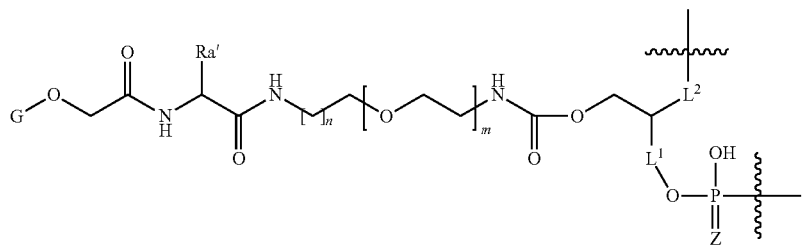

[Formula 43]

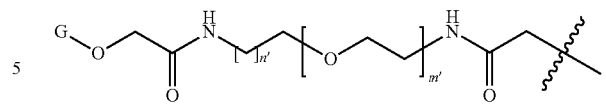

wherein n' and m' are as defined above; a group represented by the following formula:

[Formula 44]

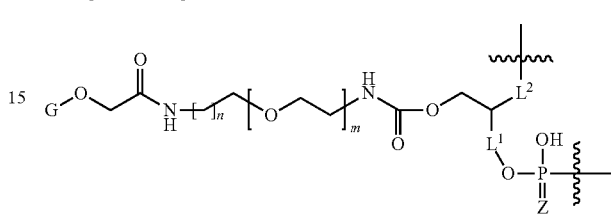

wherein G, Z, $L^1$, $L^2$, n and m are as defined above; or a group represented by the following formula:

wherein G, Z, $L^1$, $L^2$, n, m and Ra' are as defined above.

In the present invention, one example of the GalNAc unit-bound oligonucleotide is an oligonucleotide represented by the following formula:

RO-Xg-Xf-Xe-Xc-Xc-Xb-Xa-T  [Formula 46]

wherein R is a hydrogen atom, an XX group or a G group; T is an oligonucleotide which does not have a hydroxyl group at the 5' end; Xg is a GalNAc unit with a binding moiety; Xa, Xb, Xc, Xd, Xe and Xf are each independently a GalNAc unit with a binding moiety, or a single bond.

With respect to the "GalNAc unit with a binding moiety" in Xa, Xb, Xc, Xd, Xe, Xf and Xg, the following groups may be enumerated:

[Formula 47]

$X^1$

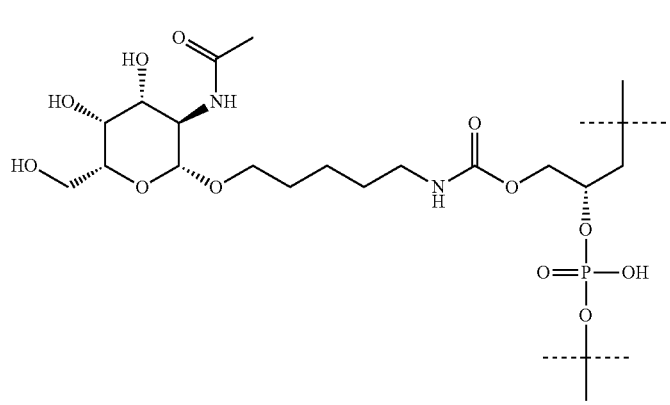

[Formula 48]
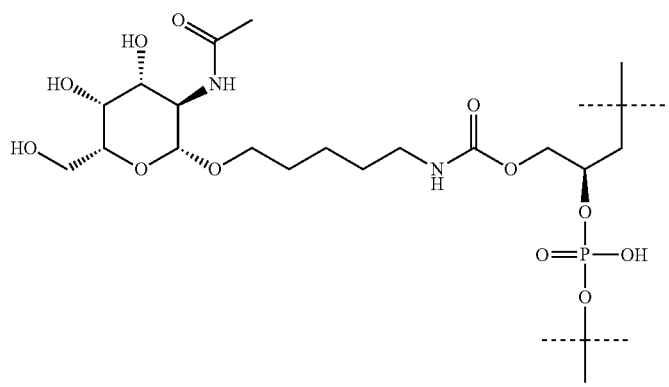
X²
[Formula 49]
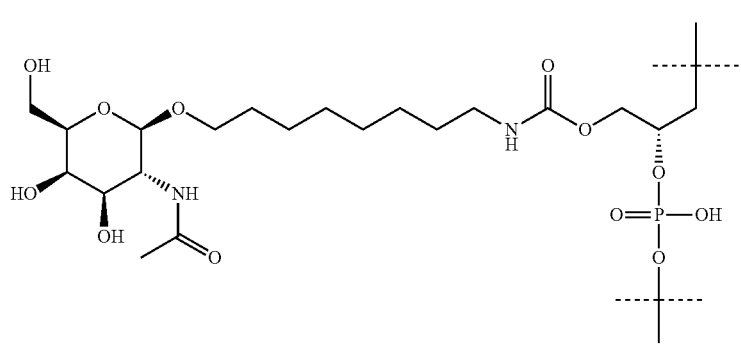
X³
[Formula 50]
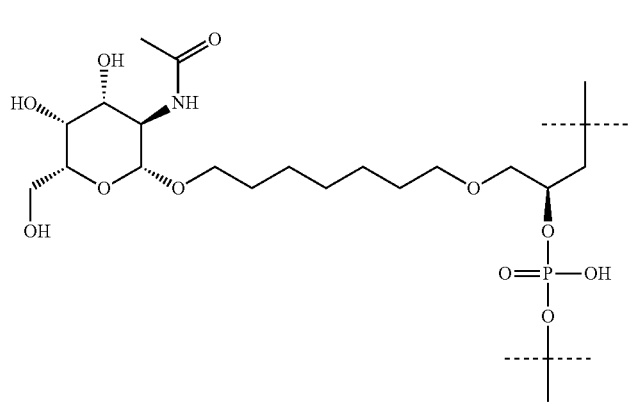
X⁴
[Formula 51]
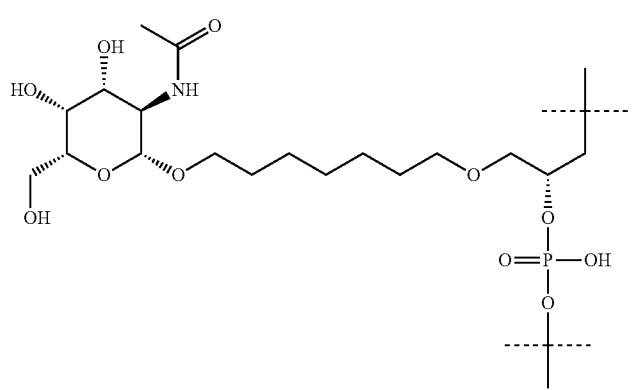
X⁵

-continued
[Formula 52]
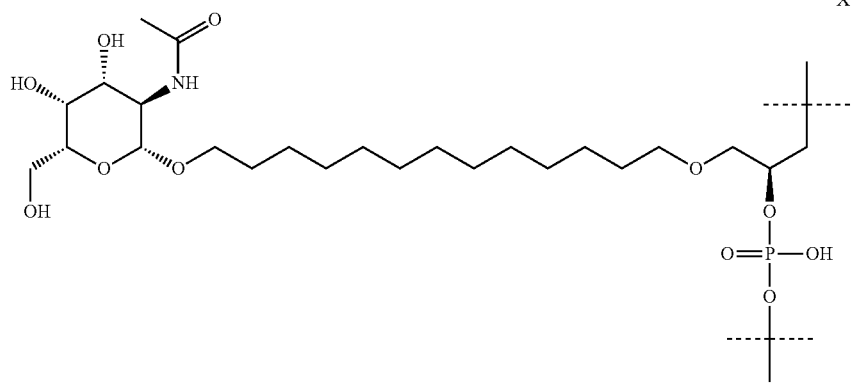
X⁶
[Formula 53]
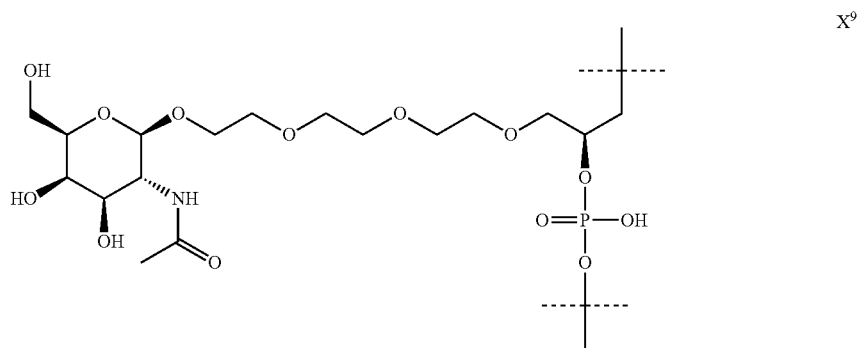
X⁹
[Formula 54]
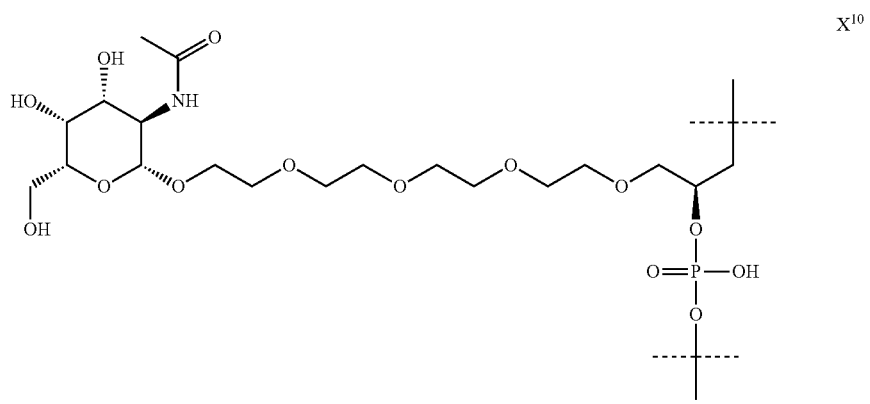
X¹⁰
[Formula 55]
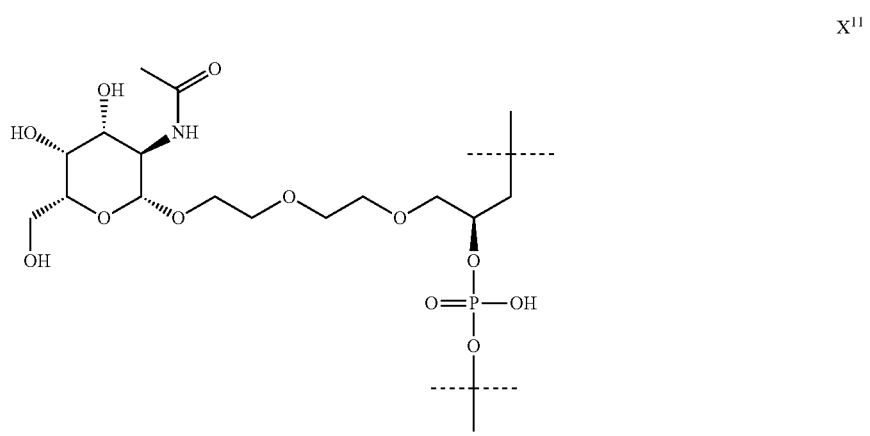
X¹¹

-continued
[Formula 56]
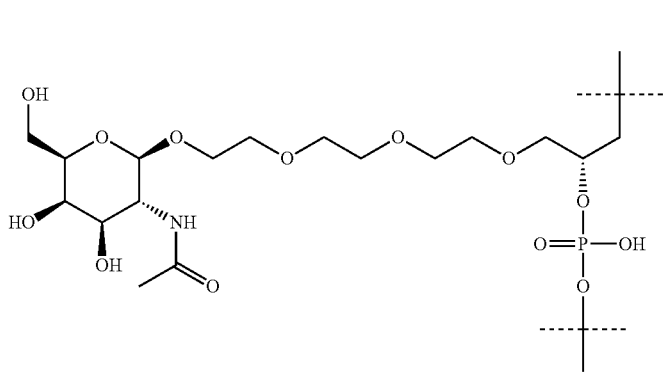
X^{12}
[Formula 57]
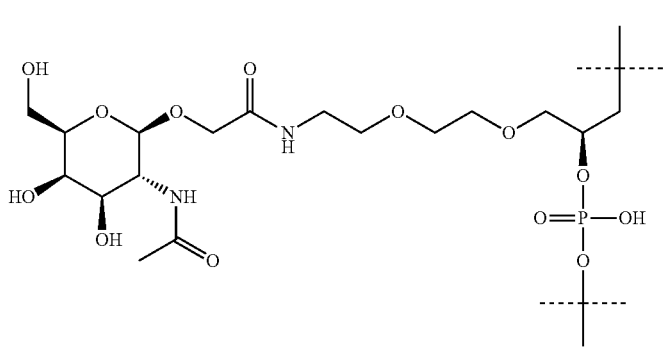
X^{13}
[Formula 58]
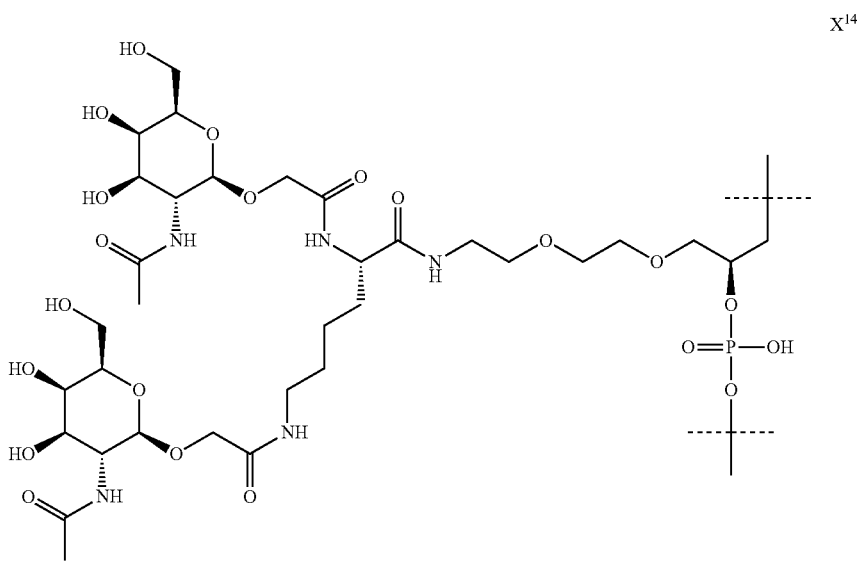
X^{14}

[Formula 59]
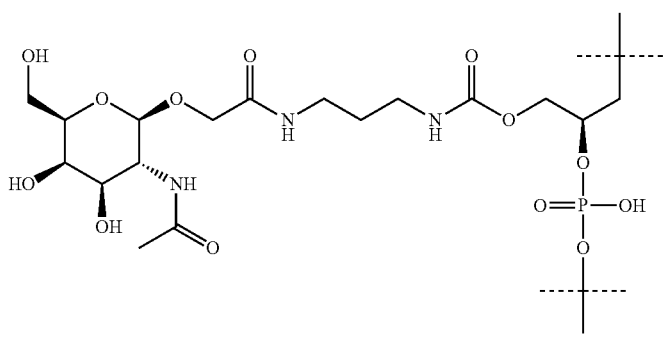
X^{15}
[Formula 60]
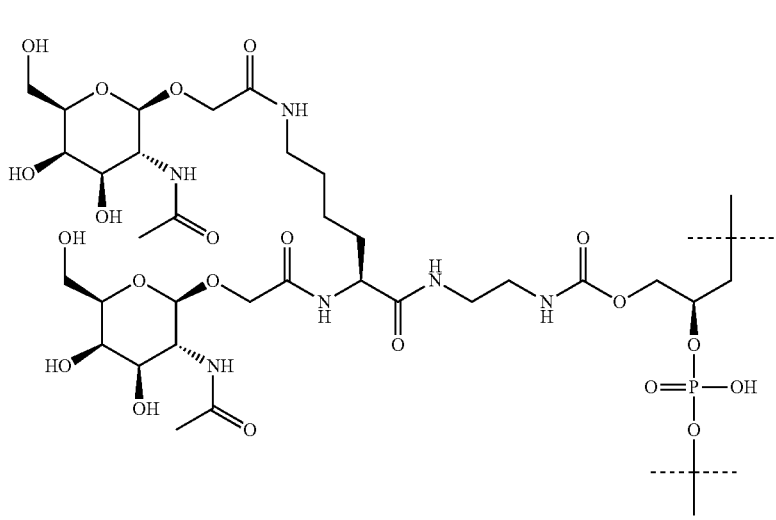
X^{16}
[Formula 61]
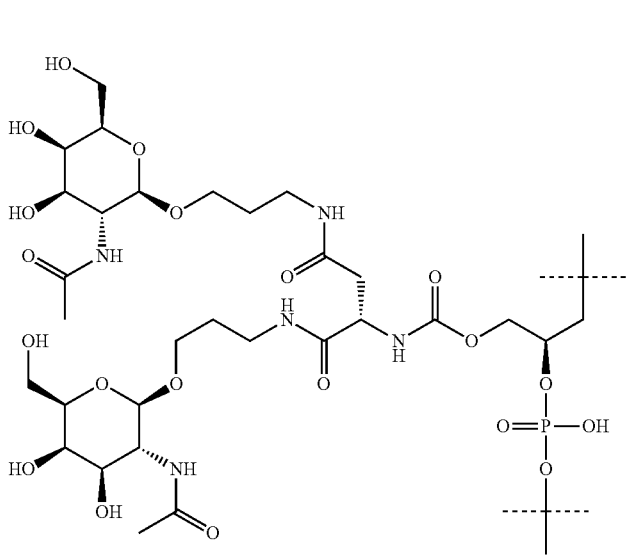
X^{17}

As non-limiting examples of Xg which is a "GalNAc unit with a binding moiety" and the "GalNAc unit" of RO-Xg- where R is an XX group or a G group, the following groups may be enumerated:
[Formula 62]
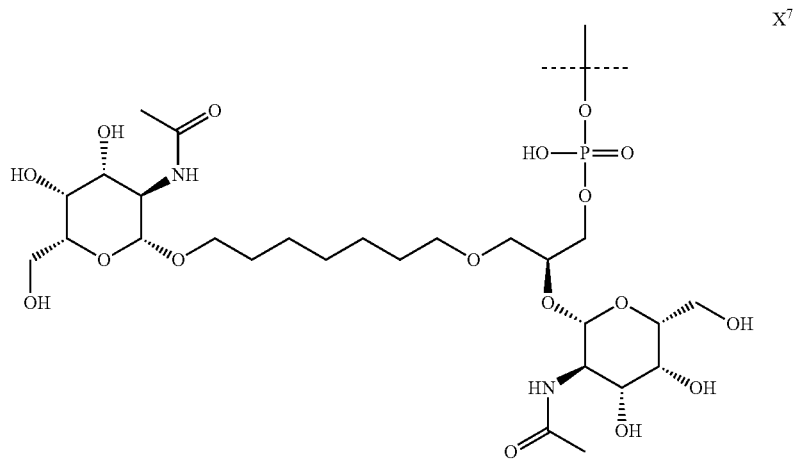
[Formula 63]
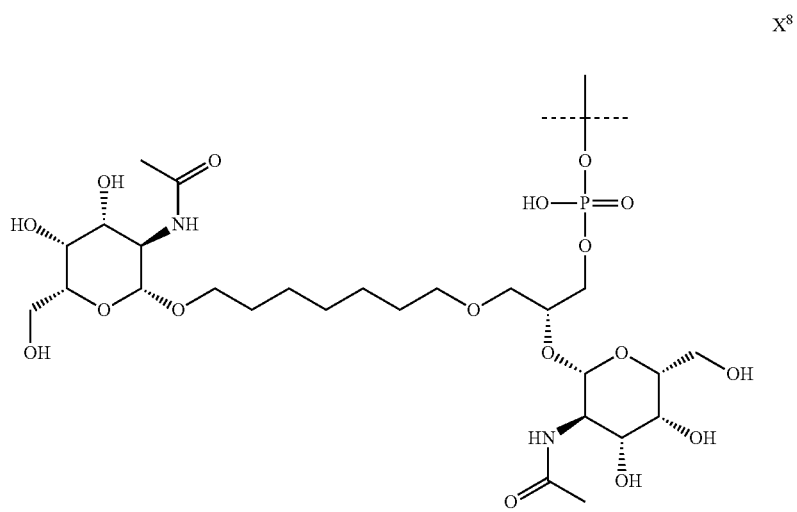

-continued
[Formula 64]
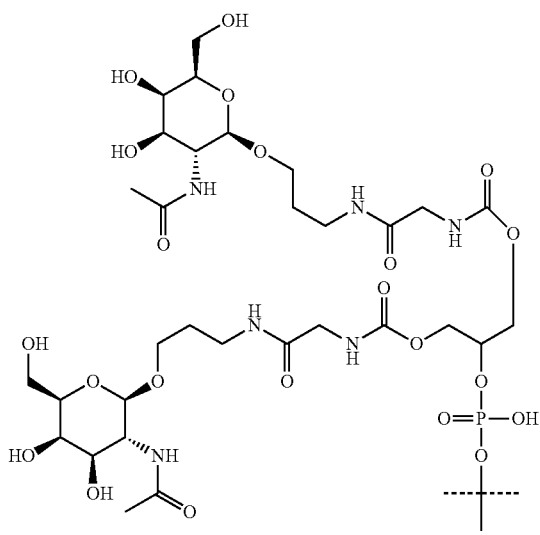
X<sup>18</sup>
[Formula 65]
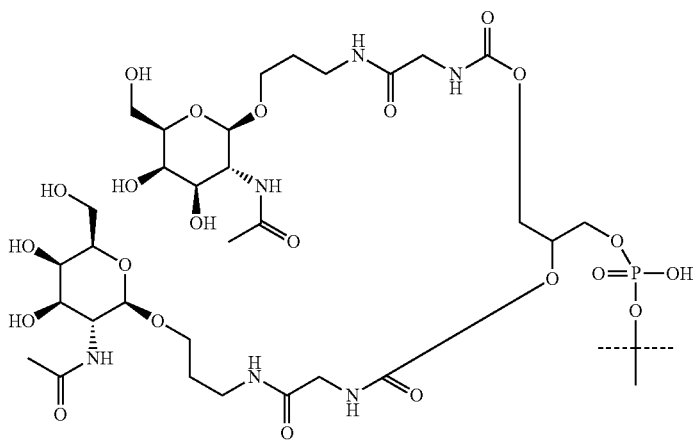
X<sup>19</sup>
[Formula 66]
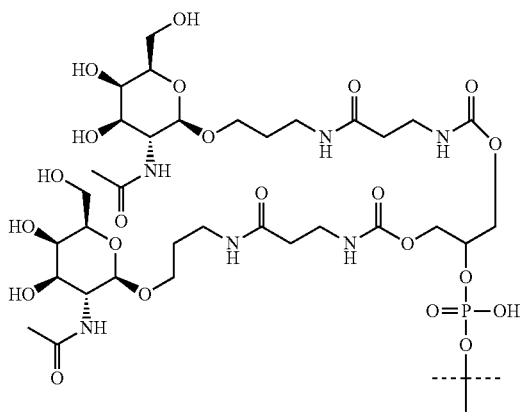
X<sup>20</sup>

[Formula 67]

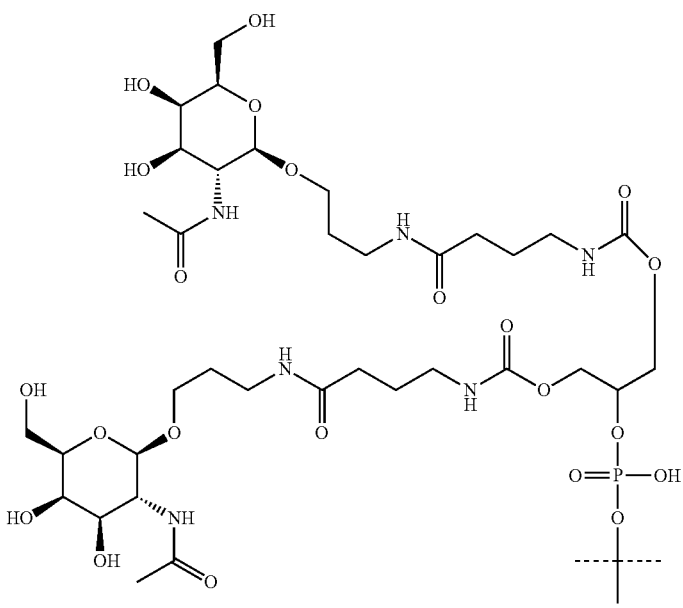

$X^{21}$

[Formula 68]

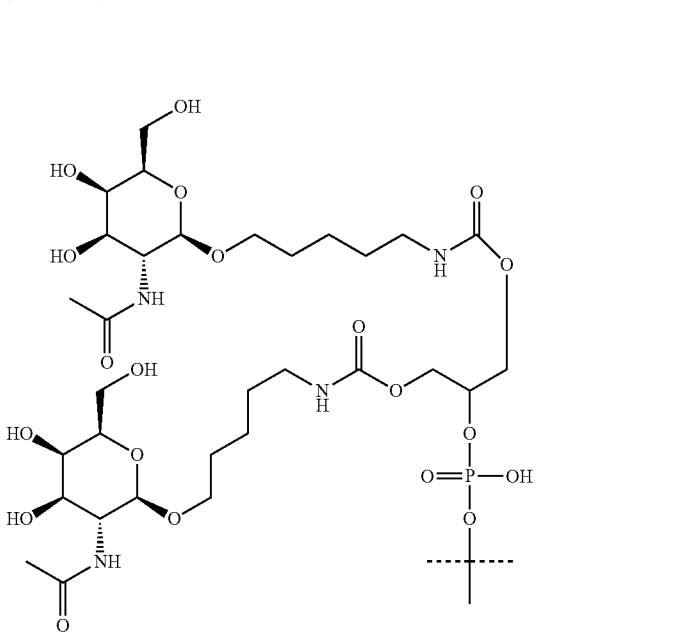

$X^{22}$

The GalNAc unit-bound oligonucleotide of the present invention may be synthesized by using GalNAc unit-containing amidites in the same manner as using amidite reagents for nucleosides, with a commercially available DNA synthesizer (e.g., PerkinElmer Model 392 based on the phosphoramidite method) according to the method described in Nucleic Acids Research, 12, 4539 (1984) with necessary modifications. When the GalNAc unit is to bind at the 5' end of the oligonucleotide, it can be synthesized by coupling the GalNAc unit-containing amidite after completion of the strand extension in the nucleotide portion. Alternatively, when the GalNAc unit is to bind at the 3' end of the oligonucleotide, a modified CPG (as disclosed in Example 12b of Japanese Unexamined Patent Publication No. Hei7-87982), 3-amino-Modifier C3 CPG, 3-amino-Modifier C7 CPG or Glyceryl CPG (Glen Research) or 3'-specer C3 SynBase CPG 1000 or 3'-specer C9 SynBase CPG 1000 (Link Technologies), etc. may be used to couple the GalNAc-containing amidite and then the strand in the oligonucleotide portion is extended, whereby an oligonucleotide can be synthesized which has a hydroxyalkylphosphate group or aminoalkylphosphate group at the 3' end, with the GalNAc unit bound thereto.

Methods of Synthesis of GalNAc Unit-Containing Amidites

The GalNAc unit-containing amidite of the present invention may be prepared according to Methods A to I described below. In Methods A to I, after completion of each reaction, the end compound of interest is collected from the reaction mixture according to conventional methods. For example, the reaction mixture is appropriately neutralized; or when insoluble matters are present therein, they are removed by filtration. Subsequently, water and an immiscible organic solvent such as ethyl acetate are added to separate the organic layer containing the compound of interest. This layer is washed with water or the like and then dried over anhydrous sodium sulfate or the like, followed by distilling off the solvent. Thus, the compound of interest is obtained. If necessary, the compound may be isolated and purified by conventional methods such as silica gel column chromatography. Alternatively, the compound may be purified by reprecipitation and recrystallization.

Method A

This is a method for preparing Compound (8). When Compound (2) with a reverse configuration is used, the configuration of the secondary hydroxyl group to which $P(R^3)R^4$ is bound will also be reversed in Compound (8).

In the above formula, $R^1$ is a common protective group for hydroxyl group, and $R^2$ is 4,4'-dimethoxytrityl group. In—P $(R^3)R^4$— of the above formula. $R^3$ and $R^4$ identically or differently represent a hydroxyl group, a protected hydroxyl group, a mercapto group, a protected mercapto group, an amino group, an alkoxy group with a carbon number of 1 to 4, an alkylthio group with a carbon number of 1 to 4, a cyanoalkoxy group with a carbon number of 1 to 5, or an amino group substituted with an alkyl group with a carbon number of 1 to 4. In the above formula, X is a carbon atom or an oxygen atom; n is an integer from 1 to 15; m is an integer from 0 to 5; provided that when n is 1, m is an integer from 0 to 5; when n is an integer from 2 to 15, m is 0.

Step A-1 is a step of preparing Compound (3), wherein Compound (1) and Compound (2) are reacted in an inert solvent in the presence of an acid to thereby generate ether bonds at the time of ring opening of epoxide.

[Formula 69]

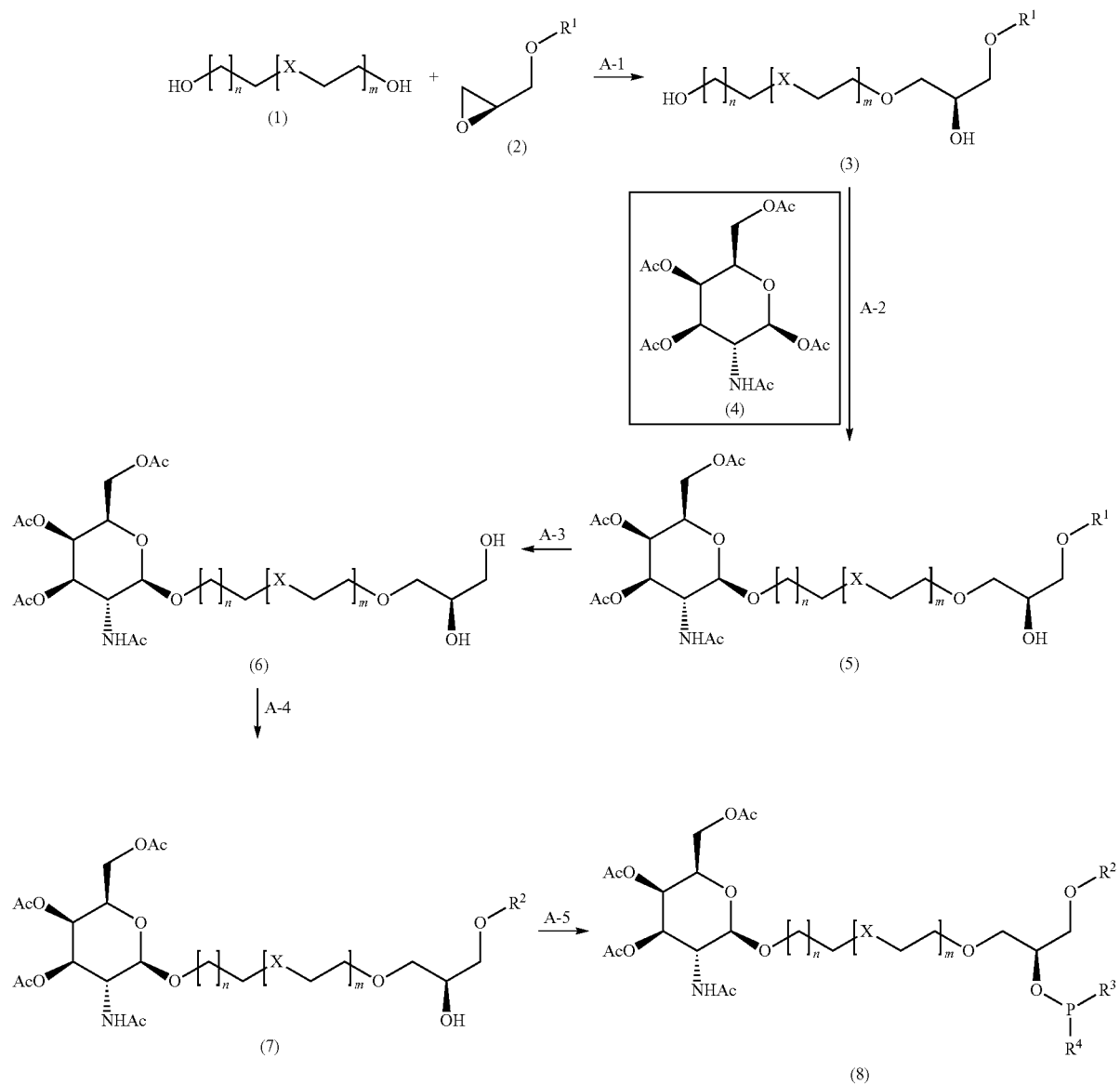

Examples of the inert solvent used in the above reaction include, but are not limited to, hydrocarbons, aromatic hydrocarbons, halogenated hydrocarbons, ethers and acetonitrile. Preferably, dichloromethane is used.

Examples of the acid used in the above reaction include, but are not limited to, organic acids and Lewis acids. As the organic acid, trifluoromethanesulfonic acid may, for example, be given. As the Lewis acid, boron trifluoride-diethylether complex may, for example, be given. Preferably, trifluoromethanesulfonic acid is used.

The reaction temperature varies depending on Compound (1) and Compound (2), the acid, the inert solvent, etc. Usually, the temperature is from −20° C. to reflux temperature, preferably from 30° C. to 45° C.

The reaction time varies depending on Compound (1) and Compound (2), the acid, the inert solvent, the reaction temperature, etc. Usually, the reaction time is from 15 min to 72 hrs, preferably from 2 to 24 hrs.

Step A-2 is a step of preparing Compound (5), wherein Compound (3) and Compound (4) are reacted in an inert solvent in the presence of an acid to thereby generate a glycoside bond.

Examples of the inert solvent used in the above reaction include, but are not limited to, hydrocarbons, aromatic hydrocarbons, halogenated hydrocarbons, ethers and acetonitrile. Preferably, dichloromethane is used.

Examples of the acid used in the above reaction include, but are not limited to, organic acids and Lewis acids. As the organic acid, trifluoromethanesulfonic acid may, for example, be given. As the Lewis acid, boron trifluoride-diethylether complex may, for example, be given. Preferably, boron trifluoride-diethylether complex is used.

The reaction temperature varies depending on Compound (3), the acid, the inert solvent, etc. Usually, the temperature is from −20° C. to reflux temperature, preferably from 30° C. to 45° C.

The reaction time varies depending on Compound (3), the acid, the inert solvent, the reaction temperature, etc. Usually, the reaction time is from 15 min to 72 hrs, preferably from 2 to 24 hrs.

Step A-3 is a step of preparing Compound (6), wherein $R^1$ that is a protective group for the hydroxyl group in Compound (5) is removed. Removal of protection groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step A-4 is a step of preparing Compound (7), wherein $R^2$ is introduced into the primary hydroxyl group in Compound (6) in an inert solvent in the presence of 4,4'-dimethoxytritylchloride and a base.

Examples of the inert solvent used in the above reaction include, but are not limited to, hydrocarbons, aromatic hydrocarbons, halogenated hydrocarbons, ethers and acetonitrile. Preferably, dichloromethane or pyridine is used.

Examples of the base used in the above reaction include, but are not limited to, trimethylamine, N,N-diisopropylethylamine, pyridine and 4-dimethylaminopyridine. Preferably, N,N-diisopropylethylamine or pyridine is used.

The reaction temperature varies depending on the base, the inert solvent, etc. Usually, the reaction temperature is from −20° C. to reflux temperature, preferably from 10° C. to 30° C.

The reaction time varies depending on the base, the inert solvent, the reaction temperature, etc. Usually, the reaction time is from 15 min to 24 hrs, preferably from 1 to 4 hrs.

Step A-5 is a step of preparing Compound (8), wherein —P($R^3$)$R^4$ is introduced into the secondary hydroxyl group in Compound (7) in an inert solvent in the presence of 2-cyanoethyl diisopropylchlorophosphoramidite and a base.

Examples of the inert solvent used in the above reaction include, but are not limited to, hydrocarbons, aromatic hydrocarbons, halogenated hydrocarbons, ethers and acetonitrile. Preferably, dichloromethane is used.

Examples of the base used in the above reaction include, but are not limited to, trimethylamine, N,N-diisopropylethylamine, pyridine and 4-dimethylaminopyridine. Preferably, N,N-diisopropylethylamine is used.

The reaction temperature varies depending on the base, the inert solvent, etc. Usually, the reaction temperature is from −20° C. to reflux temperature, preferably from 10° C. to 30° C.

The reaction time varies depending on the base, the inert solvent, the reaction temperature, etc. Usually, the reaction time is from 15 min to 24 hrs, preferably from 1 to 4 hrs.

Method B

This is a method for preparing Compound (14) or branched-type Compound (19). When Compound (2) with a reverse configuration is used, the configuration of the secondary hydroxyl group to which —P($R^3$)$R^4$ is bound will also be reversed in Compound (14) or in branched-type Compound (19)

[Formula 70]

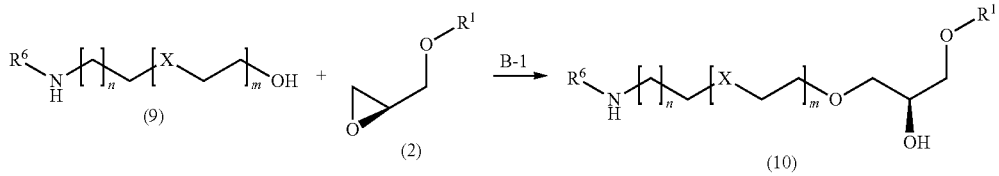

-continued
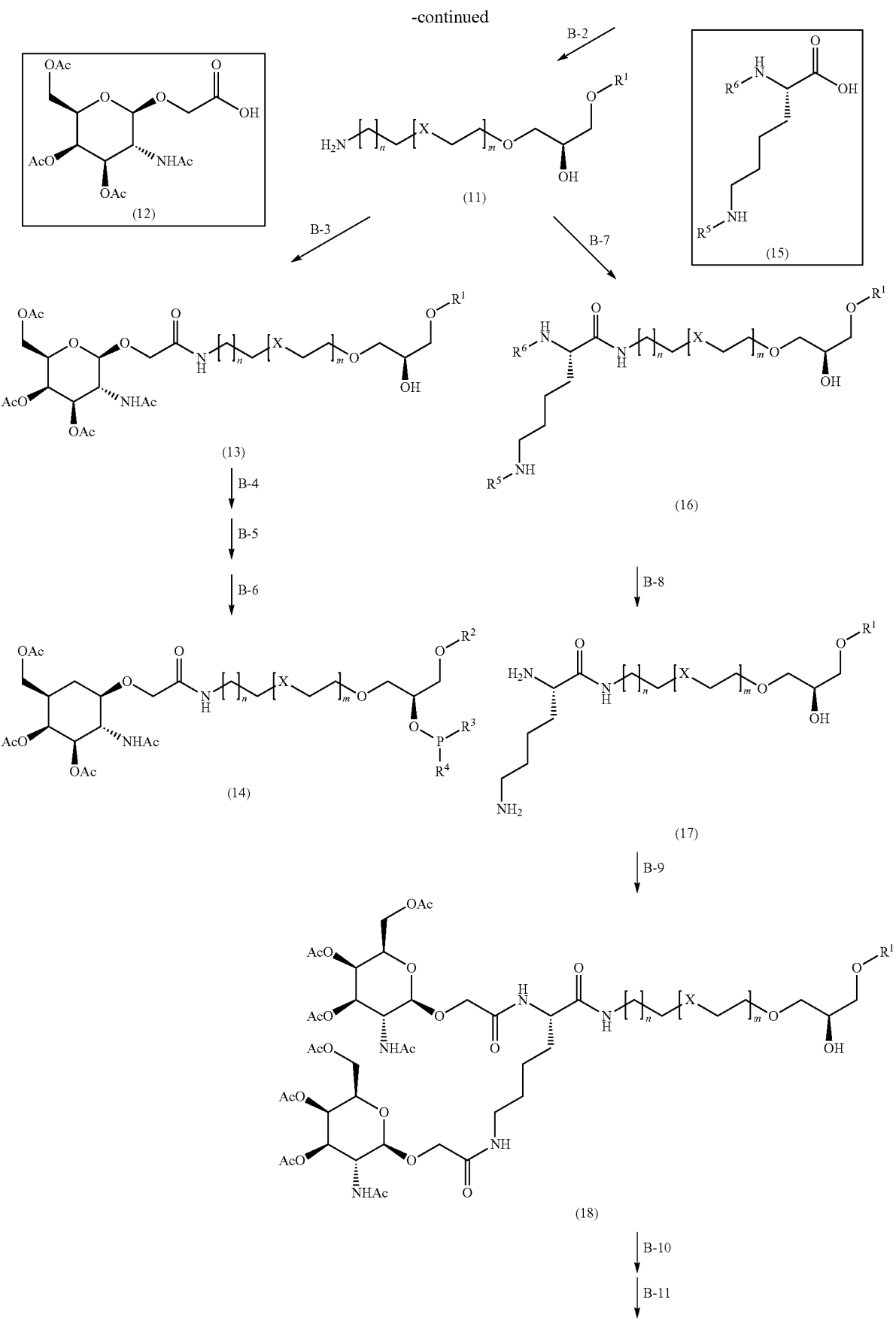

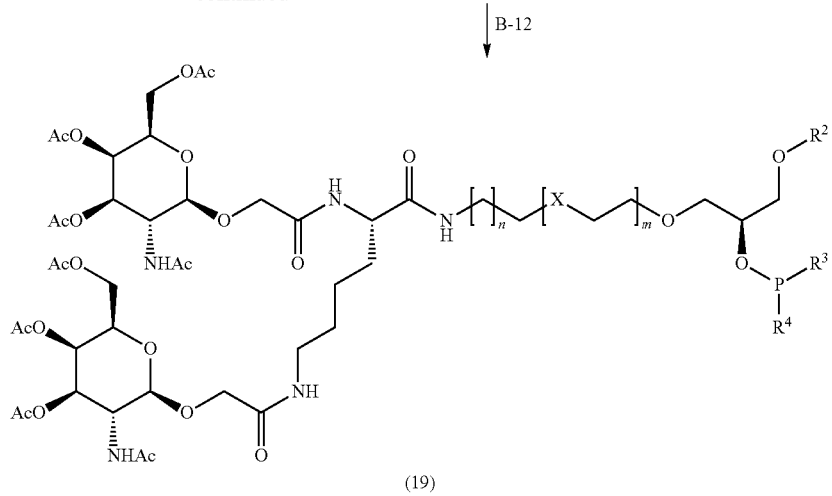

(19)

In the above Formula, $R^1$, $R^2$, $R^3$, $R^4$, X, n and m are as defined above; and $R^5$ and $R^6$ are a common protective group for amino group.

Step B-1 is a step of preparing Compound (10), wherein Compound (9) and Compound (2) are reacted in an inert solvent in the presence of an acid to thereby generate ether bonds at the time of ring opening of epoxide. This step may be performed in the same manner as described in Step A-1 above.

Step B-2 is a step of preparing Compound (11), wherein a protective group $R^5$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step B-3 is a step of preparing Compound (13), wherein Compound (11) and Compound (12) are amide-condensed in an inert solvent in the presence of a condensing agent and a base.

The inert solvent used in the above reaction may be appropriately selected depending on the type of the condensing agent used. For example, water, alcohols, aprotonic polar solvents and the like may be enumerated. Preferably, dichloromethane or N,N-dimethylformamide is used.

Examples of the base used in the above reaction include, but are not limited to, triethylamine, N,N-diisopropylethylamine, pyridine and 4-dimethylaminopyridine. Preferably, N,N-diisopropylethylamine is used.

Examples of the condensing agent used in the above reaction include, but are not limited to, carbodiimide-based condensing agents such as WSC (1-[3-(dimethylamino) propyl]-3-ethylcarbodiimide) and DIC (N,N'-diisopropylcarbodiimide); imidazole-based condensing agents such as CDI (N,N'-carbonyldiimidazole); triazine-based condensing agents such as DMT-MM (4-(4,6-dimethoxy-1,3,5-triazin-2-yl)-4-methylmorpholinium=chloride n hydrate); uronium-based condensing agents such as HATU (O-(7-azabenzotriazol-1-yl)-N, N, N', N'-tetramethyluronium hexafluorophosphate) and TSTU (O-(N-succinimidyl)-N, N, N', N'-tetramethyluronium tetrafluoroborate); and phosphonium-based condensing agents such as PyBOP (1H-benzotriazol-1-yloxytripyrrolidinophosphonium hexafluorophosphate). Preferably, WSC or HATU is used. If necessary, additives such as HOAt (1-hydroxy-7-azabenzotriazole), HOBt (1-hydroxybenzotriazole) and Oxyma (ethyl(hydroxyimino) cyanoacetate) may be added.

The reaction temperature varies depending the condensing agent, the base, the solvent, etc. Usually, the reaction temperature is from −20° C. to reflux temperature, preferably from 10° C. to 30° C.

The reaction time varies depending on the condensing agent, the base, the solvent, the reaction temperature, etc. Usually, the reaction time is from 15 min to 72 hrs, preferably from 1 to 24 hrs.

Conversion from Compound (13) to Compound (14) may be performed in the same manner as described in Method A.

Step B-4 is a step of removing a protective group $R^1$, which may be performed in the same manner as in Step A-3.

Step B-5 is a step of introducing $R^2$ into the primary hydroxyl group, which may be performed in the same manner as in Step A-4.

Step B-6 is a step of introducing —P($R^3$)$R^4$ into the secondary hydroxyl group, which may be performed in the same manner as in Step A-4.

Step B-7 is a step of preparing Compound (16), wherein Compound (11) and Compound (15) are amide-condensed in an inert solvent in the presence of a condensing agent and a base. This step may be performed in the same manner as in Step B-3 described above.

Step B-8 is a step of preparing Compound (17), wherein a protective group $R^6$ is removed. Removal of protection groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step B-9 is a step of preparing Compound (18), wherein Compound (12) and Compound (17) are amide-condensed in an inert solvent in the presence of a condensing agent and a base. This step may be performed in the same manner as in Step B-3 described above.

Conversion from Compound (18) to Compound (19) may be performed in the same manner as described in Method A.

Step B-10 is a step of removing a protective group $R^1$, which may be performed in the same manner as in Step A-3.

Step B-11 is a step of introducing $R^2$ into the primary hydroxyl group, which may be performed in the same manner as in Step A-4.

Step B-12 is a step of introducing—P($R^3$)$R^4$ into the secondary hydroxyl group, which may be performed in the same manner as in Step A-5.

Method C
This is a method for preparing Compound (26) or branched-type Compound (30). When the secondary hydroxyl group with a reverse configuration is used in Compound (23), the configuration of the secondary hydroxyl group to which —P(R$^3$)R$^4$ is bound in Compound (26) or branched-type Compound (30) will also be reversed.
[Formula 71]
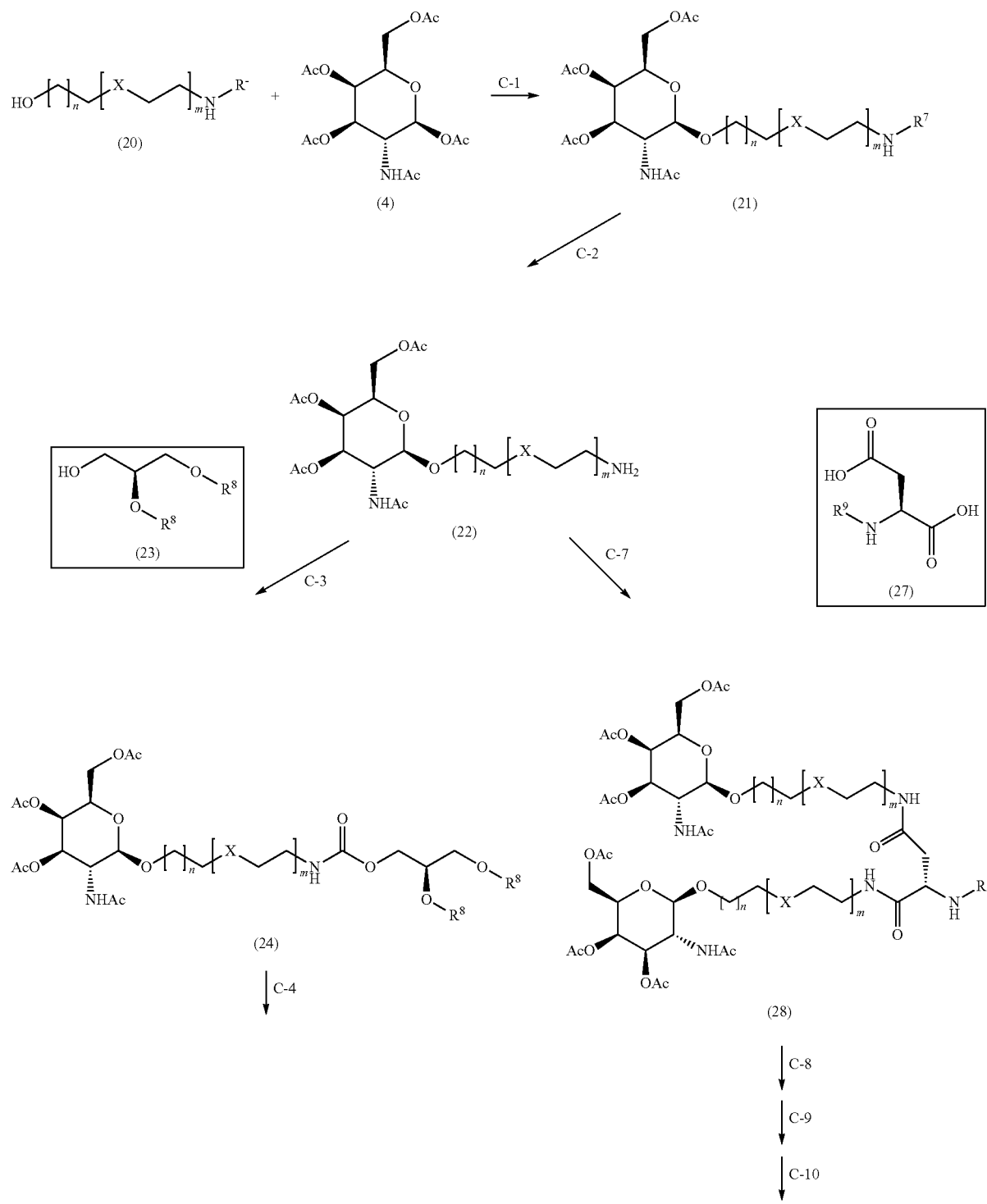

-continued

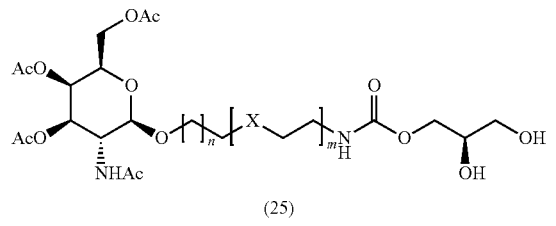

(25)

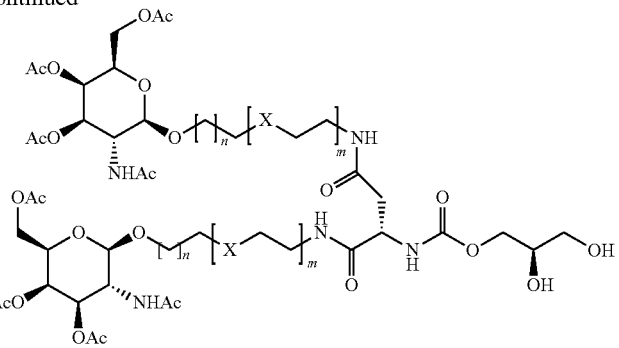

(29)

↓ C-5

↓ C-6

↓ C-11

↓ C-12

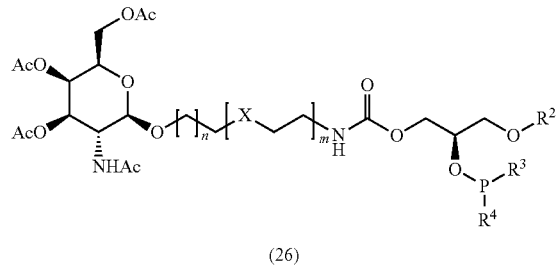

(26)

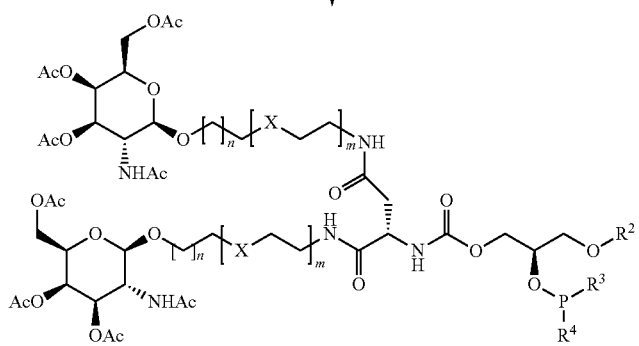

(30)

In the above Formula, $R^1$, $R^3$, $R^4$, X, n and m are as defined above; $R^8$ is a common protective group for hydroxyl group; and $R^7$ and $R^9$ are identically or differently a common protective group for amino group.

Step C-1 is a step of preparing Compound (21), wherein Compound (20) and Compound (4) are reacted in an inert solvent in the presence of an acid to thereby generate a glycoside bond. This step may be performed in the same manner as described in Step A-2 above.

Step C-2 is a step of preparing Compound (22), wherein $R^7$ that is a protective group for the amino group in Compound (21) is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step C-3 is a step of preparing Compound (24), wherein Compound (23) is converted to an active ester in an inert solvent in the presence of an activator and a base, followed by reaction with Compound (22) for carbamation.

Examples of the inert solvent used in the above reaction include, but are not limited to, hydrocarbons, aromatic hydrocarbons, halogenated hydrocarbons and ethers. Preferably, dichloromethane is used.

The activator used in the above reaction is not particularly limited as long as it forms activated esters. For example, bis(pentafluorophenyl) carbonate, bis(4-nitrophenyl) carbonate, 4-nitrophenyl chloroformate or the like may be enumerated. Preferably, 4-nitrophenyl chloroformate is used.

Examples of the base used in the above reaction include, but are not limited to, triethylamine, N,N-diisopropylethylamine, pyridine and 4-dimethylaminopyridine. Preferably, pyridine is used for preparing an active ester, and then N,N-diisopropylethylamine is added when reacting the ester with amine.

The reaction temperature varies depending the activator, the base, the inert solvent, etc. Usually, the reaction temperature is from −20° C. to reflux temperature, preferably from 10° C. to 30° C.

The reaction time varies depending on the activator, the base, the inert solvent, the reaction temperature, etc. Usually, the reaction time is from 15 min to 24 hrs, preferably from 1 to 4 hrs.

Step C-4 is a step of preparing Compound (25), wherein $R^8$ that is a protective group for the hydroxyl group in Compound (24) is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Conversion from Compound (25) to Compound (26) may be performed in the same manner as described in Method A.

Step C-5 is a step of introducing $R^2$ into primary hydroxyl group, which may be performed in the same manner as in Step A-4.

Step C-6 is a step of introducing—P(R³)R⁴ into secondary hydroxyl group, which may be performed in the same manner as in Step A-5.

Step C-7 is a step of preparing Compound (28), wherein Compound (22) and Compound (27) are amide-condensed in an inert solvent in the presence of a condensing agent and a base. This step may be performed in the same manner as described in Step B-3 in Method B.

Conversion from Compound (28) to Compound (29) may be performed as described previously.

Step C-8 is a step of removing R⁹ that is a protective group for the amino group in Compound (28), which may be performed in the same manner as in Step C-2.

Step C-9 is a step of carbamation, which may be performed in the same manner as in Step C-3.

Step C-10 is a step of removing a protective group R⁸, which may be performed in the same manner as in Step C-4.

Conversion from Compound (29) to Compound (30) may be performed in the same manner as described in Method A.

Step C-11 is a step of introducing R² into primary hydroxyl group, which may be performed in the same manner as in Step A-4.

Step C-12 is a step of introducing—P(R³)R⁴ into secondary hydroxyl group, which may be performed in the same manner as in Step A-5.

Method D

This is a method for preparing Compound (35). In this method, steps may be appropriately selected by changing the order of amide-condensation which is conducted twice, or selected depending on the state of the protective group in each compound. When the secondary hydroxyl group with a reverse configuration is used in Compound (23), the configuration of the secondary hydroxyl group to which —P(R³)R⁴ is bound in Compound (35) will also be reversed.

[Formula 72]

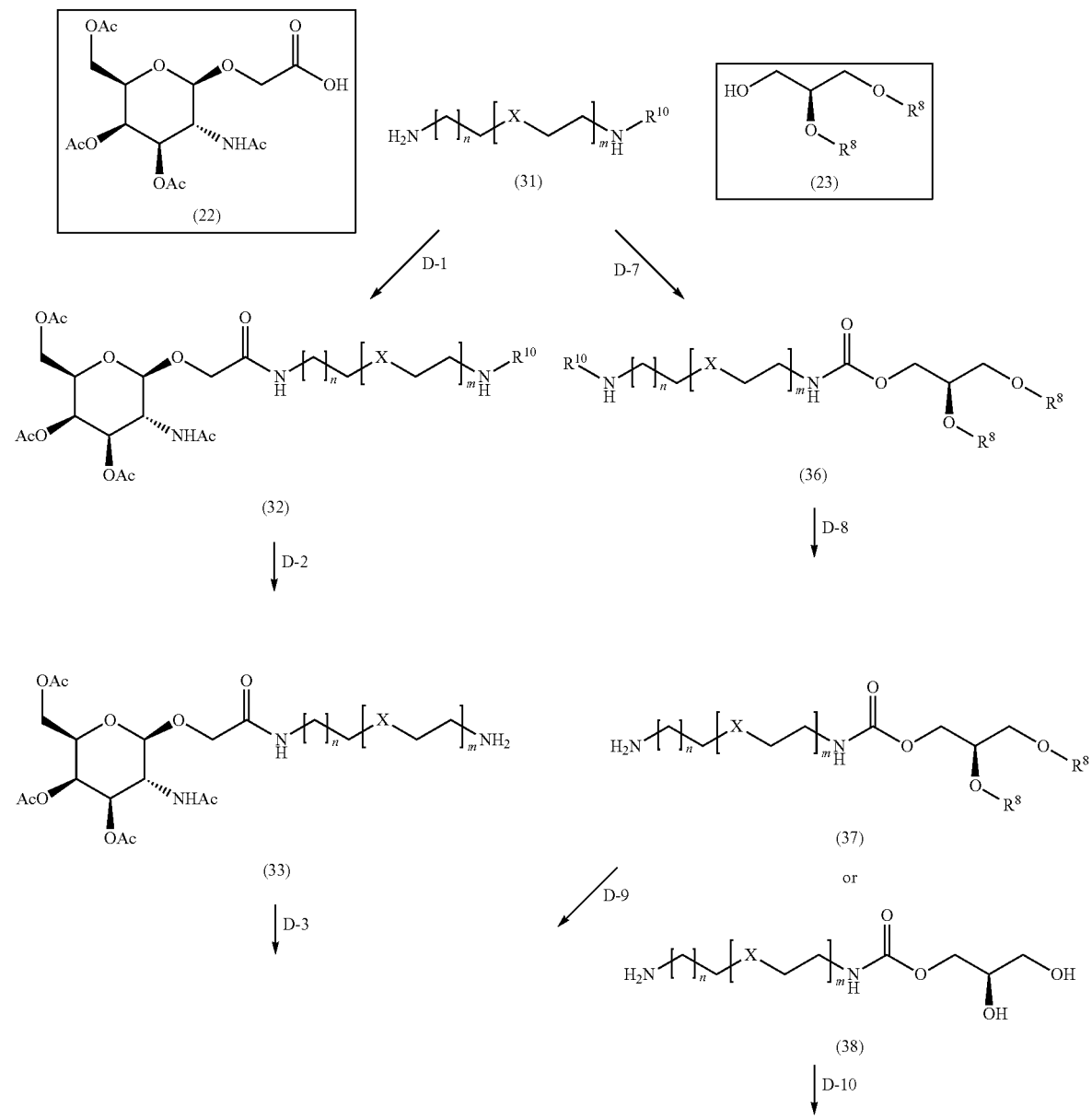

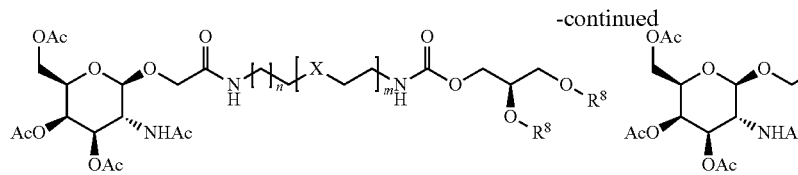
(34)

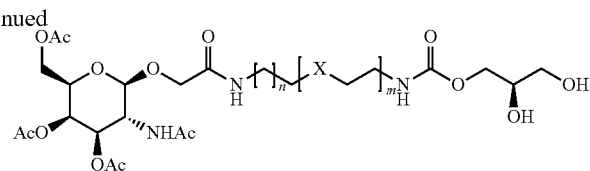
(39)

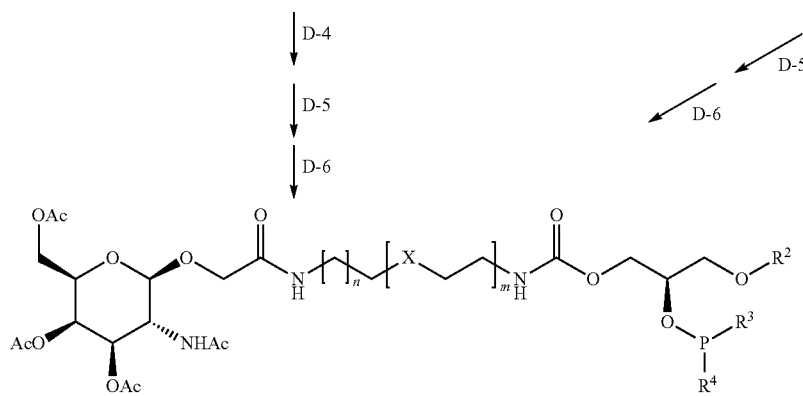
(35)

In the above Formula, $R^2$, $R^3$, $R^4$, $R^8$, X, n and m are as defined above; and $R^{10}$ is a common protective group for amino group.

Step D-1 is a step of preparing Compound (32), wherein Compound (31) and Compound (12) are amide-condensed in an inert solvent in the presence of a condensing agent and a base. This may be performed in the same manner as described in Step B-3.

Step D-2 is a step of preparing Compound (33), wherein $R^{10}$ that is a protective group for the amino group of Compound (32) is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step D-3 is a step of preparing Compound (34), wherein Compound (23) is converted to an active ester in an inert solvent in the presence of an activator and a base, followed by reaction with Compound (33) for carbamation. This step may be performed in the same manner as described in Step C-3.

Conversion from Compound (34) to Compound (35) may be performed in the same manner as described in Method C.

Step D-4 is a step of removing a protective group $R^8$, which may be performed in the same manner as in Step C-4.

Step D-5 is a step of introducing $R^2$ into primary hydroxyl group, which may be performed in the same manner as in Step C-5.

Step D-6 is a step of introducing —$P(R^3)R^4$ into secondary hydroxyl group, which may be performed in the same manner as in Step C-6.

Step D-7 is a step of preparing Compound (36), wherein Compound (23) is converted to an active ester in an inert solvent in the presence of an activator and a base, followed by reaction with Compound (31) for carbamation. This step may be performed in the same manner as described in Step C-3.

Step D-8 is a step of preparing Compound (37) by removing $R^{10}$ alone that is a protective group for the amino group of Compound (36); or it is a step of preparing Compound (38) by simultaneously removing $R^8$ that is a protective group for the hydroxyl group of Compound (36) and $R^{10}$ that is a protective group for the amino group of Compound (36). Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step D-9 is a step of preparing Compound (34), wherein Compound (37) and Compound (12) are amide-condensed in an inert solvent in the presence of a condensing agent and a base. This step may be performed in the same manner as described in Step B-3.

Step D-10 is a step of preparing Compound (39), wherein Compound (38) and Compound (12) are amide-condensed in an inert solvent in the presence of a condensing agent and a base. This step may be performed in the same manner as described in Step B-3.

Conversion from Compound (39) to Compound (35) may be performed in the same manner as described in Step D-5 and Step D-6.

Method E

This is a method for preparing branched-type Compound (44) by employing Compound (31) as used in Method D and Intermediate (38) as synthesized therein. In this method, steps may be appropriately selected by changing the order of amide-condensation which is conducted twice, or selected depending on the state of the protective group in each compound. When the secondary hydroxyl group with a reverse configuration is used in Compound (23), the configuration of the secondary hydroxyl group to which —$P(R^3)R^4$ is bound in Compound (44) will also be reversed.

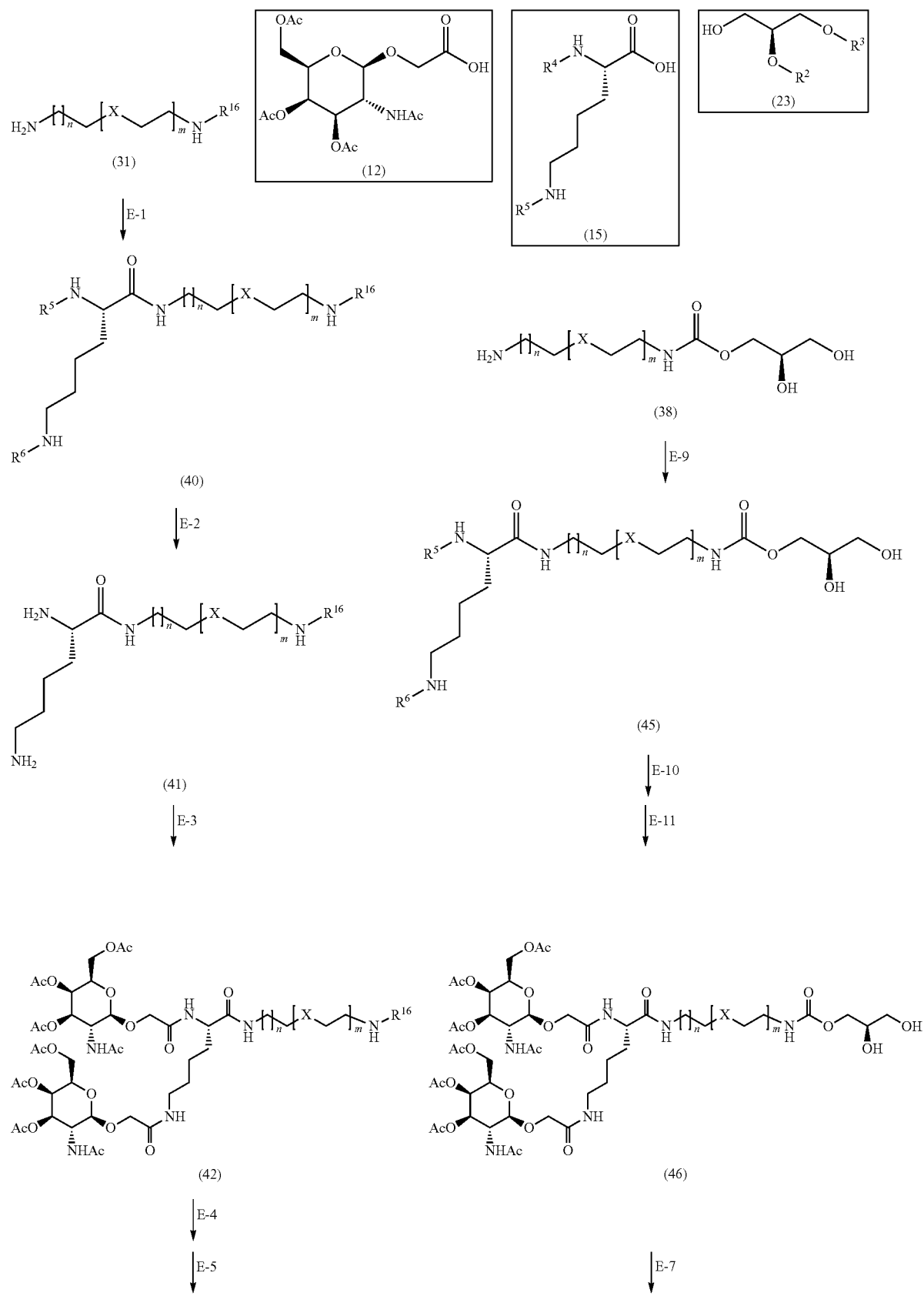
[Formula 73]

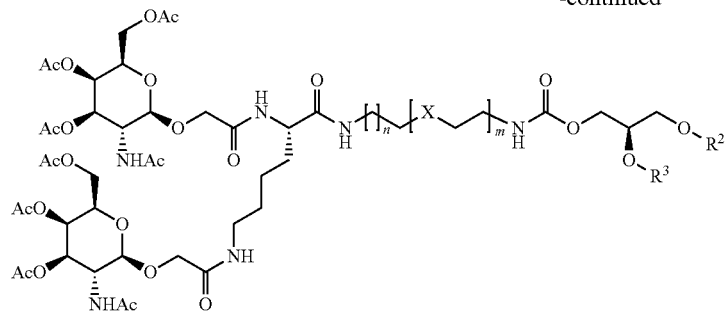

(43)

↓ E-6

↓ E-7

↓ E-8

→ E-8

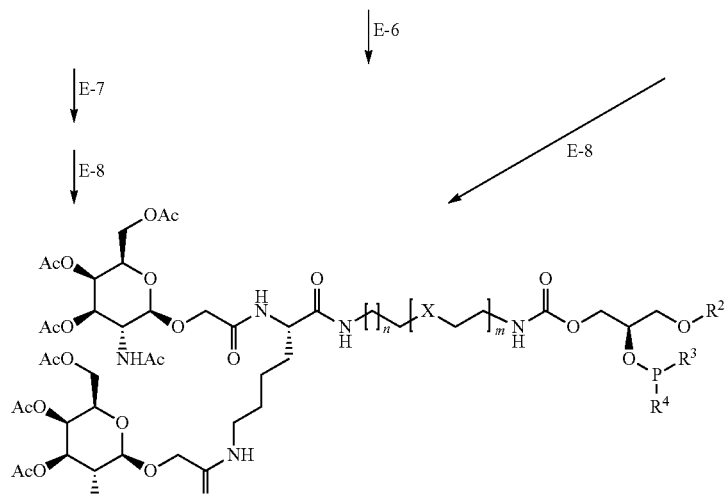

(44)

In the above formula, $R^2$, $R^3$, $R^4$, $R^6$, $R^8$, $R^{10}$, X, n and m are as defined above.

Step E-1 is a step of preparing Compound (40), wherein Compound (31) and Compound (15) are amide-condensed in an inert solvent in the presence of a condensing agent and a base. This step may be performed in the same manner as described in Step B-3.

Step E-2 is a step of preparing Compound (41) by removing $R^6$ alone that is a protective group for the amino group of Compound (40). Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step E-3 is a step of preparing Compound (42), wherein Compound (41) and Compound (12) are amide-condensed in an inert solvent in the presence of a condensing agent and a base. This step may be performed in the same manner as described in Step B-3.

Conversion from Compound (42) to Compound (43) may be performed in the same manner as described in Method D.

Step E-4 is a step of removing $R^{10}$ that is a protective group for the amino group of Compound (42). This step may be performed in the same manner as described in Step D-2.

Step E-5 is a step of carbamation, which may be performed in the same manner as described in Step D-3.

Conversion from Compound (43) to Compound (44) may be performed in the same manner as described in Method C.

Step E-6 is a step of removing $R^8$ that is a protective group for hydroxyl group of Compound (43). This step may be performed in the same manner as described in Step C-4.

Step E-7 is a step of introducing $R^2$ into primary hydroxyl group, which may be performed in the same manner as described in Step C-5.

Step E-8 is a step of introducing—P($R^3$)$R^4$ into secondary hydroxyl group, which may be performed in the same manner as described in Step C-6.

Step E-9 is a step of preparing Compound (45), wherein Compound (38) and Compound (15) are amide-condensed in an inert solvent in the presence of a condensing agent and a base. This step may be performed in the same manner as described in Step B-3.

Conversion from Compound (45) to Compound (46) may be performed in the same manner as described in Step E-2 and Step E-3.

Step E-10 is a step of removing $R^6$ that is a protective group for the amino group of Compound (45). Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step E-11 is a step of introducing Compound (15) by amide-condensation, which may be performed in the same manner as described in Step B-3.

Conversion from Compound (46) to Compound (44) may be performed by Step E-7 and Step E-8.

Method F

This is a method of preparing branched-type Compound (49) by making use of Intermediate (3) as synthesized by Method A. When the secondary hydroxyl group of Compound (3) with a reverse configuration is used, the configuration of the secondary hydroxyl group to which GalNAc is bound in Compound (49) will also be reversed.

[Formula 74]

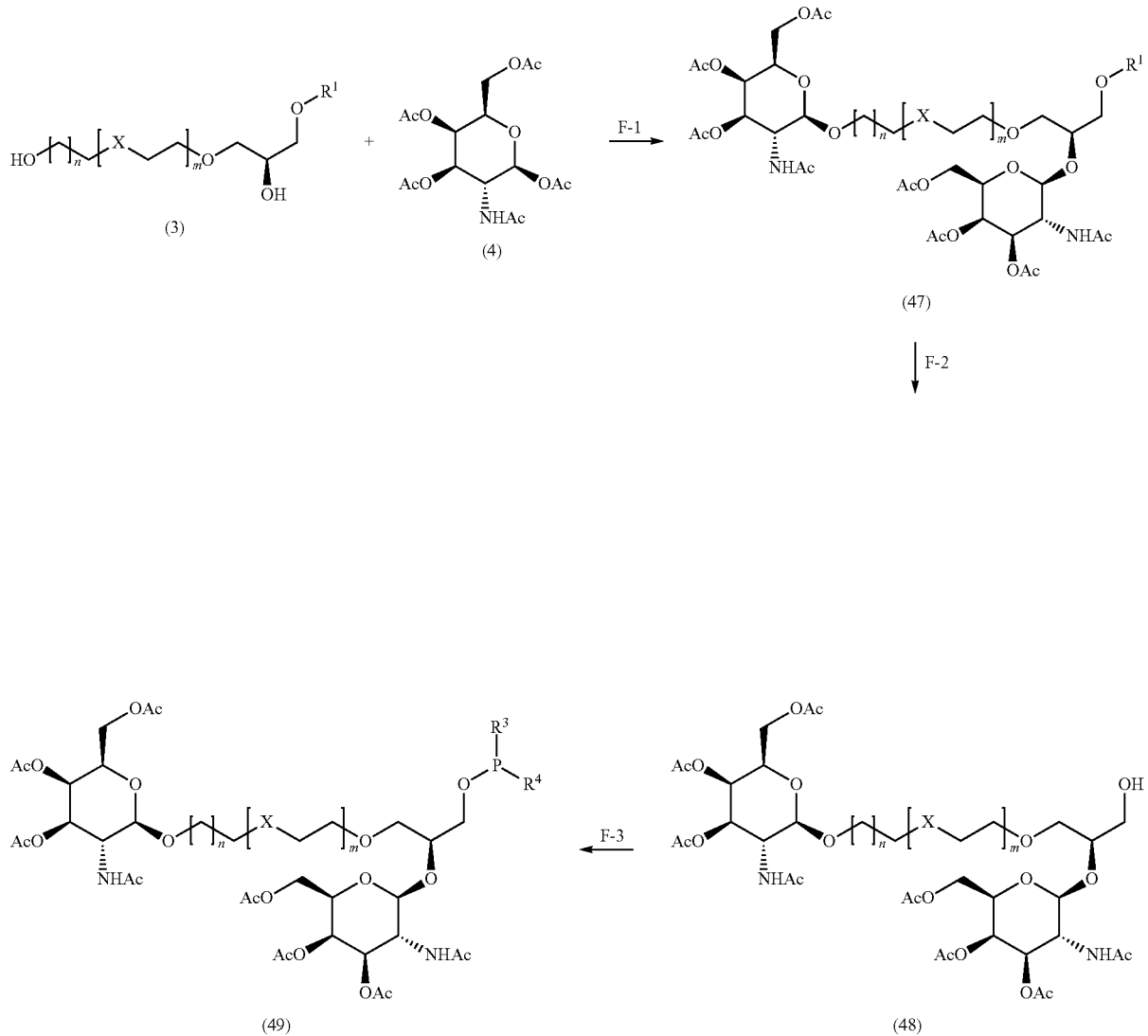

In the above formula, $R^1$, $R^3$, $R^4$, X, n and m are as defined above.

Step F-1 is a step of preparing Compound (47), wherein Compound (3) and Compound (4) are reacted in an inert solvent in the presence of an acid to thereby generate two glycoside bonds. This step may be performed in the same manner as described in Step A-2.

Step F-2 is a step of preparing Compound (48), wherein $R^1$ that is a protective group for the hydroxyl group of Compound (47) is removed. This step may be performed in the same manner as described in Step A-3.

Step F-3 is a step of preparing Compound (49), wherein —P($R^3$)$R^4$ is introduced into the hydroxyl group. This step may be performed in the same manner as described in Step A-5.

Method G

This is a method for preparing branched-type Compound (55) by utilizing Intermediate (22) as used in Method C. When the secondary hydroxyl group of Compound (52) or (56) with a reverse configuration is used, the configuration of the secondary hydroxyl group to which GalNAc is bound in Compound (55) will also be reversed.

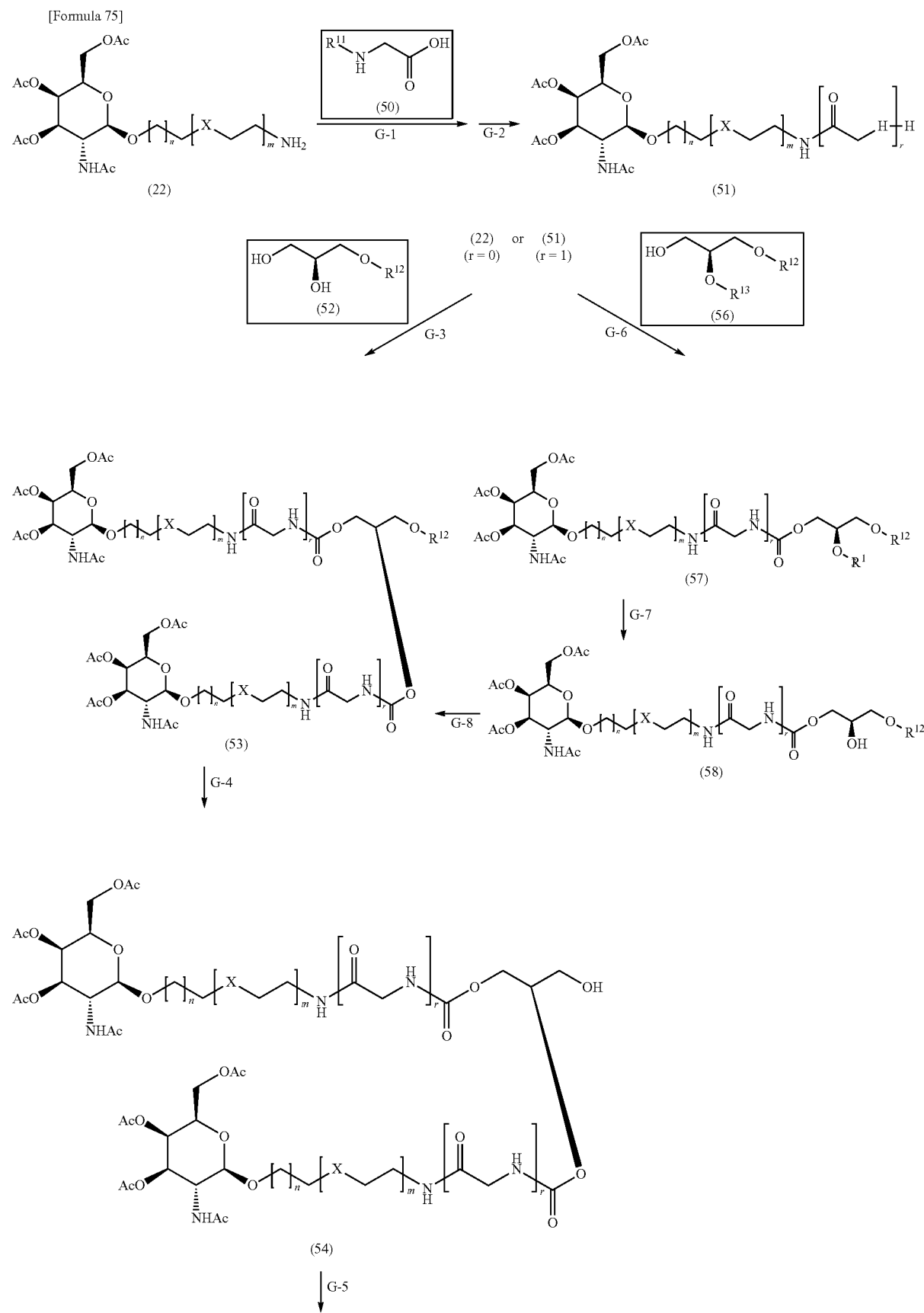

-continued

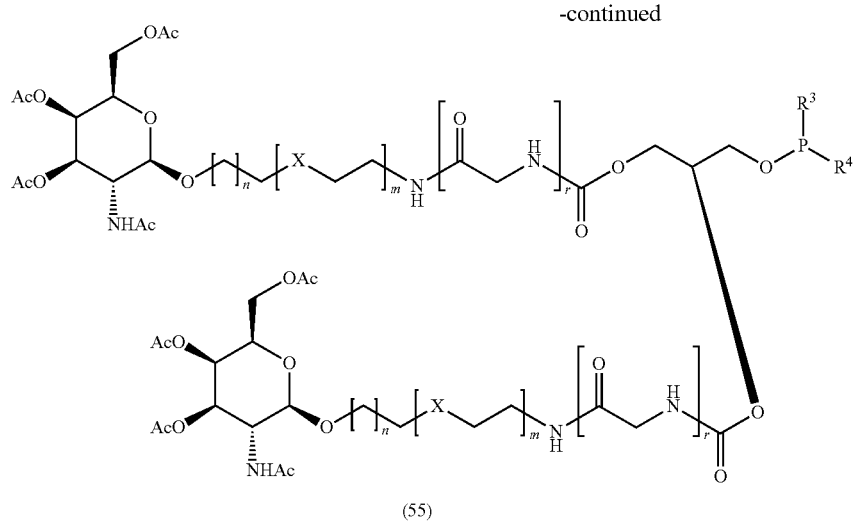

(55)

In the above Formula, $R^3$, $R^4$, X, n and m are as defined above; r is 0 or 1; $R^{11}$ is a common protective group for amino group; and $R^{12}$ and $R^{13}$ are a common protective group for hydroxyl group.

In Step G-1, Compound (22) and Compound (50) are amide-condensed in an inert solvent in the presence of a condensing agent and a base. This step may be performed in the same manner as described in Step B-3.

In Step G-2, a protective group $R^{11}$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step G-3 is a step of carbamation. This step may be performed in the same manner as described in Step C-3, provided that when r is 0, Compound (22) is carbamated; and when r is 1, Compound (52) is carbamated.

In Step G-4, a protective group $R^{12}$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step G-5 is a step of preparing Compound (55), wherein —P($R^3$)$R^4$ is introduced into the hydroxyl group. This step may be performed in the same manner as described in Step A-5.

Step G-6 is a step of carbamation. This step may be performed in the same manner as described in Step C-3, provided that when r is 0, Compound (22) is carbamated; and when r is 1, Compound (52) is carbamated.

In Step G-7, a protective group $R^{13}$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step G-8 is a step of carbamation, which may be performed in the same manner as described in C-3.

Method H

This is a method for preparing branched-type Compound (61) by utilizing Intermediate (22) as used in Method C or Intermediate (51) as used in Method G. The configuration of Compound (52) or Compound (56) is not particularly limited.

[Formual 76]

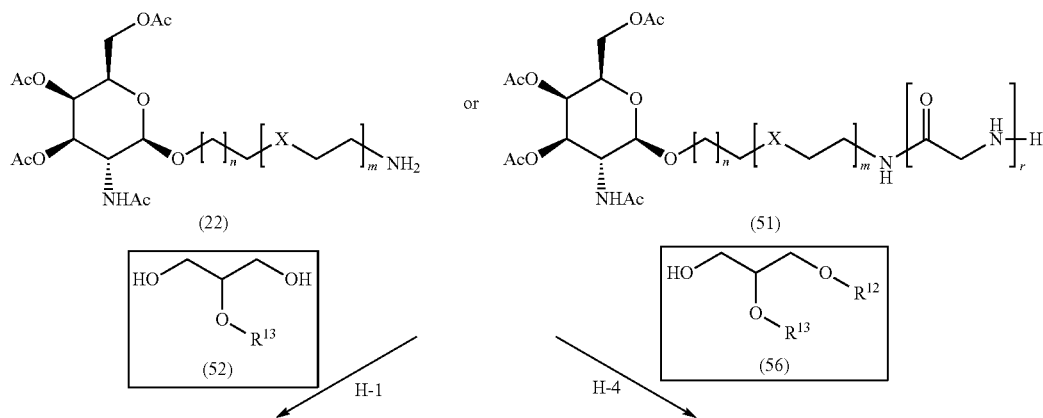

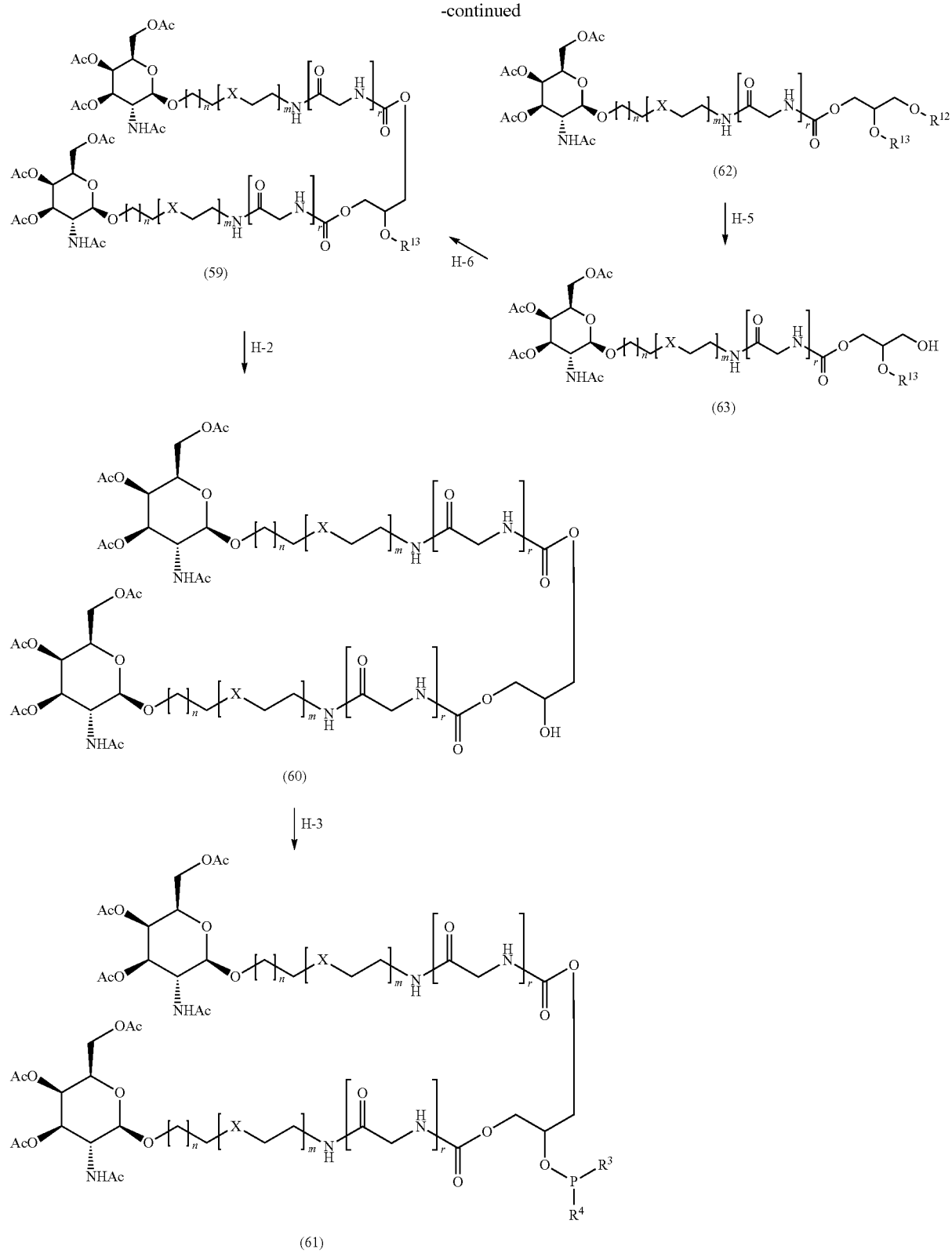
In the above Formula, $R^3$, $R^4$, X, n, m, r, $R^{12}$ and $R^{13}$ are as defined above.
Step H-1 is a step of carbamation. This step may be performed in the same manner as described in Step C-3, provided that when r is 0, Compound (22) is carbamated; and when r is 1, Compound (51) is carbamated.
In Step H-2, a protective group $R^{13}$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step H-3 is a step of preparing Compound (61), wherein —P(R$^3$)R$^4$ is introduced into the hydroxyl group. This step may be performed in the same manner as described in Step A-5.

Step H-4 is a step of carbamation. This step may be performed in the same manner as described in Step C-3, provided that when r is 0, Compound (22) is carbamated; and when r is 1, Compound (52) is carbamated.

In Step H-5, a protective group R$^{12}$ is removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

Step H-6 is a step of carbamation, which may be performed in the same manner as described in Step C-3.

Method I

This is a method for preparing branched-type Compound (73), and Compound (74). For example, by using Compound (70), the protective group for the hydroxyl group at position 6 in GalNAc portion may be appropriately selected. When R$^{14}$ is acetyl group, Compound (22) which can be synthesized by Method C is used as Compound (70). When R$^{14}$ is 4,4'-dimethoxytrityl group, a compound which can be synthesized, for example, according to the Reference Example described later is used as Compound (70).

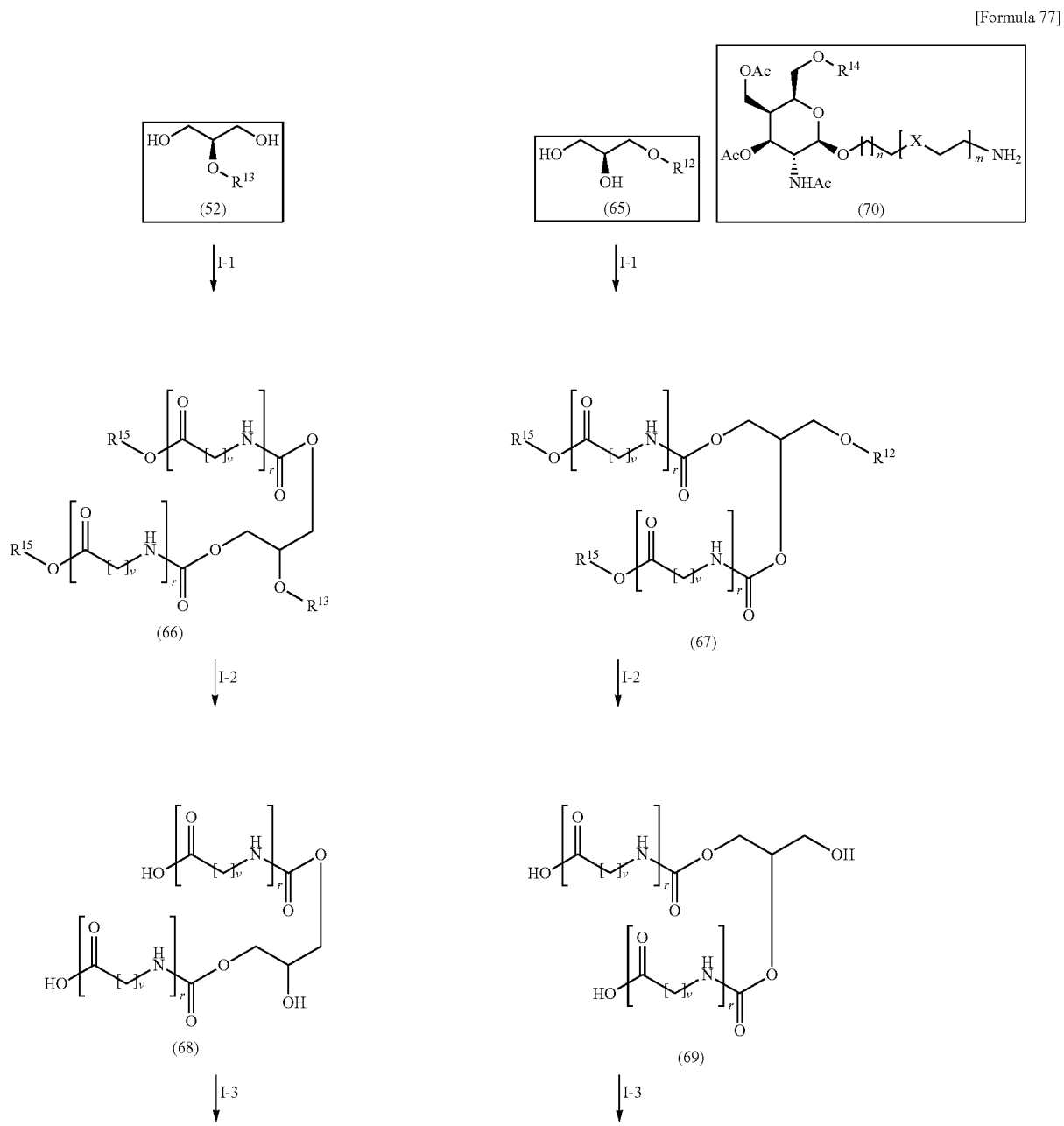

[Formula 77]

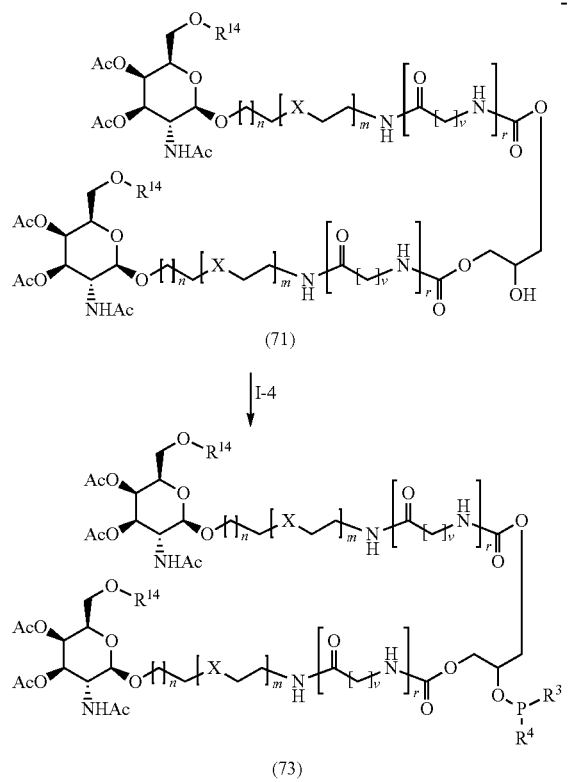
(71)

(73)

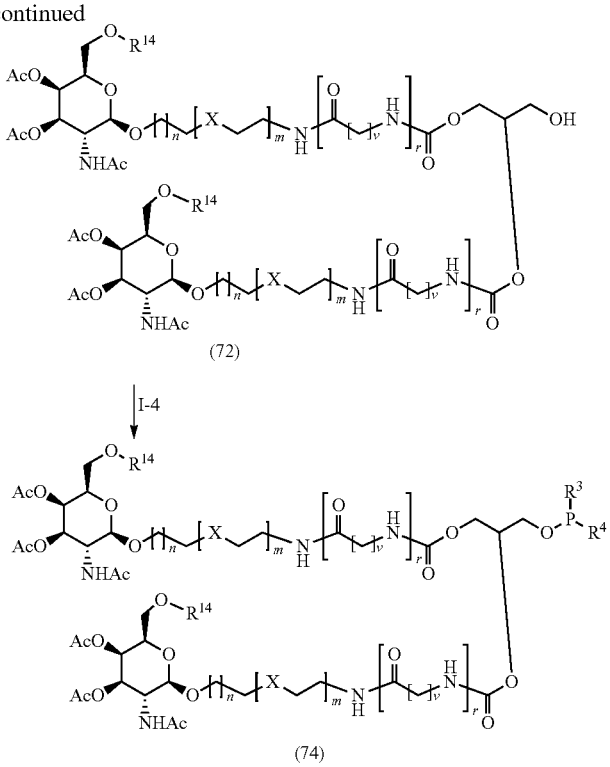
(72)

(74)

In the above formula, $R^{12}$ and $R^{13}$ which are a common protective group for hydroxyl group are preferably benzyl group. $R^{14}$ which is a common protective group for hydroxyl group is preferably acetyl group or 4,4'-dimethoxytrityl group. $R^{15}$ which is a common protective group for carbonyl group is preferably benzyl group. In —P($R^3$)$R^4$— of the above formula, $R^3$ and $R^4$ identically or differently represent a hydroxyl group, a protected hydroxyl group, a mercapto group, a protected mercapto group, an amino group, an alkoxy group with a carbon number of 1 to 4, an alkylthio group with a carbon number of 1 to 4, a cyanoalkoxy group with a carbon number of 1 to 5, or an amino group substituted with an alkyl group with a carbon number of 1 to 4. In the above formula, X is a carbon atom or an oxygen atom; n is an integer from 1 to 15; m is an integer from 0 to 5, provided that when n is 1, m is an integer from 0 to 5 and when n is an integer from 2 to 15, m is 0. In the above formula, r is independently 0 or 1; and v is an integer from 1 to 7.

StepI-1 is a step of carbamation, which may be performed in the same manner as described in Step C-3.

In Step I-2, protective groups $R^{12}$ or $R^{13}$ and $R^{15}$ are removed. Removal of protective groups varies depending on the type of the protective group used. Generally, the removal can be performed according to well-known methods in the technology of organic synthetic chemistry, e.g., the method described in T. H. Greene, P. G. Wuts, Protective Groups in Organic Synthesis. Third Edition, 1999, John Wiley & Sons, Inc.

In Step I-3, amide-condensation with Compound (22) is performed in an inert solvent in the presence of a condensing agent and a base. This step may be performed in the same manner as described in Step B-3.

Step I-4 is a step of preparing Compound (73) or Compound (74), wherein —P($R^3$)$R^4$ is introduced into the hydroxyl group. This step may be performed in the same manner as described in Step A-5.

The oligonucleotide (antisense oligonucleotide) of the present invention may be used as a pharmaceutical drug for specifically treating glycogen storage disease type Ia. Treatment is a concept encompassing both prevention and a posteriori treatment.

The oligonucleotide (antisense oligonucleotide) may be used in the form of a pharmacologically acceptable salt. The term "pharmacologically acceptable salt" as used herein refers to salts of the oligonucleotide (antisense oligonucleotide). Examples of such salts include, but are not limited to, alkaline metal salts such as sodium salts, potassium salts or lithium salts; alkaline earth metal salts such as calcium salts or magnesium salts; metal salts such as aluminum salts, iron salts, zinc salts, copper salts, nickel salts or cobalt salts; amine salts including inorganic salts such as ammonium salts and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts or tris(hydroxymethyl)aminomethane salts; inorganic acid salts including hydrohalogenic acid salts such as hydrofluorides, hydrochlorides, hydrobromides or hydroiodides, as well as nitrates, perchlorates, sulfates or phosphates; organic acid salts including lower alkane sulfonic acid salts such as methanesulfonates, trifluoromethanesulfonates or ethanesulfonates, arylsulfonic acid salts such as benzenesulfonates or p-toluenesulfonates, as well as acetates, malates, fumarates, succinates, citrates, tartrates, oxalates or maleates; and amino acid salts such as glycine salts, lysine salts, arginine salts, ornithine salts, glutamic acid salts or aspartic acid salts. Among them, alkaline metal salts are preferable; and sodium salts are more preferable. These salts may be prepared by known methods.

The oligonucleotide (antisense oligonucleotide) or a pharmacologically acceptable salt thereof sometimes occur as a solvate (e.g., hydrate). The oligonucleotide (antisense oligonucleotide) or a pharmaceutically acceptable salt thereof of the present invention may be such a solvate.

When the oligonucleotide (antisense oligonucleotide) of the present invention, a pharmacologically acceptable salt or solvate thereof is used for treatment of glycogen storage disease type Ia, they may be administered per se or mixed with appropriate, pharmacologically acceptable excipients, diluents, and the like for oral administration in the form of tablets, capsules, granules, powders, syrups, etc. or for parenteral administration in the form of injections, suppositories, patches or external preparations.

These formulations may be prepared by well-known methods using additives such as excipients (e.g., organic excipients including sugar derivatives such as lactose, sucrose, glucose, mannitol or sorbitol; starch derivatives such as corn starch, potato starch, α-starch or dextrin; cellulose derivatives such as crystalline cellulose; gum arabic; dextran; or pullulan; and inorganic excipients including silicate derivatives such as light anhydrous silicic acid, synthetic aluminum silicate, calcium silicate or magnesium aluminometasilicate; phosphates such as calcium hydrogenphosphate; carbonates such as calcium carbonate; and sulfates such as calcium sulfate), lubricants (e.g., stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; lauryl sulfates such as sodium lauryl sulfate or magnesium lauryl sulfate; silicic acid compounds such as silicic anhydride and silicic hydrate; or the starch derivatives listed above), binders (e.g., hydroxypropylcellulose, hydroxypropylmethylcellulose, polyvinylpyrrolidone, macrogol, or compounds similar to the above-listed excipients), disintegrants (e.g., cellulose derivatives such as low-substituted hydroxypropylcellulose, carboxymethylcellulose, calcium carboxymethylcellulose or internally crosslinked sodium carboxymethylcellulose; and chemically modified starch/cellulose derivatives such as carboxymethylstarch, sodium carboxymethylstarch or crosslinked polyvinylpyrrolidone), emulsifiers (e.g., colloidal clay such as bentonite or veegum; metal hydroxides such as magnesium hydroxide or aluminum hydroxide; anionic surfactants such as sodium lauryl sulfate or calcium stearate; cationic surfactants such as benzalkonium chloride; or nonionic surfactants such as polyoxyethylenealkylether, polyoxyethylene sorbitan fatty acid ester or sucrose esters of fatty acids), stabilizers (e.g., p-hydroxybenzoate esters such as methylparaben or propylparaben; alcohols such as chlorobutanol, benzyl alcohol or phenylethyl alcohol; benzalkonium chloride; phenols such as phenol or cresol; thimerosal; dehydroacetic acid; or sorbic acid), flavoring agents (e.g., conventionally used sweeteners, acidifiers, flavors and the like) or diluents.

The therapeutic drug of the present invention may comprise 0.1-250 moles/ml, preferably 1-50 mole/ml of oligonucleotide (antisense oligonucleotide), pharmacologically acceptable salt thereof or solvate thereof, 0.02-10% w/v of carbohydrate or polyalcohol; and 0.01-0.4% w/v of pharmacologically acceptable surfactant.

As the above carbohydrate, monosaccharides or disaccharides are especially preferable. Specific examples of these carbohydrates and polyalcohols include, but are not limited to, glucose, galactose, mannose, lactose, maltose, mannitol and sorbitol. These may be used alone or in combination.

Preferable examples of the surfactant include, but are not limited to, polyoxyethylene sorbitan mono-, di- or tri-ester, alkylphenylpolyoxyethylene, sodium taurocholate, sodium cholate and polyalcohol esters. Among these, polyoxyethylene sorbitan mono-, di- and tri-ester are especially preferable; the most preferable esters are oleate, laurate, stearate and palmitate. These may be used alone or in combination.

More preferably, the therapeutic drug of the present invention may comprise 0.03-0.09 M pharmacologically acceptable neutral salt such as sodium chloride, potassium chloride and/or calcium chloride.

Even more preferably, the therapeutic drug of the present invention may comprise 0.002-0.05 M pharmacologically acceptable buffer. Examples of a preferable buffer include, but are not limited to, sodium citrate, sodium glycinate, sodium phosphate and tris(hydroxymethyl)aminomethane. These buffers may be used alone or in combination.

Further, the above-described drug may be supplied in a state of solution. However, as in the case where there is a need for storage over a certain period of time, the drug is preferably lyophilized for stabilizing the oligonucleotide (antisense oligonucleotide) to thereby prevent the lowering of its therapeutic effect. When lyophilized, the drug may be reconstituted with a solution, such as distilled water for injection, just before use. Thus, the drug is returned into the state of a liquid to be administered. Therefore, the therapeutic drug of the present invention encompasses one in a lyophilized state that is used after reconstruction with a solution so that the respective components fall within specified concentration ranges. For the purpose of promoting the solubility of the lyophilized product, the drug may further comprise albumin and amino acids such as glycine.

The oligonucleotide (antisense oligonucleotide) of the present invention may be encapsulated with a lipid (e.g., one disclosed in WO 2015/005253) and administered as nucleic acid lipid nanoparticles or liposomes disclosed in WO 2015/05253, etc.

When the oligonucleotide (antisense oligonucleotide) of the invention, a pharmacologically acceptable salt or solvate thereof is administered to a human, the oligonucleotide or the like may be administered, for example, at approximately 0.01-100 mg/kg (body weight), preferably at 0.1-20 mg/kg (body weight) per adult per day either once or over several times by subcutaneous injection, intravenous infusion or intravenous injection. The dose and the number of times of administration may be changed appropriately depending on the type and symptoms of the disease, the age of the patient, administration route, etc.

Administration of the oligonucleotide (antisense oligonucleotide) of the invention, a pharmacologically acceptable salt or solvate thereof to glycogen storage disease type Ia patients may be performed, for example, as described below. Briefly, the antisense oligonucleotide, pharmacologically acceptable salt thereof or solvate thereof is prepared by methods well-known to one of ordinary skill in the art and sterilized by conventional methods to prepare, for example, 125 mg/ml of an injection solution. This solution is instilled to a patient intravenously in the form of, for example, infusion so that the dose of the oligonucleotide (antisense oligonucleotide) is, for example, 10 mg per kg body weight. This administration is repeated, for example, at 1-week intervals. Subsequently, this treatment is appropriately repeated while confirming the therapeutic effect by examining blood glucose level, blood lactate level, liver swelling as observed by CT, hepatic glycogen level, etc.

EXAMPLES

Hereinbelow, the present invention will be described more specifically with reference to the following Examples. These Examples are given only for explanation and are not intended to limit the scope of the present invention.

Examples 1 to 11

HO-$A^{e2s}$-$G^{m1s}$-$A^{m1s}$-$T^{e2s}$-$A^{m1s}$-$A^{m1s}$-$A^{e2s}$-$A^{m1s}$-$U^{m1s}$—$C^{e2s}$-$C^{m1s}$-$G^{m1s}$-$A^{e2s}$-$U^{m1s}$-$G^{m1s}$-$G^{e2s}$-$C^{m1s}$-$G^{m1s}$-$A^{e2-s}$$A^{m1s}$-$G^{e2t}$-H (21e_002) (SEQ ID NO: 1)

Synthesis was performed with an automated nucleic acid synthesizer (ABI 394 DNA/RNA Synthesizer; Applied Biosystems) by the phosphoramidite method (Nucleic Acids Research, 12, 4539 (1984)). As reagents, Activator Solution-3 (0.25 mol/L 5-Benzylthio-1H-tetrazole-Acetonitrile Solution; Wako Pure Chemical; product No. 013-20011), Cap A for AKTA (1-Methylimidazole-Acetonitrile Solution; Sigma-Aldrich; product No. L040050), Cap B1 for AKTA (Acetic Anhydride, Acetonitrile Solution; Sigma-Aldrich; product No. L050050), Cap B2 for AKTA (Pyridine-Acetonitrile Solution; Sigma-Aldrich; product No. L050150), and DCA Deblock (Dichloroacetic Acid-Toluene Solution; Sigma-Aldrich; product No. L023050) were used. As a thioation reagent for formation of phosphorothioate bond, phenylacetyl disulfide (Carbosynth; product No. FP07495) was dissolved in a 1:1 (v/v) solution of acetonitrile (dehydrated; Kanto Chemical Co., Inc.; product No. 01837-05) and pyridine (dehydrated; Kanto Chemical Co., Inc.; product No. 11339-05) to give a concentration of 0.2 M. As amidite reagents, 2'-O-Me nucleoside phosphoramidites (for adenosine: product No. ANP-5751; for cytidine: product No. ANP-5752; for guanosine: product No. ANP-5753; for uridine: product No. ANP-5754) were products from ChemGenes. Non-natural phosphoramidites used were the following compounds disclosed in the indicated Examples of Japanese Unexamined Patent Publication No. 2000-297097: Example 14 (5'-O-dimethoxytrityl-2'-O,4'-C-ethylene-6-N-benzoyladenosine-3'-O-(2-cyanoethyl N,N-diisopropyl) phosphoramidite); Example 27 (5'-O-dimethoxytrityl-2'-0,4'-C-ethylene-2-N-isobutylguanosine-3'-O-(2-cyanoethyl N,N-diisopropyl)phosphoramidite); Example 22 (5'-O-dimethoxytrityl-2'-O,4'-C-ethylene-4-N-benzoyl-5-methylcytidine-3'-O-(2-cyanoethyl N,N-diisopropyl)phosphoramidite); and Example 9 (5'-O-dimethoxytrityl-2'-0,4'-C-ethylene-5-methyluridine-3'-O-(2-cyanoethyl N,N-diisopropyl)phosphoramidite). As a solid carrier, Glen Unysupport™ 0.1 μmol (GlenResearch) was used. The program for 0.2 μmol scale attached to the nucleic acid synthesizer was used, provided that 600 seconds was set as the time required for condensation of amidites, and 150 seconds as the time required for thioation.

Protected oligonucleotide analogs with the sequence of interest were treated with 300 μl of concentrated aqueous ammonia to thereby cut out oligomers from the support and, at the same time, remove the protective group cyanoethyl on phosphorus atoms and the protective group on nucleobases. The resultant oligomer mixture was purified with Clarity QSP (Phenomenex) according to the protocol attached thereto.

The nucleotide sequence of the subject compound is complementary to a sequence from the $92^{nd}$ to $112^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 2 to 11 were also synthesized in the same manner as described in Example 1. Data from Examples 1 to 11 are summarized in Table 1 below.

TABLE 1

| Example | Designation | Sequence (5'-3') | Start | End | Molecular Weight | SEQ ID NO: |
|---|---|---|---|---|---|---|
| 1 | 21e_002 | AgaTaaAauCcgAugGcgAaG | 112 | 92 | 7544.86 | 1 |
| 2 | 21e_003 | TaaAauCcgAugGcgAagCuG | 109 | 89 | 7512.84 | 2 |
| 3 | 21e_004 | AauCcgAugGcgAagCugAaA | 106 | 86 | 7520.89 | 3 |
| 4 | 21e_005 | CcgAugGcgAagCugAaaAgG | 103 | 83 | 7575.87 | 4 |
| 5 | 21e_006 | AugGcgAagCugAaaAggAaG | 100 | 80 | 7610.88 | 5 |
| 6 | 21e_007 | GcgAagCugAaaAggAagAaG | 97 | 77 | 7633.90 | 6 |
| 7 | 21e_008 | AagCugAaaAggAagAagGuA | 94 | 74 | 7618.89 | 7 |
| 8 | 21e_009 | CugAaaAggAagAagGuaAuG | 91 | 71 | 7595.86 | 8 |
| 9 | 21e_010 | AaaAggAagAagGuaAugAgA | 88 | 68 | 7628.89 | 9 |
| 10 | 21e_011 | AggAagAagGuaAugAgaAaA | 85 | 65 | 7628.88 | 10 |
| 11 | 21e_012 | AagAagGuaAugAgaAaaTaT | 82 | 62 | 7578.93 | 11 |

In the sequences shown in Table 1, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 12 to 22

HO-$A^{m1s}$-$G^{m1s}$-$A^{m1s}$-$U^{m1s}$—$C^{m1s}$-$C^{m1s}$-$G^{m1s}$-$A^{m1s}$-$U^{m1s}$-$G^{m1s}$-$G^{m1s}$-$C^{m1s}$-$G^{m1s}$-$A^{m1s}$-$AG^{m1t}$-H (21m_002) (SEQ ID NO: 1)

Using an automated nucleic acid synthesizer (MerMade 192X; BioAutomation), synthesis and purification were performed in the same manner as described in Example 1 to thereby obtain the compound of interest.

The nucleotide sequence of the subject compound is complementary to a sequence from the $92^{nd}$ to $112^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 13 to 22 were also synthesized in the same manner as described in Example 12. Data from Examples 12 to 22 are summarized in Table 2 below.

TABLE 2

| Example | Designation | Sequence (5'-3') | Start | End | Molecular Weight | SEQ ID NO: |
|---|---|---|---|---|---|---|
| 12 | 21m_002 | agauaaaauccgauggcgaag | 112 | 92 | 7416.86 | 98 |
| 13 | 21m_003 | uaaaauccgauggcgaagcug | 109 | 89 | 7369.80 | 99 |
| 14 | 21m_004 | aauccgauggcgaagcugaaa | 106 | 86 | 7368.81 | 100 |
| 15 | 21m_005 | ccgauggcgaagcugaaaagg | 103 | 83 | 7423.81 | 101 |
| 16 | 21m_006 | auggcgaagcugaaaaggaag | 100 | 80 | 7475.89 | 102 |
| 17 | 21m_007 | gcgaagcugaaaaggaagaag | 97 | 77 | 7494.86 | 103 |
| 18 | 21m_008 | aagcugaaaaggaagaaggua | 94 | 74 | 7483.90 | 104 |
| 19 | 21m_009 | cugaaaaggaagaagguaaug | 91 | 71 | 7456.82 | 105 |
| 20 | 21m_010 | aaaaggaagaagguaaugaga | 88 | 68 | 7503.86 | 106 |
| 21 | 21m_011 | aggaagaagguaaugagaaaa | 85 | 65 | 7527.88 | 107 |
| 22 | 21m_012 | aagaagguaaugagaaaauau | 82 | 62 | 7453.87 | 108 |

In the sequences shown in Table 2, small letters represent 2'-OMe-RNA. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 23 to 50

HO-$G^{e2s}$-$A^{m1s}$-$U^{m1s}$-$A^{e2s}$-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H (21e_015) (SEQ ID NO: 12)

Synthesis and purification were performed in the same manner as described in Example 12 to thereby obtain the compound of interest.

The nucleotide sequence of the subject compound is complementary to a sequence from the 91$^{st}$ to 111$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 24 to 50 were also synthesized in the same manner as described in Example 23. Data from Examples 23 to 50 are summarized in Table 3 below.

TABLE 3

| Example | Designation | Sequence (5'-3') | Start | End | Molecular Weight | SEQ ID NO: |
|---|---|---|---|---|---|---|
| 23 | 21e_015 | GauAaaAucCgaTggCgaAgC | 111 | 91 | 7544.88 | 12 |
| 24 | 21e_016 | AuaAaaTccGauGgcGaaGcT | 110 | 90 | 7477.80 | 13 |
| 25 | 21e_017 | AaaAucCgaTggCgaAgcTgA | 108 | 88 | 7544.87 | 14 |
| 26 | 21e_018 | AaaTccGauGgcGaaGcuGaA | 107 | 87 | 7506.86 | 15 |
| 27 | 21e_019 | AucCgaTggCgaAgcTgaAaA | 105 | 85 | 7544.86 | 16 |
| 28 | 21e_020 | TccGauGgcGaaGcuGaaAaG | 104 | 84 | 7518.81 | 17 |
| 29 | 21e_021 | CgaTggCgaAgcTgaAaaGgA | 102 | 82 | 7623.82 | 18 |
| 30 | 21e_022 | GauGgcGaaGcuGaaAagGaA | 101 | 81 | 7591.85 | 19 |
| 31 | 21e_002m01 | Agauaaaauccgauggcgaag | 112 | 92 | 7432.84 | 109 |
| 32 | 21e_002m02 | agauaaaauccgauggcgaaG | 112 | 92 | 7432.84 | 110 |
| 33 | 21e_002m03 | AgauaaaauccgauggcgaaG | 112 | 92 | 7440.85 | 111 |
| 34 | 21e_002m04 | AgauaaaauccgAuggcgaaG | 112 | 92 | 7452.86 | 112 |
| 35 | 21e_002m05 | AgauaaaauCcgauggcgaaG | 112 | 92 | 7466.86 | 113 |
| 36 | 21e_002m06 | AgaTaaaauccgauggcgAaG | 112 | 92 | 7482.86 | 114 |

TABLE 3-continued

| Example | Designation | Sequence (5'-3') | Start | End | Molecular Weight | SEQ ID NO: |
|---|---|---|---|---|---|---|
| 37 | 21e_002m07 | AgauaaaauCcgAuggcgaaG | 112 | 92 | 7478.83 | 115 |
| 38 | 21e_002m08 | AgauaaaauCcgaugGcgaaG | 112 | 92 | 7478.84 | 116 |
| 39 | 21e_002m09 | AgaTaaAauccgAuggcgaaG | 112 | 92 | 7490.83 | 117 |
| 40 | 21e_002m10 | AgauaaAauccgaugGcgAaG | 112 | 92 | 7476.81 | 118 |
| 41 | 21e_002m11 | AgauaAAauccgAugGcgaaG | 112 | 92 | 7481.84 | 119 |
| 42 | 21e_002m12 | AgauaAAauCcgaugGcgaaG | 112 | 92 | 7490.85 | 120 |
| 43 | 21e_002m13 | AgaTaaAauccgAuggcgAaG | 112 | 92 | 7502.82 | 121 |
| 44 | 21e_002m14 | AgaTaaaauCcgAuggcgAaG | 112 | 92 | 7516.85 | 122 |
| 45 | 21e_002m15 | AgauaAAauCcgAugGcgaaG | 112 | 92 | 7502.82 | 123 |
| 46 | 21e_002m16 | AgaTaaAauCcgAuggegAaG | 112 | 92 | 7533.87 | 124 |
| 47 | 21e_002m17 | AgaTaaaauCcgAugGcgAaG | 112 | 92 | 7528.84 | 125 |
| 48 | 21e_002m18 | AgaTaAaaTcCgaTgGcgAaG | 112 | 92 | 7584.91 | 126 |
| 49 | 21e_002m19 | AgAuAaAuCcGaTgGcgAaG | 112 | 92 | 7564.84 | 127 |
| 50 | 21e_002m20 | AgAuAaAaTcCgAuGgCgAaG | 112 | 92 | 7594.88 | 128 |

In the sequences shown in Table 3, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 51 to 69

HO—$U^{m1s}$-$A^{e2s}$-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (18e_005) (SEQ ID NO: 20)

Synthesis was performed in the same manner as described in Example 12. Protected oligonucleotide analogs with the sequence of interest were treated with 450 μl of concentrated aqueous ammonia to thereby cut out oligomers from the support and, at the same time, remove the protective group cyanoethyl on phosphorus atoms and the protective group on nucleobases. The resultant oligomer mixture in solution was mixed with 300 μl of Clarity QSP DNA Loading Buffer (Phenomenex) and charged on Clarity SPE 96 well plates (Phenomenex). One milliliter of Clarity QSP DNA Loading Buffer:water=1:1 solution, 3 mL of water, 3 ml of 3% dichloroacetic acid (DCA) aqueous solution and 6 ml of water were added in this order. Subsequently, components extracted with a 9:1 solution of 20 mM Tris aqueous solution and acetonitrile were collected. After distilling off the solvent, the compound of interest was obtained.

The nucleotide sequence of the subject compound is complementary to a sequence from the 91st to the 109th nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T.

Compounds of Examples 52 to 69 were also synthesized in the same manner as described in Example 51. Data from Examples 51 to 69 are summarized in Table 4 below.

TABLE 4

| Example | Designation | Sequence (5'-3') | Start | End | Molecular Weight | SEQ ID NO: |
|---|---|---|---|---|---|---|
| 51 | 18e_005 | uAaaAucCgaTggCgaAg | 109 | 92 | 6437.79 | 20 |
| 52 | 18e_006 | aAaaTccGauGgcGaaGc | 108 | 91 | 6408.78 | 21 |
| 53 | 18e_007 | aAauCcgAugGcgAagCu | 107 | 90 | 6399.76 | 22 |
| 54 | 18e_008 | aAucCgaTggCgaAgcTg | 106 | 89 | 6443.80 | 23 |
| 55 | 18e_009 | aTccGauGgcGaaGcuGa | 105 | 88 | 6401.74 | 24 |
| 56 | 18e_010 | uCcgAugGcgAagCugAa | 104 | 87 | 6415.75 | 25 |
| 57 | 18e_011 | cCgaTggCgaAgcTgaAa | 103 | 86 | 6466.81 | 26 |

TABLE 4-continued

| Example | Designation | Sequence (5'-3') | Start | End | Molecular Weight | SEQ ID NO: |
|---|---|---|---|---|---|---|
| 58 | 18e_012 | cGauGgcGaaGcuGaaAa | 102 | 85 | 6434.76 | 27 |
| 59 | 18e_013 | gAugGcgAagCugAaaAg | 101 | 84 | 6488.79 | 28 |
| 60 | 18e_014 | aTggCgaAgcTgaAaaGg | 100 | 83 | 6516.82 | 29 |
| 61 | 18e_015 | uGgcGaaGcuGaaAagGa | 99 | 82 | 6474.78 | 30 |
| 62 | 18e_016 | gGcgAagCugAaaAggAa | 98 | 81 | 6511.81 | 31 |
| 63 | 18e_017 | gCgaAgcTgaAaaGgaAg | 97 | 80 | 6525.84 | 32 |
| 64 | 18e_022 | TaaaauCCgaTggCgaag | 109 | 92 | 6453.82 | 129 |
| 65 | 18e_023 | aaaauCCgaTggCgaagC | 108 | 91 | 6452.84 | 130 |
| 66 | 18e_024 | aaauCCgaTggCgaagCT | 107 | 90 | 6455.83 | 131 |
| 67 | 18e_025 | aauCCgaTggCgaagCTg | 106 | 89 | 6471.82 | 132 |
| 68 | 18e_026 | auCCgaTggCgaagCTga | 105 | 88 | 6471.83 | 133 |
| 69 | 18e_031 | TaAaaTccgauGgcGaag | 109 | 92 | 6411.77 | 134 |

In the sequences shown in Table 4, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 70 to 82

HO—U$^{mls}$-A$^{mls}$-A$^{mls}$-A$^{mls}$-A$^{mls}$-U$^{mls}$—C$^{mls}$-C$^{mls}$-G$^{mls}$-A$^{mls}$-U$^{mls}$-G$^{mls}$-G$^{mls}$-C$^{mls}$-G$^{mls}$-A$^{mls}$-A$^{mls}$-G$^{mlt}$-H (18m_005) (SEQ ID NO: 20)

Using an automated nucleic acid synthesizer (MerMade 192X; BioAutomation), synthesis and purification were performed in the same manner as described in Example 12 to thereby obtain the compound of interest.

The nucleotide sequence of the subject compound is complementary to a sequence from the 92$^{nd}$ to the 109$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 71 to 82 were also synthesized in the same manner as described in Example 70. Data from Examples 70 to 82 are summarized in Table 5 below.

TABLE 5

| Example | Designation | Sequence (5'-3') | Start | End | Molecular Weight | SEQ ID NO: |
|---|---|---|---|---|---|---|
| 70 | 18m_005 | uaaaauccgauggcgaag | 109 | 92 | 6323.74 | 135 |
| 71 | 18m_006 | aaaauccgauggcgaagc | 108 | 91 | 6322.76 | 136 |
| 72 | 18m_007 | aaauccgauggcgaagcu | 107 | 90 | 6299.74 | 137 |
| 73 | 18m_008 | aauccgauggcgaagcug | 106 | 89 | 6315.73 | 138 |
| 74 | 18m_009 | auccgauggcgaagcuga | 105 | 88 | 6315.73 | 139 |
| 75 | 18m_010 | uccgauggcgaagcugaa | 104 | 87 | 6315.73 | 140 |
| 76 | 18m_011 | ccgauggcgaagcugaaa | 103 | 86 | 6338.75 | 141 |
| 77 | 18m_012 | cgauggcgaagcugaaaa | 102 | 85 | 6362.76 | 142 |
| 78 | 18m_013 | gauggcgaagcugaaaag | 101 | 84 | 6402.77 | 143 |
| 79 | 18m_014 | auggcgaagcugaaaagg | 100 | 83 | 6402.77 | 144 |
| 80 | 18m_015 | uggcgaagcugaaaagga | 99 | 82 | 6402.77 | 145 |

TABLE 5-continued

| Example | Designation | Sequence (5'-3') | Start | End | Molecular Weight | SEQ ID NO: |
|---|---|---|---|---|---|---|
| 81 | 18m_016 | ggcgaagcugaaaaggaa | 98 | 81 | 6425.79 | 146 |
| 82 | 18m_017 | gcgaagcugaaaaggaag | 97 | 80 | 6425.80 | 157 |

In the sequences shown in Table 5, small letters represent 2'-OMe-RNA. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Reference Example 1

HO-$A^{e2s}$-$G^{m1s}$-$A^{m1s}$-$T^{e2s}$-$A^{m1s}$-$A^{m1s}$-$A^{e2s}$-$A^{m1s}$-$U^{m1s}$—$C^{e2s}$-$C^{m1s}$-$G^{m1s}$-$A^{e2s}$-$U^{m1s}$-$G^{m1s}$-$G^{e2s}$-$C^{m1s}$-$G^{m1s}$-$A^{e2s}$-$A^{m1s}$-$G^{e2t}$-H (21e_001) (SEQ ID NO: 33) Synthesis and purification were performed in the same manner as described in Example 1 to thereby obtain the compound of interest.

The nucleotide sequence of the subject compound is complementary to a sequence from the 95th to the 115th nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7520.85).

Reference Examples 2 to 3

HO-$G^{e2s}$-$C^{m1s}$-$A^{m1s}$-$G^{e2s}$-$A^{m1s}$-$U^{m1s}$-$A^{e2s}$-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{e2t}$-H (21e_013) (SEQ ID NO: 34) Synthesis and purification were performed in the same manner as described in Example 12 to thereby obtain the compound of interest.

The nucleotide sequence of the subject compound is complementary to a sequence from the 94th to the 114th nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

The compound of Reference Example 3 was also synthesized in the same manner as described in Reference Example 2. Data from Reference Examples 2 and 3 are summarized in the following Table 6.

In the sequences shown in Table 6, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Reference Examples 4 to 15

HO—$C^{m1s}$-$A^{e2s}$-$G^{m1s}$-$A^{m1s}$-$T^{e2s}$-$A^{m1s}$-$A^{m1s}$-$A^{e2s}$-$A^{m1s}$-$U^{m1s}$—$C^{e2s}$-$C^{m1s}$-$G^{m1s}$-$A^{e2s}$-$U^{m1s}$-$G^{m1s}$-$G^{e2s}$-$C^{m1t}$—H (18e_001) (SEQ ID NO: 36)

Synthesis and purification were performed in the same manner as described in Example 51 to thereby obtain the compound of interest.

The nucleotide sequence of the subject compound is complementary to a sequence from the 96th to the 113th nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Reference Examples 5 to 15 were also synthesized in the same manner as described in Reference Example 4. Data from Reference Examples 4 to 15 are summarized in the following Table 7.

TABLE 6

| Reference Example | Designation | Sequence (5'-3') | Start | End | Molecular Weight | SEQ ID NO: |
|---|---|---|---|---|---|---|
| 2 | 21e_013 | GcaGauAaaAucCgaTggCgA | 114 | 94 | 7530.86 | 34 |
| 3 | 21e_014 | CagAuaAaaTccGauGgcGaA | 113 | 93 | 7505.88 | 35 |

TABLE 7

| Reference Example | Designation | Sequence (5'-3') | Start | End | Molecular Weight | SEQ ID NO: |
|---|---|---|---|---|---|---|
| 4 | 18e_001 | cAgaTaaAauCcgAugGc | 113 | 96 | 6383.77 | 36 |
| 5 | 18e_002 | aGauAaaAucCgaTggCg | 112 | 95 | 6437.79 | 37 |
| 6 | 18e_003 | gAuaAaaTccGauGgcGa | 111 | 94 | 6409.76 | 38 |
| 7 | 18e_004 | aTaaAauCcgAugGcgAa | 110 | 93 | 6407.78 | 39 |
| 8 | 18e_018 | CagaTaaaauCCgaTggC | 113 | 96 | 6439.82 | 148 |
| 9 | 18e_019 | agaTaaaauCCgaTggCg | 112 | 95 | 6453.82 | 149 |
| 10 | 18e_020 | gaTaaaauCCgaTggCga | 111 | 94 | 6453.82 | 150 |
| 11 | 18e_021 | aTaaaauCCgaTggCgaa | 110 | 93 | 6437.83 | 151 |
| 12 | 18e_027 | CaGauAaaaucCgaTggc | 113 | 96 | 6385.78 | 152 |
| 13 | 18e_028 | AgAuaAaauccGauGgcg | 112 | 95 | 6383.74 | 153 |
| 14 | 18e_029 | GaTaaAauccgAugGcga | 111 | 94 | 6397.76 | 154 |
| 15 | 18e_030 | AuAaaAuccgaTggCgaa | 110 | 93 | 6395.78 | 155 |

In the sequences shown in Table 7, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Reference Examples 16 to 20

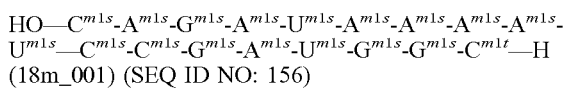
(18m_001) (SEQ ID NO: 156)

Synthesis and purification were performed in the same manner as described in Example 70 to thereby obtain the compound of interest.

The nucleotide sequence of the subject compound is complementary to a sequence from the 96th to the 113th nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Reference Examples 17 to 20 were also synthesized in the same manner as described in Reference Example 16. Data from Reference Examples 16 to 20 are summarized in Table 8 below.

TABLE 8

| Reference Example | Designation | Sequence (5'-3') | Start | End | Molecular Weight | SEQ ID NO: |
|---|---|---|---|---|---|---|
| 16 | 18m_001 | cagauaaaauccgauggc | 113 | 96 | 6283.74 | 156 |
| 17 | 18m_002 | agauaaaauccgauggcg | 112 | 95 | 6323.74 | 157 |
| 18 | 18m_003 | gauaaaauccgauggcga | 111 | 94 | 6323.75 | 158 |
| 19 | 18m_004 | auaaaauccgauggcgaa | 110 | 93 | 6307.75 | 159 |
| 20 | 21m_001 | agcagauaaaauccgauggcg | 115 | 95 | 7396.88 | 160 |

In the sequences shown in Table 8, small letters represent 2'-OMe-RNA. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 83 to 86

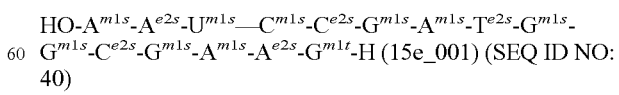
(15e_001) (SEQ ID NO: 40)

Synthesis was performed in the same manner as described in Example 1, except that AKTA Oligopilot and a solid carrier, Primer Support 5G Unylinker 350, 100 μmol (GE Healthcare), were used. Protected oligonucleotide analogs with the sequence of interest were treated with 25 ml of concentrated aqueous ammonia to thereby cut out oligomers from the support and, at the same time, remove the protective group cyanoethyl on phosphorus atoms and the protective group on nucleobases. The resultant oligomer mixture in solution was deprotected and purified with 5 g of Phenomenex Clarity QSP. After the solvent was distilled off, the compound of interest was obtained.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 84 to 86 were also synthesized in the same manner as described in Example 83. Data from Examples 83 to 86 are shown in Table 9 below.

TABLE 9

| Example | Designation | Sequence (5'-3') | Start | End | Molecular Weight | SEQ ID NO: |
|---|---|---|---|---|---|---|
| 83 | 15e_001 | aAucCgaTggCgaAg | 106 | 92 | 5371.68 | 40 |
| 84 | 15e_002 | cCgaTggCgaAgcTg | 103 | 89 | 5377.68 | 41 |
| 85 | 15ed_001 | aAtcCgaTggCgaAg | 106 | 92 | 5099.59 | 161 |
| 86 | 15ed_002 | cCgaTggCgaAgcTg | 103 | 89 | 5105.60 | 162 |

In the sequences shown in Table 9, capital letters represent 2'-O,4'-C-ethylene bridged nucleic acid and small letters 2'-OMe-RNA, with underlined small letters representing DNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Examples 87 to 90

HO-A$^{m1s}$-A$^{e2s}$-U$^{m1s}$—C$^{e2s}$-C$^{e2s}$-G$^{m1s}$-A$^{e2s}$-T$^{e2s}$-G$^{m1s}$-G$^{m1s}$-C$^{e2s}$-G$^{m1s}$-A$^{m1s}$-A$^{e2s}$-G$^{m1t}$-H (15e_001.1) (SEQ ID NO: 163)

Synthesis was performed in the same manner as described in Example 1 except that Primer Support 5G Unylinker 350, 10 μmol (GE Healthcare) was used as solid carrier and the program for 10 μmol scale was employed. Purification was performed in the same manner as described in Example 83, to thereby obtain the compound of interest.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T.

Compounds of Examples 88 to 90 were also synthesized in the same manner as described in Example 83. Data from Examples 87 to 90 are shown in Table 10 below.

TABLE 10

| Example | Designation | Sequence (5'-3') | Start | End | Molecular Weight | SEQ ID NO: |
|---|---|---|---|---|---|---|
| 87 | 15e_001.1 | aAuCCgATggCgaAg | 106 | 92 | 5409.71 | 163 |
| 88 | 15e_001.2 | aAucCgATggCgAAg | 106 | 92 | 5395.69 | 164 |
| 89 | 15e_001.3 | aAuCCgaTggCgAAg | 106 | 92 | 5409.71 | 165 |
| 90 | 15e_001.4 | aAuCCgATggCgAAg | 106 | 92 | 5421.70 | 166 |

In the sequences shown in Table 10, capital letters represent 2'-O,4'-C-ethylene bridged nucleic acid and small letters 2'-OMe-RNA. "C" in 2'-O,4'-C-ethylene bridged nucleic acid is 5-methylcytosine. For "Start" and "End", respective nucleotide numbers are shown as counted from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. Compounds were identified by negative-ion ESI mass spectrometry, and the measured molecular weights are shown in the Table.

Example 91

HO-X-X-X-A$^{P}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$ H (SEQ ID NO: 42)

Synthesis was performed in the same manner as described in Example 1 except that Primer Support 5G Unylinker 350, 10 μmol (GE Healthcare) was used as solid carrier and the program for 10 μmol scale was employed. As regards the X portion, GalNAc phosphoramidite unit 1 disclosed in Bioorg. Med. Chem. (2016) 24, 26-32 was used and condensed three times. Purification was performed in the same manner as described in Example 83 to thereby obtain the compound of interest.

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7131.24).

Example 92

HO-X-X-X-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91.

Example 93

HO-X-X-X-T$^p$-C$^p$-A$^p$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 43)

Synthesis was performed in the same manner as described in Example 91.

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7738.35).

Example 94

HO-X-X-X-A$^p$-A$^{m1s}$-A$^{e2s}$-U$^{m1s}$—C$^{e2s}$-C$^{m1s}$-G$^{e2s}$-A$^{m1s}$-T$^{e2s}$-G$^{m1s}$-G$^{e2s}$-C$^{m1s}$-G$^{e2s}$-A$^{m1s}$-A$^{e2s}$-G$^{m1t}$-H (SEQ ID NO: 167)

Synthesis was performed in the same manner as described in Example 91.

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7141.22).

Example 95

HO-X-X-X-A$^p$-A$^{e2s}$-A$^{m1s}$-T$^{e2s}$-C$^{m1s}$-C$^{e2s}$-G$^{m1s}$-A$^{e2s}$-U$^{m1s}$-G$^{e2s}$-G$^{m1s}$-C$^{e2s}$-G$^{m1s}$-A$^{e2s}$-A$^{m1s}$-G$^{e2t}$-H (SEQ ID NO: 168)

Synthesis was performed in the same manner as described in Example 91.

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7167.24).

Reference Example 21

21A

Synthesis of [(2R,3R,4R,5R,6R)-5-acetamide-3,4-diacetoxy-6-[5-(benzyloxycarbonylamino)pentoxy] tetrahydropyran-2-yl]methyl acetate (Compound 21A)

[Formula 78]

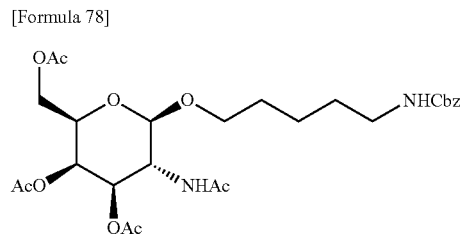 [SMILES: CC(=O)N[C@H]1[C@H](OCCCCCNC(=O)OCc2ccccc2)O[C@H](COC(C)=O)[C@H](OC(C)=O)[C@@H]1OC(C)=O]

A known documented compound N-benzyloxycarbonyl-1-hydroxypentyl-5-amine (J. Am. Chem. Soc., 2006, 128, 4058-4073) (8.05 g, 33.9 mmol) and a known documented compound [(2R,3R,4R,5R)-5-acetamide-3,4,6-triacetoxy-tetrahydropyran-2-yl]methyl acetate (WO2011053614) (12.0 g, 30.8 mmol) were suspended in dichloromethane (200 ml). Trifluoromethanesulfonic acid (450 µl, 5.23 mmol) was added, followed by stirring at 45° C. overnight. After completion of the reaction, about one half of the solvent was distilled off under vacuum to concentrate the reaction mixture, which was then added to a mixed solution of ethyl acetate/saturated aqueous sodium bicarbonate solution. The organic layer was washed with saturated aqueous sodium bicarbonate solution and saturated saline/phosphate buffer (pH 7.0), dried over anhydrous sodium sulfate and filtered. By distilling off the solvent under vacuum, a crude product was obtained. This product was purified by silica gel column chromatography (hexane:ethyl acetate=100:0-0:100, v/v) to thereby obtain the compound of interest (21A) in an amorphous state (17.0 g, yield 94%).

$^1$H-NMR (CDCl$_3$) δ: 7.37-7.32 (5H, m), 5.69 (1H, d, J=9.1 Hz), 5.35 (1H, d, J=2.4 Hz), 5.29 (1H, d, J=11.5 Hz), 5.10 (2H, s), 4.94 (1H, br), 4.68 (1H, d, J=7.9 Hz), 4.20-4.09 (2H, m), 3.97-3.86 (3H, m), 3.49-3.44 (1H, m), 3.20-3.17 (2H, m), 2.14 (3H, s), 2.05 (3H, s), 2.01 (3H, s), 1.93 (3H, s), 1.66-1.34 (6H, m).

Calcd for C$_{27}$H$_{38}$N$_2$O$_{11}$: [M+H]$^+$ 567, Found 567.

21B

Synthesis of [(2R,3R,4R,5R,6R)-5-acetamide-3,4-diacetoxy-6-(5-aminopentoxy) tetrahydropyran-2-yl] methyl acetate (Compound 21B)

[Formula 79]

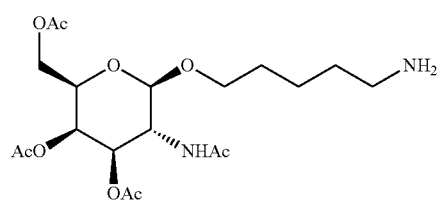

Compound 21A (17.0 g, 30.0 mmol) synthesized in Step (21A) above was dissolved in ethanol (200 ml). 10% Palladium/carbon (wet) (2 g) was added to the solution, which was then stirred vigorously at room temperature under a hydrogen atmosphere. After completion of the reaction, the reaction mixture was filtered. The filtrate was distilled off under vacuum to thereby obtain a crude product of the compound of interest (21B) (12.64 g, yield 97%), which was used in the subsequent reaction without further purification.

$^1$H-NMR (CDCl$_3$) δ: 5.78 (1H, d, J=8.5 Hz), 5.36-5.32 (2H, m), 4.72 (1H, d, J=8.5 Hz), 4.21-4.09 (2H, m), 3.96-3.88 (3H, m), 3.52-3.47 (1H, m), 2.70 (2H, t, J=6.7 Hz), 2.15 (3H, s), 2.05 (3H, s), 2.01 (3H, s), 1.96 (3H, s), 1.75-1.36 (6H, m).

Calcd for C$_{19}$H$_{32}$N$_2$O$_9$: [M+H]$^+$ 433, Found 433.

21C

Synthesis of [(2R,3R,4R,5R,6R)-5-acetamide-3,4-diacetoxy-6-[5-[[(4S)-2,2-dimethyl-1,3-dioxolan-4-yl]methoxycarbonylamino]pentoxy]tetrahydropyran-2-yl]methyl acetate Compound 21C

[Formula 80]

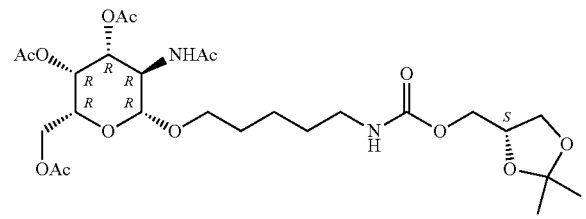

(R)-(-)-2,2-dimethyl-1,3-dioxolane-4-methanol (1.68 g, 12.8 mmol) and triethylamine (3.22 ml, 23.1 mmol) were dissolved in dichloromethane (100 ml). 4-Nitrophenyl chloroformate (2.56 g, 12.7 mmol) was added to the solution, which was then stirred at room temperature for 1 hr. Subsequently, a dichloromethane solution (20 ml) of triethylamine (5 ml, 36 mmol) and compound 21B as synthesized in Step (21B) (5.0 g, 11.56 mmol) was added to the above solution, which was stirred at 45° C. for 1 hr. After completion of the reaction, the solvent was distilled off under vacuum to obtain a crude product. This product was purified by silica gel column chromatography (hexane:ethyl acetate=100:0-0:100, v/v) to thereby obtain the compound of interest (21C) in an amorphous state (3.46 g, yield 51%).

$^1$H-NMR (CDCl$_3$) δ: 5.75 (1H, d, J=8.5 Hz), 5.36 (1H, d, J=3.0 Hz), 5.30 (1H, dd, J=11.2, 3.3 Hz), 4.97 (1H, br), 4.71 (1H, d, J=8.5 Hz), 4.33-4.29 (1H, m), 4.23-3.88 (8H, m), 3.74-3.72 (1H, m), 3.49-3.46 (1H, m), 3.19-3.14 (2H, m), 2.15 (3H, s), 2.05 (3H, s), 2.01 (3H, s), 1.96 (3H, s), 1.63-1.53 (6H, m), 1.44 (3H, s), 1.37 (3H, s).

Calcd for C$_{26}$H$_{42}$N$_2$O$_{13}$: [M+H]$^+$ 591, Found 591.

21D

Synthesis of [(2R,3R,4R,5R,6R)-5-acetamide-3,4-diacetoxy-6-[5-[[(2S)-2,3-dihydroxypropoxy]carbonylamino]pentoxy]tetrahydropyran-2-yl]methyl acetate (Compound 21D)

[Formula 81]

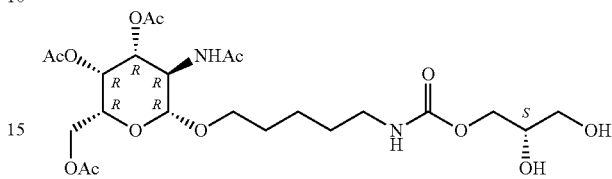

To Compound 21C synthesized in Step (21C) above (4.38 g, 7.42 mmol), 2 ml of pure water and 6 ml of trifluoroacetic acid were added. The mixture was stirred at room temperature for 1.5 hrs. After completion of the reaction, the solvent was distilled off under vacuum. Further, moisture was removed by azeotropic distillation with toluene to thereby obtain a crude product. This product was purified by silica gel column chromatography (hexane:ethyl acetate=100:0-0:100, v/v) to thereby obtain the compound of interest (21D) in an amorphous state (2.47 g, yield 61%).

$^1$H-NMR (CDCl$_3$) δ: 5.75 (1H, d, J=7.3 Hz), 5.35 (1H, d, J=3.0 Hz), 5.22 (1H, dd, J=11.5, 3.0 Hz), 5.13 (1H, br s), 4.61 (1H, d, J=8.5 Hz), 4.23-3.87 (7H, m), 3.67-3.60 (3H, m), 3.49-3.46 (1H, m), 3.22-3.16 (2H, m), 2.16 (3H, s), 2.05 (3H, s), 2.01 (3H, s), 1.97 (3H, s), 1.61-1.50 (6H, m).

Calcd for C$_{23}$H$_{38}$N$_2$O$_{13}$: [M+H]$^+$ 551, Found 551.

21E

Synthesis of [(2R,3R,4R,5R,6R)-5-acetamide-3,4-diacetoxy-6-[5-[[(2S)-3-[bis(4-methoxyphenyl)-phenyl-methoxy]-2-hydroxy-propoxy]carbonylamino]pentoxy]tetrahydropyran-2-yl]methyl acetate (Compound 21E)

[Formula 82]

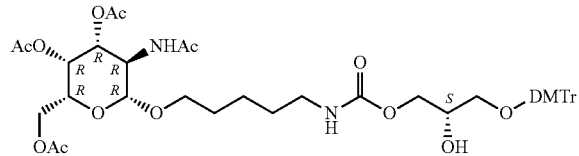

Compound 21D as synthesized in Step (21D) (2.47 g, 4.52 mmol) was dissolved in pyridine (15 mL). 4,4'-Dimethoxytrityl chloride (1.82 g, 5.38 mmol) was added and stirred at room temperature. After completion of the reaction, the solvent was distilled off under vacuum to thereby obtain a crude product. This product was purified by silica gel column chromatography (hexane:ethyl acetate=100:0-0:100, v/v; subsequently, ethyl acetate:methanol=95:5, v/v) to thereby obtain the compound of interest (21E) in an amorphous state (1.84 g, yield 48%).

$^1$H-NMR (CDCl$_3$) δ: 7.43-7.42 (2H, m), 7.32-7.29 (6H, m), 7.24-7.19 (1H, m), 6.84-6.81 (4H, m), 5.74 (1H, d, J=8.5 Hz), 5.35 (1H, d, J=3.0 Hz), 5.26 (1H, dd, J=11.2, 3.3 Hz), 4.94 (1H, br), 4.65 (1H, d, J=8.5 Hz), 4.22-4.09 (4H, m), 3.97-3.91 (4H, m), 3.79 (6H, s), 3.47-3.43 (1H, m), 3.18-3.15 (4H, m), 3.00 (1H, d, J=4.8 Hz), 2.14 (3H, s), 2.04 (3H, s), 1.99 (3H, s), 1.95 (3H, s), 1.65-1.34 (6H, m).

Calcd for C$_{44}$H$_{56}$N$_2$O$_{15}$: [M+Na]$^+$ 875, Found 875.

21F

Synthesis of [(2R,3R,4R,5R,6R)-5-acetamide-3,4-diacetoxy-6-[5-[[(2S)-3-[bis(4-methoxyphenyl)-phenyl-methoxy]-2-[2-cyanoethoxy-(diisopropylamino)phosphanyl]oxypropoxy]carbonylamino]pentoxy]tetrahydropyran-2-yl]methyl acetate (Compound 21F)

[Formula 83]

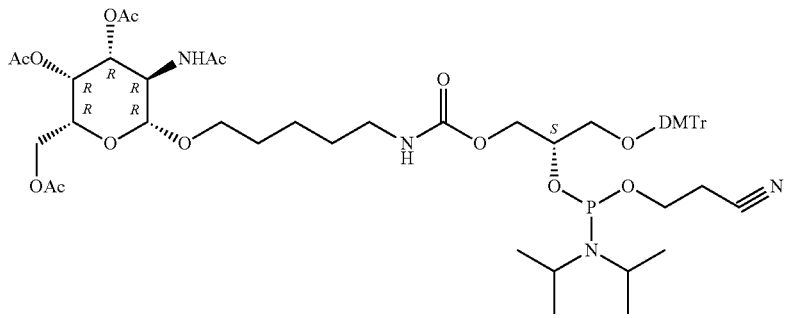

Compound 21E as synthesized in Step (21E) (1.84 g, 2.16 mmol) was added to an appropriate amount of pyridine, subjected to azeotropic distillation under vacuum, and then dissolved in dichloromethane (21 ml). To this solution, N,N-diisopropylethylamine (2.25 mL, 12.9 mmol) and 2-cyanoethyl diisopropylchlorophosphoramidite (0.96 mL, 4.31 mmol) were added. The reaction solution was stirred at room temperature for 1.5 hrs. After completion of the reaction, the solvent was distilled off under vacuum. After azeotropic distillation with an appropriate amount of toluene, a crude product was obtained. This product was purified by silica gel column chromatography (hexane:ethyl acetate=100:0-0:100, v/v, containing 1% triethylamine) to thereby obtain the compound of interest (21F) in an amorphous state (1.87 g, yield 82%).

$^1$H-NMR (CDCl$_3$) δ: 7.46-7.40 (2H, m), 7.35-7.17 (7H, m), 6.82-6.80 (4H, m), 5.73-5.63 (1H, m), 5.37-5.35 (1H, m), 5.30-5.26 (1H, m), 4.97-4.94 (0.5H, m), 4.72-4.68 (1H, m), 4.42-4.40 (0.5H, m), 4.22-4.10 (4H, m), 3.99-3.43 (14H, m), 3.18-3.12 (4H, m), 2.67-2.62 (1H, m), 2.46-2.44 (1H, m), 2.14 (3H, s), 2.01-1.96 (9H, m), 1.65-0.97 (18H, m).

Example 96

HO—X$^1$—X$^1$—X$^1$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91 except that the X portion was replaced by X$^1$. For the X$^1$ portion, Compound 21F as synthesized in Reference Example 21 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound identified by negative-ion ESI mass spectrometry (measured molecular weight: 6830.15).

Reference Example 22

22A

Synthesis of [(2R,3R,4R,5R,6R)-5-acetamide-3,4-diacetoxy-6-[5-[[(4R)-2,2-dimethyl-1,3-dioxolan-4-yl]methoxycarbonylamino]pentoxy]tetrahydropyran-2-yl]methyl acetate Compound 22A

[Formula 84]

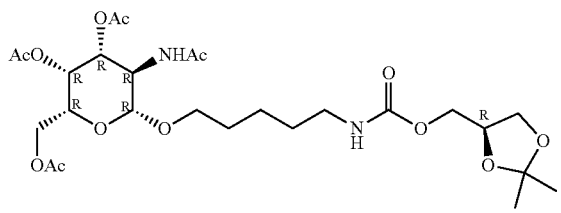

(S)-(+)-2,2-dimethyl-1,3-dioxolane-4-methanol (1.68 µg, 2.54 mmol) and triethylamine (3.22 mL, 23.1 mmol) were dissolved in dichloromethane (100 ml). 4-Nitrophenyl chloroformate (2.56 g, 12.72 mmol) was added to the solution, which was stirred at room temperature for 1 hr. Subsequently, triethylamine (5 ml, 36 mmol) and Compound 21B synthesized in Step (21B) (5.2 g, 13 mmol) were added to the solution, which was stirred at 45° C. for 1 hr. After completion of the reaction, the solvent was distilled off under vacuum to thereby obtain a crude product. This product was purified by silica gel column chromatography (hexane:ethyl acetate=100:0-0:100, v/v) to thereby obtain the compound of interest (22A) in an amorphous state (3.82 g, yield 54%).

$^1$H-NMR (CDCl$_3$) δ: 5.71 (1H, d, J=8.5 Hz), 5.36 (1H, d, J=3.0 Hz), 5.31 (1H, dd, J=11.2, 3.0 Hz), 4.97 (1H, br), 4.71 (1H, d, J=8.5 Hz), 4.33-4.30 (1H, m), 4.22-3.99 (5H, m), 3.95-3.89 (3H, m), 3.74-3.71 (1H, m), 3.50-3.46 (1H, m), 3.19-3.14 (2H, m), 2.15 (3H, s), 2.05 (3H, s), 2.01 (3H, s), 1.96 (3H, s), 1.69-1.47 (6H, m), 1.44 (3H, s), 1.37 (3H, s).

Calcd for $C_{26}H_{42}N_2O_{13}$: $[M+H]^+$ 591, Found 591.

22B

Synthesis of [(2R,3R,4R,5R,6R)-5-acetamide-3,4-diacetoxy-6-[5-[[(2R)-2,3-dihydroxypropoxy]carbonylamino]pentoxy]tetrahydropyran-2-yl]methyl acetate (Compound 22B)

[Formula 85]

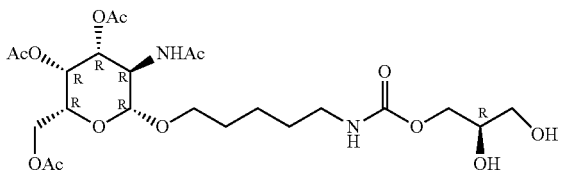

To Compound 22A synthesized in Step (22A) (3.82 g, 6.47 mmol), pure water (2 ml) and trifluoroacetic acid (6 ml) were added. The reaction mixture was stirred at room temperature for 1.5 hrs. After completion of the reaction, the solvent was distilled off under vacuum. Moisture was removed further by azeotropic distillation with toluene to thereby obtain a crude product. This product was purified by silica gel column chromatography (hexane:ethyl acetate=100:0-0:100, v/v) to thereby obtain the compound of interest (22B) in an amorphous state (2.49 g, yield 70%).

$^1$H-NMR (CDCl$_3$) δ: 5.98 (1H, d, J=8.5 Hz), 5.37-5.20 (3H, m), 4.63 (1H, d, J=8.5 Hz), 4.21-3.88 (7H, m), 3.69-3.57 (3H, m), 3.51-3.44 (1H, m), 3.21-3.14 (2H, m), 2.16 (3H, s), 2.05 (3H, s), 2.01 (3H, s), 1.97 (3H, s), 1.66-1.34 (6H, m).

Calcd for $C_{23}H_{38}N_2O_{13}$: $[M+H]^+$ 551, Found 551.

22C

Synthesis of [(2R,3R,4R,5R,6R)-5-acetamide-3,4-diacetoxy6-[5-[[(2R)-3-[bis(4-methoxyphenyl)-phenyl-methoxy]-2-hydroxy-propoxy]carbonylamino]pentoxy]tetrahydropyran-2-yl]methyl acetate (Compound 22C)

[Formula 86]

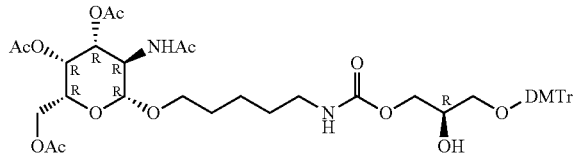

Compound 22B as synthesized in Step (22B) (2.49 g, 4.52 mmol) was dissolved in pyridine (15 ml). 4,4'-Dimethoxytrityl chloride (1.84 g, 5.43 mmol) was added to the solution, which was then stirred at room temperature. After completion of the reaction, the solvent was distilled off under vacuum to thereby obtain a crude product. This product was purified by silica gel column chromatography (hexane:ethyl acetate=100:0-0:100, v/v; subsequently, ethyl acetate:methanol=95:5, v/v) to thereby obtain the compound of interest (22C) in an amorphous state (2.1 g, yield 54%).

$^1$H-NMR (CDCl$_3$) δ: 7.42 (2H, d, J=7.9 Hz), 7.32-7.16 (6H, m), 6.83 (4H, d, J=9.1 Hz), 5.74 (1H, d, J=8.5 Hz), 5.35 (1H, d, J=3.0 Hz), 5.27 (1H, dd, J=11.2, 3.0 Hz), 4.93 (1H, br), 4.66 (1H, d, J=8.5 Hz), 4.25-4.11 (4H, m), 4.01-3.89 (4H, m), 3.79 (6H, s), 3.50-3.43 (1H, m), 3.21-3.13 (4H, m), 2.98 (1H, br), 2.13 (3H, s), 2.04 (3H, s), 1.99 (3H, s), 1.94 (3H, s), 1.65-1.34 (6H, m).

Calcd for $C_{44}H_{56}N_2O_{15}$: $[M+Na]^+$ 875, Found 875.

22D

Synthesis of [(2R,3R,4R,5R,6R)-5-acetamide-3,4-diacetoxy-6-[5-[[(2R)-3-[bis(4-methoxyphenyl)-phenyl-methoxy]-2-[2-cyanoethoxy-(diisopropylamino)phosphanyl]oxypropoxy]carbonylamino]pentoxy]tetrahydropyran-2-yl]methyl acetate (Compound 22D)

[Formula 87]

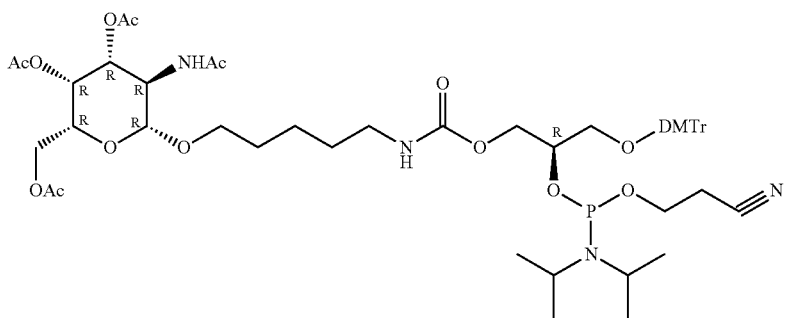

After addition of an appropriate amount of pyridine, Compound 22C as synthesized in Step (22C) (2.10 g, 2.50 mmol) was azeotropically distilled under vacuum and dissolved in dichloromethane (20 ml). N,N-diisopropylethylamine (2.6 ml, 15 mmol) and 2-cyanoethyl diisopropylchlorophosphoramidite (1.L1 ml, 4.9 mmol) were added. The reaction mixture was stirred at room temperature for 1.5 hrs. After completion of the reaction, the solvent was distilled off under vacuum. Azeotropic distillation with an appropriate amount of toluene was performed to thereby obtain a crude product. This product was purified by silica gel column chromatography (hexane:ethyl acetate=100:0-0:100, v/v, containing 1% triethylamine) to thereby obtain the compound of interest (22D) in an amorphous state (1.63 g, yield 63%).

$^1$H-NMR (CDCl$_3$) δ: 7.46-7.40 (2H, m), 7.35-7.17 (7H, m), 6.85-6.78 (4H, m), 5.70-5.57 (1H, m), 5.38-5.34 (1H, m), 5.32-5.24 (1H, m), 4.96-4.91 (0.5H, m), 4.73-4.65 (1H, m), 4.44-4.38 (0.5H, m), 4.23-4.08 (4H, m), 4.00-3.41 (14H, m), 3.27-3.03 (4H, m), 2.68-2.60 (1H, m), 2.49-2.42 (1H, m), 2.14 (3H, s), 2.07-1.91 (9H, m), 1.65-0.97 (18H, m).

Example 97

HO—X$^2$—X$^2$—X$^2$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91 except that the X portion was replaced by X$^2$. For the X$^2$ portion, Compound 22D as synthesized in Reference Example 22 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6830.14).

Reference Example 23

23A

Synthesis of [(2R,3R,4R,5R,6R)-5-acetamide-3,4-diacetoxy-6-[8-(benzyloxycarbonylamino)octoxy]tetrahydropyran-2-yl]methyl acetate (Compound 23A)

[Formula 88]

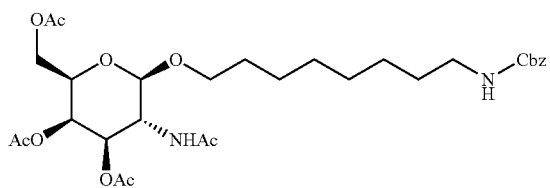

A known documented compound benzyl N-(8-hydroxyoctyl)carbamate (J. Med. Chem. 199, 3, 36, 3721-3726) (6.5 g, 23 mmol) and a known documented compound [(2R,3R,4R,5R)-5-acetamide-3,4,6-trioxy-tetrahydropyran-2-yl]methyl acetate (WO2011053614) (8.2 g, 21 mmol) were suspended in dichloromethane (150 ml). Trifluoromethanesulfonic acid (310 µl, 3.6 mmol) was added, followed by stirring at 45° C. overnight. After completion of the reaction, about one half of the solvent was distilled off under vacuum to concentrate the reaction mixture, which was then added to a mixed solution of ethyl acetate/saturated aqueous sodium bicarbonate solution. The organic layer was washed with saturated aqueous sodium bicarbonate solution and saturated saline/phosphate buffer (pH 7.0), dried over anhydrous sodium sulfate and filtered. By distilling off the solvent under vacuum, a crude product was obtained. This product was purified by silica gel column chromatography (hexane:ethyl acetate=100:0-0:100, v/v) to thereby obtain the compound of interest (23A) in an amorphous state (12.68 g, yield 99%).

$^1$H-NMR (CDCl$_3$) δ: 7.39-7.29 (5H, m), 5.65 (1H, d, J=8.5 Hz), 5.35 (1H, d, J=3.0 Hz), 5.29 (1H, dd, J=11.5, 3.0 Hz), 5.10 (2H, s), 4.83 (1H, br), 4.68 (1H, d, J=7.9 Hz), 4.20-4.09 (2H, m), 3.99-3.85 (3H, m), 3.50-3.42 (1H, m), 3.22-3.15 (2H, m), 2.14 (3H, s), 2.05 (3H, s), 2.00 (3H, s), 1.95 (3H, s), 1.62-1.27 (12H, m).

Calcd for C$_{30}$H$_{44}$N$_2$O$_{11}$: [M+H]$^+$ 609, Found 609.

23B

Synthesis of [(2R,3R,4R,5R,6R)-5-acetamide-3,4-diacetoxy-6-(8-aminooctoxy)tetrahydropyran-2-yl]methyl acetate (Compound 23B)

[Formula 89]

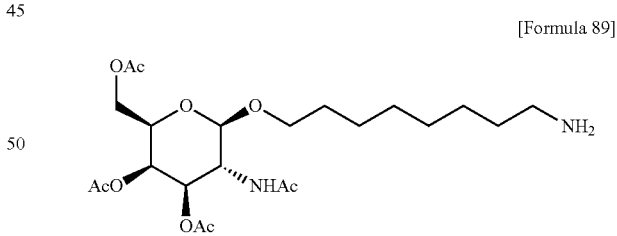

Compound 23A (12.68 g, 20.83 mmol) as synthesized in Step (23A) above was dissolved in ethanol (200 ml). 10% Palladium/carbon (wet) (2 g) was added to the solution, which was then stirred vigorously at room temperature under a hydrogen atmosphere. After completion of the reaction, the reaction mixture was filtered. The filtrate was distilled off under vacuum to thereby obtain a crude product of the compound of interest (23B) (10.1 g), which was used in the subsequent reaction without further purification.

Calcd for C$_{22}$H$_{38}$N$_2$O$_9$: [M+H]$^+$ 475, Found 475.

23C

Synthesis of [(2R,3R,4R,5R,6R)-5-acetamide-3,4-diacetoxy-6-[8-[[(4S)-2,2-dimethyl-1,3-dioxolan-4-yl]methoxycarbonylamino]octoxy]tetrahydropyran-2-yl]methyl acetate

Compound 23C

[Formula 90]

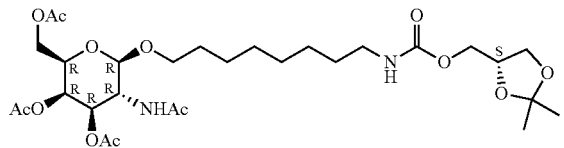

(R)-(−)-2,2-Dimethyl-1,3-dioxolane-4-methanol (1.6 g, 12 mmol) and triethylamine (3.1 ml, 22 mmol) were dissolved in dichloroethane (30 ml). 4-Nitrophenyl chloroformate (2.2 g, 12 mmol) was added to the solution, which was stirred at room temperature for 1.5 hrs. Subsequently, triethylamine (4.5 ml, 32 mmol) and Compound 23B as synthesized in Step (23B) (5.1 g, 11 mmol) were added. The reaction mixture was stirred at 45° C. for 4 hrs. After completion of the reaction, the solvent was distilled off under vacuum to thereby obtain a crude product. This product was purified by silica gel column chromatography (hexane:ethyl acetate=100:0-0:100, v/v) to thereby obtain the compound of interest (23C) in an amorphous state (2.45 g, yield 36%).

$^1$H-NMR (CDCl$_3$) δ: 5.64 (1H, d, J=7.9 Hz), 5.36 (1H, d, J=3.0 Hz), 5.29 (1H, dd, J=11.2, 3.0 Hz), 4.85 (1H, br), 4.69 (1H, d, J=7.9 Hz), 4.35-3.86 (9H, m), 3.76-3.70 (1H, m), 3.50-3.43 (1H, m), 3.20-3.12 (2H, m), 2.14 (3H, s), 2.05 (3H, s), 2.01 (3H, s), 1.96 (3H, s), 1.65-1.28 (12H, m), 1.44 (3H, s), 1.37 (3H, s).

Calcd for C29H48N2O13: [M+H]$^+$ 633, Found 633.

23D

Synthesis of [(2R,3R,4R,5R,6R)-5-acetamide-3,4-diacetoxy-6-[8-[[(2S)-2,3-dihydroxypropoxy]carbonylamino]octoxy]tetrahydropyran-2-yl]methyl acetate (Compound 23D)

[Formula 91]

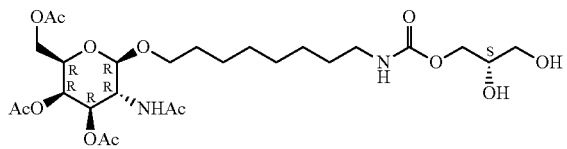

To Compound 23C synthesized in Step (23C) above (2.45 g, 3.87 mmol), pure water (2 ml) and trifluoroacetic acid (6 ml) were added. The resultant mixture was stirred at room temperature for 1.5 hrs. After completion of the reaction, the solvent was distilled off under vacuum. Further, azeotropic distillation with toluene was performed to remove moisture, thereby obtaining a crude product. This product was purified by silica gel column chromatography (hexane:ethyl acetate=100:0-0:100, v/v) to thereby obtain the compound of interest (23D) in an amorphous state (1.18 g, yield 51%).

$^1$H-NMR (CDCl$_3$) δ: 5.87 (1H, d, J=7.9 Hz), 5.35 (1H, d, J=3.0 Hz), 5.27 (1H, dd, J=11.2, 3.0 Hz), 5.07 (1H, br), 4.66 (1H, d, J=8.5 Hz), 4.27-3.86 (7H, m), 3.70-3.57 (2H, m), 3.50-3.43 (2H, m), 3.24-3.13 (2H, m), 2.15 (3H, s), 2.05 (3H, s), 2.01 (3H, s), 1.96 (3H, s), 1.67-1.24 (12H, m).

Calcd for C26H44N2O13: [M+H]$^+$ 593, Found 593.

23E

Synthesis of [(2R,3R,4R,5R,6R)-5-acetamide-3,4-diacetoxy-6-[8-[[(2S)-3-[bis(4-methoxyphenyl)-phenylmethoxy]-2-hydroxy-propoxy]carbonylamino]octoxy]tetrahydropyran-2-yl]methyl acetate (Compound 23E)

[Formula 92]

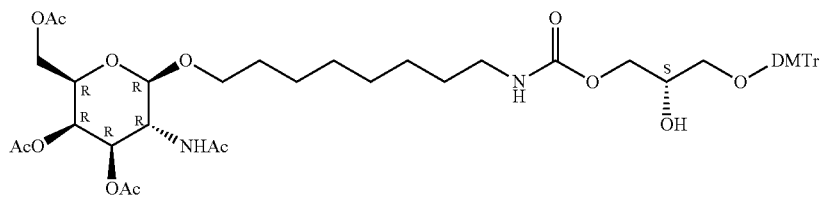

Compound 23D as synthesized in Step (23D) above (1.18 g, 1.99 mmol) was dissolved in pyridine (20 mL). 4,4'-Dimethoxytrityl chloride (0.81 g, 2.39 mmol) was added. The resultant mixture was stirred at room temperature. After completion of the reaction, the solvent was distilled off under vacuum. Azeotropic distillation was performed with an appropriate amount of toluene to obtain a crude product. This product was purified by silica gel column chromatography (hexane:ethyl acetate=100:0-0:100, v/v; subsequently, ethyl acetate:methanol=95:5, v/v) to thereby obtain the compound of interest (23E) in an amorphous state (0.6 g, yield 34%).

¹H-NMR (CDCl₃) δ: 7.44-7.40 (2H, m), 7.33-7.19 (7H, m), 6.85-6.81 (4H, m), 5.61 (1H, d, J=8.5 Hz), 5.35 (1H, d, J=3.0 Hz), 5.29 (1H, dd, J=11.2, 3.3 Hz), 4.79 (1H, br), 4.69 (1H, d, J=8.5 Hz), 4.24-4.09 (4H, m), 4.00-3.86 (4H, m), 3.79 (6H, s), 3.50-3.43 (1H, m), 3.21-3.12 (4H, m), 2.14 (3H, s), 2.04 (3H, s), 2.00 (3H, s), 1.95 (3H, s), 1.63-1.26 (12H, m).

Calcd for $C_{47}H_{62}N_2O_{15}$: $[M+Na]^+$ 917, Found 917.

23F

Synthesis of [(2R,3R,4R,5R,6R)-5-acetamide-3,4-diacetoxy-6-[8-[[(2S)-3-[bis(4-methoxyphenyl)-phenylmethoxy]-2-[2-cyanoethoxy-(diisopropylamino)phosphanyl]oxypropoxy]carbonylamino]octoxy]tetrahydropyran-2-yl]methyl acetate (Compound 23F)

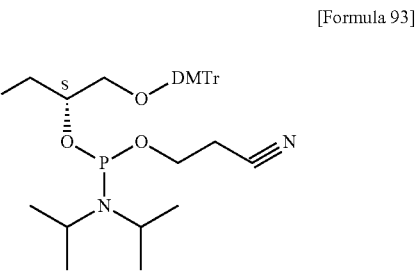

An appropriate amount of pyridine was added to Compound 23E as synthesized in Step (23E) above (0.60 g, 0.67 mmol), which was dissolved in dichloroethane (5 ml) after azeotropic distillation under vacuum. To this solution, N,N-diisopropylethylamine (0.70 ml, 4.0 mmol) and 2-cyanoethyl diisopropylchlorophosphoramidite (0.30 ml, 1.3 mmol) were added. The resultant mixture was stirred at room temperature for 1.5 hrs. After completion of the reaction, the solvent was distilled off under vacuum. Azeotropic distillation was performed with an appropriate amount of toluene to thereby obtain a crude product. This product was purified by silica gel column chromatography (hexane:ethyl acetate=100:0-0:100, v/v; containing 1% triethylamine) to thereby obtain the compound of interest (23F) in an amorphous state (0.51 g, yield 69%).

¹H-NMR (CDCl₃) δ: 7.46-7.40 (2H, m), 7.34-7.17 (7H, m), 6.84-6.78 (4H, m), 5.56-5.48 (1H, m), 5.37-5.34 (1H, m), 5.32-5.28 (1H, m), 4.87-4.80 (0.5H, m), 4.73-4.68 (1H, m), 4.43-4.37 (0.5H, m), 4.23-4.08 (4H, m), 3.97-3.43 (14H, m), 3.26-3.06 (4H, m), 2.66-2.61 (1H, m), 2.47-2.41 (1H, m), 2.14 (3H, s), 2.06-1.93 (9H, m), 1.64-1.23 (12H, m), 1.21-0.98 (12H, m).

Example 98

HO—X³—X³—X³-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$—H (SEQ ID NO: 40)

Synthesis was performed in the same manner as described in Example 91 except that the X portion was replaced by X³. For the X³ portion, Compound 23F as synthesized in Reference Example 23 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6957.27).

Reference Example 24

24A

Synthesis of 7-[(2S)-3-benzyloxy-2-hydroxypropoxy]heptan-1-ol (Compound 24A)

[Formula 94]

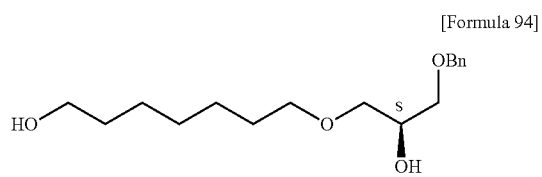

[Formula 93]

Benzyl (S)-(+)-glycidyl ether (5.0 g, 30 mmol) was dissolved in dichloromethane (150 mL). 1,7-Heptanediol (6.0 g, 45 mmol) and boron trifluoride-diethyl ether complex (0.76 ml, 6.1 mmol) were then added. The resultant mixture was stirred at room temperature for 2 days. The reaction solution was added to a mixed solution of ethyl acetate/saturated aqueous sodium bicarbonate solution and extracted with ethyl acetate. The organic layer was washed with saturated saline/saturated aqueous sodium bicarbonate solution, dried over anhydrous sodium sulfate and filtered. By distilling off the solvent under vacuum, a crude product was obtained. This product was purified by silica gel column chromatography (hexane:ethyl acetate=50:50, v/v) to thereby obtain a colorless, oily compound of interest (24A) (3.3 g, yield 37%).

¹H-NMR (CDCl₃) δ: 7.39-7.28 (5H, m), 4.57 (2H, s), 4.02-3.96 (1H, m), 3.67-3.61 (2H, m), 3.59-3.43 (6H, m), 2.48 (1H, d, J=4.2 Hz), 1.61-1.52 (4H, m), 1.37-1.30 (6H, m).

Calcd for $C_{17}H_{28}O_4$: $[M+Na]^+$ 319, Found 319.

24B

Synthesis of [(2R,3R,4R,5R,6R)-5-acetamide-3,4-diacetoxy-6-[7-[(2S)-3-benzyloxy-2-hydroxypropoxy]heptoxy]tetrahydropyran-2-yl]methyl acetate (Compound 24B-1)

[Formula 95]

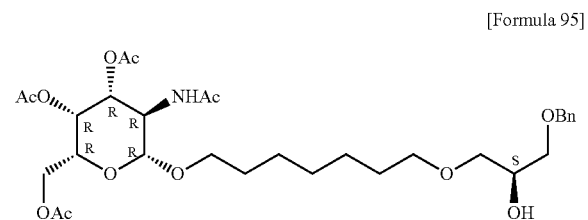

and synthesis of [(2R,3R,4R,5R,6R)-5-acetamide-6-[7-[(2S)-2-[(2R,3R,4R,5R,6R)-3-acetamide-4,5-diacetoxy-6-(acetoxymethyl)tetrahydropyran-2-yl]oxy-3-benzyloxy-propoxy]heptoxy]-3,4-diacetoxytetrahydropyran-2-yl]methyl acetate (Compound 24B-2)

[Formula 96]

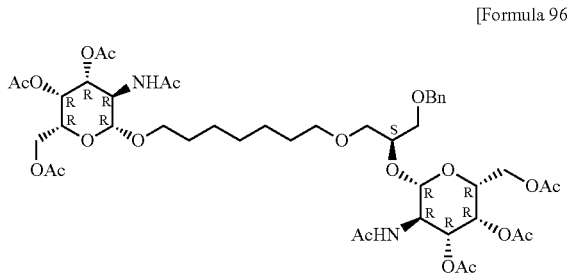

Compound 15A as synthesized in Step (24A) above (3.3 g, 11 mmol) and a known documented compound [(2R,3R,4R,5R)-5-acetamide-3,4,6-triacetoxy-tetrahydropyran-2-yl]methyl acetate (WO2011053614) (4.0 g, 10 mmol) were suspended in dichloromethane (200 ml). Trifluoromethane-sulfonic acid (0.15 ml, 1.7 mmol) was added to the suspension, which was then stirred at 45° C. for 3 days. After completion of the reaction, about one half of the solvent was distilled off under vacuum for concentration. The resultant reaction mixture was added to a mixed solution of ethyl acetate/saturated aqueous sodium bicarbonate solution and extracted with ethyl acetate. The organic layer was washed with saturated aqueous sodium bicarbonate solution and saturated saline/phosphate buffer (pH 7.0), dried over anhydrous sodium sulfate and filtered. By distilling off the solvent under vacuum, a crude product was obtained. This product was purified by silica gel column chromatography (hexane:ethyl acetate=100;0-0:100, v/v) to thereby obtain desired Compound 24B-1 (4.5 g, yield 70%) and Compound 24B-2 (1.9 g, yield 20%), both in an amorphous state.

Compound 24B-1

$^1$H-NMR (CDCl$_3$) δ: 7.39-7.28 (5H, m), 5.51 (1H, d, J=8.5 Hz), 5.37-5.29 (2H, m), 4.71 (1H, d, J=8.5 Hz), 4.56 (2H, s), 4.20-4.09 (2H, m), 4.03-3.85 (4H, m), 3.58-3.41 (7H, m), 2.58 (1H, d, J=4.2 Hz), 2.14 (3H, s), 2.05 (3H, s), 2.00 (3H, s), 1.95 (3H, s), 1.63-1.52 (4H, m), 1.36-1.29 (6H, m).

Calcd for C$_{31}$H$_{47}$NO$_{12}$: [M+H]$^+$ 626, Found 626.

Compound 24B-2

$^1$H-NMR (CDCl$_3$) δ: 7.41-7.28 (5H, m), 5.65 (1H, d, J=8.5 Hz), 5.48 (1H, d, J=8.5 Hz), 5.42-5.23 (4H, m), 4.84 (1H, d, J=8.5 Hz), 4.72 (1H, d, J=8.5 Hz), 4.59-4.49 (2H, m), 4.20-3.38 (17H, m), 2.19-1.92 (24H, m), 1.61-1.47 (4H, m), 1.38-1.26 (6H, m).

Calcd for C$_{45}$H$_{66}$N$_2$O$_{20}$: [M+H]$^+$ 955, Found 955.

24C

Synthesis of [(2R,3R,4R,5R,6R)-5-acetamide-3,4-diacetoxy-6-[7-[(2R)-2,3-dihydroxypropoxy]heptoxy]tetrahydropyran-2-yl]methyl acetate (Compound 24C)

[Formula 97]

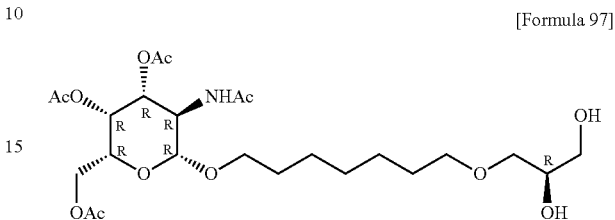

Compound 24B-1 as synthesized in Step (24B) above (4.5 g, 7.2 mmol) was dissolved in ethanol (100 ml). 10% Palladium/carbon (wet) (2.0 g) was added to the solution, which was then stirred vigorously at room temperature for 5 hrs under a hydrogen atmosphere. After completion of the reaction, the reaction mixture was filtered. The filtrate was distilled off under vacuum. Azeotropic distillation was performed, first with an appropriate amount of toluene and then with an appropriate amount of pyridine, to thereby obtain a crude product of Compound 24C, which was used in the subsequent reaction without further purification.

$^1$H-NMR (CDCl$_3$) δ: 5.55 (1H, d, J=9.1 Hz), 5.37-5.27 (2H, m), 4.69 (1H, d, J=8.5 Hz), 4.21-4.09 (2H, m), 3.99-3.42 (11H, m), 2.69 (1H, d, J=5.4 Hz), 2.15 (3H, s), 2.05 (3H, s), 2.01 (3H, s), 1.96 (3H, s), 1.65-1.52 (4H, m), 1.40-1.29 (6H, m).

Calcd for C$_{24}$H$_{41}$NO$_{12}$: [M+H]$^+$ 536, Found 536.

24D

Synthesis of [(2R,3R,4R,5R,6R)-5-acetamide-3,4-diacetoxy-6-[7-[(2S)-3-[bis(4-methoxyphenyl)-phenyl-methoxy]-2-hydroxy-propoxy]heptoxy]tetrahydropyran-2-yl]methyl acetate (Compound 24D)

[Formula 98]

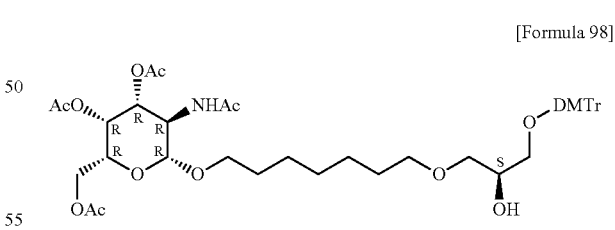

The crude product of Compound 24C as synthesized in Step (24C) above was dissolved in pyridine (30 ml). 4,4'-Dimethoxytrityl chloride (2.7 g, 7.9 mmol) was added to the solution. The resultant mixture was stirred at room temperature for 13 hrs. After completion of the reaction, the solvent was distilled off under vacuum. Azeotropic distillation with toluene was conducted to obtain a crude product. This product was purified by silica gel column chromatography (hexane:ethyl acetate=50:50-0:100, v/v, containing 1% triethylamine) to thereby obtain the compound of interest (24D) in an amorphous state (3.0 g; yield: 2 steps, 49%).

$^1$H-NMR (CDCl$_3$) δ: 7.45-7.41 (2H, m), 7.34-7.20 (7H, m), 6.85-6.80 (4H, m), 5.50 (1H, d, J=8.5 Hz), 5.37-5.29 (2H, m), 4.71 (1H, d, J=8.5 Hz), 4.20-4.09 (2H, m), 3.98-3.85 (4H, m), 3.79 (6H, s), 3.55-3.40 (5H, m), 3.22-3.13 (2H, m), 2.51 (1H, d, J=4.2 Hz), 2.14 (3H, s), 2.05 (3H, s), 2.00 (3H, s), 1.93 (3H, s), 1.60-1.52 (4H, m), 1.35-1.27 (6H, m).

Calcd for C$_{45}$H$_{59}$NO$_{14}$: [M+Na]$^+$ 860, Found 860.

24E

Synthesis of [(2R,3R,4R,5R,6R)-5-acetamide-3,4-diacetoxy-6-[7-[(2S)-3-[bis(4-methoxyphenyl)-phenyl-methoxy]-2-[2-cyanoethyl-(diisopropylamino)phosphanyl]oxypropoxy]heptoxy]tetrahydropyran-2-yl]methyl acetate Compound 24E

[Formula 99]

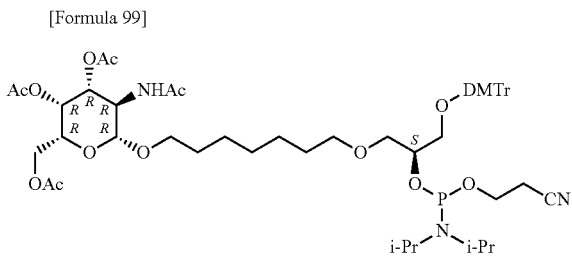

Compound 24D as synthesized in Step (24D) above (3.0 g, 3.6 mmol) was azeotropically distilled with an appropriate amount of pyridine and then dissolved in dichloromethane (50 ml). N,N-Diisopropylethylamine (2.5 ml, 14 mmol) and 2-cyanoethyl diisopropylchlorophosphoramidite (0.88 ml, 3.9 mmol) were added to the solution. The reaction mixture was stirred at room temperature for 1.5 hrs. After completion of the reaction, the solvent was distilled off under vacuum to obtain a crude product. This product was purified by silica gel column chromatography (hexane:ethyl acetate=50:50-0:100, v/v, containing 1% triethylamine) to thereby obtain the compound of interest (24E) in an amorphous state (3.0 g, yield 82%).

$^1$H-NMR (CDCl$_3$) δ: 7.48-7.41 (2H, m), 7.36-7.15 (7H, m), 6.85-6.77 (4H, m), 5.59-5.41 (1H, m), 5.38-5.26 (2H, m), 4.75-4.68 (1H, m), 4.20-4.07 (2H, m), 3.97-3.06 (21H, m), 2.67-2.40 (2H, m), 2.14 (3H, s), 2.04 (3H, s), 2.00 (3H, s), 1.92 (3H, s), 1.64-1.46 (4H, m), 1.37-1.22 (6H, m), 1.22-0.97 (12H, m).

Example 99

HO—X$^4$—X$^4$—X$^4$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91 except that the X portion was replaced by X$^4$. For the X$^4$ portion, Compound 24E as synthesized in Reference Example 24 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6785.22).

Reference Example 25

25A

Synthesis of 7-[(2R)-3-benzyloxy-2-hydroxy-propoxy]heptan-1-ol (Compound 25A)

[Formula 100]

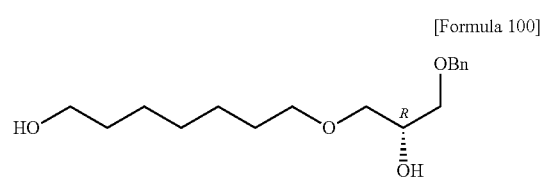

Benzyl (R)-(−)-glycidyl ether (5.0 g, 30 mmol) was dissolved in dichloromethane (150 ml). 1,7-Heptanediol (6.0 g, 45 mmol) and boron trifluoride-diethyl ether complex (0.76 ml, 6.1 mmol) were added to the solution. The resultant mixture was stirred at room temperature for 2 days. The reaction solution was added to a mixed solution of ethyl acetate/saturated aqueous sodium bicarbonate solution and extracted with ethyl acetate. The organic layer was washed with saturated saline/saturated aqueous sodium bicarbonate solution, dried over anhydrous sodium sulfate and filtered. By distilling off the solvent under vacuum, a crude product was obtained. This product was purified by silica gel column chromatography (hexane:ethyl acetate=50:50, v/v) to thereby obtain a colorless, oily compound of interest (25A) (4.0 g, yield 44%).

$^1$H-NMR (CDCl$_3$) δ: 7.39-7.27 (5H, m), 4.56 (2H, s), 4.04-3.94 (1H, m), 3.67-3.59 (2H, m), 3.58-3.40 (6H, m), 2.51 (1H, d, J=4.2 Hz), 1.63-1.49 (4H, m), 1.41-1.30 (6H, m).

Calcd for C$_{17}$H$_{28}$O$_4$: [M+Na]$^+$ 319, Found 319.

25B

Synthesis of [(2R,3R,4R,5R,6R)-5-acetamide-3,4-diacetoxy-6-[7-[(2R)-3-benzyloxy-2-hydroxy-propoxy]heptoxy]tetrahydropyran-2-yl]methyl acetate (Compound 25B-1)

[Formula 101]

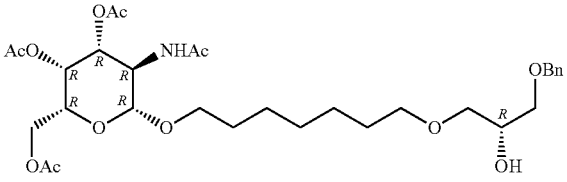

and Synthesis of [(2R,3R,4R,5R,6R)-5-acetamide-6-[7-[(2R)-2-[(2R,3R,4R,5R,6R)-3-acetamide-4,5-diacetoxy-6-(acetoxymethyl)tetrahydropyran-2-yl]oxy-3-benzyloxy-propoxy]heptoxy]-3,4-diacetoxytetrahydropyran-2-yl]methyl acetate (Compound 25B-2)

[Formula 102]

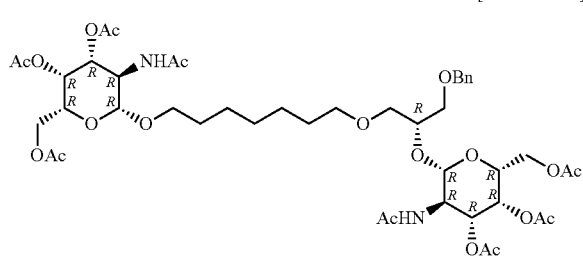

Compound 25A as synthesized in Step (25A) above (4.0 g, 14 mmol) and a known documented compound [(2R,3R,4R,5R)-5-acetamide-3,4,6-triacetoxy-tetrahydropyran-2-yl]methyl acetate (WO2011053614) (4.8 g, 12 mmol) were suspended in dichloromethane (200 ml). Trifluoromethanesulfonic acid (0.18 ml, 2.1 mmol) was added to the suspension, which was then stirred at 45° C. for 3 days. After completion of the reaction, about one half of the solvent was distilled off under vacuum for concentration. The resultant reaction mixture was added to a mixed solution of ethyl acetate/saturated aqueous sodium bicarbonate solution, and extracted with ethyl acetate. The organic layer was washed with saturated aqueous sodium bicarbonate solution and saturated saline/phosphate buffer (pH 7.0), dried over anhydrous sodium sulfate, and filtered. By distilling off the solvent under vacuum, a crude product was obtained. This product was purified by silica gel column chromatography (hexane:ethyl acetate=100;0-0:100, v/v) to thereby obtain desired Compound 25B-1 (4.8 g, yield 62%) and Compound 25B-2 (1.9 g, yield 16%), both in an amorphous state.

Compound 25B-1

$^1$H-NMR (CDCl$_3$) δ: 7.39-7.27 (5H, m), 5.50 (1H, d, J=9.1 Hz), 5.37-5.28 (2H, m), 4.70 (1H, d, J=8.5 Hz), 4.57 (2H, s), 4.20-4.08 (2H, m), 4.03-3.85 (4H, m), 3.58-3.42 (7H, m), 2.58 (1H, d, J=4.2 Hz), 2.14 (3H, s), 2.05 (3H, s), 2.00 (3H, s), 1.95 (3H, s), 1.64-1.50 (4H, m), 1.38-1.29 (6H, m).

Calcd for C31H47NO12: [M+H]$^+$ 626, Found 626.

Compound 25B-2

$^1$H-NMR (CDCl$_3$) δ: 7.39-7.28 (5H, m), 5.85-5.21 (6H, m), 4.90-4.73 (2H, m), 4.53 (2H, s), 4.22-3.38 (17H, m), 2.20-1.91 (24H, m), 1.63-1.51 (4H, m), 1.41-1.30 (6H, m).
Calcd for C45H66N2O20: [M+H]$^+$ 955, Found 955.

25C

Synthesis of [(2R,3R,4R,5R,6R)-5-acetamide-3,4-diacetoxy-6-[7-[(2S)-2,3-dihydroxypropoxy]heptoxy]tetrahydropyran-2-yl]methyl acetate (Compound 25C)

[Formula 103]

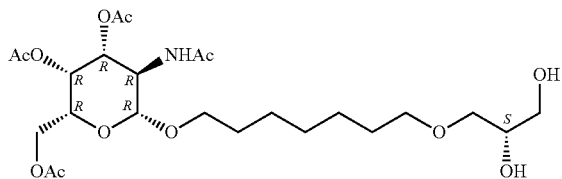

Compound 25B-1 as synthesized in Step (25B) above (4.8 g, 7.7 mmol) was dissolved in ethanol (100 ml). 10% Palladium/carbon (wet) (2.0 g) was added to the solution, which was then stirred vigorously at room temperature for 5 hrs under a hydrogen atmosphere. After completion of the reaction, the reaction mixture was filtered. The filtrate was distilled off under vacuum. Azeotropic distillation was performed, first with an appropriate amount of toluene and then with an appropriate amount of pyridine, to thereby obtain a crude product of desired Compound 25C, which was used in the subsequent reaction without further purification.

$^1$H-NMR (CDCl$_3$) δ: 5.62 (1H, d, J=8.5 Hz), 5.38-5.26 (2H, m), 4.69 (1H, d, J=8.5 Hz), 4.21-4.09 (2H, m), 4.00-3.43 (11H, m), 2.74 (1H, br s), 2.15 (3H, s), 2.05 (3H, s), 2.01 (3H, s), 1.96 (3H, s), 1.68-1.50 (4H, m), 1.41-1.29 (6H, m).

Calcd for C24H41NO12: [M+H]$^+$ 536, Found 536.

25D

Synthesis of [(2R,3R,4R,5R,6R)-5-acetamide-3,4-diacetoxy-6-[7-[(2R)-3-[bis(4-methoxyphenyl)-phenyl-methoxy]-2-hydroxy-propoxy]heptoxy]tetrahydropyran-2-yl]methyl acetate (Compound 25D)

[Formula 104]

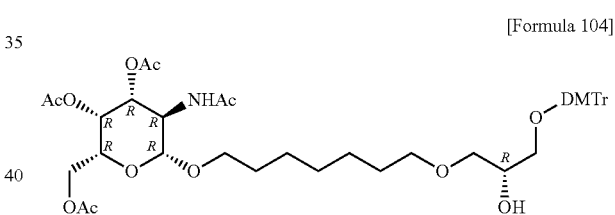

The crude product of Compound 25C as synthesized in Step (25C) above was dissolved in pyridine (30 ml). 4,4'-Dimethoxytrityl chloride (2.7 g, 8.0 mmol) was added to the solution. The resultant mixture was stirred at room temperature for 1.5 hrs. After completion of the reaction, the solvent was distilled off under vacuum. Azeotropic distillation with toluene was conducted to obtain a crude product. This product was purified by silica gel column chromatography (hexane:ethyl acetate=50:50-0:100, v/v, containing 1% triethylamine) to thereby obtain the compound of interest (25D) in an amorphous state (4.5 g; yield: 2 steps, 70%).

$^1$H-NMR (CDCl$_3$) δ: 7.46-7.40 (2H, m), 7.34-7.18 (7H, m), 6.86-6.79 (4H, m), 5.50 (1H, d, J=8.5 Hz), 5.37-5.28 (2H, m), 4.70 (1H, d, J=8.5 Hz), 4.20-4.08 (2H, m), 3.98-3.84 (4H, m), 3.79 (6H, s), 3.55-3.39 (5H, m), 3.21-3.14 (2H, m), 2.51 (1H, d, J=4.2 Hz), 2.14 (3H, s), 2.04 (3H, s), 2.00 (3H, s), 1.94 (3H, s), 1.65-1.47 (4H, m), 1.36-1.27 (6H, m).

Calcd for C45H59NO14: [M+Na]$^+$ 860, Found 860.

25E

Synthesis of [(2R,3R,4R,5R,6R)-5-acetamide-3,4-diacetoxy-6-[7-[(2R)-3-[bis(4-methoxyphenyl)-phenyl-methoxy]-2-[2-cyanoethyl-(diisopropylamino)phosphanyl]oxypropoxy]heptoxy]tetrahydropyran-2-yl]methyl acetate Compound 25E

[Formula 105]

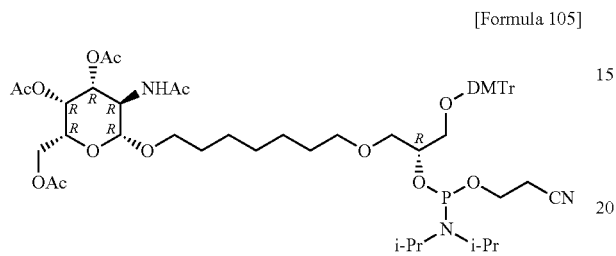

Compound 25D as synthesized in Step (25D) above (4.5 g, 5.4 mmol) was azeotropically distilled with an appropriate amount of pyridine and then dissolved in dichloromethane (50 ml). N,N-Diisopropylethylamine (3.7 ml, 21 mmol) and 2-cyanoethyl diisopropylchlorophosphoramidite (1.3 ml, 5.9 mmol) were added to the solution. The reaction mixture was stirred at room temperature for 1 hr. After completion of the reaction, the solvent was distilled off under vacuum. Azeotropic distillation with an appropriate amount of toluene was conducted to obtain a crude product. This product was purified by silica gel column chromatography (hexane:ethyl acetate=50:50-0:100, v/v, containing 1% triethylamine) to thereby obtain the compound of interest (25E) in an amorphous state (4.5 g, yield 81%).

$^1$H-NMR (CDCl$_3$) δ: 7.48-7.40 (2H, m), 7.36-7.16 (7H, m), 6.84-6.77 (4H, m), 5.58-5.42 (1H, m), 5.37-5.27 (2H, m), 4.74-4.68 (1H, m), 4.20-4.07 (2H, m), 3.97-3.06 (21H, m), 2.67-2.39 (2H, m), 2.14 (3H, s), 2.05 (3H, s), 2.00 (3H, s), 1.92 (3H, s), 1.63-1.45 (4H, m), 1.36-1.23 (6H, m), 1.21-0.98 (12H, m).

Example 100

HO—X$^5$—X$^5$—X$^5$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91 except that the X portion was replaced by X$^5$. For the X$^5$ portion, Compound 25E as synthesized in Reference Example 16 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6785.21).

Reference Example 26

26A

Synthesis of 13-[(2S)-3-benzyloxy-2-hydroxy-propoxy]tridecan-1-ol (Compound 26A)

[Formula 106]

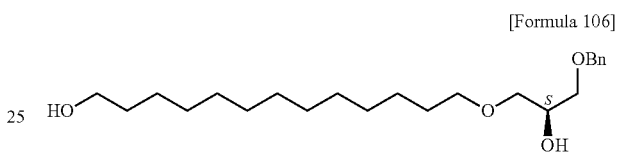

Benzyl (S)-(+)-glycidyl ether (5.0 g, 30 mmol) was dissolved in dichloromethane (150 ml). Tridecane-1,13-diol (7.6 g, 35 mmol) and boron trifluoride-diethyl ether complex (0.61 ml, 4.9 mmol) were added to the solution. The resultant mixture was stirred at room temperature for 2 days. The reaction mixture was added to a mixed solution of ethyl acetate/saturated aqueous sodium bicarbonate solution and extracted with ethyl acetate. The organic layer was washed with saturated saline/saturated aqueous sodium bicarbonate solution, dried over anhydrous sodium sulfate and filtered. By distilling off the solvent under vacuum, a crude product was obtained. This product was purified by silica gel column chromatography (hexane:ethyl acetate=50:50, v/v) to thereby obtain a colorless, oily compound of interest (26A) (3.8 g, yield 41%).

$^1$H-NMR (CDCl$_3$) δ: 7.38-7.27 (5H, m), 4.56 (2H, s), 4.02-3.94 (1H, m), 3.69-3.39 (8H, m), 2.49 (1H, d, J=4.2 Hz), 1.61-1.50 (4H, m), 1.39-1.21 (18H, m).

Calcd for C$_{23}$H$_{40}$O$_4$: [M+H]$^+$ 381, Found 381.

26B

Synthesis of [(2R,3R,4R,5R,6R)-5-acetamide-3,4-diacetoxy-6-[13-[(2S)-3-benzyloxy-2-hydroxy-propoxy]tridecoxy]tetrahydropyran-2-yl]methyl acetate (Compound 26B)

[Formula 107]

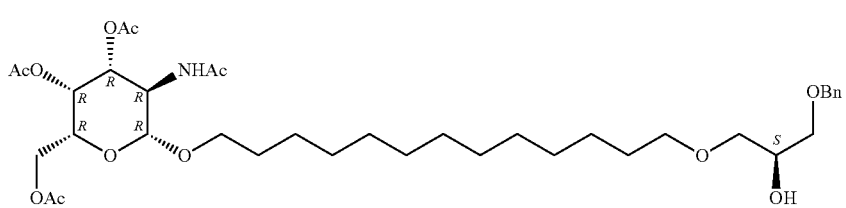

Compound 26A as synthesized in Step (26A) above (3.8 g, 9.9 mmol) and a known documented compound [(2R,3R,4R,5R)-5-acetamide-3,4,6-triacetoxy-tetrahydropyran-2-yl] methyl acetate (WO2011053614) (3.5 g, 9.0 mmol) were suspended in dichloromethane (60 ml). Trifluoromethanesulfonic acid (0.13 ml, 1.5 mmol) was added to the suspension, which was then stirred at 45° C. for 17 hrs. After completion of the reaction, about one half of the solvent was distilled off under vacuum for concentration. The resultant reaction mixture was added to a mixed solution of ethyl acetate/saturated aqueous sodium bicarbonate solution, and extracted with ethyl acetate. The organic layer was washed with saturated aqueous sodium bicarbonate solution and saturated saline/phosphate buffer (pH 7.0), dried over anhydrous sodium sulfate, and filtered. By distilling off the solvent under vacuum, a crude product was obtained. This product was purified by silica gel column chromatography (hexane:ethyl acetate=100:0-0:100, v/v) to thereby obtain desired Compound 26B in an amorphous state (3.7 g, yield 58%).

$^1$H-NMR (CDCl$_3$) δ: 7.38-7.27 (5H, m), 5.39-5.30 (3H, m), 4.72 (1H, d, J=8.5 Hz), 4.57 (2H, s), 4.20-4.09 (2H, m), 4.02-3.85 (4H, m), 3.58-3.40 (7H, m), 2.48 (1H, d, J=4.2 Hz), 2.14 (3H, s), 2.05 (3H, s), 2.01 (3H, s), 1.96 (3H, s), 1.63-1.51 (4H, m), 1.37-1.21 (18H, m).

Calcd for C$_{37}$H$_{59}$NO$_{12}$: [M+H]$^+$ 710, Found 710.

26C

Synthesis of [(2R,3R,4R,5R,6R)-5-acetamide-3,4-diacetoxy-6-[13-[(2R)-2,3-dihydroxypropoxy]tridecoxy]tetrahydropyran-2-yl]methyl acetate (Compound of 26C)

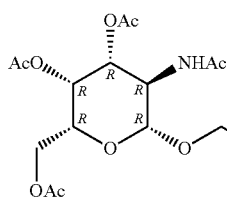

Compound 26B as synthesized in Step (26B) above (3.7 g, 5.2 mmol) was dissolved in ethanol (100 ml). 10% Palladium/carbon (wet) (2.0 g) was added to the solution, which was then stirred vigorously at room temperature for 5 hrs under a hydrogen atmosphere. After completion of the reaction, the reaction mixture was filtered. The filtrate was distilled off under vacuum to obtain a crude product. This product was purified by silica gel column chromatography (hexane:ethyl acetate=100:0-90:10, v/v) to thereby obtain a colorless, oily compound of interest (26C) (1.4 g, yield 43%).

$^1$H-NMR (CDCl$_3$) δ: 5.42-5.29 (3H, m), 4.57 (1H, d, J=8.5 Hz), 4.21-4.09 (2H, m), 3.95-3.44 (11H, m), 2.60 (1H, d, J=4.8 Hz), 2.14 (3H, s), 2.05 (3H, s), 2.01 (3H, s), 1.96 (3H, s), 1.64-1.51 (4H, m), 1.37-1.22 (18H, m).

Calcd for C$_{30}$H$_{53}$NO$_{12}$: [M+Na]$^+$ 642, Found 642.

26D

Synthesis of [(2R,3R,4R,5R,6R)-5-acetamide-3,4-diacetoxy-6-[13-[(2S)-3-[bis(4-methoxyphenyl)-phenylmethoxy]-2-hydroxy-propoxy]tridecoxy]tetrahydropyran-2-yl]methyl acetate (Compound 26D)

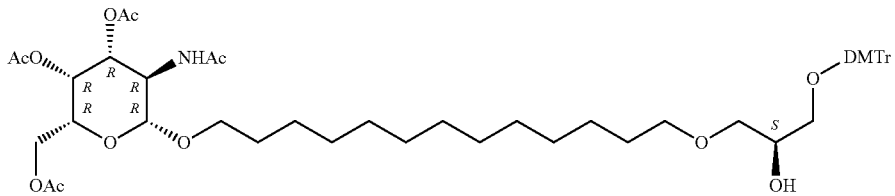

Compound 26C as synthesized in Step (26C) above (1.4 g, 2.3 mmol) was dissolved in pyridine (10 ml). 4,4'-Dimethoxytrityl chloride (0.84 g, 2.5 mmol) was added to the solution. The resultant mixture was stirred at room temperature for 15 hrs. After completion of the reaction, the solvent was distilled off under vacuum. Azeotropic distillation with toluene was conducted to obtain a crude product. This product was purified by silica gel column chromatography (hexane:ethyl acetate=50:50-20:80, v/v, containing 1% triethylamine) to thereby obtain the compound of interest (26D) in an amorphous state (1.9 g; yield 91%).

$^1$H-NMR (CDCl$_3$) δ: 7.45-7.41 (2H, m), 7.34-7.18 (7H, m), 6.85-6.80 (4H, m), 5.40-5.30 (3H, m), 4.72 (1H, d, J=8.5 Hz), 4.20-4.09 (2H, m), 3.97-3.84 (4H, m), 3.79 (6H, s), 3.56-3.40 (5H, m), 3.22-3.13 (2H, m), 2.43 (1H, d, J=4.8 Hz), 2.14 (3H, s), 2.05 (3H, s), 2.01 (3H, s), 1.95 (3H, s), 1.63-1.50 (4H, m), 1.35-1.21 (18H, m).

Calcd for C$_{51}$H$_{71}$NO$_{14}$: [M+Na]$^+$ 944, Found 944.

26E

Synthesis of [(2R,3R,4R,5R,6R)-5-acetamide-3,4-diacetoxy-6-[13-[(2S)-3-[bis(4-methoxyphenyl)-phenylmethoxy]-2-[2-cyanoethyl-(diisopropylamino)phosphanyl]oxypropoxy]tridecoxy]tetrahydropyran-2-yl]methyl acetate Compound 26E

[Formula 110]

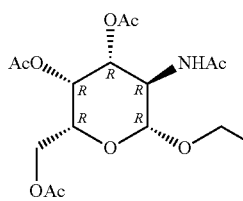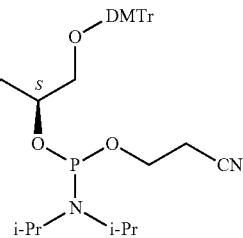

Compound 26D as synthesized in Step (26D) above (1.9 g, 2.1 mmol) was azeotropically distilled with an appropriate amount of pyridine and then dissolved in dichloromethane (50 ml). N,N-Diisopropylethylamine (1.4 ml, 8.0 mmol) and 2-cyanoethyl diisopropylchlorophosphoramidite (0.49 ml, 2.2 mmol) were added to the solution. The resultant mixture was stirred at room temperature for 1.5 hrs. After completion of the reaction, the solvent was distilled off under vacuum to obtain a crude product. This product was purified by silica gel column chromatography (hexane:ethyl acetate=100:0-50:50, v/v, containing 1% triethylamine) to thereby obtain the compound of interest (26E) in an amorphous state (1.7 g, yield 75%).

$^1$H-NMR (CDCl$_3$) δ: 7.48-7.41 (2H, m), 7.36-7.16 (7H, m), 6.84-6.78 (4H, m), 5.41-5.30 (3H, m), 4.72 (1H, d, J=8.5 Hz), 4.20-4.09 (2H, m), 3.95-3.07 (21H, m), 2.66-2.40 (2H, m), 2.14 (3H, s), 2.05 (3H, s), 2.00 (3H, s), 1.95 (3H, s), 1.63-1.45 (4H, m), 1.35-1.21 (18H, m), 1.21-0.99 (12H, m).

Example 101

HO—X$^6$—X$^6$—X$^6$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91 except that the X portion was replaced by X$^6$. For the X$^6$ portion, Compound 26E as synthesized in Reference Example 26 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7037.48).

Reference Example 27

27A

Synthesis of [(2R,3R,4R,5R,6R)-5-acetamide-6-[7-[(2R)-2-[(2R,3R,4R,5R,6R)-3-acetamide-4,5-diacetoxy-6-(acetoxymethyl)tetrahydropyran-2-yl]oxy-3-hydroxy-propoxy]heptoxy]-3,4-diacetoxytetrahydropyran-2-yl]methyl acetate (Compound 27A)

[Formula 111]

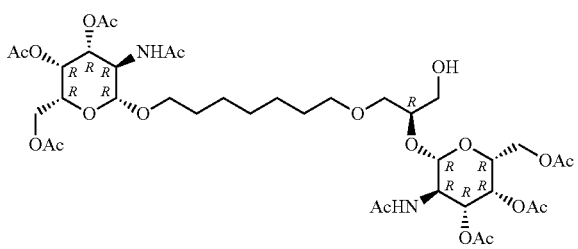

Compound 24B-2 as synthesized in Step (24B) above (1.9 g, 2.0 mmol) was dissolved in ethanol (60 ml). 10% Palladium/carbon (wet) (2.0 g) was added to the solution, which was then stirred vigorously at room temperature for 8 hrs under a hydrogen atmosphere. After completion of the reaction, the reaction mixture was filtered. The filtrate was distilled off under vacuum. Azeotropic distillation was performed, first with an appropriate amount of toluene and then with an appropriate amount of pyridine, to thereby obtain a crude product (1.3 g) of desired Compound 27A, which was used in the subsequent reaction without further purification.

$^1$H-NMR (CDCl$_3$) δ: 5.84 (1H, d, J=8.5 Hz), 5.69 (1H, d, J=8.5 Hz), 5.41-5.14 (4H, m), 4.85 (1H, d, J=8.5 Hz), 4.70 (1H, d, J=8.5 Hz), 4.22-3.40 (17H, m), 2.86-2.81 (1H, m), 2.20-1.93 (24H, m), 1.65-1.49 (4H, m), 1.39-1.23 (6H, m).

Calcd for C$_{38}$H$_{60}$N$_2$O$_{20}$: [M+H]$^+$ 865, Found 865.

27B

Synthesis of [(2R,3R,4R,5R,6R)-5-acetamide-6-[7-[(2S)-2-[(2R,3R,4R,5R,6R)-3-acetamide-4,5-diacetoxy-6-(acetoxymethyl)tetrahydropyran-2-yl]oxy-3-[2-cyanoethoxy-(diisopropylamino)phosphanyl]oxypropoxy]heptoxy]-3,4-diacetoxytetrahydropyran-2-yl]methyl acetate (Compound 27B)

[Formula 112]

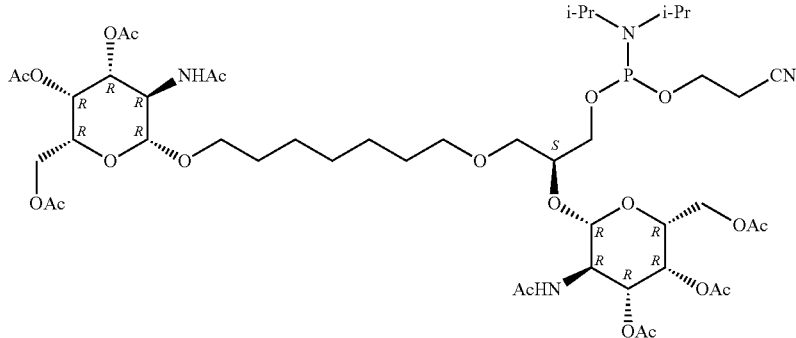

The crude product of Compound 27A as synthesized in Step (27A) (1.3 g) was dissolved in dichloromethane (50 ml). Diisopropylethylamine (1.0 ml, 5.8 mmol) and 2-cyanoethyl diisopropylchlorophosphoramidite (0.36 ml, 1.6 mmol) were added to the solution, which was then stirred at room temperature for 1 hr. Further, 2-cyanoethyl diisopropylchlorophosphoramidite (0.36 ml, 1.6 mmol) was added, followed by stirring at room temperature for 1 hr. After completion of the reaction, the solvent was distilled off under vacuum. Azeotropic distillation with an appropriate amount of toluene was conducted to obtain a crude product. This product was purified by silica gel column chromatography (ethyl acetate:acetonitrile=100:0-90:10, v/v) to thereby obtain the compound of interest (27B) in an amorphous state (0.56 g; yield: 2 steps 26%).

$^1$H-NMR (CDCl$_3$) δ: 6.04-5.69 (2H, m), 5.39-5.06 (4H, m), 4.86-4.69 (2H, m), 4.25-3.40 (21H, m), 2.80-2.67 (2H, m), 2.21-1.92 (24H, m), 1.66-1.48 (4H, m), 1.38-1.15 (18H, m).

Example 102

HO—X$^7$—X$^4$-A$^{mls}$-A$^{e2s}$-U$^{mls}$—C$^{mls}$-C$^{e2s}$-G$^{mls}$-A$^{mls}$-T$^{e2s}$-G$^{mls}$-G$^{mls}$-C$^{e2s}$-G$^{mls}$-A$^{mls}$-A$^{e2s}$-G$^{mlt}$-H (SEQ ID NO: 40)

Synthesis was performed in the same manner as described in Example 91, except that the X portion was replaced by X$^4$ and X$^7$. For the X$^4$ portion, Compound 24E as synthesized in Reference Example 15 was used and condensed once. For the X$^7$ portion, Compound 27B as synthesized in Reference Example 27 was used and condensed once.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6517.17).

Reference Example 28

28A

Synthesis of [(2R,3R,4R,5R,6R)-5-acetamide-6-[7-[(2S)-2-[(2R,3R,4R,5R,6R)-3-acetamide-4,5-diacetoxy-6-(acetoxymethyl)tetrahydropyran-2-yl]oxy-3-hydroxy-propoxy]heptoxy]-3,4-diacetoxytetrahydropyran-2-yl]methyl acetate (Compound 28A)

[Formula 113]

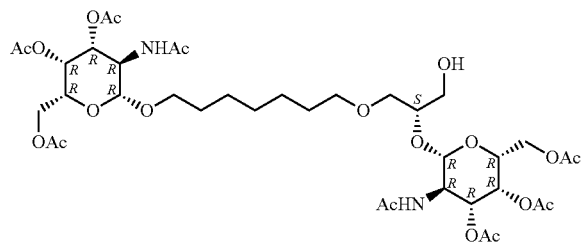

Compound 25B-2 as synthesized in Step (25B) above (1.9 g, 2.0 mmol) was dissolved in ethanol (60 ml). 10% Palladium/carbon (wet) (2.0 g) was added to the solution, which was then stirred vigorously at room temperature for 5 hrs under a hydrogen atmosphere. After completion of the reaction, the reaction mixture was filtered. The filtrate was distilled off under vacuum. Azeotropic distillation was performed, first with an appropriate amount of toluene and then with an appropriate amount of pyridine, to thereby obtain a crude product (1.8 g) of desired Compound 28A, which was used in the subsequent reaction without further purification.

$^1$H-NMR (CDCl$_3$) δ: 5.93 (1H, d, J=8.5 Hz), 5.71 (1H, d, J=8.5 Hz), 5.42-5.22 (4H, m), 4.82-4.73 (2H, m), 4.23-3.35 (17H, m), 2.98-2.92 (1H, m), 2.21-1.92 (24H, m), 1.66-1.48 (4H, m), 1.42-1.23 (6H, m).

Calcd for C$_{38}$H$_{60}$N$_2$O$_{20}$: [M+H]$^+$ 865, Found 865.

28B

Synthesis of [(2R,3R,4R,5R,6R)-5-acetamide-6-[7-[(2R)-2-[(2R,3R,4R,5R,6R)-3-acetamide-4,5-diacetoxy-6-(acetoxymethyl)tetrahydropyran-2-yl]oxy-3-[2-cyanoethoxy-(diisopropylamino)phosphanyl]oxypropoxy]heptoxy]-3,4-diacetoxtetrahydropyran-2-yl]methyl acetate (Compound 28B)

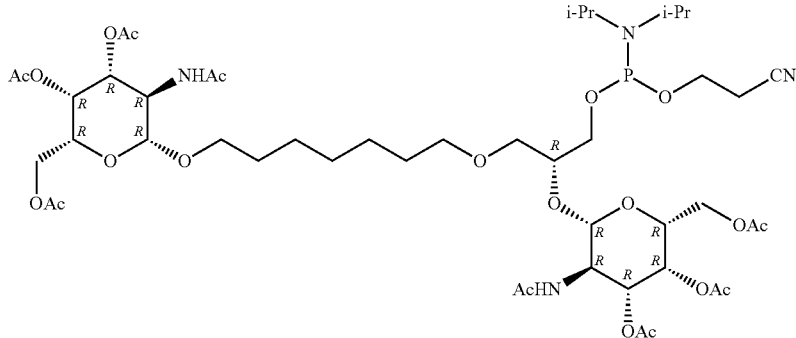

[Formula 114]

The crude product of Compound 28A as synthesized in Step (28A) (1.8 g) was dissolved in dichloromethane (50 ml). Diisopropylethylamine (1.5 ml, 8.4 mmol) and 2-cyanoethyl diisopropylchlorophosphoramidite (0.51 ml, 2.3 mmol) were added to the solution, which was then stirred at room temperature for 5.5 hrs. Further, 2-cyanoethyl diisopropylchlorophosphoramidite (0.51 ml, 2.3 mmol) was added, followed by stirring at room temperature for 1 hr. After completion of the reaction, the solvent was distilled off under vacuum. Azeotropic distillation with an appropriate amount of toluene was conducted to obtain a crude product. This product was purified by silica gel column chromatography (ethyl acetate:acetonitrile=100:0-90:10, v/v) to thereby obtain the compound of interest (28B) in an amorphous state (1.5 g; yield: 2 steps 71%).

$^1$H-NMR (CDCl$_3$) δ: 5.91-5.67 (2H, m), 5.41-5.18 (4H, m), 4.91-4.72 (2H, m), 4.26-3.35 (21H, m), 2.79-2.63 (2H, m), 2.20-1.92 (24H, m), 1.67-1.50 (4H, m), 1.40-1.13 (18H, m).

Example 103

HO—X$^8$—X$^5$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^5$ and X$^8$. For the X$^5$ portion, Compound 25E as synthesized in Reference Example 25 was used and condensed once. For the X$^8$ portion, Compound 28B as synthesized in Reference Example 28 was used and condensed once.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6517.10).

Reference Example 29

29A

Synthesis of (2R)-1-benzyloxy-3-[2-[2-(2-hydroxyethoxy)ethoxy]ethoxy]propan-2-ol Compound 29A

[Formula 115]

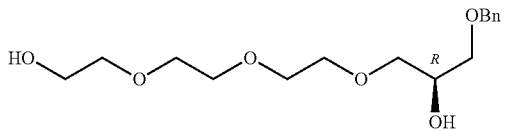

Triethylene glycol (6.9 g, 46 mmol) and benzyl (S)-(+)-glycidyl ether (5.0 g, 30 mmol) were dissolved in dichloromethane (75 ml). Boron trifluoride-diethyl ether complex (0.77 ml, 6.1 mmol) were added to the solution. The resultant mixture was stirred at room temperature for 16 hrs. After completion of the reaction, saturated aqueous sodium bicarbonate solution was added to the reaction mixture, which was then extracted with dichloromethane. The organic layer was washed with saturated saline/saturated aqueous sodium bicarbonate solution, dried over anhydrous sodium sulfate and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in dichloromethane. The organic layer was washed with saturated saline, and saturated saline/saturated aqueous sodium bicarbonate solution, dried over anhydrous sodium sulfate and filtered. The solvent was distilled off under vacuum to thereby obtain an oily compound of interest (29A) (5.6 g, yield 58%).

$^1$H-NMR (CDCl$_3$) δ: 7.37-7.25 (5H, m), 4.55 (2H, s), 4.05-3.97 (1H, m), 3.65-3.56 (16H, m).

Calcd for C$_{16}$H$_{26}$O$_6$: [M+H]$^+$ 315, Found 315.

29B

Synthesis of [(2R,3R,4R,5R,6R)-5-acetamide-3,4-diacetoxy-6-[2-[2-[2-[(2R)-3-benzyloxy-2-hydroxy-propoxy]ethoxy]ethoxy]ethoxy]tetrahydropyran-2-yl]methyl acetate (Compound 29B)

[Formula 116]

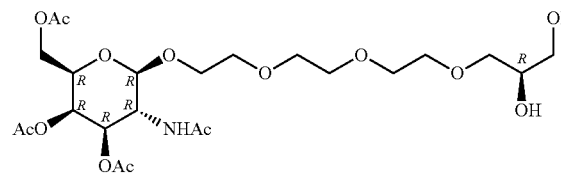

Compound 29A as synthesized in Step (29A) above (5.6 g, 18 mmol) and a known documented compound [(2R,3R,4R,5R)-5-acetamide-3,4,6-triacetoxy-tetrahydropyran-2-yl]methyl acetate (WO2011053614) (6.3 g, 16 mmol) were suspended in dichloromethane (100 ml). Trifluoromethanesulfonic acid (0.24 ml, 2.8 mmol) was added to the suspension, which was then stirred at 45° C. for 16 hrs. After completion of the reaction, saturated aqueous sodium bicarbonate solution was added to the reaction mixture, followed by extraction with dichloromethane. The organic layer was washed with saturated saline/saturated aqueous sodium bicarbonate solution, dried over anhydrous sodium sulfate and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in ethyl acetate. The organic layer was washed with saturated saline, and saturated saline/saturated aqueous sodium bicarbonate solution, dried over anhydrous sodium sulfate and filtered. The solvent was distilled off under vacuum to thereby obtain the compound of interest (29B) in an amorphous state (4.9 g, yield 47%).

$^1$H-NMR (CDCl$_3$) δ: 7.38-7.27 (5H, m), 6.69 (1H, d, J=9.1 Hz), 5.28 (1H, d, J=3.0 Hz), 5.02 (1H, dd, J=11.2, 3.0 Hz), 4.77 (1H, d, J=8.5 Hz), 4.56 (2H, s), 4.29-3.47 (21H, m), 2.15 (3H, s), 2.04 (3H, s), 1.97 (3H, s), 1.96 (3H, s).

Calcd for C$_{30}$H$_{45}$NO$_{14}$: [M+H]$^+$ 644, Found 644.

29C

Synthesis of [(2R,3R,4R,5R,6R)-5-acetamide-3,4-diacetoxy-6-[2-[2-[2-[(2R)-2,3-dihydroxypropoxy]ethoxy]ethoxy]ethoxy]tetrahydropyran-2-yl]methyl acetate (Compound 29C)

[Formula 117]

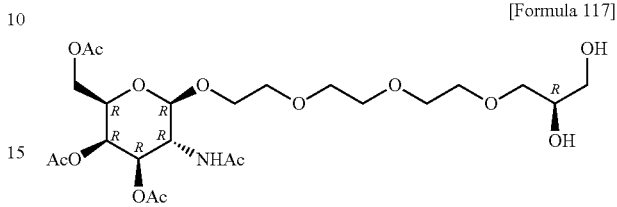

Compound 29B as synthesized in Step (29B) above (4.9 g, 7.6 mmol) was dissolved in ethanol (100 ml). 10% Palladium/carbon (wet) (4.0 g) was added to the solution, which was then stirred vigorously at room temperature for 8 hrs under a hydrogen atmosphere. After completion of the reaction, the reaction mixture was filtered. The filtrate was distilled off under vacuum. Azeotropic distillation with an appropriate amount of toluene was performed to thereby obtain an oily compound of interest (29C) (4.0 g, yield 95%).

$^1$H-NMR (CDCl$_3$) δ: 6.83-6.76 (1H, m), 5.32 (1H, d, J=3.0 Hz), 5.11 (1H, dd, J=11.2, 3.0 Hz), 4.79 (1H, d, J=9.1 Hz), 4.27-4.08 (3H, m), 3.97-3.53 (18H, m), 2.16 (3H, s), 2.06 (3H, s), 2.00 (3H, s), 1.97 (3H, s).

Calcd for C$_{23}$H$_{39}$NO$_{14}$: [M+H]$^+$ 554, Found 554.

29D

Synthesis of [(2R,3R,4R,5R,6R)-5-acetamide-3,4-diacetoxy-6-[2-[2-[2-[(2S)-3-[bis (4-methoxyphenyl)-phenylmethoxy]-2-hydroxy-propoxy]ethoxy]ethoxy]ethoxy]tetrahydropyran-2-yl]methyl acetate (Compound 29D)

[Formula 118]

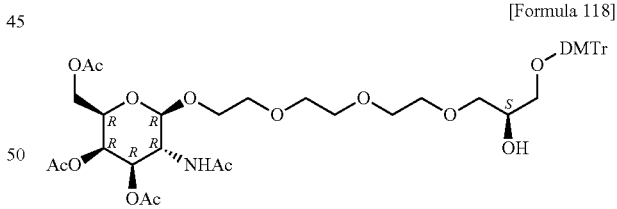

Compound 29C (4.0 g, 7.2 mmol) as synthesized in Step (29C) above was azeotropically distilled with an appropriate amount of pyridine under vacuum. The resultant compound was dissolved in pyridine (30 ml), to which 4,4'-dimethoxytrityl chloride (2.7 g, 8.0 mmol) was added. The mixture was stirred at room temperature for 3 hrs. After completion of the reaction, the solvent was distilled off under vacuum. Azeotropic distillation with an appropriate amount of toluene was conducted to obtain a crude product. This product was purified by silica gel column chromatography (ethyl acetate:ethyl acetate/methanol (5/1)=100:0-50:50, v/v, containing 1% triethylamine) to thereby obtain the compound of interest (29D) in an amorphous state (3.5 g, yield 57%).

$^1$H-NMR (CDCl$_3$) δ: 7.44-7.40 (2H, m), 7.33-7.18 (7H, m), 6.85-6.80 (4H, m), 6.59 (1H, d, J=9.7 Hz), 5.29 (1H, d, J=3.0 Hz), 5.00 (1H, dd, J=11.2, 3.0 Hz), 4.77 (1H, d, J=8.5 Hz), 4.27-4.07 (3H, m), 4.00-3.82 (4H, m), 3.79 (6H, s), 3.71-3.49 (12H, m), 3.20-3.10 (2H, m), 2.14 (3H, s), 2.01 (3H, s), 1.93 (6H, s).

Calcd for C$_{44}$H$_{57}$NO$_{16}$: [M+Na]$^+$ 878, Found 878.

29E

Synthesis of [(2R,3R,4R,5R,6R)-5-acetamide-3,4-diacetoxy-6-[2-[2-[2-[(2S)-3-[bis(4-methoxyphenyl)-phenylmethoxy]-2-[2-cyanoethoxy-(diisopropylamino)phosphanyl]oxypropoxy]ethoxy]ethoxy]ethoxy]tetrahydropyran-2-yl]methyl acetate (Compound 29E)

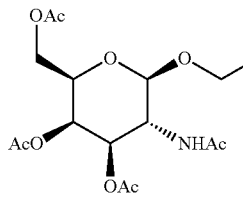

Compound 29D (3.5 g, 4.1 mmol) as synthesized in Step (29D) was azeotropically distilled with an appropriate amount of pyridine and then dissolved in dichloromethane (40 ml) N,N-Diisopropylethylamine (2.8 ml, 16 mmol) and 2-cyanoethyl diisopropylchlorophosphoramidite (1.1 ml, 4.9 mmol) were added to the solution, which was then stirred at room temperature for 3 hrs. After completion of the reaction, the solvent was distilled off under vacuum. Azeotropic distillation with an appropriate amount of toluene was performed to obtain a crude product. This product was purified by silica gel column chromatography (hexane:ethyl acetate=50:50-0:100, v/v, containing 1% triethylamine) to thereby obtain the compound of interest (29E) in an amorphous state (2.2 g, yield 51%).

$^1$H-NMR (CDCl$_3$) δ: 7.47-7.40 (2H, m), 7.35-7.16 (7H, m), 6.85-6.77 (4H, m), 6.40 (1H, d, J=9.1 Hz), 5.33-5.28 (1H, m), 5.03-4.93 (1H, m), 4.81-4.74 (1H, m), 4.28-4.08 (3H, m), 3.96-3.46 (26H, m), 3.27-3.04 (2H, m), 2.69-2.41 (2H, m), 2.15 (3H, s), 2.04 (3H, s), 1.97-1.90 (6H, m), 1.30-0.98 (12H, m).

Example 104

HO—X$^9$—X$^9$—X$^9$—A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^9$. For the X$^9$ portion, Compound 29E as synthesized in Reference Example 29 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6839.16).

Reference Example 30

30A

Synthesis of (2R)-1-benzyloxy-3-[2-[2-[2-(2-hydroxyethoxy)ethoxy]ethoxy]ethoxy]propan-2-ol (Compound 30A)

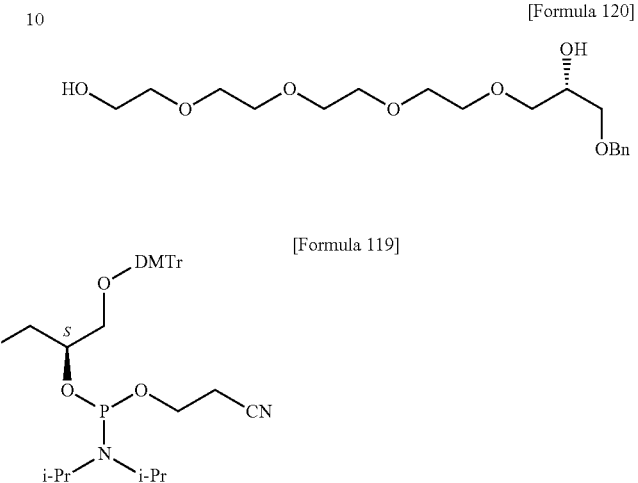

Tetraethylene glycol (8.87 g, 45.7 mmol) and benzyl (S)-(+)-glycidyl ether (4.66 ml, 30 mmol) were dissolved in dichloromethane (75 ml), and boron trifluoride-diethyl ether complex (0.76 ml, 6.1 mmol) was added to the solution. The resultant mixture was stirred at room temperature overnight. After completion of the reaction, saturated aqueous sodium bicarbonate solution was added. The organic layer was washed with saturated aqueous sodium bicarbonate solution and saturated saline, dried over anhydrous sodium sulfate and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in dichloromethane. The organic layer was washed with saturated aqueous sodium bicarbonate solution and saturated saline, dried over anhydrous sodium sulfate, and filtered. The solvent was distilled off under vacuum to thereby obtain an oily compound of interest (30A) (5.3 g, yield 49%).

$^1$H-NMR (CDCl$_3$) δ: 7.37-7.23 (5H, m), 4.56 (2H, s), 4.01 (1H, br), 3.75-3.41 (20H, m).

Calcd for C$_{18}$H$_{30}$O$_7$: [M+H]$^+$ 359, Found 359.

30B

Synthesis of [(2R,3R,4R,5R,6R)-5-acetamide-3,4-diacetoxy-6-[2-[2-[2-[2-[(2R)-3-benzyloxy-2-hydroxy-propoxy]ethoxy]ethoxy]ethoxy]tetrahydropyran-2-yl]methyl acetate Compound 30B

[Formula 121]

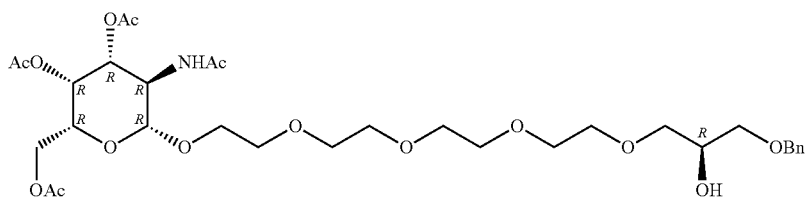

Compound 30A synthesized in Step (30A) above (5.3 g, 15 mmol) and a known documented compound [(2R,3R,4R,5R)-5-acetamide-3,4,6-triacetoxy-tetrahydropyran-2-yl]methyl (WO2011053614) (5.2 g, 13 mmol) were suspended in dichloromethane (100 ml). Trifluoromethanesulfonic acid (0.2 ml, 2.3 mmol) was added to the suspension, which was then stirred at 45° C. for 22 hrs. After completion of the reaction, the solvent was distilled off under vacuum for concentration. Then, ethyl acetate was added to the resultant reaction mixture. The organic layer was washed with saturated aqueous sodium bicarbonate solution and saturated saline, dried over anhydrous sodium sulfate, and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in dichloromethane. The organic layer was washed with saturated aqueous sodium bicarbonate solution and saturated saline, dried over anhydrous sodium sulfate, and filtered. The solvent was distilled off under vacuum to thereby obtain the compound of interest (30B) in an amorphous state (4.5 g, yield 49%).

$^1$H-NMR (CDCl$_3$) δ: 7.38-7.24 (5H, m), 6.72 (1H, d, J=8.5 Hz), 5.29 (1H, d, J=3.0 Hz), 5.00 (1H, dd, J=11.2, 3.3 Hz), 4.76 (1H, d, J=8.5 Hz), 4.56 (2H, s), 4.31-4.21 (1H, m), 4.18-3.46 (24H, m), 2.15 (3H, s), 2.04 (3H, s), 1.97 (6H, s).

Calcd for $C_{32}H_{49}NO_{15}$: [M+H]$^+$ 688, Found 688.

30C

Synthesis of [(2R,3R,4R,5R,6R)-5-acetamide-3,4-diacetoxy-6-[2-[2-[2-[2-[(2R)-2,3-dihydroxy-propoxy]ethoxy]ethoxy]ethoxy]ethoxy]tetrahydropyran-2-yl]methyl acetate Compound 30C

[Formula 122]

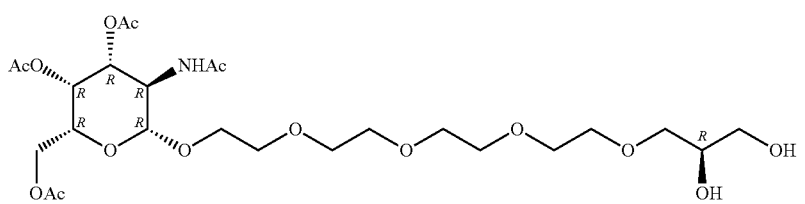

Compound 30B as synthesized in Step (30B) above (4.5 g, 6.5 mmol) was dissolved in ethanol (80 ml). 10% Palladium/carbon (wet) (4 g) was added to the solution, which was then stirred vigorously at room temperature for 8 hrs under a hydrogen atmosphere. After completion of the reaction, the reaction mixture was filtered. The filtrate was distilled off under vacuum to thereby obtain a crude product of the compound of interest (30C) (3.9 g, yield quant.). This product was used in the subsequent reaction without further purification.

$^1$H-NMR (CDCl$_3$) δ: 6.85 (1H, d, J=9.7 Hz), 5.32 (1H, d, J=3.0 Hz), 5.10 (1H, dd, J=11.2, 3.0 Hz), 4.74 (1H, d, J=8.5 Hz), 4.32-4.09 (2H, m), 3.99-3.56 (23H, m), 2.16 (3H, s), 2.05 (3H, s), 2.00 (3H, s), 1.99 (3H, s).

Calcd for $C_{25}H_{43}NO_{15}$: $[M+H]^+$ 598, Found 598.

30D

Synthesis of [(2R,3R,4R,5R,6R)-5-acetamide-3,4-diacetoxy-6-[2-[2-[2-[2-[(2S)-3-[bis(4-methoxyphenyl)-phenyl-methoxy]-2-hydroxy-propoxy]ethoxy]ethoxy]ethoxy]ethoxy]tetrahydropyran-2-yl]methyl acetate (Compound 30D)

[Formula 123]

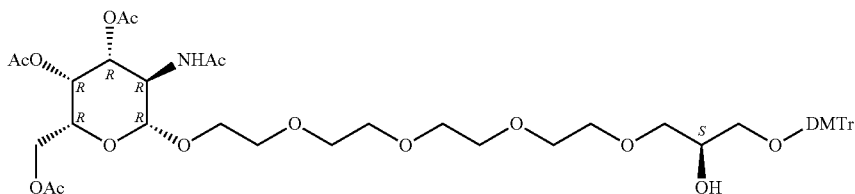

Compound 30C as synthesized in Step (30C) (3.9 g, 6.5 mmol) was azeotropically distilled with an appropriate amount of pyridine under vacuum, and dissolved in pyridine (22 ml). 4,4'-Dimethoxytrityl chloride (2.4 g, 7.2 mmol) was added to the solution, which was then stirred at room temperature for 2 hrs. After completion of the reaction, the solvent was distilled off under vacuum. Azeotropic distillation with an appropriate amount of toluene was performed to obtain a crude product. This product was purified by silica gel column chromatography (ethyl acetate:ethyl acetate/methanol (5/1)=100:0-50:50, v/v, containing 1% triethylamine) to thereby obtain the compound of interest (30D) in an amorphous state (3.12 g, yield 53%).

$^1$H-NMR (CDCl$_3$) δ: 7.44-7.40 (2H, m), 7.33-7.18 (7H, m), 6.85-6.79 (4H, m), 6.63 (1H, d, J=9.1 Hz), 5.29 (1H, d, J=3.0 Hz), 4.96 (1H, dd, J=11.2, 3.3 Hz), 4.75 (1H, d, J=8.5 Hz), 4.29-4.21 (1H, m), 4.17-4.07 (2H, m), 4.00-3.81 (4H, m), 3.79 (6H, s), 3.71-3.58 (14H, m), 3.53-3.43 (2H, m), 3.21-3.10 (2H, m), 2.14 (3H, s), 2.02 (3H, s), 1.95 (6H, s).

Calcd for $C_{46}H_{61}NO_{17}$: $[M+Na]^+$ 922, Found 922.

30E

Synthesis of [(2R,3R,4R,5R,6R)-5-acetamide-3,4-diacetoxy-6-[2-[2-[2-[2-[(2S)-3-[bis(4-methoxyphenyl)-phenyl-methoxy]-2-[2-cyanoethoxy-(diisopropylamino)phosphanyl]oxy-propoxy]ethoxy]ethoxy]ethoxy]ethoxy]tetrahydropyran-2-yl]methyl acetate (Compound 30E)

[Formula 124]

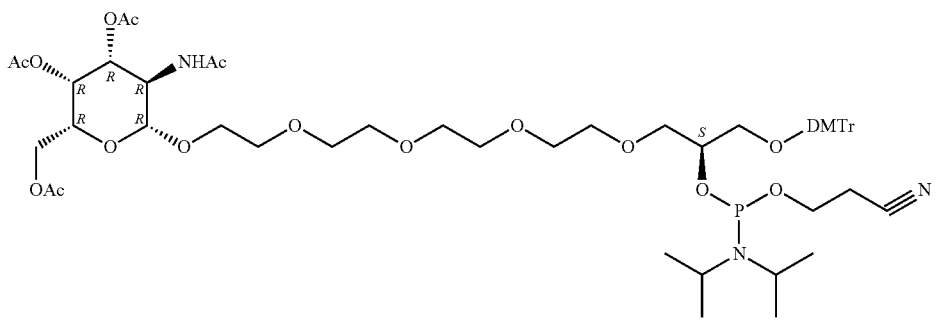

Compound 30D (3.12 g, 3.47 mmol) as synthesized in Step (30D) was azeotropically distilled with an appropriate amount of pyridine under vacuum and then dissolved in dichloromethane (35 ml). N,N-Diisopropylethylamine (2.42 ml, 13.9 mmol) and 2-cyanoethyl diisopropylchlorophosphoramidite (0.93 ml, 4.16 mmol) were added to the solution, which was then stirred at room temperature for 1 hr. After completion of the reaction, the solvent was distilled off under vacuum. Azeotropic distillation with an appropriate amount of toluene was performed under vacuum to obtain a crude product. This product was purified by silica gel column chromatography (hexane:ethyl acetate=100:0-0:100, v/v, containing 1% triethylamine) to thereby obtain the compound of interest (30E) in an amorphous state (2.98 g, yield 78%).

$^1$H-NMR (CDCl$_3$) δ: 7.46-7.40 (2H, m), 7.35-7.17 (7H, m), 6.84-6.78 (4H, m), 6.43 (1H, d, J=9.1 Hz), 5.31 (1H, br), 5.00-4.93 (1H, m), 4.78 (1H, d, J=8.5 Hz), 4.29-4.08 (3H, m), 3.91-3.48 (30H, m), 3.27-3.04 (2H, m), 2.67-2.62 (1H, m), 2.46-2.41 (1H, m), 2.15 (3H, s), 2.04 (3H, s), 1.97-1.94 (6H, m), 1.30-0.99 (12H, m).

Example 105

HO—X$^{10}$—X$^{10}$—X$^{10}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^{10}$. For the X$^{10}$ portion, Compound 30E as synthesized in Reference Example 30 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6971.21).

Reference Example 31

31A

Synthesis of (2R)-1-benzyloxy-3-[2-(2-hydroxyethoxy)ethoxy]propan-2-ol (Compound 31A)

[Formula 125]

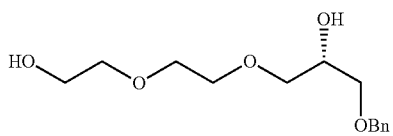

Diethylene glycol (5.0 g, 30.5 mmol) and benzyl (S)-(+)-glycidyl ether (6.5 g, 60.9 mmol) were dissolved in dichloromethane (75 ml), and boron trifluoride-diethyl ether complex (0.76 ml, 6.1 mmol) was added to the solution. The resultant mixture was stirred at room temperature for 2 hrs. After completion of the reaction, saturated aqueous sodium bicarbonate solution was added. The organic layer was washed with saturated aqueous sodium bicarbonate solution and saturated saline, dried over anhydrous sodium sulfate, and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum.

The compound of interest was dissolved in dichloromethane. The organic layer was washed with saturated aqueous sodium bicarbonate solution and saturated saline, dried over anhydrous sodium sulfate, and filtered. The solvent was distilled off under vacuum to thereby obtain an oily compound of interest (31A) (5.3 g, yield 64%).

$^1$H-NMR (CDCl$_3$) δ: 7.38-7.27 (5H, m), 4.56 (2H, s), 4.05-3.97 (1H, m), 3.77-3.48 (12H, m), 2.85-2.82 (1H, m), 2.47-2.42 (1H, m).

Calcd for C$_{14}$H$_{22}$O$_5$: [M+Na]$^+$ 293, Found 293.

31B

Synthesis of [(2R,3R,4R,5R,6R)-5-acetamide-3,4-diacetoxy-6-[2-[2-[(2R)-3-benzyloxy-2-hydroxypropoxy]ethoxy]ethoxy]tetrahydropyran-2-yl]methyl acetate (Compound 31B)

[Formula 126]

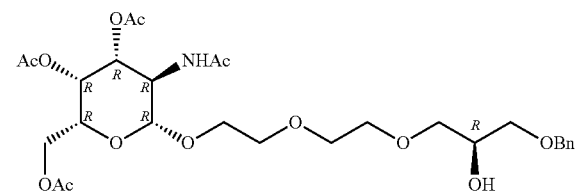

Compound 31A (4.0 g, 15 mmol) as synthesized in Step (31A) above and a known documented compound [(2R,3R,4R,5R)-5-acetamide-3,4,6-triacetoxy-tetrahydropyran-2-yl]methyl acetate (WO2011053614) (5.2 g, 13 mmol) were suspended in dichloromethane (100 ml). Trifluoromethanesulfonic acid (0.2 ml, 2.3 mmol) was added to the suspension, which was then stirred at 45° C. for 22 hrs. After completion of the reaction, the solvent was distilled off under vacuum for concentration. Then, ethyl acetate was added to the resultant reaction mixture. The organic layer was washed with saturated aqueous sodium bicarbonate solution and saturated saline, dried over anhydrous sodium sulfate, and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in dichloromethane. The organic layer was washed with saturated aqueous sodium bicarbonate solution and saturated saline, dried over anhydrous sodium sulfate, and filtered. The solvent was distilled off under vacuum to thereby obtain the compound of interest (31B) in an amorphous state (4.15 g, yield 52%).

$^1$H-NMR (CDCl$_3$) δ: 7.37-7.28 (5H, m), 6.71 (1H, d, J=9.7 Hz), 5.30 (1H, d, J=3.0 Hz), 5.12 (1H, dd, J=11.2, 3.3

Hz), 4.77 (1H, d, J=8.5 Hz), 4.57 (2H, s), 4.27-4.05 (1H, m), 3.93-3.45 (16H, m), 2.15 (3H, s), 2.05 (3H, s), 1.98 (3H, s), 1.95 (3H, s).

Calcd for $C_{28}H_{41}NO_{13}$: $[M+Na]^+$ 622, Found 622.

31C

Synthesis of [(2R,3R,4R,5R,6R)-5-acetamide-3,4-diacetoxy-6-[2-[2-[(2R)-2,3-dihydroxypropoxy]ethoxy]ethoxy]tetrahydropyran-2-yl]methyl acetate (Compound 31C)

[Formula 127]

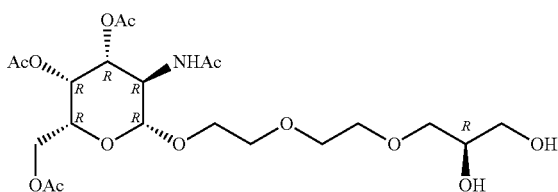

Compound 31B (4.15 g, 6.9 mmol) synthesized in Step (31B) above was dissolved in ethanol (80 ml). 10% Palladium/carbon (wet) (4 g) was added to the solution, which was then stirred vigorously at room temperature for 8 hrs under a hydrogen atmosphere. 10% Palladium/carbon (wet) (1 g) was added further, and the reaction mixture was stirred vigorously at 50° C. for 4 hrs under a hydrogen atmosphere. 10% Palladium/carbon (wet) (1 g) was added further, and the reaction mixture was stirred vigorously at 50° C. for 8 hrs under a hydrogen atmosphere. After completion of the reaction, the reaction mixture was filtered. The filtrate was distilled off under vacuum to thereby obtain a crude product of the compound of interest (31C) (3.0 g, yield 86%). This product was used in the subsequent reaction without further purification.

$^1$H-NMR (CDCl$_3$) δ: 6.58 (1H, d, J=9.1 Hz), 5.32-5.30 (1H, m), 5.16 (1H, dd, J=11.2, 3.3 Hz), 4.78 (1H, d, J=8.5 Hz), 4.26-4.09 (2H, m), 3.95-3.58 (15H, m), 2.16 (3H, s), 2.06 (3H, s), 2.01 (3H, s), 1.98 (3H, s).

Calcd for $C_{21}H_{35}NO_{13}$: $[M+H]^+$ 510, Found 510.

31D

Synthesis of [(2R,3R,4R,5R,6R)-5-acetamide-3,4-diacetoxy-6-[2-[2-[(2S)-3-[bis(4-methoxyphenyl)-phenylmethoxy]-2-hydroxy-propoxy]ethoxy]ethoxy]tetrahydropyran-2-yl]methyl acetate (Compound 31D)

[Formula 128]

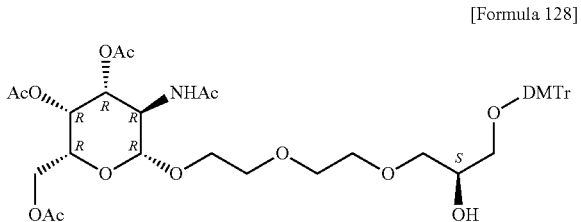

Compound 31C (3.0 g, 5.9 mmol) as synthesized in Step (31C) was azeotropically distilled with an appropriate amount of pyridine under vacuum, and dissolved in pyridine (25 ml). 4,4'-Dimethoxytrityl chloride (2.2 g, 6.5 mmol) was added to the solution, which was then stirred at room temperature for 2 hrs. After completion of the reaction, the solvent was distilled off under vacuum. Azeotropic distillation with an appropriate amount of toluene was performed to obtain a crude product. This product was purified by silica gel column chromatography (ethyl acetate:ethyl acetate/methanol (5/1)=100:0-50:50, v/v, containing 1% triethylamine) to thereby obtain the compound of interest (31D) in an amorphous state (1.7 g, yield 36%).

$^1$H-NMR (CDCl$_3$) δ: 7.47-7.42 (2H, m), 7.35-7.18 (7H, m), 6.86-6.80 (4H, m), 6.73 (1H, d, J=9.7 Hz), 5.31 (1H, d, J=3.0 Hz), 5.14 (1H, dd, J=11.2, 3.0 Hz), 4.76 (1H, d, J=8.5 Hz), 4.28-4.09 (3H, m), 4.07-3.83 (4H, m), 3.79 (6H, s), 3.72-3.49 (8H, m), 3.26 (1H, d, J=3.6 Hz), 3.18-3.13 (2H, m), 2.14 (3H, s), 2.04 (3H, s), 1.94 (3H, s), 1.90 (3H, s).

Calcd for $C_{42}H_{53}NO_{15}$: $[M+Na]^+$ 834, Found 834.

31E

Synthesis of [(2R,3R,4R,5R,6R)-5-acetamide-3,4-diacetoxy-6-[2-[2-[(2S)-3-[bis(4-methoxyphenyl)-phenylmethoxy]-2-[2-cyanoethoxy-(diisopropylamino)phosphanyl]oxypropoxy]ethoxy]ethoxy]tetrahydropyran-2-yl]methyl acetate (Compound 31E)

[Formula 129]

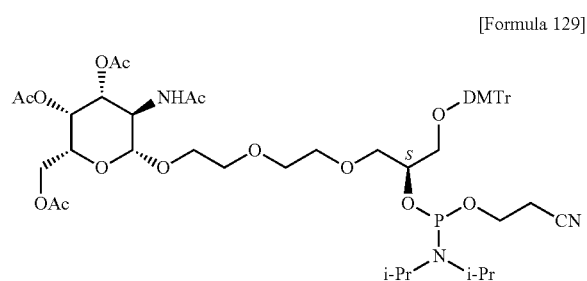

Compound 31D (1.7 g, 2.1 mmol) as synthesized in Step (31D) was azeotropically distilled with an appropriate amount of pyridine and then dissolved in dichloromethane (20 ml). N,N-Diisopropylethylamine (1.5 ml, 8.4 mmol) and 2-cyanoethyl diisopropylchlorophosphoramidite (0.56 ml, 2.5 mmol) were added to the solution, which was then stirred at room temperature for 3 hrs. After completion of the reaction, the solvent was distilled off under vacuum. Azeotropic distillation with an appropriate amount of toluene was performed to obtain a crude product. This product was purified by silica gel column chromatography (hexane:ethyl acetate=50:50-0:100, v/v, containing 1% triethylamine) to thereby obtain the compound of interest (31E) in an amorphous state (1.5 g, yield 71%).

$^1$H-NMR (CDCl$_3$) δ: 7.47-7.40 (2H, m), 7.37-7.17 (7H, m), 6.86-6.77 (4H, m), 6.08-5.95 (1H, m), 5.34-5.29 (1H, m), 5.16-5.06 (1H, m), 4.76-4.69 (1H, m), 4.20-4.02 (3H, m), 3.95-3.47 (22H, m), 3.31-3.08 (2H, m), 2.69-2.40 (2H, m), 2.14 (3H, s), 2.04-2.02 (3H, m), 1.97-1.94 (3H, m), 1.91-1.88 (3H, m), 1.21-1.01 (12H, m).

Example 106

HO—X$^{11}$-X$^{11}$-X$^{11}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^{11}$. For the X$^{11}$ portion, Compound 31E as synthesized in Reference Example 31 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6708.09).

Reference Example 32

32A

Synthesis of (2S)-1-benzyloxy-3-[2-[2-(2-hydroxy-ethoxy)ethoxy]ethoxy]propan-2-ol Compound 32A

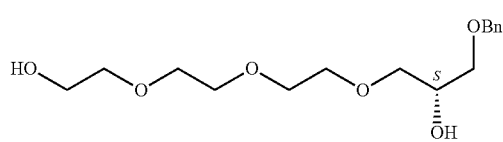
[Formula 130]

Triethylene glycol (9.2 g, 61 mmol) and benzyl (R)-(-)-glycidyl ether (5.0 g, 30 mmol) were dissolved in dichloromethane (75 ml), and boron trifluoride-diethyl ether complex (0.77 ml, 6.1 mmol) was added to the solution. The resultant mixture was stirred at room temperature for 4 hrs. After completion of the reaction, saturated aqueous sodium bicarbonate solution was added, followed by extraction with dichloromethane. The organic layer was washed with saturated saline/saturated aqueous sodium bicarbonate solution, dried over anhydrous sodium sulfate, and filtered. By distilling off the solvent under vacuum, a crude product was obtained. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in dichloromethane. The organic layer was washed with saturated saline and saturated saline/saturated aqueous sodium bicarbonate solution, dried over anhydrous sodium sulfate, and filtered. The solvent was distilled off under vacuum to thereby obtain an oily compound of interest (32A) (6.4 g, yield 67%).

$^1$H-NMR (CDCl$_3$) δ: 7.38-7.25 (5H, m), 4.56 (2H, s), 4.19-3.45 (17H, m).

Calcd for C$_{16}$H$_{26}$O$_6$: [M+H]$^+$ 315, Found 315.

32B

Synthesis of [(2R,3R,4R,5R,6R)-5-acetamide-3,4-diacetoxy-6-[2-[2-[2-[(2S)-3-benzyloxy-2-hydroxy-propoxy]ethoxy]ethoxy]ethoxy]tetrahydropyran-2-yl]methyl acetate (Compound 32B)

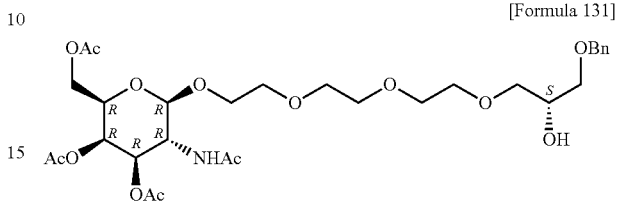
[Formula 131]

Compound 32A (6.4 g, 20 mmol) as synthesized in Step (32A) above and a known documented compound [(2R,3R,4R,5R)-5-acetamide-3,4,6-triacetoxy-tetrahydropyran-2-yl]methyl (WO2011053614) (7.2 g, 18 mmol) were suspended in dichloromethane (200 ml). Trifluoromethanesulfonic acid (0.28 ml, 3.1 mmol) was added to the suspension, which was then stirred at 45° C. for 20 hrs. After completion of the reaction, saturated aqueous sodium bicarbonate solution was added, followed by extraction with dichloromethane. The organic layer was washed with saturated saline/saturated aqueous sodium bicarbonate solution, dried over anhydrous sodium sulfate, and filtered. The solvent was distilled off under vacuum to obtain a crude product. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum. The compound of interest was dissolved in ethyl acetate. The organic layer was washed with saturated saline and saturated saline/saturated aqueous sodium bicarbonate solution, dried over anhydrous sodium sulfate, and filtered. The solvent was distilled off under vacuum to thereby obtain the compound of interest (32B) in an amorphous state (5.6 g, yield 47%).

$^1$H-NMR (CDCl$_3$) δ: 7.39-7.25 (5H, m), 6.68 (1H, d, J=9.1 Hz), 5.33-5.27 (1H, m), 5.07-4.95 (1H, m), 4.78 (1H, d, J=8.5 Hz), 4.55 (2H, s), 4.25-3.24 (21H, m), 2.15 (3H, s), 2.04 (3H, s), 1.97 (3H, s), 1.96 (3H, s).

Calcd for C$_{30}$H$_{45}$NO$_{14}$: [M+H]$^+$ 644, Found 644.

32C

Synthesis of [(2R,3R,4R,5R,6R)-5-acetamide-3,4-diacetoxy-6-[2-[2-[2-[(2S)-2,3-dihydroxypropoxy]ethoxy]ethoxy]ethoxy]tetrahydropyran-2-yl]methyl acetate (Compound 32C)

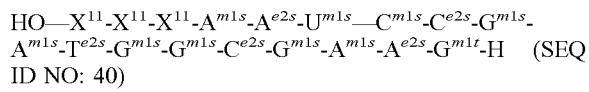
[Formula 132]

Compound 32B (5.6 g, 8.7 mmol) as synthesized in Step (32B) was dissolved in ethanol (100 ml). 20% Palladium hydroxide (wet) (1.5 g) was added to the solution, which was then stirred vigorously at 50° C. for 8 hrs under a hydrogen atmosphere. After completion of the reaction, the reaction mixture was filtered. The resultant filtrate was distilled off under vacuum. Azeotropic distillation with an appropriate amount of toluene was performed to thereby obtain an oily compound of interest (32C) (4.1 g, yield 85%).

$^1$H-NMR (CDCl$_3$) δ: 6.80 (1H, d, J=9.1 Hz), 5.34-5.30 (1H, m), 5.15-5.03 (1H, m), 4.81 (1H, d, J=8.5 Hz), 4.33-4.08 (3H, m), 3.99-3.48 (18H, m), 2.16 (3H, s), 2.06 (3H, s), 2.00 (3H, s), 1.98 (3H, s).

Calcd for C$_{23}$H$_{39}$NO$_{14}$: [M+H]$^+$ 554, Found 554.

32D

Synthesis of [(2R,3R,4R,5R,6R)-5-acetamide-3,4-diacetoxy-6-[2-[2-[2-[(2R)-3-[bis(4-methoxyphenyl)-phenylmethoxy]-2-hydroxy-propoxy]ethoxy]ethoxy]ethoxy]tetrahydropyran-2-yl]methyl acetate (Compound 32D)

[Formula 133]

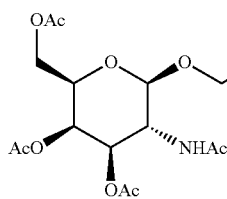

Compound 32C (4.1 g, 7.4 mmol) as synthesized in Step (32C) was azeotropically distilled with an appropriate amount of pyridine under vacuum, and then dissolved in pyridine (30 ml). 4,4'-Dimethoxytrityl chloride (2.8 g, 8.2 mmol) was added to the solution, which was then stirred at room temperature for 3 hrs. After completion of the reaction, the solvent was distilled off under vacuum. Azeotropic distillation with an appropriate amount of toluene was performed to obtain a crude product. This product was purified by silica gel column chromatography (ethyl acetate: ethyl acetate/methanol (5/1)=100:0-50:50, v/v, containing 1% triethylamine) to thereby obtain the compound of interest (32D) in an amorphous state (1.9 g, yield 30%).

$^1$H-NMR (CDCl$_3$) δ: 7.44-7.40 (2H, m), 7.35-7.18 (7H, m), 6.86-6.79 (4H, m), 6.67 (1H, d, J=9.1 Hz), 5.29 (1H, d, J=3.0 Hz), 5.03 (1H, dd, J=11.2, 3.0 Hz), 4.77 (1H, d, J=9.1 Hz), 4.26-4.06 (3H, m), 4.00-3.81 (4H, m), 3.79 (6H, s), 3.75-3.50 (12H, m), 3.23-3.11 (2H, m), 2.15 (3H, s), 2.01 (3H, s), 1.94 (6H, s).

Calcd for C$_{44}$H$_{57}$NO$_{16}$: [M+Na]$^+$ 878, Found 878.

32E

Synthesis of [(2R,3R,4R,5R,6R)-5-acetamide-3,4-diacetoxy-6-[2-[2-[2-[(2R)-3-[bis(4-methoxyphenyl)-phenylmethoxy]-2-[2-cyanoethoxy-(diisopropylamino)phosphanyl]oxypropoxy]ethoxy]ethoxy]ethoxy]tetrahydropyran-2-yl]methyl acetate (Compound 32E)

[Formula 134]

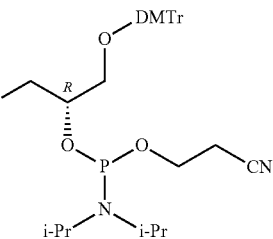

Compound 32D (1.9 g, 2.2 mmol) as synthesized in Step (32D) was azeotropically distilled with an appropriate amount of toluene and then dissolved in dichloromethane (20 ml). N,N-Diisopropylethylamine (1.6 ml, 9.0 mmol) and 2-cyanoethyl diisopropylchlorophosphoramidite (0.59 ml, 2.7 mmol) were added to the solution, which was then stirred at room temperature for 1 hr. After completion of the reaction, the solvent was distilled off under vacuum to obtain a crude product. This product was purified by silica gel column chromatography (hexane:ethyl acetate=50:50-0:100, v/v, containing 1% triethylamine) to thereby obtain the compound of interest (32E) in an amorphous state (1.5 g, yield 64%).

$^1$H-NMR (CDCl$_3$) δ: 7.47-7.40 (2H, m), 7.36-7.16 (7H, m), 6.85-6.78 (4H, m), 6.45-6.38 (1H, m), 5.33-5.28 (1H, m), 5.03-4.94 (1H, m), 4.80-4.75 (1H, m), 4.27-4.08 (3H, m), 3.93-3.45 (26H, m), 3.28-3.04 (2H, m), 2.69-2.40 (2H, m), 2.15 (3H, s), 2.04 (3H, s), 1.97-1.92 (6H, m), 1.21-1.01 (12H, m).

Example 107

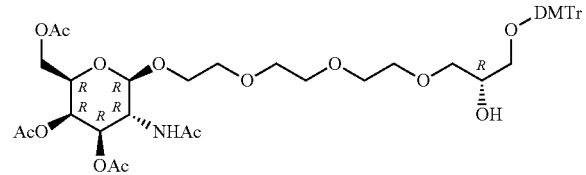

Synthesis was performed in the same manner as described in Example 91, except that the X portion was replaced by X$^{12}$. For the X$^{12}$ portion, Compound 32E as synthesized in Reference Example 32 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6839.16).

Example 108

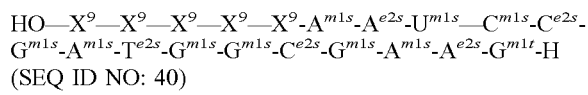
(SEQ ID NO: 40)

Synthesis was performed in the same manner as described in Example 91, except that the X portion was replaced by $X^9$. For the $X^9$ portion, Compound 29E as synthesized in Reference Example 29 was used and condensed five times.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7817.33).

Example 109

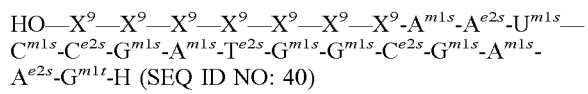
(SEQ ID NO: 40)

Synthesis was performed in the same manner as described in Example 91, except that the X portion was replaced by $X^9$. For the $X^9$ portion, Compound 29E as synthesized in Reference Example 29 was used and condensed seven times.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 8796.73).

Reference Example 33

33A

Synthesis of 9H-fluoren-9-ylmethyl N-[2-[2-[(2R)-3-benzyloxy-2-hydroxypropoxy]ethoxy]ethyl]carbamate (Compound 33A)

[Formula 135]

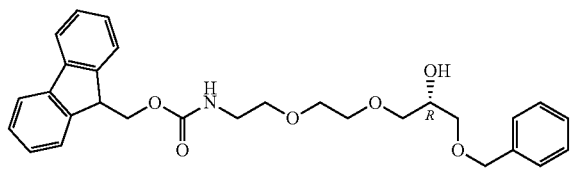

A known documented compound 9H-fluoren-9-ylmethyl N-[2-(2-hydroxyethoxy)ethyl]carbamate (Bioconjugate Chemistry, 2000, 11, 755-761) (3.11 g, 10 mmol) and benzyl (S)-(+)-glycidyl ether (0.8 g, 5 mmol) were dissolved in dichloromethane (30 ml), and boron trifluoride-diethyl ether complex (0.1 ml, 1 mmol) was added to the solution. The resultant mixture was stirred at room temperature for 16 hrs. After completion of the reaction, saturated aqueous sodium bicarbonate solution was added. The organic layer was washed with saturated aqueous sodium bicarbonate solution and saturated saline, dried over anhydrous sodium sulfate, and filtered. The solvent was distilled off under vacuum to obtain a crude product. This product was purified by silica gel column chromatography (hexane:ethyl acetate=80:20-0:100, v/v) to thereby obtain an oily compound of interest (33A) (0.74 g, yield 30%).

$^1$H-NMR (CDCl$_3$) δ: 7.76 (2H, d, J=7.9 Hz), 7.60 (2H, d, J=7.3 Hz), 7.42-7.37 (2H, m), 7.35-7.27 (7H, m), 5.40 (1H, s), 4.53 (2H, s), 4.39 (2H, d, J=6.7 Hz), 4.25-4.19 (1H, m), 4.04-3.97 (1H, m), 3.69-3.35 (12H, m).

Calcd for C29H33NO6: [M+H]$^+$ 492, Found 492.

33B

Synthesis of (2R)-1-[2-(2-aminoethoxy)ethoxy]-3-benzyloxy-propan-2-ol trifluoroacetate Compound 33B

[Formula 136]

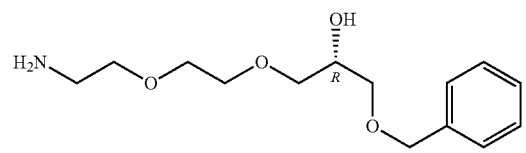

Compound 33A (13.8 g, 28.1 mmol) as synthesized in Step (33A) was dissolved in ethanol/tetrahydrofuran (50 ml/50 ml). 1 N Sodium hydroxide aqueous solution (100 ml) was added to the solution, which was then stirred at room temperature for 2 hrs. After completion of the reaction, the organic solvent was distilled off under vacuum and 1 N hydrochloric acid (100 ml) was added. The solid matter generated was removed by filtration. The byproduct contained in the aqueous layer (filtrate) was extracted with ethyl acetate. After distillation under vacuum, acetonitrile was added to the resultant residue, followed by filtration. The filtrate was distilled off under vacuum to thereby obtain a crude product. This product was isolated/purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together and the solvent was distilled off under vacuum to thereby obtain an oily compound of interest (33B) (7.1 g, yield 66%).

$^1$H-NMR (CDCl$_3$) δ: 7.38-7.27 (5H, m), 4.55 (2H, s), 4.07-3.99 (1H, m), 3.77-3.48 (10H, m), 2.96-2.88 (2H, m).

33C

Synthesis of [(2R,3R,4R,5R,6R)-5-acetamide-3,4-diacetoxy-6-[2-[2-[2-[(2R)-3-benzyloxy-2-hydroxy-propoxy]ethoxy]ethylamino]-2-oxo-ethoxy]tetrahydropyran-2-yl]methyl acetate Compound 33C

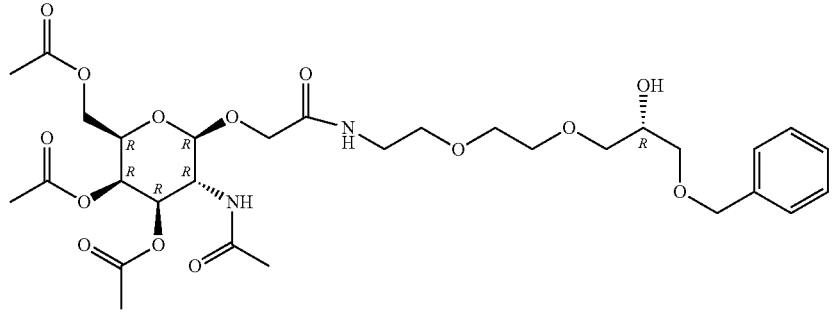

[Formula 137]

A known documented compound 2-[(2R,3R,4R,5R,6R)-3-acetamide-4,5-diacetoxy-6-(acetoxymethyl)tetrahydropyran-2-yl]oxyacetic acid (WO2012037254) (6 g, 14.8 mmol), 1-(-3-dimethylaminopropyl)-3-ethylcarbodiimide hydrochloride (3.4 g, 17.8 mmol), 3H-1,2,3-triazole[4,5-b]pyridin-3-ol (2.0 g, 14.8 mmol), N,N-diisopropylethylamine (9.0 ml, 51.8 mmol) and Compound 33B (6.7 g, 17.5 mmol) as synthesized in Step (33B) were dissolved in dichloromethane (130 ml) and the solution was stirred at room temperature for 4 hrs. After completion of the reaction, the organic layer was washed with 1 N hydrochloric acid, saturated aqueous sodium bicarbonate solution and saturated saline, dried over anhydrous sodium sulfate and filtered. The solvent was distilled off under vacuum to obtain a crude product. This product was purified by silica gel column chromatography (ethyl acetate:methanol=100:0-90:10, v/v) to thereby obtain the compound of interest (33C) in an amorphous state (7.9 g, yield 81%).

$^1$H-NMR (CDCl$_3$) δ: 7.39-7.28 (5H, m), 7.00-6.93 (1H, m), 6.50-6.44 (1H, m), 5.33-5.29 (1H, m), 5.16 (1H, dd, J=11.5, 3.6 Hz), 4.63-4.53 (3H, m), 4.34 (1H, d, J=15.1 Hz), 4.22-3.83 (5H, m), 3.73-3.26 (13H, m), 2.15 (3H, s), 2.05 (3H, s), 1.99 (6H, s).

Calcd for C$_{30}$H$_{44}$N$_2$O$_{14}$: [M+H]$^+$ 657, Found 657.

33D

Synthesis of [(2R,3R,4R,5R,6R)-5-acetamide-3,4-diacetoxy-6-[2-[2-[2-[(2R)-2,3-dihydroxypropoxy]ethoxy]ethylamino]-2-oxo-ethoxy]tetrahydropyran-2-yl]methyl acetate Compound 33D

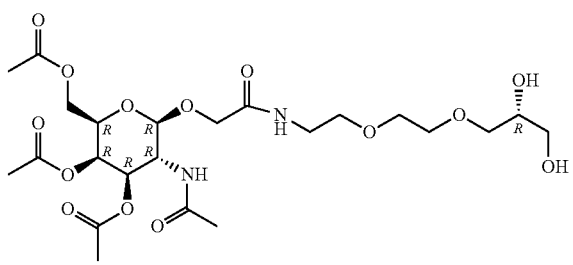

[Formula 138]

Compound 33C (7.9 g, 12 mmol) as synthesized in Step (33C) above was dissolved in ethanol (80 ml). 20% Palladium hydroxide (wet) (2.0 g) was added to the solution, which was then stirred vigorously at 50° C. for 8 hrs under a hydrogen atmosphere. After completion of the reaction, the reaction mixture was filtered and the resultant filtrate was distilled off under vacuum to thereby obtain the compound of interest (33D) (6.7 g, yield 98%) in an amorphous state.

$^1$H-NMR (CDCl$_3$) δ: 7.03-6.98 (1H, m), 6.43 (1H, d, J=9.1 Hz), 5.35 (1H, d, J=3.3 Hz), 5.15 (1H, dd, J=11.2, 3.3 Hz), 4.58 (1H, d, J=7.9 Hz), 4.35 (1H, d, J=15.7 Hz), 4.28-3.82 (5H, m), 3.77-3.34 (13H, m), 2.18 (3H, s), 2.06 (3H, s), 2.03 (3H, s), 2.01 (3H, s).

Calcd for C$_{23}$H$_{38}$N$_2$O$_{14}$: [M+H]$^+$ 568, Found 568.

33E

Synthesis of [(2R,3R,4R,5R,6R)-5-acetamide-3,4-diacetoxy-6-[2-[2-[2-[(2S)-3-[bis(4-methoxyphenyl)-phenyl-methoxy]-2-hydroxy-propoxy]ethoxy]ethyl-amino]-2-oxo-ethoxy]tetrahydropyran-2-yl]methyl acetate (Compound 33E)

[Formula 139]

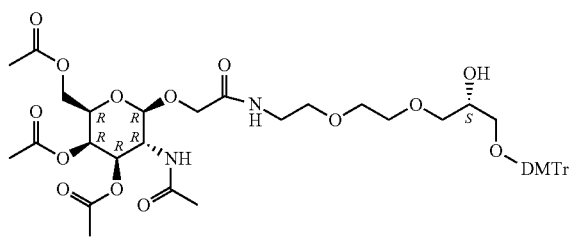

Compound 33D (6.8 g, 12 mmol) as synthesized in Step (33D) above was azeotropically distilled with an appropriate amount of pyridine under vacuum, and then dissolved in pyridine (40 ml). 4,4'-Dimethoxytrityl chloride (4.5 g, 13 mmol) was added to the solution, which was then stirred at room temperature for 2 hrs. After completion of the reaction, the solvent was distilled off under vacuum. Azeotroppic distillation with an appropriate amount of toluene was performed to obtain a crude product. This product was purified by silica gel column chromatography (ethyl acetate: ethyl acetate/methanol (5/1)=100:0-50:50, v/v, containing 1% triethylamine) to thereby obtain the compound of interest (33E) in an amorphous state (6.9 g, yield 66%).

$^1$H-NMR (CDCl$_3$) δ: 7.42 (2H, d, J=7.9 Hz), 7.33-7.19 (7H, m), 7.01-6.94 (1H, m), 6.83 (4H, d, J=9.1 Hz), 6.37 (1H, d, J=8.5 Hz), 5.33 (1H, d, J=3.3 Hz), 5.15 (1H, dd, J=11.2, 3.3 Hz), 4.58 (1H, d, J=7.9 Hz), 4.32 (1H, d, J=15.7 Hz), 4.22-3.86 (5H, m), 3.79 (6H, s), 3.66-3.12 (13H, m), 2.13 (3H, s), 2.03 (3H, s), 1.97 (3H, s), 1.95 (3H, s).

Calcd for C$_{44}$H$_{56}$N$_2$O$_{16}$: [M+Na]$^+$ 893, Found 892.

33F

Synthesis of [(2R,3R,4R,5R,6R)-5-acetamide-3,4-diacetoxy-6-[2-[2-[2-[(2S)-3-[bis(4-methoxyphenyl)-phenyl-methoxy]-2-[2-cyanoethoxy-(diisopropylamino)phosphanyl]oxy-propoxy]ethoxy]ethylamino]-2-oxo-ethoxy]tetrahydropyran-2-yl]methyl acetate (Compound 33F)

[Formula 140]

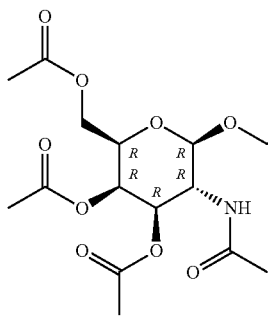 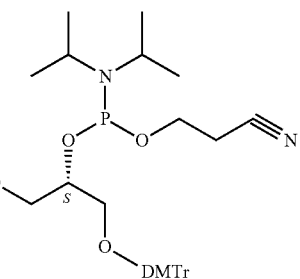

Compound 33E (6.9 g, 7.9 mmol) as synthesized in Step 33E was azeotropically distilled with an appropriate amount of toluene and dissolved in dichloromethane (80 ml). N,N-Diisopropylethylamine (5.5 ml, 32 mmol) and 2-cyanoethyl diisopropylchlorophosphoramidite (2.1 ml, 9.5 mmol) were added to the solution, which was then stirred at room temperature for 1 hr. After completion of the reaction, the solvent was distilled off under vacuum to obtain a crude product. This product was purified by silica gel column chromatography (ethyl acetate:ethyl acetate/methanol (5/1)= 100:0-50:50, v/v, containing 1% triethylamine) to thereby obtain the compound of interest (33F) in an amorphous state (6.6 g, yield 78%).

$^1$H-NMR (CDCl$_3$) δ: 7.47-7.40 (2H, m), 7.35-7.17 (7H, m), 6.98-6.91 (1H, m), 6.85-6.78 (4H, m), 6.05-5.89 (1H, m), 5.37-5.33 (1H, m), 5.17-5.07 (1H, m), 4.59-4.49 (1H, m), 4.37-4.30 (1H, m), 4.23-3.06 (28H, m), 2.69-2.42 (2H, m), 2.15 (3H, s), 2.05 (3H, s), 2.02-1.98 (3H, m), 1.97-1.94 (3H, m), 1.30-1.00 (12H, m).

Example 110

HO—X$^{13}$—X$^{13}$—X$^{13}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^{13}$. For the X$^{13}$ portion, Compound 33F as synthesized in Reference Example 33 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6878.11).

Example 111

HO—X$^{13}$—X$^{13}$—X$^{13}$—X$^{13}$—X$^{13}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^{13}$. For the X$^{13}$ portion, Compound 33F as synthesized in Reference Example 33 was used and condensed five times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7882.43).

Example 112

HO—X$^{13}$—X$^{13}$—X$^{13}$—X$^{13}$—X$^{13}$—X$^{13}$—X$^{13}$-A$^{m1s}$-A$^{e2s}$-U$^{m1s}$—C$^{m1s}$-C$^{e2s}$-G$^{m1s}$-A$^{m1s}$-T$^{e2s}$-G$^{m1s}$-G$^{m1s}$- C$^{e2s}$-G$^{m1s}$-A$^{m1s}$-A$^{e2s}$-G$^{m1t}$-H (SEQ ID NO: 40)

Synthesis was performed in the same manner as described in Example 91, except that the X portion was replaced by X$^{13}$. For the X$^{13}$ portion, Compound 33F as synthesized in Reference Example 33 was used and condensed seven times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was analyzed under the HPLC conditions described below: analysis column was Clarity Oligo-MS C18 (Phenomenex) (2.6 m, 50×2.1 mm); Mobile Phase A consisted of 100 mM hexafluoroisopropanol and 8 mM triethylamine aqueous solution whereas Mobile Phase B consisted of methanol; analysis was performed with a gradient of Mobile Phase B changing from 10% to 25% in 4 min, at a flow rate of 0.5 ml/min and at 60° C.; HPLC retention time of the compound was 3.0 min.

Reference Example 34

34A

Synthesis of tert-butyl N-[(5S)-6-[2-[2-[(2R)-3-benzyloxy-2-hydroxy-propoxy]ethoxy]ethylamino]-5-(tert-butoxycarbonylamino)-6-oxo-hexyl]carbamate Compound 34A

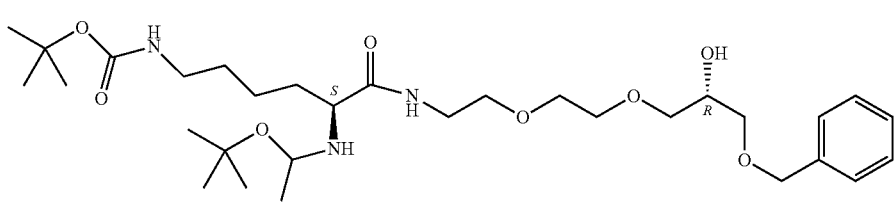

[Formula 141]

(2S)-2,6-Bis(tert-butoxycarbonylamino)hexanoic acid (1.7 g, 4.9 mmol), 1-(-3-dimethylaminopropyl)-3-ethylcarbodiimide hydrochloride (1.3 g, 6.9 mmol), 3H-1,2,3-triazole[4,5-b]pyridin-3-ol (0.67 g, 4.9 mmol), N,N-diisopropylethylamine (3.0 ml, 17 mmol) and compound 33B (2.1 g, 5.4 mmol) as synthesized in Step (33B) above were dissolved in dichloromethane (40 ml) and the solution was stirred at room temperature for 4 hrs. Further, 1-(-3-dimethylaminopropyl)-3-ethylcarbodiamide hydrochloride (1.3 g, 6.9 mmol) and N,N-diisopropylethylamine (1.0 ml, 5.7 mmol) were added to the reaction mixture, which was then stirred overnight. After completion of the reaction, the organic layer was washed with 1 N hydrochloric acid, saturated aqueous sodium bicarbonate solution and saturated saline, dried over anhydrous sodium sulfate, and filtered. The solvent was distilled off under vacuum to thereby obtain a crude product (3.1 g) containing Compound 34A. The whole volume of this crude product was used in the subsequent reaction without further purification.

Calcd for $C_{30}H_{51}N_3O_9$: $[M+H]^+$ 599, Found 599.

34B

Synthesis of (2S)-2,6-diamino-N-[2-[2-[(2R)-3-benzyloxy-2-hydroxy-propoxy]ethoxy]ethyl]hexanamide trifluoroacetate (Compound 34B)

The crude product (3.1 g) containing Compound 34A as synthesized in Step (34A) above was dissolved in dichloromethane (24 ml)/trifluoroacetic acid (6 ml) and stirred at room temperature for 90 min. After completion of the reaction, the solvent was distilled off under vacuum. After addition of an appropriate amount of dichloromethane, the solvent was re-distilled off under vacuum. Subsequently, an appropriate amount of acetonitrile/distilled water (4/1) was added, and the solvent was again distilled off under vacuum. The above-described operations were repeated until excessive trifluoroacetic acid was removed to thereby obtain a crude product (3.8 g) containing Compound 34B. The whole volume of this crude product was used in the subsequent reaction without further purification.

Calcd for $C_{20}H_{35}N_3O_5$: $[M+H]^+$ 399, Found 398.

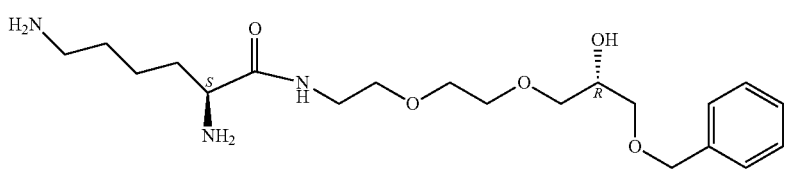

[Formula 142]

34C

Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[2-[(2R)-3-benzyloxy-2-hydroxy-propoxy]ethoxy]ethylamino]-6-oxo-hexyl]amino]-2-oxo-ethoxy]-3,4-diacetoxy-tetrahydropyran-2-yl]methyl acetate (Compound 34C)

[Formula 143]

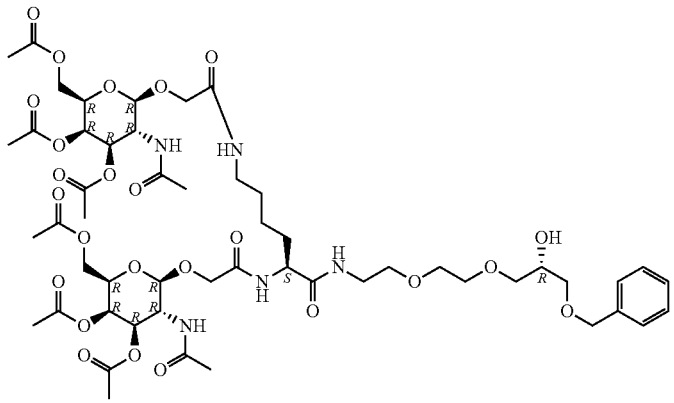

A known documented compound 2-[(2R,3R,4R,5R,6R)-3-acetamide-4,5-diacetoxy-6-(acetoxymethyl)tetrahydropyran-2-yl]oxyacetic acid (WO2012037254) (3.5 g, 8.6 mmol), 1-(-3-dimethylaminopropyl)-3-ethylcarbodiimide hydrochloride (2.3 g, 12 mmol), 3H-1,2,3-triazole[4,5-b]pyridin-3-ol (1.3 g, 9.6 mmol), N,N-diisopropylethylamine (10 ml, 59 mmol) and the crude product containing Compound 34B as synthesized in Step (34B) were dissolved in dichloromethane (80 ml) and stirred at room temperature overnight. After completion of the reaction, the organic layer was washed with 1 N hydrochloric acid, saturated aqueous sodium bicarbonate solution and saturated saline, dried over anhydrous sodium sulfate, and filtered. The solvent was distilled off under vacuum to thereby obtain a crude product. This product was purified by silica gel column chromatography (ethyl acetate:methanol (5/1)=100:0-70:30, v/v) to thereby obtain the compound of interest (34C) in an amorphous state (3.5 g, yield 62% (3 steps)).

$^1$H-NMR (CDCl$_3$) δ: 7.50-7.44 (1H, m), 7.39-7.28 (5H, m), 7.17-7.11 (2H, m), 6.94-6.88 (1H, m), 6.30-6.26 (1H, m), 5.37-5.32 (2H, m), 5.09-4.99 (2H, m), 4.57 (2H, s), 4.56-3.11 (30H, m), 2.18 (3H, s), 2.16 (3H, s), 2.07-1.99 (15H, m), 1.97 (3H, s), 1.96-1.34 (6H, m).

Calcd for $C_{52}H_{77}N_{50}O_{25}$: [M+H]$^+$ 1172, Found 1173.

34D

Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[2-[(2R)-2,3-dihydroxypropoxy]ethoxy]ethylamino]-6-oxo-hexyl]amino]-2-oxo-ethoxy]-3,4-diacetoxy-tetrahydropyran-2-yl]methyl acetate (Compound 34D)

[Formula 144]

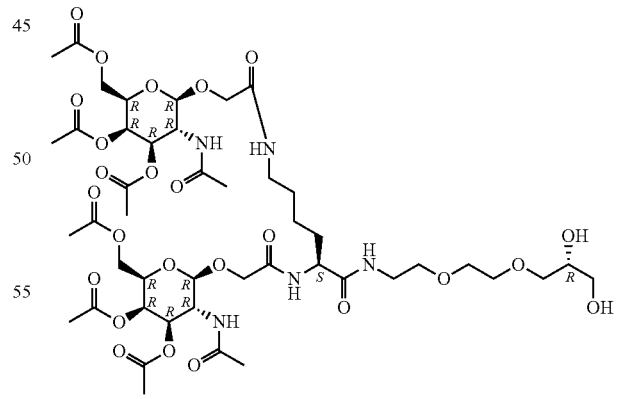

Compound 34C (3.5 g, 3.0 mmol) as synthesized in Step (34C) above was dissolved in ethanol (40 ml). 200% Palladium hydroxide (wet) (1.2 g) was added to the solution, which was then stirred vigorously at 50° C. for 8 hrs under a hydrogen atmosphere. After completion of the reaction, the reaction mixture was filtered and the resultant filtrate was distilled off under vacuum to thereby obtain the compound of interest (34D) (3.14 g, yield 970%) in an amorphous state.
$^1$H-NM/R (CDCl$_3$) δ: 7.72-7.67 (1H, in), 7.16 (2H, d, J=9.1 Hz), 7.04-6.98 (1H, in), 6.27 (1H, d, J=9.1 Hz), 5.36 (2H, d, J=3.0 Hz), 5.10-4.99 (2H, in), 4.67-3.07 (30H, in), 2.18 (3H, s), 2.17 (3H, s), 2.08-2.00 (15H, in), 1.98 (3H, s), 1.93-1.33 (6H, in).
Calcd for C$_{45}$H$_{71}$N$_5$O$_{25}$. [M+H]$^+$ 1082, Found 1083.

34E

Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[2-[(2S)-3-[bis(4-methoxyphenyl)-phenyl-methoxy]-2-hydroxy-propoxy]ethoxy]ethylamino]-6-oxo-hexyl]amino]-2-oxo-ethoxy]-3,4-diacetoxy-tetrahydropyran-2-yl]methyl acetate Compound 34E

[Formula 145]

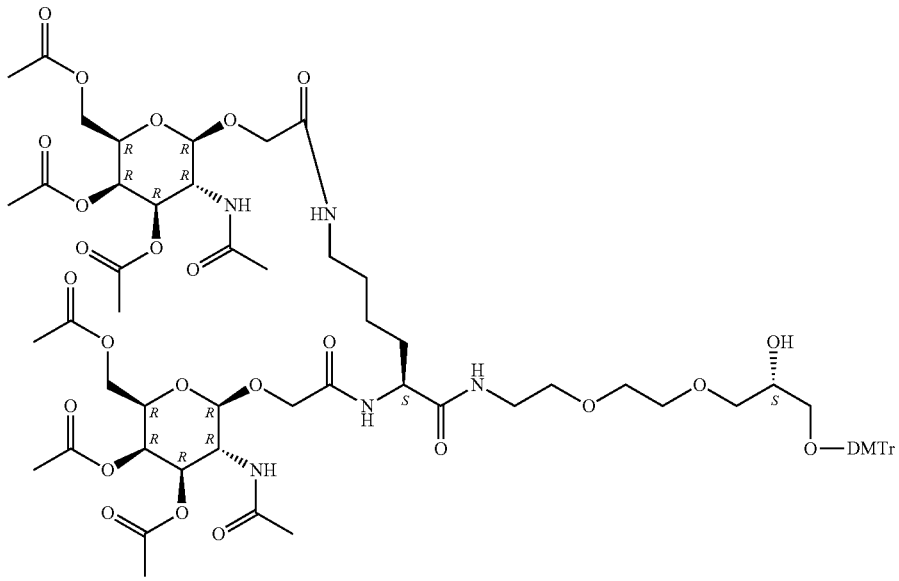

Compound 34D (3.14 g, 2.9 mmol) as synthesized in Step (34D) above was azeotropically distilled with an appropriate amount of pyridine under vacuum and dissolved in pyridine (10 ml). 4,4'-Dimethoxytrityl chloride (1.1 g, 3.2 mmol) was added to the solution, which was then stirred at room temperature for 2 hrs. After completion of the reaction, toluene (20 ml), ethanol (1 ml) and N,N-diisopropylethylamine (1 ml) were added and the solvent was distilled off under vacuum to obtain a crude product. This product was purified by silica gel column chromatography (ethyl acetate: ethyl acetate/methanol (5/1)=100:0-50:50, v/v, containing 1% triethylamine) to thereby obtain the compound of interest (34E) in an amorphous state (2.5 g, yield 62%).
$^1$H-NMR (CDCl$_3$) δ: 7.60-7.55 (1H, m), 7.43 (2H, d, J=7.3 Hz), 7.35-7.20 (7H, m), 7.17-7.10 (2H, m), 6.92-6.87 (1H, m), 6.83 (4H, d, J=9.1 Hz), 6.30 (1H, d, J=9.1 Hz), 5.36-5.30 (2H, m), 5.09-4.95 (2H, m), 4.60-3.07 (36H, m), 2.19-2.14 (6H, m), 2.06-1.99 (15H, m), 1.97 (3H, s), 1.70-1.34 (6H, m).
Calcd for C$_{66}$H$_{89}$N$_5$O$_7$: [M+Na]$^+$ 1407, Found 1407.

34F

Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[2-[(2S)-3-[bis(4-methoxyphenyl)-phenyl-methoxy]-2-[2-cyanoethoxy-(diisopropylamino)phosphanyl]oxy-propoxy]ethoxy]ethylamino]-6-oxo-hexyl]amino]-2-oxo-ethoxy]-3,4-diacetoxy-tetrahydropyran-2-yl]methyl acetate (Compound 34F)

[Formula 146]

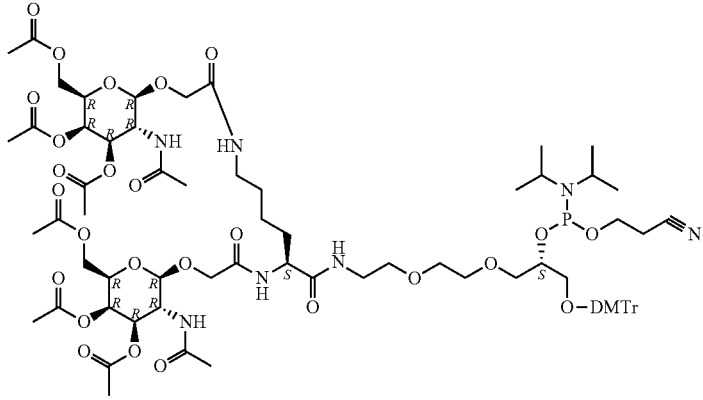

Compound 34E (2.5 g, 1.8 mmol) as synthesized in Step (34E) was azeotropically distilled with an appropriate amount of toluene/dichloromethane (3/1) and dissolved in dichloromethane (18 ml). N,N-Diisopropylethylamine (1.3 ml, 7.2 mmol) and 2-cyanoethyl diisopropylchlorophosphoramidite (0.48 ml, 2.2 mmol) were added to the solution, which was then stirred at room temperature for 1 hr. After completion of the reaction, the solvent was distilled off under vacuum to obtain a crude product. This product was purified by silica gel column chromatography (ethyl acetate: ethyl acetate/methanol (5/1)=100:0-50:50, v/v, containing 100 triethylamine) to thereby obtain the compound of interest (34F) in an amorphous state (2.1 g, yield 73%).

$^1$H-NMR (CDCl$_3$) δ: 7.47-7.41 (2H, m), 7.35-7.05 (10H, m), 6.89-6.78 (5H, m), 6.35-6.25 (1H, m), 5.37-5.34 (2H, m), 5.11-4.98 (2H, m), 4.55-3.08 (40H, m), 2.70-2.45 (2H, m), 2.18 (3H, s), 2.17 (3H, s), 2.07-1.99 (15H, m), 1.98-1.94 (3H, m), 1.91-1.31 (6H, m), 1.21-1.02 (12H, m).

Example 113

HO—$X^{14}$-$A^{m1s}$-$A^{e2s}$-$U^{m1s}$—$C^{m1s}$-$C^{e2s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ TD NO: 40)

Synthesis was performed in the same manner as described in Example 91, except that the X portion was replaced by $X^{14}$. For the $X^{14}$ portion, Compound 34F as synthesized in Reference Example 34 was used and condensed once.

The nucleotide sequence of the subject compound is complementary to a sequence from the 92$^{th}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6263.04).

Example 114

HO—$X^{14}$—$X^{14}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 40)

Synthesis was performed in the same manner as described in Example 91, except that the X portion was replaced by $X^{14}$. For the $X^{14}$ portioin, Compound 34F as synthesized in Reference Example 34 was used and condensed twice.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 7154.36).

Example 115

HO—$X^{14}$—$X^{14}$—$X^{14}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 40)

Synthesis was performed in the same manner as described in Example 91, except that the X portion was replaced by $X^{14}$. For the $X^{14}$ portion, Compound 34F as synthesized in Reference Example 34 was used and condensed three times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 8046.64).

Examples 116 to 127

Preparation of Nucleic Acid Lipid Particles Encapsulating Oligonucleotide Distearoylphosphatidylcholine (1,2-distearoyl-sn-glycero-3-phosphocholine; hereinafter designated "DSPC"; NOF CORPORATION), cholesterol (hereinafter designated "Chol"; Sigma-Aldrich, Inc.), the compound disclosed in Example 8 of WO 2015/005253 (hereinafter designated "LP") and N-[methoxy poly(ethylene glycol) 2000]carbamoyl]-1,2-dimyristyloxypropyl-3-amine (hereinafter designated "PEG-C-DMA"; NOF CORPORATION) were dissolved in ethanol at a molar ratio of DSPC:Chol:LP:PEG-C-DMA=10:48:40:2 to prepare a lipid solution having a total lipid concentration of 5 mM.

Oligonucleotides (21e_002, 18e_005, 21m_002, 18e_005, 18m_022, 15e_001, 15ed_001, 18e_008, 18e_025, 18m_008, 15e_002 and 15ed_002) were individually dissolved in citrate buffer (20 mM, pH 4.0) to prepare oligonucleotide solutions.

The above-described lipid solution and the oligonucleotide solution were mixed in the microchannel cartridge (flow rate: 12 ml/min; mixed volume ratio: lipid solution/oligonucleotide solution=⅓; temperature: room temperature) of NanoAssemblr Benchtop™ (Precision Nanosystems) so that the ratio of LP-derived nitrogen atom (N) to oligonucleotide-derived phosphorus atom (P) (N/P) would be 3 to thereby obtain a dispersion of nucleic acid lipid particles. Subsequently, this dispersion was dialyzed with approximately 2 liters of phosphate buffer (pH 7.4) for 12-18 hrs (Float-A-Lyzer G2, MWCO: 1000 kD, Spectra/Por) for ethanol removal and neutralization. Thus, a purified dispersion of oligonucleotide-encapsulating nucleic acid lipid particles was obtained. For adjusting the concentration, the dispersion was appropriately concentrated by ultrafiltration (Amicon-Ultra, MWCO: 100 kD, Millipore).

The properties of the oligonucleotide-encapsulating nucleic acid lipid particles of Examples 116 to 127 were evaluated. The method of each property evaluation is described below.

(1) Oligonucleotide Encapsulation Rate

Oligonucleotide encapsulation rate was determined using Quant-iT RiboGreen RNA Assay kit (Invitrogen) according to the attached protocol with necessary modifications. Briefly, in the presence and absence of 0.015% Triton X-100 surfactant, oligonucleotide in the dispersion of nucleic acid lipid particles was quantified. Then, encapsulation rate was calculated by the formula below:

{[amount of oligonucleotide in the presence of surfactant]−[amount of oligonucleotide in the absence of surfactant]}/[amount of oligonucleotide in the presence of surfactant]}×100(%)

(2) Ratio of Oligonucleotide to Lipids

The amount of phospholipids in the dispersion of nucleic acid lipid particles was measured with Phospholipid C-Test Wako (Wako Pure Chemical) according to the attached protocol with necessary modifications. Briefly, phospholipids in samples were quantified in the presence of 1% Triton X-100 surfactant.

The amounts of cholesterol and LP in the dispersion of nucleic acid lipid particles were measured by reversed-phase chromatography (System: Agilent 1100 series; Column: Chromolith Performance RP-18 endcapped 100-3 monolithic HPLC-column (Merck); Buffer A: 0.01% trifluoroacetic acid; Buffer B: 0.01% trifluoroacetic acid, methanol; Gradient (B %): 82-97% (0-17 min); Flow Rate: 2 ml/min; Temperature: 50° C.; Detection: 205 nm).

The amount of total lipid was calculated from the amounts of phospholipids, cholesterols and LPs and the composition ratios of lipid components constituting the liposome.

Then, using the "amount of oligonucleotide in the presence of surfactant" described in (1) above, the ratio of oligonucleotide to lipids was calculated from the following formula:

[Oligonucleotide concentration in the presence of surfactant]/[Total lipid concentration](wt/wt)

(3) Average Particle Size

The particle size of liposome was measured with Zeta Potential/Particle Sizer NICOMP™ 380ZLS (Particle Sizing Systems). Average particle size in the following Table represents volume average particle size, and the ±sign indicates deviation.

The results are summarized in Table 11 below.

TABLE 11

| Nucleic Acid Lipid Particles | ASO | Encapsulation Rate (%) | ASO/Lipid (wt/wt)* | Particle Size (nm) |
|---|---|---|---|---|
| Example 116 | 21e_002 | 98 | 12 | 60 ± 35 |
| Example 117 | 18e_005 | 98 | 12 | 69 ± 36 |
| Example 118 | 21m_002 | 98 | 13 | 67 ± 33 |
| Example 119 | 18e_005 | 98 | 12 | 61 ± 31 |
| Example 120 | 18m_022 | 98 | 13 | 59 ± 21 |
| Example 121 | 15e_001 | 98 | 13 | 57 ± 20 |
| Example 122 | 15ed_001 | 99 | 15 | 58 ± 19 |
| Example 123 | 18e_008 | 97 | 14 | 62 ± 36 |
| Example 124 | 18e_025 | 98 | 14 | 58 ± 25 |
| Example 125 | 18m_008 | 98 | 13 | 62 ± 28 |
| Example 126 | 15e_002 | 98 | 13 | 62 ± 33 |
| Example 127 | 15ed_002 | 98 | 14 | 54 ± 21 |

*ASO/Lipid (wt/wt): weight ratio of oligonucleotide to lipid.

From the above-described results, it has become clear that oligonucleotide is encapsulated in lipid particles to form nucleic acid lipid particles having an average particle size of approx. 50 nm to approx. 70 nm.

Example 128

HO—$X^{14}$-$A^{m1s}$-$T^{e2s}$-$C^{m1s}$-$C^{m1s}$-$G^{e2s}$-$A^{m1s}$-$U^{m1s}$-$G^{e2s}$-$G^{m1s}$-$C^{m1s}$-$G^{e2s}$-$A^{m1s}$-$A^{m1s}$-$G^{e2s}$-$C^{m1t}$—H (SEQ ID NO: 44)

Synthesis was performed in the same manner as described in Example 113, except that the above-described sequence (designated 15e_005) was substituted for the sequence used in Example 113.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6210.94).

Example 129

HO—$X^{14}$—$U^{m1s}$—$C^{e2s}$-$C^{m1s}$-$G^{m1s}$-$A^{e2s}$-$U^{m1s}$-$G^{m1s}$-$G^{e2s}$-$C^{m1s}$-$G^{m1s}$-$A^{e2s}$-$A^{m1s}$-$G^{m1s}$-$C^{e2s}$—$U^{m1t}$—H (SEQ ID NO: 45)

Synthesis was performed in the same manner as described in Example 113, except that the above-described sequence (designated 15e_006) was substituted for the sequence used in Example 113.

The nucleotide sequence of the subject compound is complementary to a sequence from the 90$^{th}$ to the 104$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6201.95).

Example 130

HO—X$^{14}$—C$^{m1s}$-C$^{e2s}$-G$^{m1s}$-A$^{m1s}$-T$^{e2s}$-G$^{m1s}$-G$^{m1s}$-C$^{e2s}$-G$^{m1s}$-A$^{m1s}$-A$^{e2s}$-G$^{m1s}$-C$^{m1s}$-T$^{e2s}$-G$^{m1t}$-H (SEQ ID NO: 41)

Synthesis was performed in the same manner as described in Example 113, except that the above-described sequence (designated 15e_002) was substituted for the sequence used in Example 113.

The nucleotide sequence of the subject compound is complementary to a sequence from the 89$^{th}$ to the 103$^{rd}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6268.98).

Reference Example 35

(35A) Synthesis of [(2R,3R,4R,5R,6R)-5-acet-amide3,4-diacetoxy-6-[2-[3-(tert-butoxycarbo-nylamino)propylamino]-2-oxo-ethoxy]tetrahydropy-ran-2-yl]methyl acetate Compound 35A

[Formula 147]

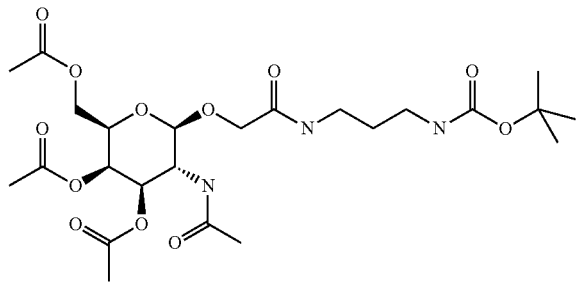

A known documented compound 2-[(2R,3R,4R,5R,6R)-3-acetamide-4,5-diacetoxy-6-(acetoxymethyl)tetrahydropy-ran-2-yl]oxyacetic acid (WO2012037254) (10 g, 24.7 mmol) and N-(3-aminopropyl)carbamic acid tert-butyl ester (4.7 ml, 27.1 mmol) were dissolved in N,N-dimethylforma-mide (70 ml). To this solution, 1-[bis(dimethylamino)meth-ylene]-1H-1,2,3-triazolo[4,5-b]pyridinium 3-oxide hexafluorophosphate (11.3 g, 29.6 mmol) and N,N-diisopro-pylethylamine (8.6 ml, 49.3 mmol) were added. The resul-tant mixture was stirred at room temperature for 40 min. After completion of the reaction, ethyl acetate was added. The organic layer was washed with 15% saline, 0.5 N hydrochloric acid, saturated saline, saturated aqueous sodium bicarbonate solution and saturated saline, dried over anhydrous sodium sulfate, and filtered. The solvent was distilled off under vacuum to obtain a crude product (approx. 14 g) containing the subject compound of interest. This crude product was used in the subsequent reaction without further purification.

(35B) Synthesis of [(2R,3R,4R,5R,6R)-5-acet-amide-3,4-diacetoxy-6-[2-(3-aminopropylamino)-2-oxo-ethoxy]tetrahydropyran-2-yl]methyl acetate trifluoroacetate Compound 35B

[Formula 148]

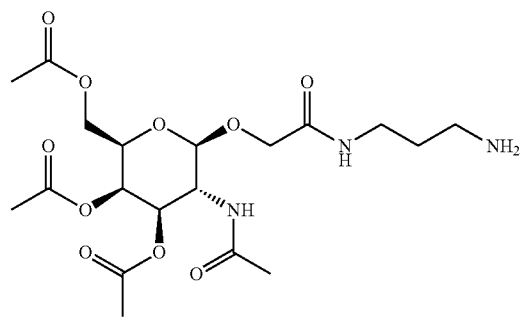

The crude product as synthesized in Step (35A) (14 g) was dissolved in dichloromethane (40 ml), and 16 ml in total of trifluoroacetic acid was added to the solution until the reaction was completed. After completion of the reaction, the solvent was distilled off under vacuum to obtain a crude product. An appropriate amount of diethyl ether was added and decantation was performed. An appropriate amount of acetonitrile was added and distilled off under vacuum. Further, an appropriate amount of dichloromethane was added and distilled off under vacuum to thereby obtain approx. 15.9 g of a crude product containing the subject compound of interest. This crude product was used in the subsequent reaction without further purification.

Calcd for $C_{19}H_{31}N_3O_{10}$: [M+H]$^+$ 462, Found 462.

(35C) Synthesis of [(2R,3R,4R,5R,6R)-5-acet-amide-3,4-diacetoxy-6-[2-[3-[[(4R)-2,2-dimethyl-1,3-dioxolan-4-yl]methoxycarbonylamino]propy-lamino]-2-oxo-ethoxy]tetrahydropyran-2-yl]methyl acetate (Compound 35C)

[Formula 149]

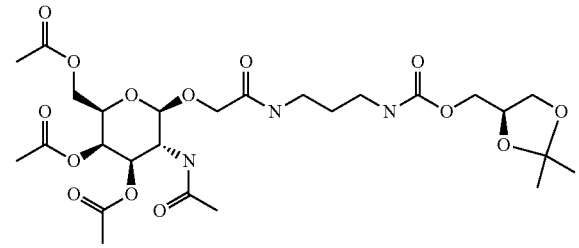

(S)-+)-1,2-Isopropylideneglycerol (6.52 g, 49.4 mmol) and chloroformic acid 4-nitrophenyl ester (9.96 g, 49.4 mmol) were dissolved in dichloromethane (200 ml), and pyridine (7.95 ml, 98.8 mmol) was added to the solution. The resultant mixture was stirred at room temperature for 30 min. To this reaction mixture, a dichioromethane solution (100 in) of the crude product as synthesized in Step (35B) above (15.9 g) and triethylamine (20.5 ml, 148 mmol) were added and stirred at room temperature overnight After completion of the reaction, the organic layer was washed with 0.5 N hydrochloric acid, saturated saline, saturated aqueous sodium bicarbonate solution and saturated saline, dried over anhydrous sodium sulfate, and filtered. The solvent was distilled off under vacuum to obtain a crude product. This product was purified by silica gel column chromatography (ethyl acetate:methanol=100:0-65:35, v/v) to thereby obtain the compound of interest (35C) as a solid (9.0 g, yield 59% (3 steps)).

$^1$H-NMR (CDCl$_3$) δ: 7.09-7.01 (1H, m), 6.16 (1H, d, J=8.5 Hz), 5.53-5.46 (1H, m), 5.37 (1H, d, J=3.6 Hz), 5.22-5.14 (1H, m), 4.53 (1H, d, J=8.5 Hz), 4.41-3.99 (9H-m, 3.96-3.89 (1H, n), 3.79-3.71 (1H, m), 3.44-3.15 (4H, m), 2.17 (3H, s), 2.06 (3H, s), 2.04 (3H, s), 1.98 (3H, s), 1.80-1.58 (2H, m), 1.43 (3H, s), 1.37 (3H, s).

Calcd for $C_{26}H_{41}N_3O_{14}$: [M+Na]$^+$ 642, Found 642.

(35D) Synthesis of [(2R,3R,4R, 6R$^5$-acetamide-3,4-diacetoxy-6-[2-[3-[[(2R)-2,3-dihydroxypropoxy] carbonylamino]propylamino]-2-oxo-ethoxy]tetrahydropyran-2-yl]methyl acetate (Compound 35D)

[Formula 150]

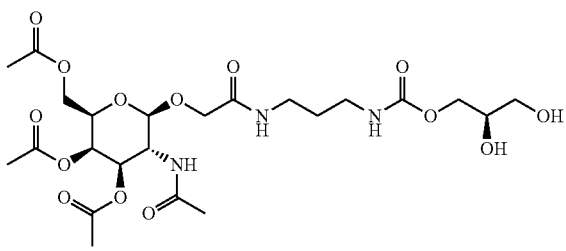

To a methanol solution (160 ml) of the compound as synthesized in Step (35C) above (7.87 g, 12.7 mmol), p-toluenesulfonic acid (0.242 g, 1.27 mmol) was added and stirred overnight. After completion of the reaction, the solvent was distilled off under vacuum to thereby obtain 7.36 g of a crude product containing the subject compound of interest. This product was used in the subsequent reaction without further purification.

Calcd for $C_{23}H_{37}N_3O_{14}$: [M+Na]+ 580, Found 580, [M+Na]+ 602, Found 602.

(35E) Synthesis of [(2R,3R,4R,5R,6R)-5-acetamide-3,4-diacetoxy-6-[2-[3[[(2R)-3-[bis(4-methoxyphenyl)-phenyl-methoxy]~2-hydroxypropoxy]carbonylamino]propylamino]-2-oxo-ethoxy] tetrahydropyran-2-yl]methyl acetate (Compound 35E)

[Formula 151]

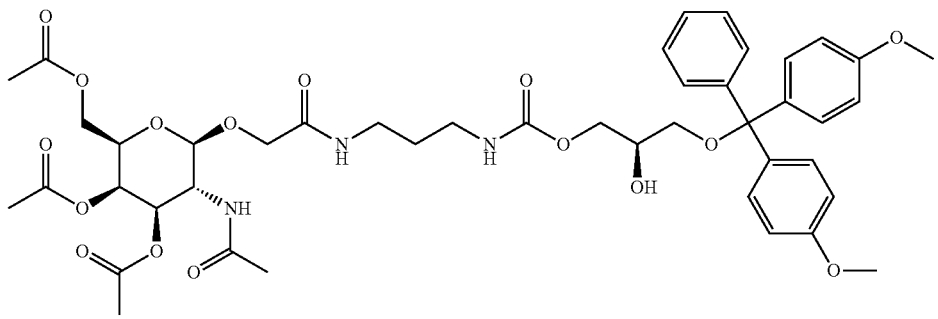

Dichloromethane (150 ml) and pyridine (10 ml) were added to the crude product as synthesized in Step (35D) (7.36 g), and the solvent was distilled off under vacuum Subsequently, the resultant product was dissolved in pyridine (60 ml). 4,4-Dimethoxytrityl chloride (5.59 g 16.5 mmol) was added to the solution which was then stirred at room temperature for 30 min. After completion of the reaction, solvents methanol (1.03 ml, 25.4 mmol) and N,N-diisopropylethylamine (4.42 ml, 25.4 mmol) were distilled off under vacuum. The resultant product was purified by silica gel column chromatography (ethyl acetate:ethyl acetate/methanol (5/1)=100:0-0:100, v/v, containing 1% triethylamine) to thereby obtain the compound of interest (35E) as a solid (4.51 g, yield 40%).

$^1$H-NMR (CDCl$_3$) δ: 745-7.39 (2H, n), 7.34-7.28 (6H, m), 7.24-7.18 (1H, m), 7.07-6.99 (1H, m), (6.86-6.80 (4H, m), 6.21 (1H, d, J=8.5 Hz), 5.48-5.41 (1H, m), 5.36 (1H, d, J=3.6 Hz), 5.19-5.13 (1H, m), 4.52 (1H, d, J=8.5 Hz), 4.39-3.88 (9H, m), 3.79 (6H, s) 3.50-3.12 (6H, m), 2.92 (1H, d, 3=4.8 Hz), 2.16 (3H, s), 2.05 (3H, s), 1.99 (3H, s), 1.95 (3H, s), 1.80-1.54 (2H, m).

Calcd for $C_{44}H_{55}N_3O_{16}$: [M+Na]+ 904, Found 904.

(35F) Synthesis of [(2R,3R,4R,5R,6R)-5-acetamide-3,4-diacetoxy-6-[2-[3-[[(2R)-3-[bis(4-methoxyphenyl)-phenyl-methoxy]-2-[2-cyanoethoxy-(diisopropylamino)phosphanyl]oxy-propoxy]carbonylamino]propylamino]-2-oxo-ethoxy]tetrahydropyran-2-yl]methyl acetate Compound 35F

[Formula 152]

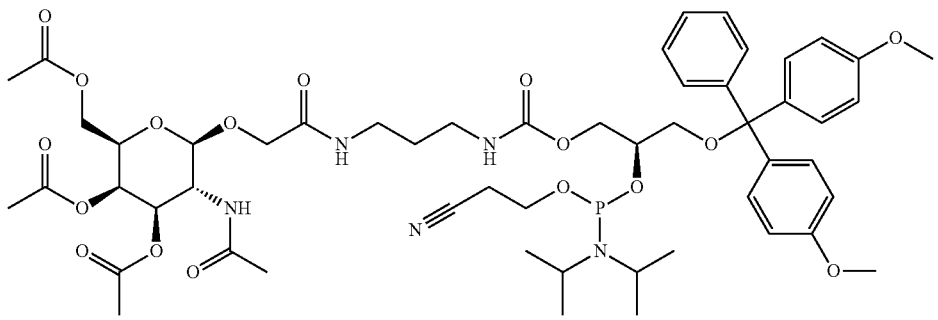

Compound 35E (4.51 g, 5.11 mmol) as synthesized in Step (35E) above was azeotropically distilled with an appropriate amount of ethyl acetate/toluene (¼) and then dissolved in dichloromethane (90 ml). N,N-Diisopropylethylamine (3.56 ml, 20.5 mmol) and 2-cyanoethyl diisopropylchlorophosphoramidite (1.57 ml, 5.63 mmol) were added and stirred at room temperature for 1 hr. After completion of the reaction, the solvent was distilled off under vacuum to obtain a crude product. This product was purified by silica gel column chromatography (ethyl acetate: ethyl acetate/methanol (5/1)=100:0-50:50, v/v, containing 1% triethylamine) to thereby obtain the compound of interest (35F) as a solid (3.97 g, yield 72%).

$^1$H-NMR (CDCl$_3$) δ: 7.47-7.38 (2H, m), 7.35-7.16 (7H, m), 7.12-7.04 (1H, m), 6.86-6.76 (4H, m), 6.25-6.12 (1H, m), 5.58-5.18 (3H, m), 4.61-4.53 (1H, m), 4.46-3.42 (19H, m), 3.39-3.02 (6H, m), 2.68-2.41 (2H, m), 2.19-2.13 (3H, m), 2.08-2.02 (3H, m), 2.01-1.91 (6H, m), 1.78-1.54 (2H, m), 1.31-0.94 (12H, m).

Reference Example 36

(36A) Synthesis of [(4R)-2,2-dimethyl-1,3-dioxolan-4-yl]methyl N-[2-(tert-butoxycarbonylamino)ethyl]carbamate (Compound 36A)

[Formula 153]

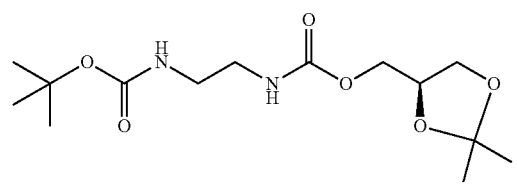

(S)-(+)-1,2-Isopropylideneglycerol (5.0 g, 37.5 mmol) and chloroformic acid 4-nitrophenyl ester (7.55 g, 37.5 mmol) were dissolved in dichloromethane (150 ml), and pyridine (5.0 ml, 61.8 mmol) was added to the solution. The resultant mixture was stirred at room temperature for 1 hr. To this reaction mixture, a dichloromethane solution (40 ml) of N-(2-aminoethyl)carbamic acid tut-butyl ester (6 g, 37.5 mmol) and triethylamine (8.8 ml, 63.7 mmol) were added and stirred at room temperature for 1 hr. After completion of the reaction, the organic layer was washed with 0.5 N hydrochloric acid, saturated saline, saturated aqueous sodium bicarbonate solution and saturated saline, dried overt anhydrous sodium sulfate, and filtered. The solvent was distilled off under vacuum, whereby a crude product (10.6 g) containing the compound of interest was obtained as a solid. This product was used in the subsequent reaction without further purification.

(36B) Synthesis of [(2R)-2,3-dihydroxypropyl] N-(2-aminoethyl)carbamate trifluoroacetate Compound 36B

[Formula 154]

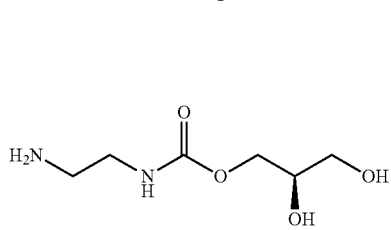

Trifluoroacetic acid (15.6 ml) and purified water (5.55 ml) were added to the crude product synthesized in Step (36A) above (10.6 g). The mixture was stirred at room temperature for 1 hr. After completion of the reaction, the solvent was distilled off under vacuum. Subsequently, acetonitrile was added thereto, and the solvent was distilled off under vacuum. Further, acetonitrile/purified water (4/1) was added thereto. After distilling off the solvent under vacuum, the resultant product was dried under vacuum. An oily crude product (14.3 g) containing the compound of interest was obtained. This crude product was used in the subsequent reaction without further purification.

(36C) Synthesis of benzyl N-[(5S)-5-(benzyloxycarbonylamino)-6-2[[(2R)-2,3-dihydroxypropoxy]carbonylamino]ethylamino]-6-oxo-hexyl]carbamate (Compound 36C)

[Formula 155]

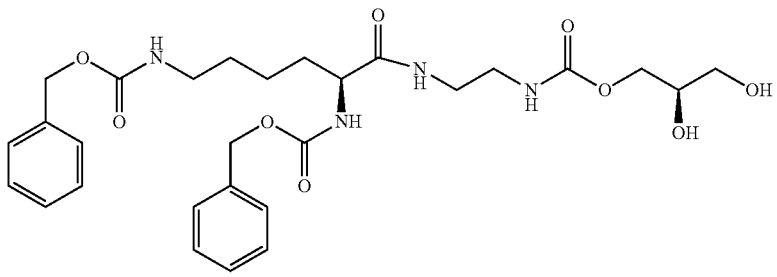

To an N,N-dimethylformamide solution (100 ml) of N,N'-Di-Cbz-L-lysine (13.7 g), 1-[bis(dimethylamino)methylene]-1H-1,2,3-triazolo[4,5-b]pyridinium 3-oxide hexafluorophosphate (15.0 g, 40 mmol) and N,N-diisopropylethylamine (12 ml, 66 mmol) were added. Further, the crude product synthesized in Step (36B) above (9.7 g) and an N,N-dimethylformamide solution (20 ml) of N,N-diisopropylethylamine (12 ml, 66 mmol) were added thereto. The resultant mixture was stirred at room temperature for 40 min. After completion of the reaction, ethyl acetate was added. The organic layer was washed with 15% saline, 0.5 N hydrochloric acid, saturated saline, saturated aqueous sodium bicarbonate solution and saturated saline, dried over anhydrous sodium sulfate, and filtered. The solvent was distilled off under vacuum to obtain a solid matter. This solid matter was washed with 1 N hydrochloric acid and purified water, and then with dichloromethane and diethyl ether, and dried under vacuum to thereby obtain a crude product (10.5 g) containing the compound of interest.

Calcd for $C_{28}H_{38}N_4O_9$: $[M+H]^+$ 575, Found 575.

(36D) Synthesis of [(2R)-2,3-dihydroxypropyl] N-[2-[[(2S)-2,6-diaminohexanoyl]amino]ethyl]carbamate hydrochloride (Compound 36D)

[Formula 156]

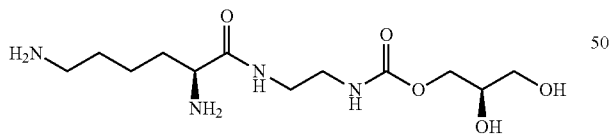

The crude product synthesized in Step (36C) above (9.5 g) was dissolved in tetrahydrofuran/1 N hydrochloric acid (36 ml), and 10% palladium/carbon (2.0 g) was added thereto. The mixture was stirred at room temperature for 2.5 hrs under a hydrogen atmosphere.

After completion of the reaction, the reaction solution was filtered. The solvent was distilled off under vacuum. Then, the resultant product was dried under vacuum with Biotage™ V-10 high speed concentration system to thereby obtain a crude product (6.4 g) of the subject compound of interest. This crude product was used in the subsequent reaction without further purification.

(36E) Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[[(2R)-2,3-dihydroxypropoxy]carbonylamino]ethylamino]-6-oxo-hexyl]amino]-2-oxo-ethoxy]-3,4-diacetoxy-tetrahydropyran-2-yl]methyl acetate (Compound 36E)

[Formula 157]

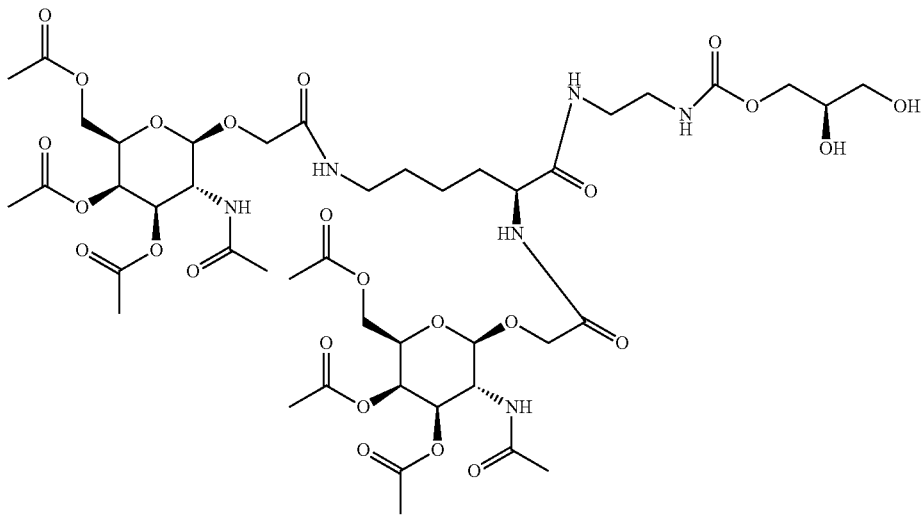

To an N,N-dimethylformamide solution (30 ml) of a known compound in the literature 2-[(2R,3R,4R,5R,6R)-3-acetamide-4,5-diacetoxy-6-(acetoxymethyl)tetrahydropyran-2-yl]oxyacetic acid (WO2012037254) (2.64 g, 6.5 mmol) and the crude compound (1.37 g, 3.6 mmol) synthesized in Step (36D) above, 1-[bis(dimethylamino)methylene]-1H-1,2,3-triazolo[4,5-b]pyridinium 3-oxide hexafluorophosphate (3.0 g, 8.0 mmol) and N,N-diisopropylethylamine (3.8 ml, 21.7 mmol) were added and stirred at room temperature for 40 min. After completion of the reaction, diethyl ether (500 ml) was added thereto to obtain precipitated residue. This residue was isolated and purified by reversed-phase HPLC (GLSciencd, Inertsil ODS-3) using 0.1% trifluoroacetic acid aqueous solution and 0.1% trifluoroacetic acid acetonitrile solution as eluents. Fractions containing the compound of interest were collected together, and the solvent was distilled off under vacuum to thereby obtain the compound of interest in an amorphous state (2.23 g, yield 57%).

$^1$H-NMR (DMSO-D$_6$) δ: 8.14-8.08 (1H, m), 8.03-7.91 (2H, m), 7.33-7.22 (2H, m), 7.16-7.10 (1H, m), 5.27-5.23 (2H, m), 5.01-4.93 (2H, m), 4.59-4.52 (2H, m), 4.26-3.55 (17H, m), 3.36-3.30 (2H, m), 3.18-2.86 (7H, m), 2.14-2.06 (6H, m), 2.04-1.98 (6H, m), 1.94-1.89 (6H, m), 1.88-1.79 (6H, m), 1.71-1.48 (2H, m), 1.47-1.35 (2H, m), 1.32-1.15 (2H, m).

Calcd for $C_{44}H_{68}N_6O_{25}$: [M+H]$^+$ 1081, Found 1081.

(36F) Synthesis of [(2R,3R,4R,5R,6R)-5-acetamide-6-[2-[[(5S)-5-[[2-[(2R,3R,4R,5R,6R)-3-acetamide-4,5-diacetoxy-6-(acetoxymethyl)tetrahydropyran-2-yl]oxyacetyl]amino]-6-[2-[[(2R)-3-[bis(4-methoxyphenyl)-phenyl-methoxy]-2-hydroxy-propoxy]carbonylamino]ethylamino]-6-oxo-hexyl]amino]-2-oxo-ethoxy]-3,4-diacetoxy-tetrahydropyran-2-yl]methyl acetate (Compound 36F)

[Formula 158]

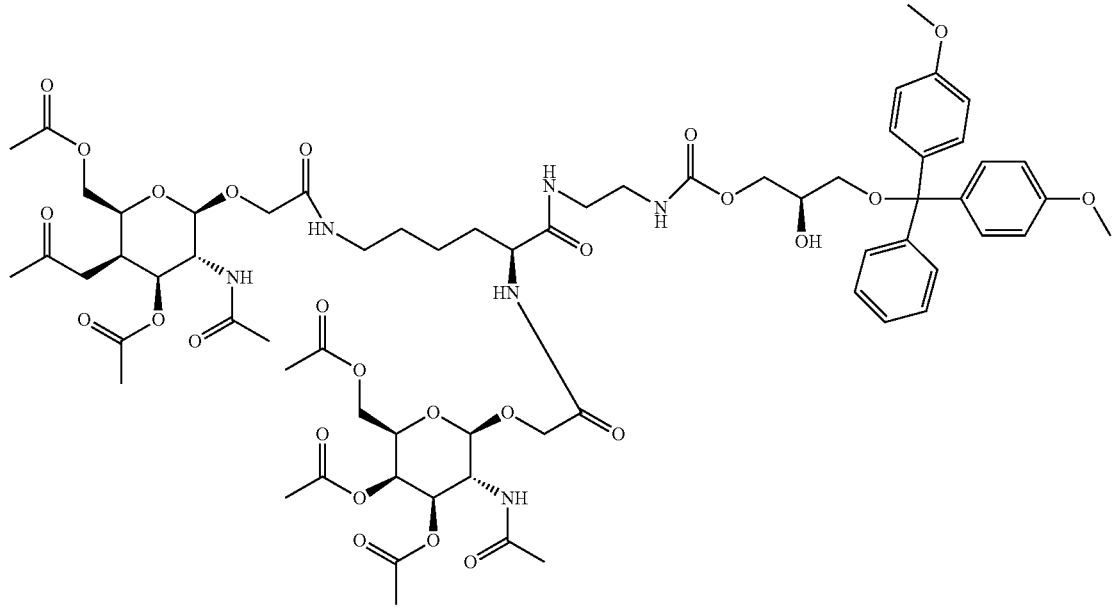

Pyridine (10 ml) was added to the compound synthesized in Step (36E) above (7.36 g, 2.1 mmol) and the solvent was distilled off under vacuum. This operation was repeated 3 times. Subsequently, the residue was dissolved in pyridine (10 ml), and 4,4'-dimethoxytrityl chloride (0.77 g, 2.3 mmol) was added thereto. The resultant mixture was stirred at room temperature for 30 min. After completion of the reaction, ethanol (1.0 ml) and N,N-diisopropylethylamine (1.0 ml) was added thereto and the solvent was distilled off under vacuum to obtain a crude product. This product was purified by silica gel column chromatography (ethyl acetate: ethyl acetate/methanol (5/1)=100:0-0:100, v/v, containing 1% triethylamine) to thereby obtain the compound of interest in an amorphous state (1.17 g, yield 41%).

$^1$H-NMR (CDCl$_3$) δ: 7.47-7.38 (2H, m), 7.36-6.95 (10H, m), 6.86-6.79 (4H, m), 6.33-6.27 (1H, m), 5.53-4.99 (4H, m), 4.57-3.07 (30H, m), 2.21-2.14 (6H, m), 2.08-1.94 (18H, m), 1.92-1.07 (6H, m).

Calcd for $C_{65}H_{86}N_6O_{27}$: [M+Na]+ 1406, Found 1406.

(36G) Synthesis of [(2R,3R,4R,5R,6R)-5-acet-
amide-6-[2-[[(5S)-5-[[2-[(2R,3R,4R,5R,6R)-3-acet-
amide-4,5-diacetoxy-6-(acetoxymethyl)tetrahydro-
pyran-2-yl]oxyacetyl]amino]-6-[2-[[(2R)-3-[bis(4-
methoxyphenyl)-phenyl-methoxy]-2-[2-cyanoethyl-
(diisopropylamino)phosphanyl]oxy-propoxy]
carbonylamino]ethylamino]-6-oxo-hexyl]amino]-2-
oxo-ethoxy]-3,4-diacetoxy-tetrahydropyran-2-yl]
methyl acetate (Compound 36G)

[Formula 159]

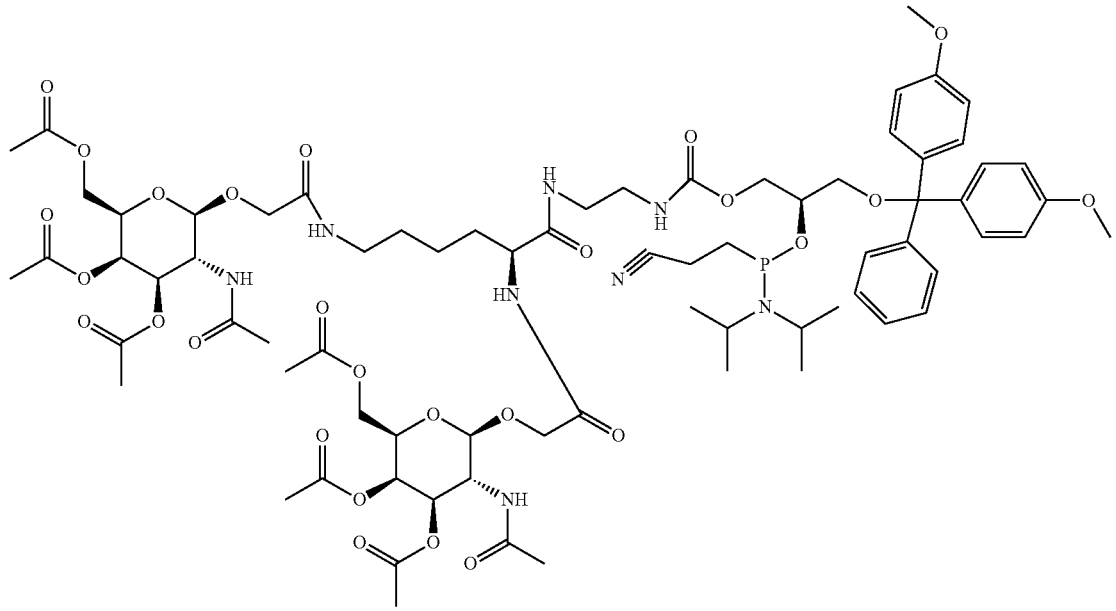

Compound 36F synthesized in Step (36F) above (1.17 g, 0.85 mmol) was azeotropically distilled with an appropriate amount of dichloromethane/toluene (¼) and then dissolved in dichloromethane (8 ml). N,N-Diisopropylethylamine (0.59 ml, 3.4 mmol) and 2-cyanoethyl-diisopropylchloro-phosphoramidite (0.23 ml, 1.0 mmol) were added thereto and stirred at room temperature for 1 hr. After completion of the reaction, the solvent was distilled off under vacuum to obtain a crude product. This product was purified by silica gel column chromatography (ethyl acetate:ethyl acetate/methanol (5/1)=100:0-0:100, v/v, containing 1% triethylamine) to thereby obtain the compound of interest (36G) in an amorphous state (0.81 g, yield 61%).

$^1$H-NMR (CDCl$_3$) δ: 7.47-7.40 (2H, m), 7.36-7.10 (11H, m), 6.95-6.86 (1H, m), 6.85-6.78 (4H, m), 6.34-6.28 (1H, m), 5.56-5.33 (2H, m), 5.12-4.98 (2H, m), 4.52-3.04 (36H, m), 2.72-2.46 (2H, m), 2.20-2.15 (6H, m), 2.08-1.94 (18H, m), 1.93-1.81 (2H, m), 1.67-1.52 (2H, m), 1.46-1.34 (2H, m), 1.22-0.98 (12H, m).

Reference Example 37

(37A) Synthesis of [(2R,3R,4R,5R)-5-acetamide-3,
4-diacetoxy-6-[3-(benzyloxycarbonylamino)
propoxy]tetrahydropyran-2-yl]methyl acetate (Compound 37A)

[Formula 160]

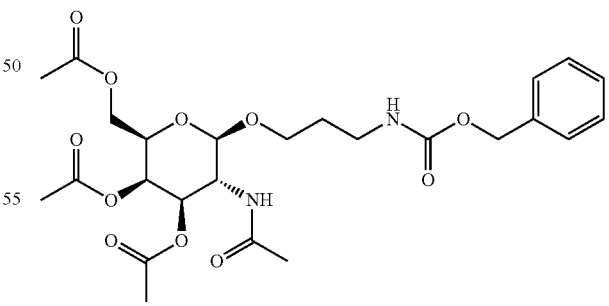

N-(3-Hydroxypropyl)carbamic acid benzyl ester (6.4 g, 30.8 mmol) and a known compound in the literature [(2R, 3R,4R,5R)-5-acetamide-3,4,6-triacetoxy-tetrahydropyran-2-yl]methyl acetate (WO2011053614) (10 g, 25.7 mmol) were suspended in dichloromethane (200 ml). To this suspension, trifluoromethanesulfonic acid (450 µl, 5.1 mmol) was added and stirred at 45° C. for 4 hrs. After completion of the reaction, about one half of the solvent was distilled off under vacuum for concentration. The organic layer was washed with saturated aqueous sodium bicarbonate solution and saturated saline, dried over anhydrous sodium sulfate, and filtered. The solvent was distilled off under vacuum to obtain a crude product. Isopropyl ether (100 m) was added to the crude product, followed by stirring for 3 hrs. The resultant solid matter was filtered to thereby obtain the compound of interest (37A) (11.9 g), which was used in the subsequent reaction without further purification. 1H-NMR (CDCl$_3$) δ: 7.43-7.29 (5H, m), 6.26 (1H, d, J=8.5 Hz), 5.36-5.29 (1H, m), 5.12 (1H, d, J=12.1 Hz), 5.08 (1H, d, J=12.1 Hz), 5.03-4.95 (2H, m), 4.33 (1H, d, J=9.1 Hz), 4.21-4.06 (3H, m), 4.01-3.93 (1H, m), 3.80-3.73 (1H, m), 3.62-3.49 (1H, m), 3.44-3.35 (1H, m), 3.14-3.04 (1H, m), 2.15 (3H, s), 2.05 (3H, s), 2.01 (3H, s), 1.95 (3H, s), 1.88-1.75 (1H, m), 1.69-1.56 (1H, m).

Calcd for $C_{25}H_{34}N_2O_{11}$: [M+H]$^+$ 539, Found 539.

(37B) Synthesis of [(2R,3R,4R,5R)-5-acetamide-3, 4-diacetoxy-6-(3-aminopropoxy)tetrahydropyran-2-yl]methyl acetate hydrochloride (Compound 37B)

[Formula 161]

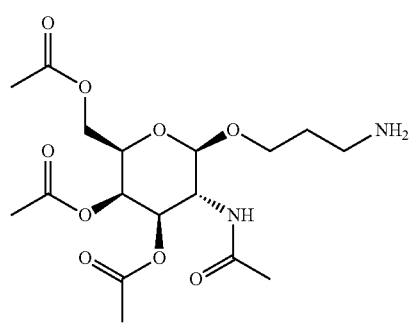

Compound 37A synthesized in Step (37A) above (10 g, 18.6 mmol) was dissolved in tetrahydrofuran (200 ml)/1 N hydrochloric acid (20 ml). 10% Palladium/carbon (wet) (1 g) was added and stirred vigorously at room temperature for 1 hr under a hydrogen atmosphere. After completion of the reaction, the reaction solution was filtered. The filtrate was distilled off under vacuum to thereby obtain a crude product (8.97 g) containing the compound of interest (37B), which was used in the subsequent reaction without further purification.

Calcd for $C_{17}H_{28}N_2O_9$: [M+H]$^+$ 405, Found 405.

(37C) Synthesis of [(2R,3R,4R,5R,6R)-5-acetamide-6-[3-[[(3S)-4-[3-[(2R,3R,4R,5R,6R)-3-acetamide-4,5-diacetoxy-6-(acetoxymethyl)tetrahydropyran-2-yl]oxypropylamide]-3-(9H-fluoren-9-ylmethoxycarbonylamino)-4-oxo-butanoyl]amino] propoxy]-3,4-diacetoxy-tetrahydropyran-2-yl]methyl acetate (Compound 37C)

[Formula 162]

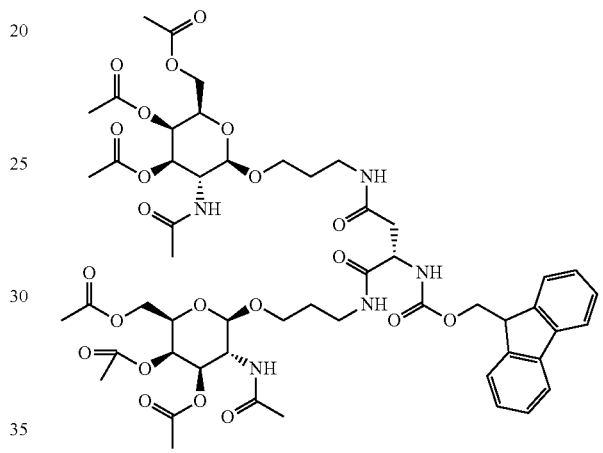

To an N,N-dimethylformamide solution (15 ml) of N-[(9H-fluoren-9-ylmethoxy)carbonyl]-L-aspartic acid (1.7 g, 4.78 mmol) and the compound synthesized in Step (37B) above (5.48 g, 12.4 mmol), 1-[bis(dimethylamino)methylene]-1H-1,2,3-triazolo[4,5-b]pyridinium 3-oxide hexafluorophosphate (4.7 g, 12.4 mmol) and N,N-diisopropylethylamine (5.8 ml, 33.5 mmol) were added and stirred at room temperature for 1 hr. Ethyl acetate was added to the reaction solution, and the organic layer was 15% saline, 0.5 N hydrochloric acid, saturated saline, saturated aqueous sodium bicarbonate solution and saturated saline, dried over anhydrous sodium sulfate, and filtered. The solvent was distilled off under vacuum to obtain a solid matter. This solid matter was washed with isopropyl ether and then dried under vacuum to thereby obtain a crude product (5.4 g) containing the compound of interest (37C). This crude product was used in the subsequent reaction without further purification.

Calcd for $C_{53}H_{69}N_5O_{22}$: [M+H]$^+$ 1128, Found 1129,[M+Na]$^+$ 1151, Found 1151.

(37D) Synthesis of [(2R,3R,4R,5R,6R)-5-acetamide-6-[3-[[(3S)-4-[3-[(2R,3R,4R,5R,6R)-3-acetamide-4,5-diacetoxy-6-(acetoxymethyl)tetrahydropyran-2-yl]oxypropylamino]-3-amino-4-oxo-butanoyl]amino]propoxy]-3,4-diacetoxy-tetrahydropyran-2-yl]methyl acetate trifluoroacetate (Compound 37D)

(37E) [(2R,3R,4R,5R,6R)-5-acetamide-6-[3-[[(3S)-4-[3-[(2R,3R,4R,5R,6R)-3-acetamide-4,5-diacetoxy-6-(acetoxymethyl)tetrahydropyran-2-yl]oxypropylamino]-3-[[(4R)-2,2-dimethyl-1,3-dioxolane-4-yl]methoxycarbonylamino]-4-oxo-butanoyl]amino]propoxy]-3,4-diacetoxy-tetrahydropyran-2-yl]methyl acetate (Compound 37E)

[Formula 163]

[Formula 164]

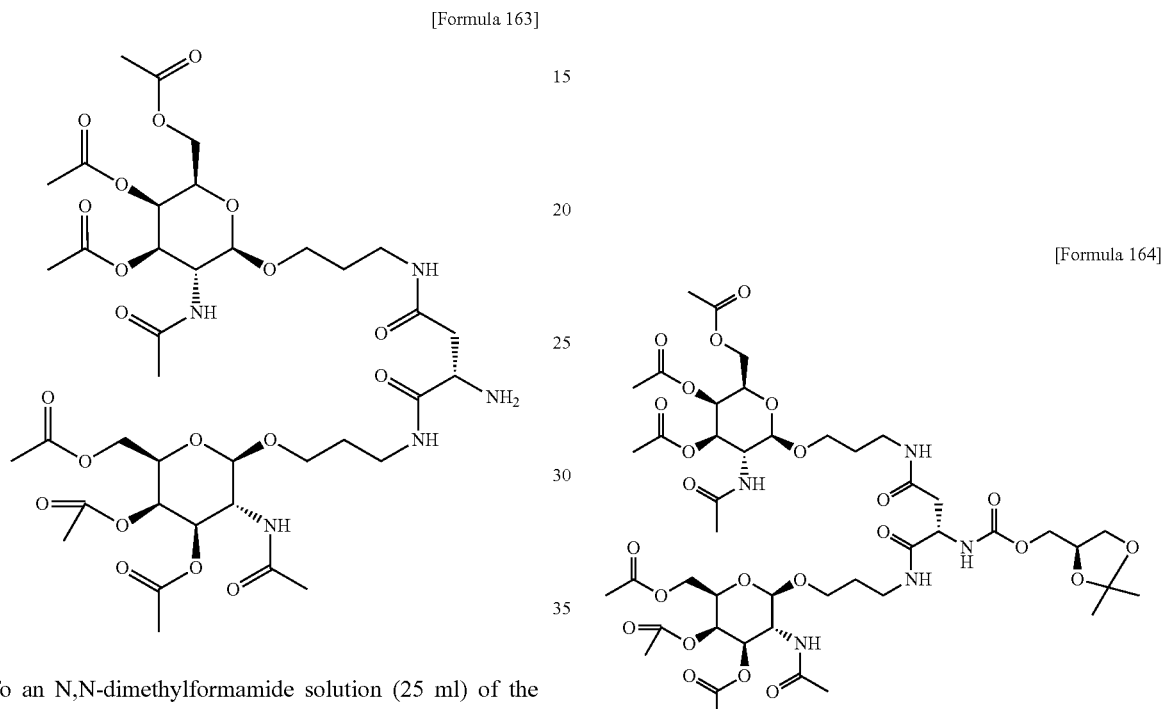

To an N,N-dimethylformamide solution (25 ml) of the compound synthesized in Step (37C) above (5.4 g, 4.8 mmol), piperidine (0.57 ml, 5.7 mmol) was added and stirred at room temperature for 1.5 hrs. After completion of the reaction, trifluoroacetic acid (0.31 ml) was added. The reaction solution was added to an appropriate amount of diethyl ether to thereby obtain precipitated residue. The residue was isolated and purified by reversed-phase HPLC (GL Science, Inertsil ODS-3) using 0.1% trifluoroacetic acid aqueous solution and 0.1% trifluoroacetic acid acetonitrile solution as eluents. Fractions containing the compound of interest were collected together. The solvent was distilled off under vacuum to thereby obtain the compound of interest in an amorphous state (2.7 g, yield 55%).

$^1$H-NMR (DMSO-D$_6$) δ: 8.34-8.26 (1H, m), 8.14-8.05 (4H, m), 7.90-7.82 (2H, m), 5.25-5.21 (2H, m), 5.00-4.92 (2H, m), 4.50-4.45 (2H, m), 4.08-3.82 (5H, m), 3.80-3.63 (3H, m), 3.51-3.39 (3H, m), 3.19-3.02 (4H, m), 2.70-2.53 (2H, m), 2.14-2.05 (6H, m), 2.04-1.96 (6H, m), 1.93-1.86 (6H, m), 1.84-1.75 (6H, m), 1.69-1.57 (4H, m).

Calcd for C$_{38}$H$_{59}$N$_5$O$_{20}$: [M+H]$^+$ 905, Found 906.

Using the compound synthesized in Step (37D) above (2.7 g, 2.6 mmol), synthesis was performed in the same manner as described in Step (35C) to thereby obtain the compound of interest in an amorphous state (0.77 g, yield 27%).

$^1$H-NMR (CDCl$_3$) δ: 7.19-7.12 (1H, m), 6.96-6.85 (2H, m), 6.83-6.75 (1H, m), 6.16 (1H, d, J=9.1 Hz), 5.41-5.34 (2H, m), 5.25-5.08 (2H, m), 4.66 (1H, d, J=8.5 Hz), 4.51-3.87 (16H, m), 3.79-3.72 (1H, m), 3.64-3.14 (6H, m), 3.01-2.91 (1H, m), 2.68-2.57 (1H, m), 2.22-2.14 (6H, m), 2.10-1.93 (18H, m), 1.90-1.63 (4H, m), 1.42 (3H, s), 1.35 (3H, s).

Calcd for C$_{45}$H$_{69}$N$_5$O$_{24}$: [M+Na]$^+$ 1086, Found 1086.

(37F) Synthesis of [(2R,3R,4R,5R,6R)-5-acetamide-6-[3-[[(3S)-4-[3-[(2R,3R,4R,5R,6R)-3-acetamide-4,5-diacetoxy-6-(acetoxymethyl)tetrahydropyran-2-yl]oxypropylamino]-3-[[(2R)-2,3-dihydroxypropoxy]carbonylamino]-4-oxo-butanoyl]amino]propoxy]-3,4-diacetoxy-tetrahydropyran-2-yl]methyl acetate (Compound 37F)

[Formula 165]

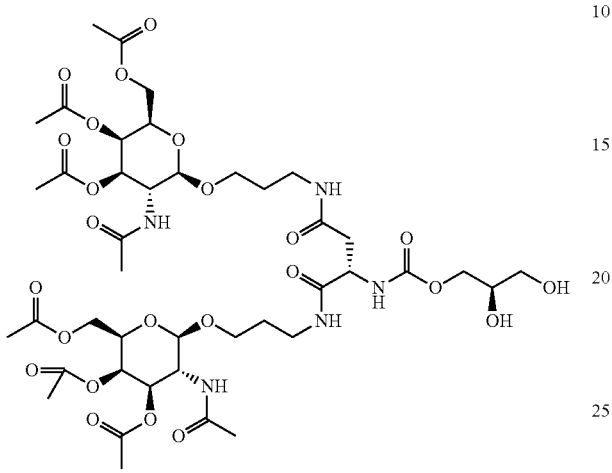

Using the compound synthesized in Step (37E) above (0.77 g, 0.72 mmol), synthesis was performed in the same manner as described in Step (35D) to thereby obtain a crude product (0.74 g) containing Compound 37F. This crude product was used in the subsequent reaction without further purification.

Calcd for $C_{42}H_{65}N_5O_{24}$: [M+H]$^+$ 1024, Found 1024.

(37G) Synthesis of [(2R,3R,4R,5R,6R)-5-acetamide-6-[3-[[(3S)-4-[3-[(2R,3R,4R,5R,6R)-3-acetamide-4,5-diacetoxy-6-(acetoxymethyl)tetrahydropyran-2-yl]oxypropylamino]-3-[[(2R)-3-[bis(4-methoxyphenyl)-phenyl-methoxy]-2-hydroxypropoxy]carbonylamino]-4-oxo-butanoyl]amino]propoxy]-3,4-diacetoxy-tetrahydropyran-2-yl]methyl acetate (Compound 37G)

[Formula 166]

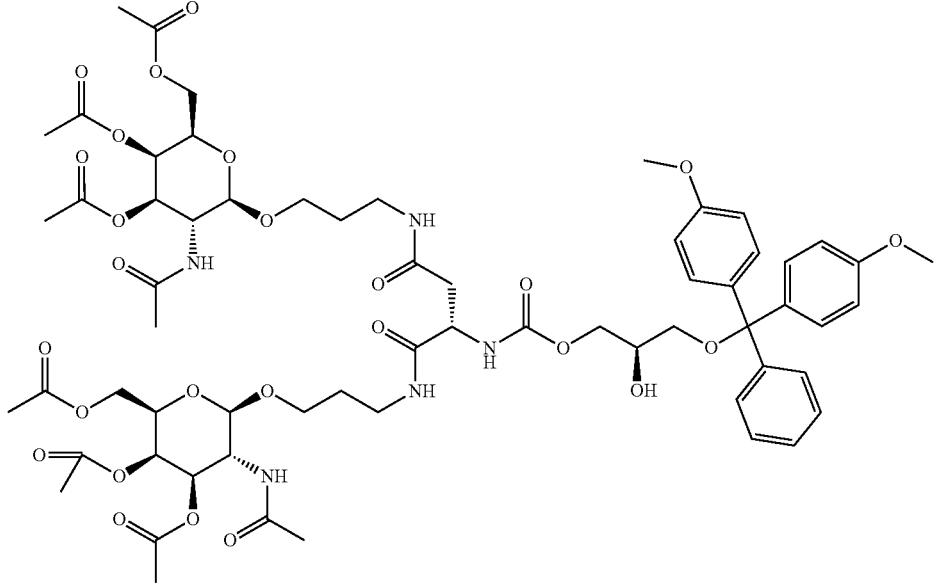

Using the compound synthesized in Step (37F) above (0.74 g), synthesis was performed in the same manner as described in Step (35E) to thereby obtain the compound of interest in an amorphous state (0.63 g, yield 66% (2 steps)).

$^1$H-NMR (CDCl$_3$) δ: 7.44-7.38 (2H, m), 7.33-7.09 (9H, m), 6.86-6.69 (6H, m), 6.22 (1H, d, J=7.9 Hz), 5.38-5.33 (2H, m), 5.23-5.09 (2H, m), 4.66 (1H, d, J=7.9 Hz), 4.54-4.42 (2H, m), 4.24-3.87 (16H, m), 3.79 (6H, s), 3.57-3.14 (8H, m), 2.97-2.87 (1H, m), 2.66-2.50 (1H, m), 2.19-2.13 (6H, m), 2.08-1.91 (10H, m), 1.87-1.65 (4H, m).

Calcd for C$_{63}$H$_{83}$N$_5$O$_{26}$: [M+Na]$^+$ 1349, Found 1349.

(37H) Synthesis of [(2R,3R,4R,5R,6R)-5-acet-amide-6-[3-[[(3S)-4-[3-[(2R,3R,4R,5R,6R)-3-acet-amide-4,5-diacetoxy-6-(acetoxymethyl)tetrahydro-pyran-2-yl]oxypropylamino]-3-[[(2R)-3-[bis(4-methoxyphenyl)-phenyl-methoxy]-2-[2-cyanoethoxy-(diisopropylamino)phosphanyl]oxy-propoxy]carbonylamino]-4-oxo-butanoyl]amino] propoxy]-3,4-diacetoxy-tetrahydropyran-2-yl]methyl acetate (Compound 37H)

Reference Example 38

(38A) Synthesis of benzyl N-[3-[(2R,3R,4R,5R,6R)-3-acetamide-4,5-dihydroxy-6-(hydroxymethyl)tetrahydropyran-2-yl]oxypropyl]carbamate (Compound 38A)

[Formula 168]

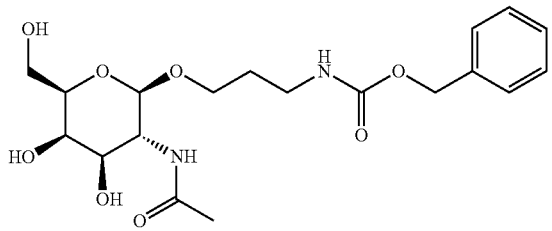

[Formula 167]

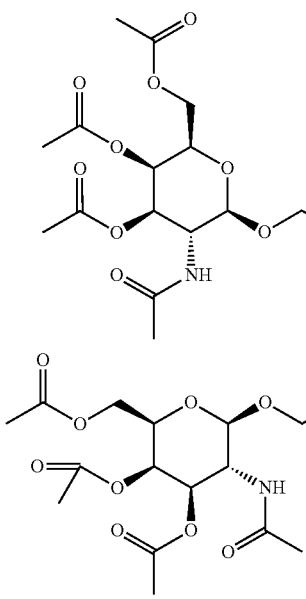

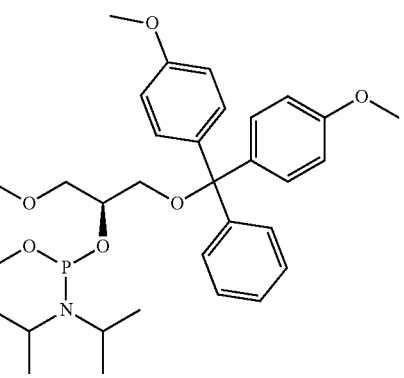

Using the compound synthesized in Step (37G) above (0.63 g, 0.48 mmol), synthesis was performed in the same manner as described in Step (35F) to thereby obtain the compound of interest in an amorphous state (0.52 g, yield 71%).

$^1$H-NMR (CDCl$_3$) δ: 7.45-7.38 (2H, m), 7.34-6.95 (9H, m), 6.88-6.62 (6H, m), 6.18-6.10 (1H, m), 5.39-5.32 (2H, m), 5.24-5.05 (2H, m), 4.69-4.60 (1H, m), 4.52-4.41 (2H, m), 4.34-2.90 (32H, m), 2.68-2.42 (3H, m), 2.20-2.14 (6H, m), 2.09-1.91 (18H, m), 1.87-1.66 (4H, m), 1.21-0.97 (12H, m).

To a suspension of the compound synthesized in Step (37A) (12.4 g, 23 mmol) in ethyl alcohol (200 ml), 28% sodium methoxide methanol solution (0.85 ml) was added and stirred at room temperature. As the reaction proceeds, the reaction solution once becomes a clear solution. When the solution was left for 60 min, precipitate was obtained. The precipitate was filtered, washed with ethyl alcohol and diisopropyl ether, and then dried under vacuum to thereby obtain a crude product (10 g) containing the compound of interest (38A) as solid. This crude product was used in the subsequent reaction without further purification. 1H-NMR (DMSO-D$_6$) δ: 7.60 (1H, d, J=9.1 Hz), 7.40-7.17 (5H, m), 5.01 (2H, s), 4.62-4.55 (2H, m), 4.49 (1H, d, J=4.2 Hz), 4.20 (1H, d, J=8.5 Hz), 3.76-3.27 (6H, m), 3.08-2.99 (2H, m), 1.81 (3H, s), 1.66-1.56 (2H, m).

Calcd for C$_{19}$H$_{28}$N$_2$O$_8$: [M+Na]$^+$ 435, Found 435.

(38B) Synthesis of N-[(2R,3R,4R,5R,6R)-2-(3-aminopropoxy)-4,5-dihydroxy-6-(hydroxymethyl)tetrahydropyran-3-yl]acetamide hydrochloride (Compound 38B)

[Formula 169]

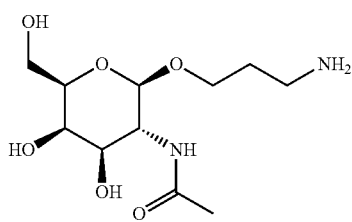

The compound synthesized in Step (38A) (22.8 g, 55.3 mmol) was dissolved in tetrahydrofuran (280 ml)/1 N hydrochloric acid (61 ml). 10% Palladium/carbon (wet) (5.56 g) was added thereto and stirred vigorously at room temperature under a hydrogen atmosphere for 3.5 hrs. After completion of the reaction, the reaction solution was filtered. The resultant filtrate was distilled off under vacuum. After addition of an appropriate amount of ethyl alcohol, the generated solid matter was filtered, washed with ethyl alcohol and diethyl ether, and then dried under vacuum to thereby obtain a crude product (17 g) containing the compound of interest (38B). This crude product was used in the subsequent reaction without further purification. 1H-NMR (D$_2$O) δ: 4.27 (1H, d, J=8.5 Hz), 3.90-3.50 (8H, m), 2.93 (2H, t, J=7.0 Hz), 1.89 (3H, s), 1.82-1.75 (2H, m).

(38C) Synthesis of 9H-fluoren-9-ylmethyl N-[3-[(2R,3R,4R,5R,6R)-3-acetamide-4,5-dihydroxy-6-(hydroxymethyl)tetrahydropyran-2-yl]oxypropyl]carbamate (Compound 38C)

[Formula 170]

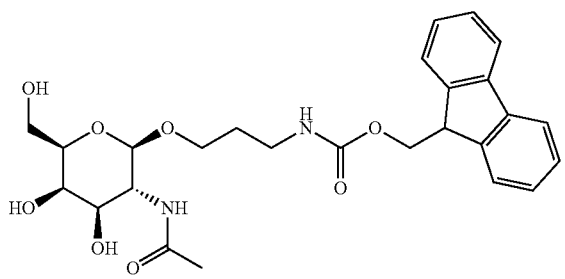

The compound synthesized in Step (38B) above (16.4 g, 52.1 mmol) was dissolved in tetrahydrofuran (200 ml)/purified water (50 ml), and N,N-diisopropylethylamine (12.7 ml, 72.9 mmol) was added thereto. Under ice cooling, N-[(9H-fluoren-9-ylmethoxy)carbonyloxy]succinimide (21.1 g, 62.5 mmol) was added to the mixed solution, which was then stirred at room temperature for 1.5 hrs. After completion of the reaction, the solvent was distilled off under vacuum. Diethyl ether (100 ml) was added and stirred for 1 hr. The resultant solid matter was washed with ethyl alcohol, ethyl acetate and diethyl ether in this order, and then dried under vacuum to thereby obtain a crude product (22.9 g) containing the compound of interest (38C).

1H-NMR (DMSO-D$_6$) δ: 7.89 (2H, d, J=7.3 Hz), 7.69 (2H, d, J=7.3 Hz), 7.61 (1H, d, J=9.1 Hz), 7.42 (2H, t, J=7.3 Hz), 7.33 (2H, t, J=7.3 Hz), 7.24 (1H, t, J=5.7 Hz), 4.60-4.57 (2H, m), 4.49 (1H, d, J=4.2 Hz), 4.31-4.18 (4H, m), 3.76-3.28 (8H, m), 3.05-2.97 (2H, m), 1.81 (3H, s), 1.62-1.57 (2H, m).

Calcd for C$_{26}$H$_{32}$N$_2$O$_8$: [M+Na]$^+$ 523, Found 523.

(38D) Synthesis of [(2R,3R,4R,5R,6R)-5-acetamide-4-acetoxy-2-[[bis(4-methoxyphenyl)-phenylmethoxy]methyl]-6-[3-(9H-fluoren-9-ylmethoxycarbonylamino)propoxy]tetrahydropyran-3-yl] acetate (Compound 38D)

[Formula 171]

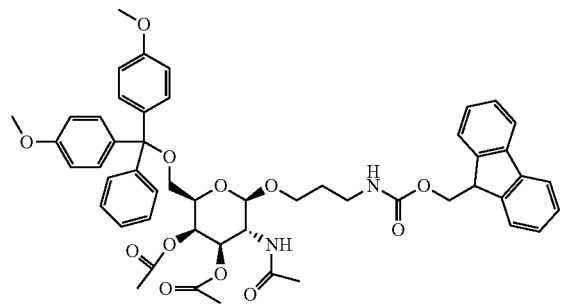

To a suspension of the compound synthesized in Step (38C) above (1.56 g, 3.1 mmol) in pyridine (20 ml), 4,4'-dimethoxytrityl chloride (1.27 g, 3.7 mmol) was added and stirred at room temperature for 30 min. Subsequently, acetic anhydride (1.18 ml, 12.5 mmol) was added and stirred at room temperature for 20 hrs. After completion of the reaction, N,N-diisopropylethylamine (1.1 ml, 6.2 mmol) and ethyl alcohol (2 ml) were added. The solvent was distilled off under vacuum to obtain a crude product. This product was purified by silica gel column chromatography (hexane: ethyl acetate=75:25-0:100, v/v, containing 1% triethylamine) to thereby obtain the compound of interest (38D) in an amorphous state (2.8 g, quant.).

1H-NMR (CDCl$_3$) δ: 7.77 (2H, d, J=7.3 Hz), 7.62 (2H, d, J=7.3 Hz), 7.43-7.18 (13H, m), 6.83-6.79 (4H, m), 6.03 (1H, d, J=9.1 Hz), 5.55 (1H, d, J=3.0 Hz), 5.14-5.03 (2H, m), 4.46-4.43 (3H, m), 4.24-4.04 (2H, m), 3.97-3.91 (1H, m), 3.85-3.82 (1H, m), 3.77 (6H, s), 3.72-3.71 (1H, m), 3.54-3.33 (3H, m), 3.09-3.04 (2H, m), 2.03 (3H, s), 1.89 (6H, s), 1.65-1.56 (2H, m).

Calcd for C52H$_{55}$NO$_{12}$: [M+Na]$^+$ 908, Found 909.

(38E) Synthesis of [(2R,3R,4R,5R,6R)-5-acetamide-4-acetoxy-6-(3-aminopropoxy)-2-[[bis(4-methoxyphenyl)-phenyl-methoxy]methyl]tetrahydropyran-3-yl] acetate (Compound 38E)

[Formula 172]

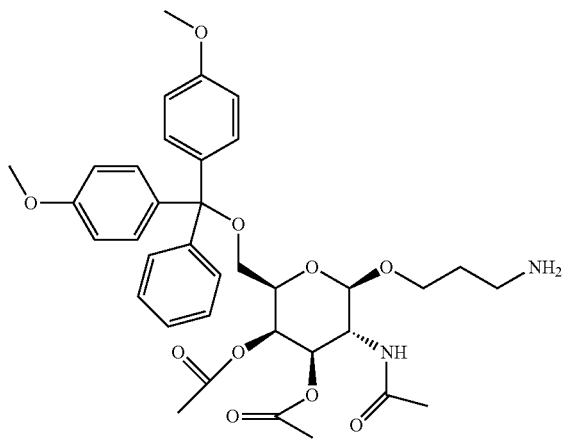

To a dichloromethane solution (8 ml) of the compound synthesized in Step (38D) above (2.49 g, 2.8 mmol), piperidine (0.45 ml, 4.5 mmol) was added and stirred at room temperature. When the reaction was not completed, piperidine was added further appropriately. After completion of the reaction, the solvent was distilled off under vacuum to obtain a crude product. This product was purified by NH-silica gel column chromatography (dichloromethane:methanol=100:0-85:15, v/v) to thereby obtain the compound of interest (38E) in an amorphous state (1.48 g, yield 79%).

$^1$H-NMR (CDCl$_3$) δ: 7.39-7.18 (9H, m), 6.83-6.80 (4H, m), 5.55 (1H, d, J=3.0 Hz), 5.51 (1H, d, J=9.1 Hz), 5.27 (1H, dd, J=11.2, 3.3 Hz), 4.64 (1H, d, J=8.5 Hz), 3.98-3.90 (2H, m), 3.84-3.82 (1H, m), 3.79 (6H, s), 3.75-3.74 (1H, m), 3.58-3.56 (1H, m), 3.35 (1H, dd, J=9.1, 5.4 Hz), 3.07 (1H, t, J=8.5 Hz), 2.82-2.74 (4H, m), 2.01 (3H, s), 1.96 (3H, s), 1.89 (3H, s), 1.74-1.69 (2H, m).

Calcd for C$_{37}$H$_{45}$NO$_{10}$: [M+Na]$^+$ 687, Found 687.

Reference Example 39

(39A) Synthesis of benzyl 2-[[2-benzyloxy-3-[(2-benzyloxy-2-oxo-ethyl)carbamoyloxy]propoxy]carbonylamino]acetate (Compound 39A)

[Formula 173]

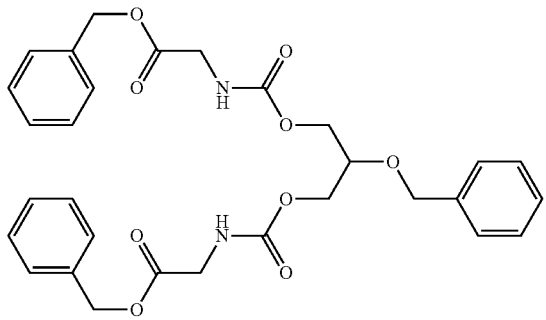

2-Benzyloxy-1,3-propanediol (2.5 g, 14 mmol) and chloroformic acid 4-nitrophenyl ester (5.8 g, 29 mmol) were dissolved in tetrahydrofuran (100 ml), and pyridine (5.0 ml, 61.8 mmol) was added thereto. The resultant mixture was stirred at room temperature for 20 min. The deposited solid matter was filtered, and then tetrahydrofuran (70 ml) was added. Subsequently, glycine benzyl ester trifluoroacetate (9.2 g, 33 mmol) and N,N-diisopropylethylamine (9.6 ml, 55 mmol) were added and stirred at room temperature overnight. After completion of the reaction, the solvent was distilled off under vacuum to obtain a crude product. This product was purified by silica gel column chromatography (hexane:ethyl acetate=100:0-40:60, v/v) to thereby obtain a gum-like compound of interest (39A) (6.5 g, yield 84%).

1H-NMR (CDCl$_3$) δ: 7.37-7.33 (15H, m), 5.48 (2H, t, J=5.4 Hz), 5.18 (4H, s), 4.64 (2H, s), 4.23 (4H, d, J=5.4 Hz), 3.99 (4H, d, J=5.4 Hz), 3.84 (1H, t, J=5.4 Hz).

Calcd for C$_{30}$H$_{32}$N$_2$O$_9$: [M+H]$^+$ 565, Found 565, [M+Na]$^+$ 587, Found 587

(39B) Synthesis of 2-[[3-(carboxymethylcarbamoyloxy)-2-hydroxy-propoxy]carbonylamino]acetate (Compound 39B)

[Formula 174]

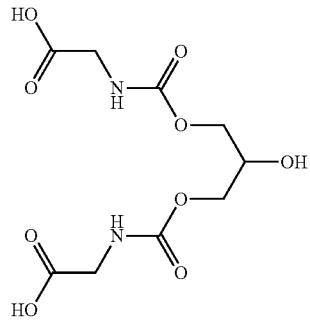

Compound 39A (7.3 g, 2.8 mmol) synthesized in Step (39A) above was dissolved in tetrahydrofuran (200 ml)/purified water (50 ml). 20% Palladium hydroxide/active carbon (moisture content: approx. 50%) (3 g) was added and stirred vigorously at room temperature under a hydrogen atmosphere for 5 hrs. After completion of the reaction, the reaction mixture was filtered. The resultant filtrate was distilled off under vacuum to obtain a crude product (3.2 g) containing the compound of interest (39B). This crude product was used in the subsequent reaction without further purification.

1H-NMR (D$_2$O) δ: 4.21-4.14 (5H, m), 3.86 (4H, s).

(39C) Synthesis of [(2R,3R,4R,5R,6R)-5-acet-
amide-6-[3-[[2-[[3-[[2-[3-[(2R,3R,4R,5R,6R)-3-
acetamide-4,5-diacetoxy-6-[[bis(4-methoxyphenyl)-
phenyl-1-methoxy]methyl]tetrahydropyran-2-yl]
oxypropylamino]-2-oxo-ethyl]carbamoyloxy]-2-
hydroxy-propoxy]carbonylamino]acetyl]amino]
propoxy]-4-acetoxy-2-[[bis(4-methoxyphenyl)-
phenyl-methoxy]methyl]tetrahydropyran-3-yl]
acetate (Compound 39C)

[Formula 175]

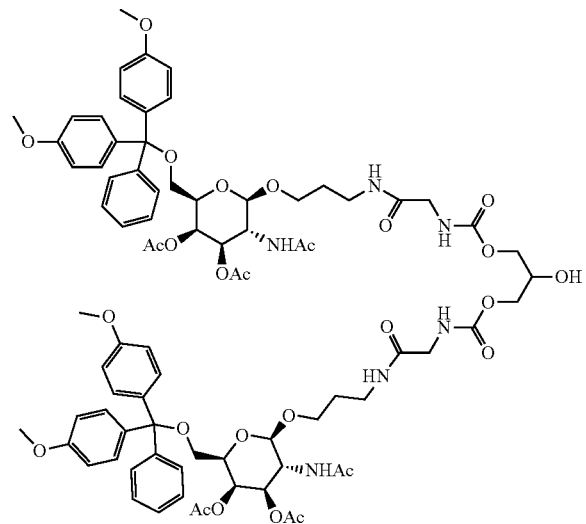

To an N,N-dimethylformamide solution (9 ml) of Compound 39B (0.31 g, 1.05 mmol) synthesized in Step (39B), Compound 38E (1.47 g, 2.21 mmol) synthesized in Step (38E) and N,N-diisopropylethylamine (0.91 ml, 5.27 mmol), 1-[bis(dimethylamino)methylene]-1H-1,2,3-triazolo[4,5-b]pyridinium 3-oxide hexafluorophosphate (11.3 g, 29.6 mmol) was added and stirred at room temperature for 3 hrs. After completion of the reaction, the reaction solution was added dropwise to diethyl ether (total 185 ml). After removal of the solvent (supernatant), a gelatinous crude product was obtained. This product was purified by silica gel column chromatography (dichloromethane:methanol=100:0-15:85, v/v, containing 1% triethylamine) to thereby obtain the compound of interest (39C) as a solid (1.05 g, yield 63%).

1H-NMR (CDCl$_3$) δ: 7.39-7.17 (18H, m), 6.83-6.80 (8H, m), 6.70-6.27 (2H, m), 5.56-5.54 (2H, m), 5.10 (2H, d, J=10.9 Hz), 4.49-3.02 (44H, m), 2.01 (6H, s), 1.96 (6H, s), 1.90 (6H, s), 1.80-1.63 (4H, m).

Calcd for $C_{81}H_{98}N_6O_{27}$: [M+Na]$^+$ 1611, Found 1611

(39D) Synthesis of [(2R,3R,4R,5R,6R)-5-acet-
amide-6-[3-[[2-[[3-[[2-[3-[(2R,3R,4R,5R,6R)-3-
acetamide-4,5-diacetoxy-6-[[bis(4-methoxyphenyl)-
phenyl-methoxy]methyl]tetrahydropyran-2-yl]
oxypropylamino]-2-oxo-ethyl]carbamoyloxy]-2-[2-
cyanoethoxy-(diisopropylamino)phosphanyl]oxy-
propoxy]carbonylamino]acetyl]amio]propoxy]-4-
acetoxy-2-[[bis(4-methoxyphenyl)-phenyl-methoxy]
methyl]tetrahydropyran-3-yl] acetate (Compound
39D)

[Formula 176]

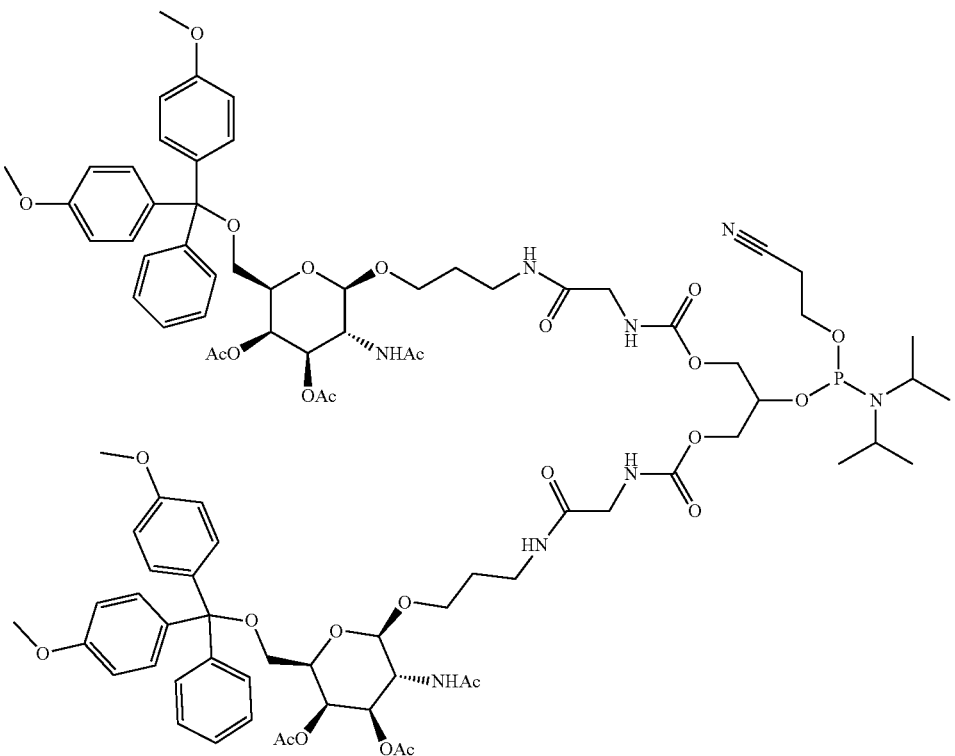

Compound 39C (0.47 g, 0.30 mmol) synthesized in Step (39C) above was azeotropically distilled with an appropriate amount of ethyl acetate/toluene (1/1) and then dissolved in dichloromethane (3 ml). N,N-Diisopropylethylamine (210 µl, 1.18 mmol) and 2-cyanoethyl diisopropylchlorophosphoramidite (79 µl, 0.36 mmol) were added and stirred at room temperature for 1 hr. Further, 2-cyanoethyl diisopropylchlorophosphoramidite (20 µl, 0.09 mmol) was added and stirred at room temperature for 15 min. After completion of the reaction, the solvent was distilled off under vacuum to obtain a crude product. This product was purified by silica gel column chromatography (ethyl acetate:methanol=100:0-85:15, v/v, containing 1% triethylamine) to thereby obtain the compound of interest (39D) in an amorphous state (0.34 g, yield 64%).

1H-NMR (CDCl$_3$) δ: 7.39-7.17 (18H, m), 6.87-6.70 (8H, m), 6.29-6.06 (2H, m), 5.55 (2H, d, J=3.0 Hz), 5.11 (2H, d, J=10.9 Hz), 4.47-3.02 (47H, m), 2.63 (2H, t, J=6.3 Hz), 2.02 (6H, s), 1.96 (6H, s), 1.90 (6H, s), 1.80-1.64 (4H, m), 1.17 (12H, d, J=6.7 Hz).

Reference Example 40

(40A) Synthesis of benzyl 2-[[3-benzyloxy-2-[(2-benzyloxy-2-oxo-ethyl)carbamoyloxy]propoxy]carbonylamino]acetate (Compound 40A)

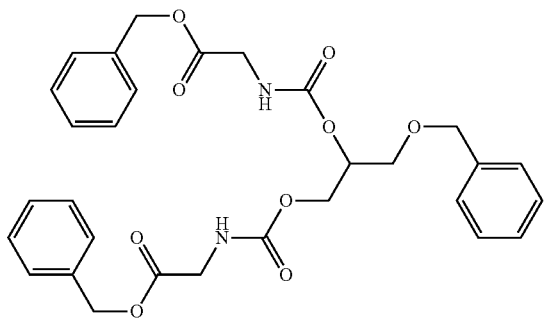

[Formula 177]

Synthesis was performed in the same manner as described in Step (39A), except that (+/−)-3-benzyloxy-1,2-propanediol (1.0 g, 5.5 mmol) was used instead of 2-benzyloxy-1,3-propanediol. As a result, Compound 40A was obtained (2.8 g, yield 90%).

1H-NMR (CDCl$_3$) δ: 7.39-7.30 (15H, m), 5.37-5.35 (2H, m), 5.17-5.12 (5H, m), 4.56-4.51 (2H, m), 4.33-4.30 (2H, m), 4.03-3.94 (4H, m), 3.61 (2H, d, J=5.4 Hz).

Calcd for C$_{30}$H$_{32}$N$_2$O$_9$: [M+Na]$^+$ 587, Found 587

(40B) Synthesis of 2-[[2-(carboxymethylcarbamoyloxy)-3-hydroxy-propoxy]carbonylamino]acetate (Compound 40B)

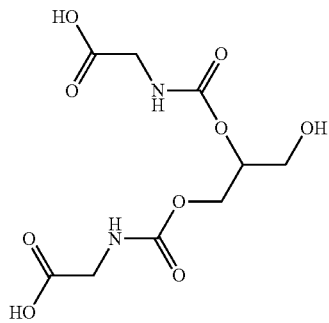

[Formula 178]

Synthesis was performed in the same manner as described in Step (39B), except that Compound 40A (2.8 g, 5.0 mmol) was used instead of Compound 39A. As a result, a crude product (1.2 g) containing Compound 40B was obtained 1H-NMR (D$_2$O) δ: 4.32-4.19 (3H, m), 3.94-3.87 (4H, m), 3.81-3.71 (2H, m). (40C) Synthesis of [(2R,3R,4R,5R,6R)-5-acetamide-6-[3-[[2-[[2-[[2-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-2-oxo-ethyl]carbamoyloxy]-3-hydroxy-propoxy]carbonylamino]acetyl]amino]propoxy]-4-acetoxy-2-[[bis(4-methoxyphenyl)-phenyl-1-methoxy]methyl]tetrahydropyran-3-yl] acetate (Compound 40C)

[Formula 179]

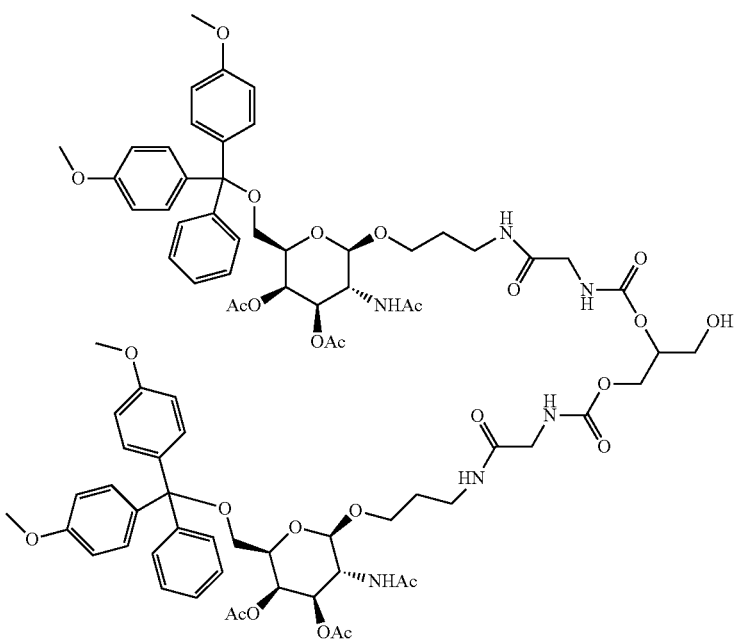

Synthesis was performed in the same manner as described in Step (39C), except that Compound 40B (0.31 g, 1.05 mmol) was used instead of Compound 39B. As a result, Compound 40C was obtained (0.74 g, yield 44%).

1H-NMR (CDCl$_3$) δ: 7.40-7.18 (18H, m), 6.81 (8H, dd, J=9.1, 3.0 Hz), 6.70-6.50 (1H, m), 6.16-6.02 (1H, m), 5.56-5.54 (2H, br), 5.11-5.00 (2H, m), 4.53-2.99 (44H, m), 2.01 (6H, s), 1.95 (6H, s), 1.88 (6H, s), 1.77-1.68 (4H, m)

Calcd for $C_{81}H_{98}N_6O_{27}$: [M+Na]$^+$ 1611, Found 1611

(40D) Synthesis of [(2R,3R,4R,5R,6R)-5-acetamide-6-[3-[[2-[[2-[[2-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-2-oxo-ethyl]carbamoyloxy]-3-[2-cyanoethoxy-(diisopropylamino)phosphanyl]oxy-propoxy]carbonylamino]acetyl]amino]propoxy]-4-acetoxy-2-[[bis(4-methoxyphenyl)-phenyl-methoxy]methyl]tetrahydropyran-3-yl]acetate (Compound 40D)

[Formula 180]

Synthesis was performed in the same manner as described in Step (39D), except that Compound 40C (0.31 g, 1.05 mmol) was used instead of Compound 39C. As a result, Compound 40D was obtained (0.60 g, yield 72%).

1H-NMR (CDCl$_3$) δ: 7.38-7.18 (18H, m), 7.13-6.97 (1H, m), 6.83-6.81 (8H, m), 6.58-6.36 (1H, m), 5.56-5.52 (2H, m), 5.10-5.04 (2H, m), 4.46-2.97 (47H, m), 2.65-2.63 (2H, m), 2.02 (6H, s), 1.95 (3H, s), 1.94 (3H, s), 1.90 (3H, s), 1.89 (3H, s), 1.77-1.67 (4H, m), 1.20-1.16 (12H, m)

Example 131

HO—$X^{16}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H) (SEQ ID NO: 40)

Synthesis was performed in the same manner as described in Example 91, except that the X portion was substituted with $X^{16}$. As regards $X^{16}$, Compound 36G synthesized in Reference Example 36 was used and condensed once.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6261.97).

Example 132

HO—$X^{15}$—$X^{15}$—$X^{15}$-$A^{m1s}$-$A^{e2s}$-$U^{m1s}$—$C^{m1s}$-$c^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 40)

Synthesis was performed in the same manner as described in Example 91, except that the X portion was substituted with $X^{15}$. As regards $X^{15}$, Compound 35F synthesized in Reference Example 35 was used and condensed 3 times.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6917.09).

Example 133

$X^{18}$-$A^{m1s}$-$A^{e2s}$-$U^{m1s}$—$C^{m1s}$-$C^{e2s}$-$G^{m1s}$-$A^{m1s}$-$G^{m1s}$-$A^{m1s}$-$A^{e2s}$-$G^{m1t}$-H (SEQ ID NO: 40)

Synthesis was performed in the same manner as described in Example 91, except that the X portion was substituted with $X^{18}$. As regards $X^{18}$, Compound 39D synthesized in Reference Example 39 was used and condensed once.

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6247.96).

Example 134

HO—$X^{15}$—$X^{15}$—$X^{15}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 169)

Synthesis was performed in the same manner as described in Example 132, except that the above-described sequence (designation: 15e_005.1) was used instead of the sequence used therein.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6919.09).

Example 135

HO—$X^{15}$—$X^{15}$—$X^{15}$—$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-$C^{e2s}$—$U^{m1t}$—H (SEQ ID NO: 170)

Synthesis was performed in the same manner as described in Example 132, except that the above-described sequence (designation: 15e_006.1) was used instead of the sequence used therein.

The nucleotide sequence of the subject compound is complementary to a sequence from the 90$^{th}$ to the 104$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6884.07).

Example 136

HO—$X^{15}$—$X^5$-$X^5$$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 42)

Synthesis was performed in the same manner as described in Example 132, except that the above-described sequence (designation: 16e_001) was used instead of the sequence used therein.

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 7276.10)

Example 137

HO—$X^1$—$X^1$—$X^1$-$A^{m1s}$-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 46)

Synthesis was performed in the same manner as described in Example 132, except that the above-described sequence (designation: 17e_001) was used instead of the sequence used therein.

Example 138

$X^{18}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 171)

Synthesis was performed in the same manner as described in Example 133, except that the above-described sequence (designation: 15e_005.1) was used instead of the sequence used therein.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6250.00).

Example 139

$X^{18}$—$U^{m1s}$—$C^{m1s}$-$C^{e2s}$-$G^{m1s}$-$A^{m1s}$-$A^{e2s}$-$G^{m1s}$-$C^{e2s}$—$U^{m1t}$H (SEQ ID NO: 172)

Synthesis was performed in the same manner as described in Example 133, except that the above-described sequence (designation: 15e_006.1) was used instead of the sequence used therein.

The nucleotide sequence of the subject compound is complementary to a sequence from the $90^{th}$ to the $104^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6214.96).

Example 140

$X^{18}$-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 42)

Synthesis was performed in the same manner as described in Example 133, except that the above-described sequence (designation: 16e_001) was used instead of the sequence used therein.

The nucleotide sequence of the subject compound is complementary to a sequence from the $92^{nd}$ to the $107^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6607.02).

The nucleotide sequence of the subject compound is complementary to a sequence from the $92^{nd}$ to the $108^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 7636.19)

Example 141

$X^{18}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 47)

Synthesis was performed in the same manner as described in Example 133, except that the above-described sequence (designation: 16e_002) was used instead of the sequence used therein.

The nucleotide sequence of the subject compound is complementary to a sequence from the $91^{st}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6609.03).

Example 142

$X^{18}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H (SEQ ID NO: 48)

Synthesis was performed in the same manner as described in Example 133, except that the above-described sequence (designation: 16e_003) was used instead of the sequence used therein.

The nucleotide sequence of the subject compound is complementary to a sequence from the $90^{th}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6586.00).

Example 143

$X^{18}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H (SEQ ID NO: 173)

Synthesis was performed in the same manner as described in Example 133, except that the above-described sequence (designation: 15e_001.5) was used instead of the sequence used therein.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6233.97).

Example 144

$X^{18}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 174)

Synthesis was performed in the same manner as described in Example 133, except that the above-described sequence (designation: 15e_005.5) was used instead of the sequence used therein.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6235.97).

Example 145

$X^{18}$—$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H (SEQ ID NO: 175)

Synthesis was performed in the same manner as described in Example 133, except that the above-described sequence (designation: 15e_006.5) was used instead of the sequence used therein.

The nucleotide sequence of the subject compound is complementary to a sequence from the $90^{th}$ to the $104^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6200.94).

Example 146

$X^{18}$-$A^{m1s}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H (SEQ ID NO: 176)

Synthesis was performed in the same manner as described in Example 133, except that the above-described sequence (designation: 16e_001.5) was used instead of the sequence used therein.

The nucleotide sequence of the subject compound is complementary to a sequence from the $92^{nd}$ to the $107^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6593.02).

Example 147

$X^{18}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 177)

Synthesis was performed in the same manner as described in Example 133, except that the above-described sequence (designation: 16e_002.5) was used instead of the sequence used therein.

The nucleotide sequence of the subject compound is complementary to a sequence from the $91^{st}$ to the $106^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6595.01).

Example 148

$X^{18}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H (SEQ ID NO: 178)

Synthesis was performed in the same manner as described in Example 133, except that the above-described sequence (designation: 16e_003.5) was used instead of the sequence used therein.

The nucleotide sequence of the subject compound is complementary to a sequence from the $90^{th}$ to the $105^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6571.98).

Example 149

HO—$X^{16}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H (SEQ ID NO: 173)

Synthesis was performed in the same manner as described in Example 131, except that the above-described sequence (designation: 15e_001.5) was used instead of the sequence used therein.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6247.99).

Example 150

$X^{19}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 40)

Synthesis was performed in the same manner as described in Example 91, except that the X portion was substituted with $X^{19}$. As regards $X^{19}$, Compound 40D synthesized in Reference Example 40 was used and condensed once.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6247.99).

Example 151

$X^{17}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H (SEQ ID NO: 40)

Synthesis was performed in the same manner as described in Example 91, except that the X portion was substituted with $X^{17}$. As regards $X^{17}$, Compound 37H synthesized in Reference Example 37 was used and condensed once.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of Homo sapiens glucose-6-phosphatase catalytic subunit (G6PC), transcript variant 1, mRNA (NCBI-GenBank accession No. NM_000151.3) is mutated from G to T. The compound was Reference Example 41

(41A) Synthesis of 3-[[2-benzyloxy-3-[(3-benzyloxy-3-oxo-propyl)carbamoyloxy]propoxy]carbonylamino] propanoic acid benzyl ester (Compound 41A)

[Formula 181]

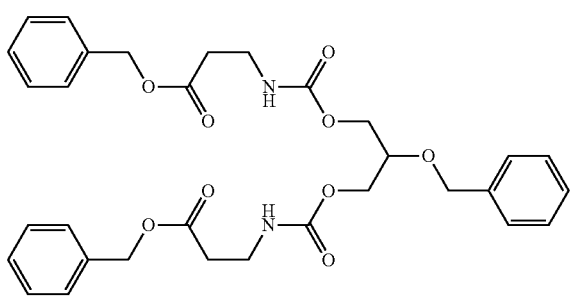

Synthesis was performed in the same manner as described in Step (39A), except that 3-aminopropionic acid benzyl ester trifluoroacetate (2.4 g, 8.17 mmol) was used instead of glycine benzyl ester trifluoroacetate used in Step (39A). As a result, Compound 41A was obtained (1.62 g, yield 80%).

1H-NMR (CDCl3) δ: 7.39-7.27 (15H, m), 5.21 (2H, br s), 5.14 (4H, s), 4.63 (2H, s), 4.24-4.10 (4H, m), 3.79-3.74 (1H, m), 3.48-3.44 (4H, m), 2.59 (4H, t, J=6.0 Hz). Calcd for $C_{32}H_{36}N_2O_9$: $[M+H]^+$ 593, Found 593, $[M+Na]^+$ 615, Found 615

(41B) Synthesis of 3-[[3-(2-carboxyethylcarbamoyloxy)-2-hydroxy-propoxy]carbonylamino]propanoate (Compound 41B)

[Formula 182]

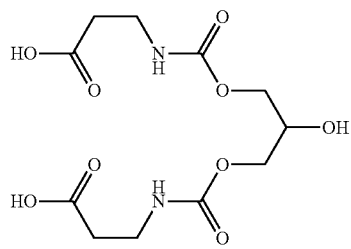

Synthesis was performed in the same manner as described in Step (39B), except that Compound 41A (1.62 g, 2.73 mmol) was used instead of Compound 39A used in Step (39B).

As a result, Compound 41B was obtained (0.89 g, quant).

1H-NMR (D2O) δ: 4.22-4.04 (5H, m), 3.46-3.32 (4H, m), 2.57 (4H, t, J=6.7 Hz).

(41C) Synthesis of [(2R,3R,4R,5R,6R)-5-acetamide-6-[3-[3-[[3-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-3-oxo-propyl]carbamoyloxy]-2-hydroxy-propoxy]carbonylamino]propanoylamino]propoxy]-4-acetoxy-2-[[bis(4-methoxyphenyl)-phenyl-methoxy]methyl]tetrahydropyran-3-yl]acetate (Compound 41C)

[Formula 183]

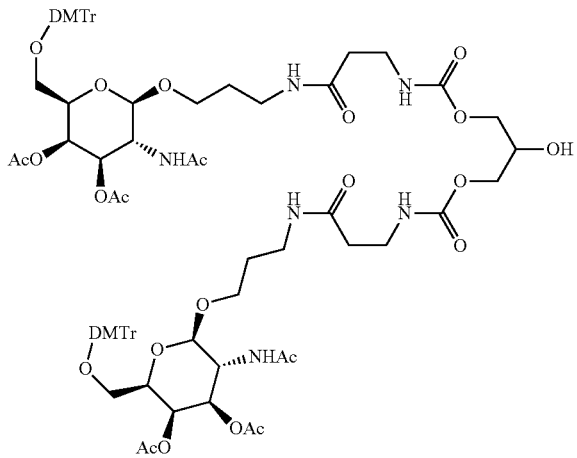

Synthesis was performed in the same manner as in Step (39C), except that Compound 41B (300 mg, 0.93 mmol) was used instead of Compound 39B used in Step (39C). As a result, Compound 41C was obtained (950 mg, yield 63%).

1H-NMR (CDCl3) δ: 7.32-7.24 (18H, m), 6.82-6.80 (8H, m), 6.64-6.61 (1H, br), 6.27-6.24 (1H, br), 5.91-5.88 (1H, br), 5.56 (2H, d, J=3.0 Hz), 5.10 (2H, d, J=11.5 Hz), 4.46-3.05 (43H, m), 2.47-2.37 (4H, m), 2.02 (6H, s), 1.98 (6H, s), 1.90 (6H, s), 1.78-1.67 (4H, m).

Calcd for $C_{83}H_{102}N_6O_{27}$: $[M+Na]^+$ 1638, Found 1638

(41D) Synthesis of [(2R,3R,4R,5R,6R)-5-acetamide-6-[3-[3-[[3-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-3-oxo-propyl]carbamoyloxy]-2-[2-cyanoethoxy-(diisopropylamino)phosphanyl1]oxy-propoxy]carbonylamino]propanoylamino]propoxy]-4-acetoxy-2-[[bis(4-methoxyphenyl)-phenyl-methoxy]methyl]tetrahydropyran-3-yl]acetate (Compound 41D)

[Formula 184]

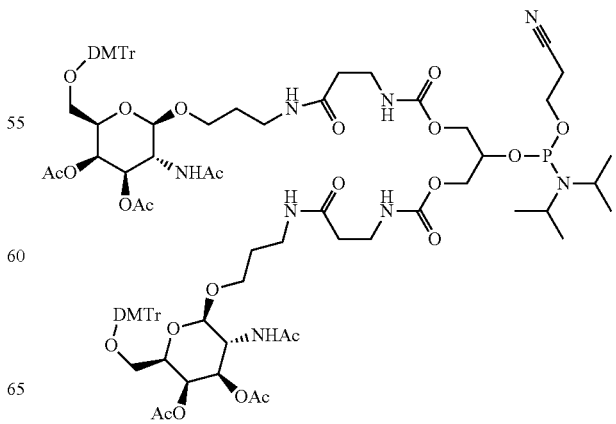

Synthesis was performed in the same manner as described in Step (39D), except that Compound 41C (945 mg, 0.58 mmol) was used instead of Compound 39C used in Step (39D). As a result, Compound 41D was obtained (638 mg, yield 60%).

1H-NMR (CDCl$_3$) δ: 7.39-7.18 (18H, m), 6.85-6.78 (8H, m), 6.73-6.64 (1H, m), 6.40-6.23 (1H, m), 5.83-5.72 (1H, m), 5.56 (2H, d, J=3.0 Hz), 5.13-5.04 (2H, m), 4.45-4.35 (2H, m), 4.22-3.30 (40H, m), 3.22-3.03 (4H, m), 2.64 (2H, t, J=6.0 Hz), 2.54-2.32 (4H, m), 2.02 (6H, s), 2.00-1.95 (6H, m), 1.90 (6H, s), 1.83-1.59 (4H, m), 1.20-1.10 (12H, m).

Reference Example 42

(42A) Synthesis of 4-[[2-benzyloxy-3-[(4-benzyloxy-4-oxo-butyl)carbamoyloxy]propoxy]carbonylamino]butanoic acid benzyl ester (Compound 42A)

[Formula 185]

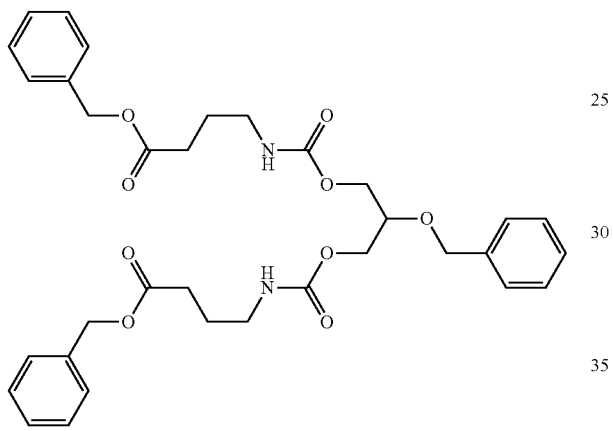

Synthesis was performed in the same manner as described in Step (39A), except that 4-aminobutanoic acid benzyl ester trifluoroacetate (1.30 g, 4.21 mmol) was used instead of glycine benzyl ester trifluoroacetate used in Step (39A). As a result, Compound 42A was obtained (0.85 g, yield 78%).

1H-NMR (CDCl3) δ: 7.38-7.27 (15H, m), 5.11 (4H, s), 4.80 (2H, br s), 4.63 (2H, s), 4.19-4.15 (4H, m), 3.77-3.75 (1H, m), 3.23-3.18 (4H, m), 2.40 (4H, t, J=7.3 Hz), 1.88-1.81 (4H, m).

Calcd for $C_{34}H_4N_2O_9$: [M+H]$^+$ 621, Found 622, [M+Na]$^+$ 643, Found 644

(42B) Synthesis of 4-[[3-(3-carboxypropylcarbamoyloxy)-2-hydroxy-propoxy]carbonylamino]butanoic acid (Compound 42B)

[Formula 186]

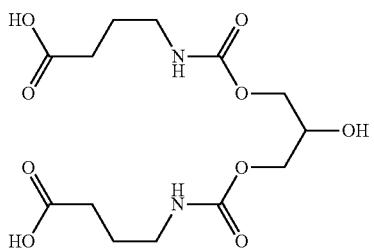

Synthesis was performed in the same manner as described in Step (39B), except that Compound 42A (0.85 g, 1.4 mmol) was used instead of Compound 39A used in Step (39B). As a result, Compound 42B was obtained (0.49 g, quant).

1H-NMR (D2O) δ: 4.19-4.05 (5H, m), 3.19-3.12 (4H, m), 2.36-2.27 (4H, m), 1.83-1.73 (4H, m).

(42C) Synthesis of [(2R,3R,4R,5R,6R)-5-acetamide-6-[3-[4-[[3-[[4-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-4-oxo-butyl]carbamoyloxy]-2-hydroxy-propoxy]carbonylamino]butanoylamino]propoxy]-4-acetoxy-2-[[bis(4-methoxyphenyl)-phenyl-methoxy]methyl]tetrahydropyran-3-yl] acetate (Compound 42C)

[Formula 187]

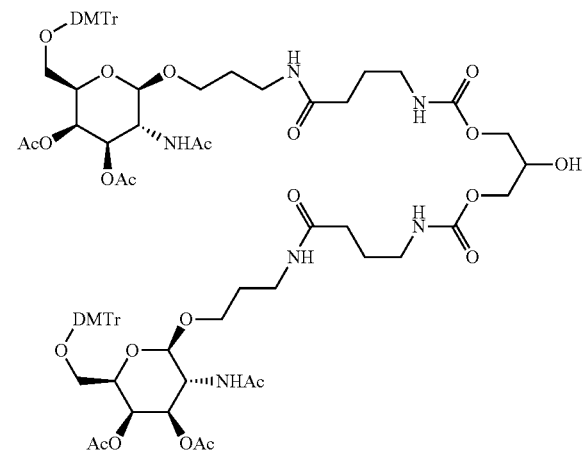

Synthesis was performed in the same manner as described in Step (39C), except that Compound 42B (300 mg, 0.86 mmol) was used instead of Compound 39B used in Step (39C). As a result, Compound 42C was obtained (1.16 g, yield 82%).

1H-NMR (CDCl3) δ: 7.31-7.24 (18H, m), 6.82-6.80 (8H, m), 6.68-6.65 (3H, m), 5.91-5.84 (1H, m), 5.56 (2H, d, J=3.0 Hz), 5.10 (2H, d, J=10.9 Hz), 4.45 (2H, d, J=8.5 Hz), 4.23-3.12 (40H, m), 2.31-2.22 (4H, m), 2.01 (6H, s), 1.98 (6H, s), 1.90 (6H, s), 1.81-1.68 (8H, m).

Calcd for $C85H_{106}N_6O_{27}$: [M+Na]$^+$ 1666, Found 1667

(42D) Synthesis of [(2R,3R,4R,5R,6R)-5-acetamide-6-[3-[3-[[3-[[3-[3-[(2R,3R,4R,5R,6R)-3-acetamide-4,5-diacetoxy-6-[[bis(4-methoxyphenyl)-phenyl-methoxy]methyl]tetrahydropyran-2-yl]oxypropylamino]-4-oxo-butyl]carbamoyloxy]-2-[2-cyanoethoxy-(diisopropylamino)phosphanyl]oxypropoxy]carbonylamino]butanoylamino]propoxy]-4-acetoxy-2-[[bis(4-methoxyphenyl)-phenyl-methoxy]methyl]tetrahydropyran-3-yl]acetate (Compound 42D)

chloric acid (8 ml). 10% Palladium/carbon (wet) (2 g) was added and stirred vigorously at room temperature under a hydrogen atmosphere. After completion of the reaction, the reaction solution was filtered. The resultant filtrate was distilled off under vacuum to thereby obtain a crude product of Compound 43A (3.1 g, yield 97%). This product was used in the subsequent reaction without further purification.

Calcd for $C_{19}H_{32}N_2O_9$: $[M+H]^+$ 433, Found 433.

[Formula 188]

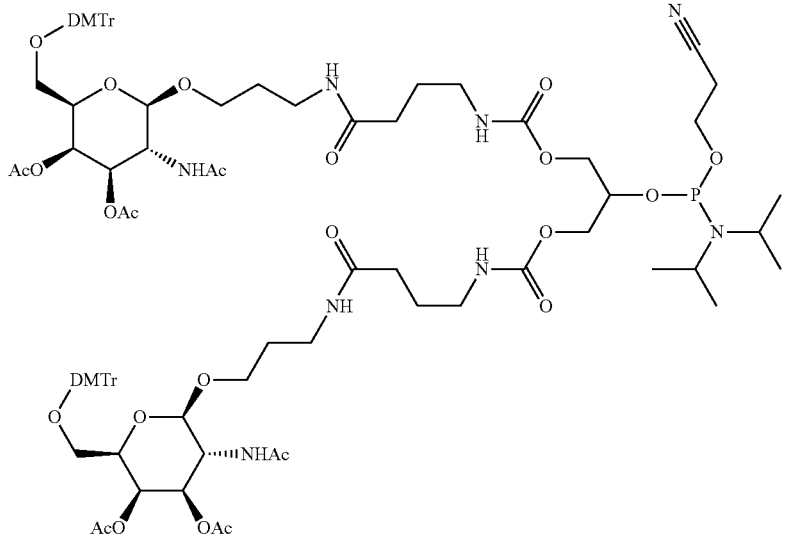

Synthesis was performed in the same manner as described in Step (39D), except that Compound 42C (1.16 g, 0.71 mmol) was used instead of Compound 39C used in Step (39D). As a result, Compound 42D was obtained (795 mg, yield 61%).

1H-NMR (CDCl$_3$) δ: 7.40-7.17 (18H, m), 6.85-6.77 (8H, m), 6.72-5.65 (5H, m), 5.56 (2H, d, J=3.0 Hz), 5.11-5.03 (2H, m), 4.46-4.35 (2H, m), 4.25-3.02 (42H, m), 2.65 (2H, t, J=6.0 Hz), 2.39-2.16 (4H, m), 2.02 (6H, s), 1.99-1.94 (6H, m), 1.90 (6H, s), 1.87-1.59 (8H, m), 1.18 (12H, d, J=6.7 Hz).

Reference Example 43

(43A) Synthesis of [(2R,3R,4R,5R,6R)-5-acetamide-3,4-diacetoxy-6-(5-aminopentoxy)tetrahydropyran-2-yl]methyl acetate hydrochloride (Compound 43A)

[Formula 189]

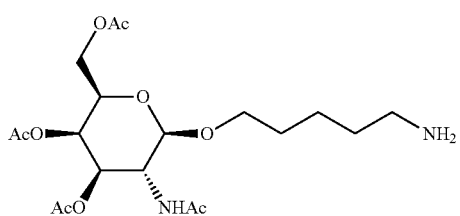

Compound 21A (3.87 g, 6.83 mmol synthesized in Step (21A1 was dissolved in tetrahydropyran (32 ml)/1 N hydro- (43B) Synthesis of [(2R,3R,4R,5R,6R)-5-acetamide-6-[5-[[3-[5-[(2R,3R,4R,5R,6R)-3-acetamide-4,5-diacetoxy-6-(acetoxymethyl)tetrahydropyran-2-yl]oxypentylcarbamoyloxy]-2-benzyloxy-propoxy]carbamoylamino]pentoxy]-3,4-diacetoxy-tetrahydropyran-2-yl]methyl acetate (Compound 43B)

[Formula 190]

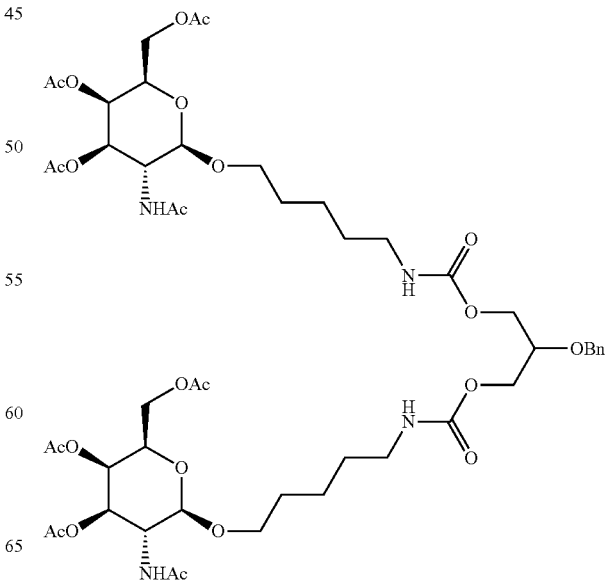

2-Benzyloxy-1,3-propanediol (600 mg, 3.29 mmol) and chloroformic acid 4-nitrophenyl ester (1.39 g, 6.91 mmol) were dissolved in tetrahydrofuran (22 ml), and pyridine (1.1 ml, 13.2 mmol) was added thereto. The resultant mixture was stirred at room temperature for 15 min. The solid matter deposited was filtered, and then tetrahydrofuran (16 ml) was added. Subsequently, a tetrahydrofuran (15 ml)/dichloromethane (5 ml) solution of Compound 43A (3.09 g, 6.59 mmol) synthesized in Step (43A) and N,N-diisopropylethylamine (3.4 ml, 19.8 mmol) were added and stirred at 40° C. for 2 hrs. After completion of the reaction, the solvent was distilled off under vacuum. Dichloromethane was added, and the organic layer was washed with 0.5 N hydrochloric acid, saturated saline, 0.2 N sodium hydroxide aqueous solution and saturated saline, dried over anhydrous sodium sulfate, and filtered. The solvent was distilled off under vacuum to thereby obtain a crude product. This product was purified by silica gel column chromatography (dichloromethane:methanol=100:0-90:10, v/v) to thereby obtain a mixture (2.1 g) mainly containing the compound of interest (43B).

Calcd for $C_{50}H_{74}N_4O_{23}$: $[M+H]^+$ 1099, Found 1099. $[M+Na]^+$ 1121, Found 1121.

(43C) Synthesis of [(2R,3R,4R,5R,6R)-5-acetamide-6-[5-[[3-[5-[(2R,3R,4R,5R,6R)-3-acetamide-4,5-diacetoxy-6-(acetoxymethyl)tetrahydropyran-2-yl]oxypentylcarbamoyloxy]-2-hydroxy-propoxy]carbonylamino]pentoxy]-3,4-diacetoxy-tetrahydropyran-2-yl]methyl acetate (Compound 43C)

[Formula 191]

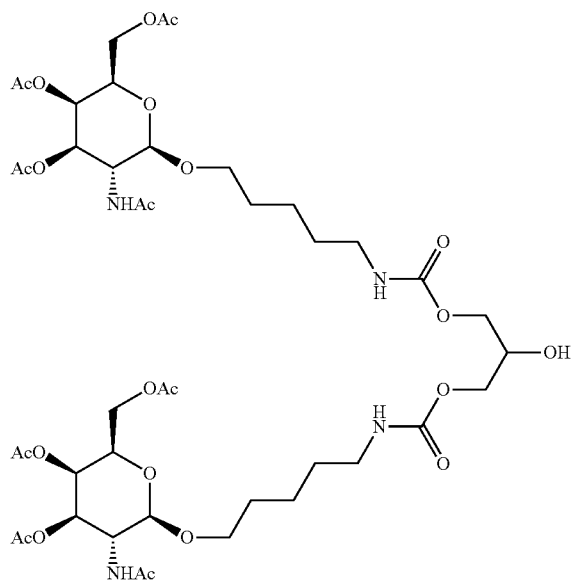

The mixture (2.1 g) containing Compound 43B obtained in Step (43B) above was dissolved in tetrahydropyran (20 ml)/purified water (1 ml). 1 N Hydrochloric acid (0.38 ml) and 10% palladium/carbon (wet) (1 g) were added and stirred vigorously at room temperature under a hydrogen atmosphere. After completion of the reaction, the reaction solution was filtered. The resultant filtrate was distilled off under vacuum to obtain a crude product. This product was purified by silica gel column chromatography (ethyl acetate:methanol=100:0-90:15, v/v) to thereby obtain Compound 43C as a solid (1.38 g, yield 72%).

$^1$H-NMR (CDCl$_3$) δ: 6.10-5.96 (1H, m), 5.38-4.94 (6H, m), 4.70-4.64 (2H, m), 4.23-3.44 (19H, m), 3.20-3.15 (4H, m), 2.15 (6H, s), 2.05 (6H, s), 2.01 (6H, s), 1.97 (6H, s), 1.67-1.38 (12H, m).

Calcd for $C_{43}H_{68}N_4O_{23}$: $[M+H]^+$ 1009, Found 1009. $[M+Na]^+$ 1031, Found 1031.

(43D) Synthesis of [(2R,3R,4R,5R,6R)-5-acetamide-6-[5-[[3-[5-[(2R,3R,4R,5R,6R)-3-acetamide-4,5-diacetoxy-6-(acetoxymethyl)tetrahydropyran-2-yl]oxypentylcarbamoyloxy]-2-[2-cyanoethoxy-(diisopropylamino)phosphanyl]oxy-propoxy]carbamoylamino]pentoxy]-3,4-diacetoxy-tetrahydropyran-2-yl]methyl acetate (Compound 43D)

[Formula 192]

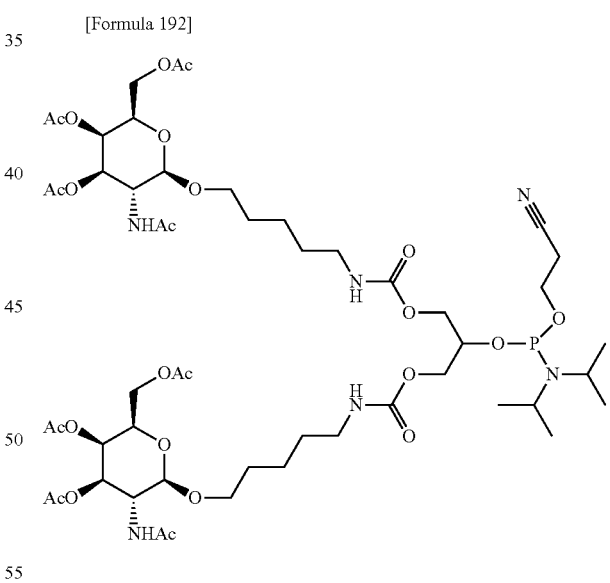

Synthesis was performed in the same manner as described in Step (39D), except that Compound 43C (1.38 g, 1.37 mmol) was used instead of Compound 39C used in Step (39D). As a result, Compound 43D was obtained (850 mg, yield 51%).

$^1$H-NMR (CDCl$_3$) δ: 5.95-5.89 (1H, m), 5.38-5.26 (4H, m), 5.20-5.16 (1H, m), 5.00-4.95 (1H, m), 4.71-4.68 (2H, m), 4.36-3.44 (22H, m), 3.15 (4H, q, J=6.4 Hz), 2.67 (2H, t, J=6.3 Hz), 2.15 (6H, s), 2.05 (6H, s), 2.01 (6H, s), 1.96 (6H, s), 1.67-1.33 (12H, m), 1.18 (12H, d, J=6.7 Hz).

Reference Example 44

(44A) Synthesis of [(2R,3R,4R,5R,6R)-5-acet-amide-6-[3-[3-[[3-[[3-[3-[(2R,3R,4R,5R,6R)-3-acet-amide-4,5-diacetoxy-6-(acetoxymethyl)tetrahydro-pyran-2-yl]oxypropylamino]-3-oxo-propyl]carbamoyloxy]-2-hydroxy-propoxy]carbonylamino]propanoylamino]propoxy]-3,4-diacetoxy-tetrahydropyran-2-yl]methyl acetate (Compound 44A)

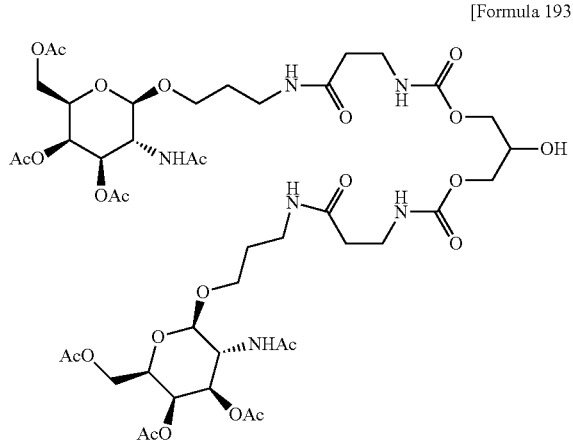 [SMILES: CC(=O)N[C@H]1[C@H](OCCCNC(=O)CCNC(=O)OCC(O)COC(=O)NCCC(=O)NCCCO[C@@H]2O[C@H](COC(C)=O)[C@H](OC(C)=O)[C@H](OC(C)=O)[C@H]2NC(C)=O)O[C@H](COC(C)=O)[C@H](OC(C)=O)[C@@H]1OC(C)=O]

[Formula 193]

To an N,N-dimethylformamide solution (2 ml) of Compound 41B (200 mg, 0.62 mmol) synthesized in Step (41B), O—(N-Succinimidyl)-N,N,N',N'-tetramethyluronium tetrafluoroborate (411 mg, 1.37 mmol) and N,N-diisopropylethylamine (0.32 ml, 1.86 mmol) were added and stirred at room temperature for 20 min. This reaction solution was added to an N,N-dimethylformamide solution (2 ml) of Compound 37B (657 mg, 1.49 mmol) synthesized in Step (37B), and then N,N-diisopropylethylamine (0.32 ml, 1.86 mmol) was added thereto. The resultant mixture was stirred at room temperature for 60 min. After completion of the reaction, the reaction solution was added dropwise to diethyl ether (total 80 ml). After removal of the solvent (supernatant), a gelatinous crude product was obtained. This product was purified by silica gel column chromatography (dichloromethane:methanol=100:0-75:25, v/v) to thereby obtain the compound of interest (44A) in an amorphous state (408 mg, yield 60%).

$^1$H-NMR (CDCl$_3$) δ: 6.76 (2H, br), 6.69-6.63 (2H, m), 5.96 (1H, br), 5.36 (2H, d, J=3.0 Hz), 5.13-5.08 (2H, m), 4.53 (2H, d, J=8.5 Hz), 4.25-3.07 (27H, m), 2.51-2.44 (4H, m), 2.17 (6H, s), 2.06 (6H, s), 2.02 (6H, s), 2.00 (6H, s), 1.86-1.73 (4H, m).

Calcd for C$_{45}$H$_{70}$N$_6$O$_{25}$: [M+H]$^+$ 1095, Found 1096. [M+Na]$^+$ 1117, Found 1117.

(44B) Synthesis of [(2R,3R,4R,5R,6R)-5-acet-amide-6-[3-[3-[[3-[[3-[3-[(2R,3R,4R,5R,6R)-3-acet-amide-4,5-diacetoxy-6-(acetoxymethyl)tetrahydro-pyran-2-yl]oxypropylamino]-3-oxo-propyl]carbamoyloxy]-2-[2-cyanoethoxy-(diisopropylamino)phosphanyl]oxy-propoxy]carbonylamino]propanoylamino]propoxy]-3,4-diacetoxy-tetrahydropyran-2-yl]methyl acetate (Compound 44B)

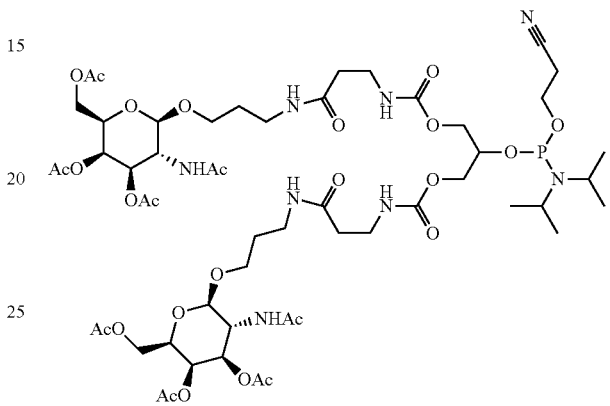

[Formula 194]

Synthesis was performed in the same manner as described in Step (39D), except that Compound 44A (1.53 g, 1.40 mmol) was used instead of Compound 39C used in Step (39D). As a result, Compound 44B was obtained (510 mg, yield 28%).

$^1$H-NMR (CDCl$_3$) δ: 6.60-6.44 (4H, m), 5.76-5.68 (1H, m), 5.36 (2H, d, J=3.0 Hz), 5.09-5.05 (2H, m), 4.50-4.45 (2H, m), 4.26-3.37 (28H, m), 3.17 (2H, br), 2.67 (2H, t, J=6.3 Hz), 2.52-2.42 (4H, m), 2.17 (6H, s), 2.05 (6H, s), 2.02 (6H, s), 1.99 (6H, s), 1.81-1.70 (4H, m), 1.18 (12H, d, J=6.7 Hz).

Example 152

X$^{20}$-A$^{m1s}$-A$^{e2s}$-U$^{m1s}$—C$^{m1s}$-C$^{e2s}$-G$^{m1s}$-A$^{e2s}$-U$^{m1s}$-G$^{m1s}$-G$^{m1s}$-C$^{e2s}$-G$^{m1s}$-A$^{m1s}$-A$^{e2s}$-G$^{m1t}$-H (SEQ ID NO: 173)

Synthesis was performed in the same manner as described in Example 143, except that X$^{18}$ was substituted with X$^{20}$. The sequence used was the above-described sequence (designation: 15e_001.5).

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6261.98).

Example 153

X$^{20}$-A$^{e2s}$-U$^{m1s}$—C$^{m1s}$-C$^{e2s}$-G$^{m1s}$-A$^{e2s}$-U$^{m1s}$-G$^{m1s}$-G$^{m1s}$-C$^{e2s}$-G$^{m1s}$-A$^{m1s}$-A$^{e2s}$-G$^{m1s}$-C$^{e2t}$—H (SEQ ID NO: 174)

Synthesis was performed in the same manner as described in Example 144, except that X$^{18}$ was substituted with X$^{20}$. The sequence used was the above-described sequence (designation: 15e_005.5).

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6264.00).

Example 154

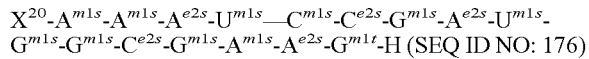
$G^{m1s}$-$G^{m1s}$-$C^{e2s}$-$G^{m1s}$-$A^{m1s}$-$A^{e2s}$-$G^{m1t}$-H (SEQ ID NO: 176)

Synthesis was performed in the same manner as described in Example 146, except that $X^{18}$ was substituted with $X^{20}$. The sequence used was the above-described sequence (designation: 16e_001.5).

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6621.04).

Example 155

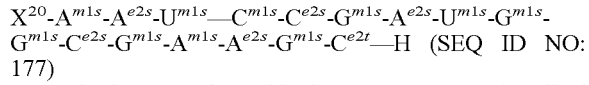
$G^{m1s}$-$C^{e2s}$-$G^{m1s}$-$A^{m1s}$-$A^{e2s}$-$G^{m1s}$-$C^{e2t}$—H (SEQ ID NO: 177)

Synthesis was performed in the same manner as described in Example 147, except that $X^{18}$ was substituted with $X^{20}$. The sequence used was the above-described sequence (designation: 16e_002.5).

The nucleotide sequence of the subject compound is complementary to a sequence from the 91$^{st}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6623.05).

Example 156

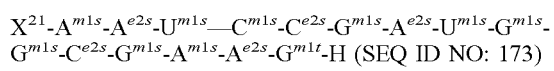
$G^{m1s}$-$C^{e2s}$-$G^{m1s}$-$A^{m1s}$-$A^{e2s}$-$G^{m1t}$-H (SEQ ID NO: 173)

Synthesis was performed in the same manner as described in Example 143, except that $X^{18}$ was substituted with $X^{21}$. The sequence used was the above-described sequence (designation: 15e_001.5).

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6290.02).

Example 157

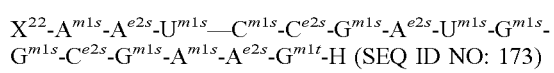
$G^{m1s}$-$C^{e2s}$-$G^{m1s}$-$A^{m1s}$-$A^{e2s}$-$G^{m1t}$-H (SEQ ID NO: 173)

Synthesis was performed in the same manner as described in Example 143, except that $X^{18}$ was substituted with $X^{22}$. The sequence used was the above-described sequence (designation: 15e_001.5).

The nucleotide sequence of the subject compound is complementary to a sequence from the 92$^{nd}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6175.96).

Example 158

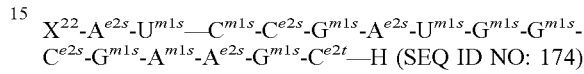
$C^{e2s}$-$G^{m1s}$-$A^{m1s}$-$A^{e2s}$-$G^{m1s}$-$C^{e2t}$—H (SEQ ID NO: 174)

Synthesis was performed in the same manner as described in Example 144, except that $X^{18}$ was substituted with $X^{22}$. The sequence used was the above-described sequence (designation: 15e_005.5).

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6177.98).

Example 159

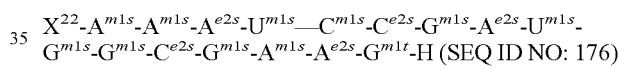
$G^{m1s}$-$G^{m1s}$-$C^{e2s}$-$G^{m1s}$-$A^{m1s}$-$A^{e2s}$-$G^{m1t}$-H (SEQ ID NO: 176)

Synthesis was performed in the same manner as described in Example 146, except that $X^{18}$ was substituted with $X^{22}$. The sequence used was the above-described sequence (designation: 16e_001.5).

The nucleotide sequence of the subject compound is complementary to a sequence from the 92$^{nd}$ to the 107$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6535.03).

Example 160

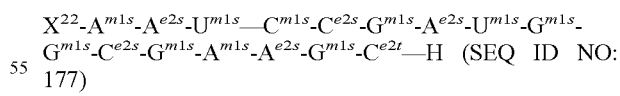
$G^{m1s}$-$C^{e2s}$-$G^{m1s}$-$A^{m1s}$-$A^{e2s}$-$G^{m1s}$-$C^{e2t}$—H (SEQ ID NO: 177)

Synthesis was performed in the same manner as described in Example 147, except that $X^{18}$ was substituted with $X^{22}$. The sequence used was the above-described sequence (designation: 16e_002.5).

The nucleotide sequence of the subject compound is complementary to a sequence from the 91$^{st}$ to the 106$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (actually measured molecular weight: 6537.05).

Test Example 1

Evaluation of Repair of Abnormal Splicing with Compounds of Examples in Cultured Cells
Culture of 293A Cells (Human Embryonic Kidney Cells)
293A cells (R705-07 Invitrogen) were cultured as described below.
Briefly, 293A cells were maintenance-cultured in a maintenance medium (DMEM, 10% FBS). For experiments, cells were seeded on 6-well plates at a density of $2 \times 10^5$ cells/well and on 12-well plates at $1 \times 10^5$ cells/well. On the next day, cells were co-transfected with a Compound of Example and a plasmid vector as described later, fand the transfected cells were used for following evaluations.
Preparation of Human G6PC Full-Length Plasmid Vectors
Human G6PC full-length plasmid vectors (pcDNA hG6PC and pcDNA hG6PC (c.648G>T)+Int4) were prepared as described below.
Briefly, using Human Multiple Tissue cDNA Panel as a template and the G6PC cDNA Amplified primer pair described below, G6PC cDNA was amplified, and then further amplified with G6PC cDNA IF primer pair. The amplified fragment was inserted into the BamHI site of pcDNA3.1 with InFusion System (pcDNA hG6PC).

```
G6PC cDNA Amplified primer:
Forward primer:
                                       (SEQ ID NO: 49)
5'-ATAGCAGAGCAATCACCACCAAGCC-3'

Reverse primer:
                                       (SEQ ID NO: 50)
5'-ATTCCACGACGGCAGAATGGATGGC-3'

G6PC IF primer:
Forward primer:
                                       (SEQ ID NO: 51)
5'-TACCGAGCTCGGATCCACCACCAAGCCTGGAATAACTGC-3'

Reverse primer:
                                       (SEQ ID NO: 52)
5'-CTGGACTAGTGGATCCTGGCATGGTTGTTGACTTTAAAC-3'
```

Using Human Genomic DNA as a template and the G6PC Int4 Amplified primer pair described below, a region comprising G6PC Intron 4 and part of Exon 5 was amplified. Further, G6PC Intron 4 was amplified with G6PC Int4 IF primer pair. On the other hand, pcDNA hG6PC prepared in STEP 1-1 was amplified with the hG6PC vector 1F primer pair described below. Further, c.648G>T mutation in exon 5 was introduced into InFusion primer. Both fragments were ligated using InFusion System to introduce G6PC Intron 4 sequence into pcDNA hG6PC (pcDNA hG6PC (c.648G>T)+Int4).

```
G6PC Int4 Amplified primer:
Forward primer:
5'-TCTGGGCTGTGCAGCTGAATGTCTG-3'        (SEQ ID NO: 53)

Reverse primer:
5'-GTAGGGATGACACTGACGGATGCC-3'         (SEQ ID NO: 54)

G6PC Int4 IF primer:
Forward primer:
5'-CTGGAGTCCTGTCAGGTATGGGC-3'          (SEQ ID NO: 55)
```

```
Reverse primer:
5'-AGCTGAAAAGGAAGAAGGTAATGAG-3'        (SEQ ID NO: 56)

hG6PC vector IF primer:
Forward primer:
5'-TCTTCCTTTTCAGCTTCGCCATCGG-3'        (SEQ ID NO: 57)

Reverse primer:
5'-CTGACAGGACTCCAGCAACAAC-3'           (SEQ ID NO: 58)
```

Co-Transfection with Compounds of Examples and Plasmid Vector
Co-transfection of cells with compounds of examples and the plasmid vector was performed as described below.
Briefly, solution A and solution B described below were prepared and mixed.
When 6-well plates were used, solution A [250 μl of Opti-MEM Medium (Gibco), 0.50 μl of plasmid vector (1 mg/ml), 4.0 μl (final: 20 nM) of Compound prepared in Example (12.5 μM)] and solution B [250 μl of Opti-MEM Medium (Gibco), 6.0 μl of Lipofectamine 2000 (Invitrogen)] were prepared per well and mixed. When 12-well plates were used, solution A [125 μl of Opti-MEM Medium (Gibco), 0.25 μl of plasmid vector (1 mg/ml), 2.0 μl (final: 20 nM) of Compound prepared in Example (12.5 μM)] and solution B [125 μl of Opti-MEM Medium (Gibco), 3.0 μl of Lipofectamine 2000 (Invitrogen)] were prepared per well and mixed.
The above-described mixed solution was incubated at room temperature for 20 min and then added to cells one day after passaging (co-transfection). Six hours after the addition, the medium was exchanged with fresh maintenance medium. Then, cells were incubated in a $CO_2$ incubator for 24 hrs following the addition of the mixed solution.
RNA Extraction (In Vitro)
RNA was extracted as described below.
Cells which had been incubated for 24 hrs after co-transfection were washed once with cold PBS. Cell Lysis Solution in RNeasy mini kit or RNeasy 96 kit (Qiagen) was added to each well (300 μl/well). After incubation at room temperature for 5 min, the solution was collected and subjected to RNA purification according to the protocol of the kit including DNase treatment. For DNase treatment, RNase-Free DNase set (Qiagen 89254) was used. With the thus purified/eluted RNA, the following reverse transcription was performed.
Reverse Transcription
Reverse transcription was performed as described below.
Briefly, the extracted RNA was adjusted to give a concentration of 25-100 mg/ml. Then, using High Capacity RNA-to-cDNA kit (Applied Biosystems), a mixture was prepared that contained 10 μl of Buffer mix, 1 μl of Enzyme mix, 9 μl of purified water and extracted RNA per sample, and subjected to reverse transcription (37° C. 60 min, 95° C. 5 min, 4° C. Hold).
To 20 μl of reverse transcription product, 80 μl of purified water was added to make a 5-fold dilution, which was stored at −30° C.
qRT-PCR (SYBR Green)
qRT-PCR primer pairs (SYBR Green) were designed as follows.

```
Repaired hG6PC primer (SYBR):
Forward primer:
5'-TTGTGGTTGGGATTCTGGGC-3'             (SEQ ID NO: 59)
```

-continued

```
Reverse primer:
5'-ATGCTGTGGATGTGGCTGAA-3'         (SEQ ID NO: 60)

hActin primer (SYBR):
Forward primer:
5'-TGGCACCCAGCACAATGAA-3'          (SEQ ID NO: 61)

Reverse primer:
5'-CTAAGTCATAGTCCGCCTAGAAGCA-3'    (SEQ ID NO: 62)
```

PCR reaction solution was prepared as follows: 5 µl of 2× FAST SYBR Green Master Mix (Applied Biosystems), 2 µl of purified water, 1 µl of Primer mix (10 µM) and 2 µl of cDNA (5-fold dilution) were suspended per well. PCR reaction was performed with Viia7 (Applied Biosystems) (program: SYBR Green Regents, FAST, including Melt curve).

qRT-PCR (Taqman Assay)

Repaired hG6PC primer set and Total hG6PC primer set were designed as described below, and 20×primer probe mix (primer concentration: 1000 nM, probe concentration: 250 nM) was prepared. For hActin primer set and mActin primer set, undiluted solutions were used.

```
Repaired hG6PC primer set (Taqman):
Forward primer:
5'-GCTGCTCATTTTCCTCATCAAGTT-3'     (SEQ ID NO: 63)

Reverse primer:
5'-TGGATGTGGCTGAAAGTTTCTGTA-3'     (SEQ ID NO: 64)

Probe:
5'-TCCTGTCAGGCATTGC-3' FAM         (SEQ ID NO: 65)
``` hActin primer set (Tagman): ABI Hs01060665_g1 FAM
mActin primer set (Tagman): ABI Mm02619580_g1 FAM
18s primer set (Tagman): ABI Hs99999901_s1 FAM PCR reaction solution was prepared as follows: 5 µl of 2× Taqman Fast Advanced Master Mix (Applied Biosystems), 2.5 µl of purified water, 0.5 µl of 20×Primer probe mix (10 M), 2 µl of cDNA (5-fold dilution) were suspended per well. PCR reaction was performed with viia7 or Quantstadio7 (Applied Biosystems) (program: Taqman regents, FAST).

Quantification of Normal Human G6PC Specific Polypeptide by LC-MS/MS

Protein extraction and LC-MS/MS quantification of normal human G6PC specific peptide were performed as described below.

Extraction and Adjustment of Protein Lysate

Cells incubated for 24 hrs after co-transfection were washed once with cold PBS. RIPA buffer (nacalai tesque) was added (100 µl/well). After incubation on ice, the resultant liquid was collected. The collected liquid was incubated on ice for 20 min and then centrifuged at 10000 g for 10 min at 4° C. to recover the supernatant. The amount of the total protein in the supernatant was quantified. Then, the supernatant was adjusted to give a protein concentration of 0.4 mg/ml, to thereby prepare a protein lysate.

Preparation of Reagents

DS264_100u: Stable isotope-labeled peptide GLGVD (L*)LWT(L*)EK (Scrum, L*: L-Leucine-$^{13}C_6$, $^{15}N$) was adjusted to 100 µM with 50% cn (purified water/acetonitrile).

DS266_100u: Stable isotope-labeled peptide WCEQPEW (V*)HIDTTPFAS(L*)LK (L*: L-Leucine-$^{13}C_6$, $^{15}N$, V*:L-Valine-$^{13}C_5$, $^{15}N$) was adjusted to 100 µM with 50% cn (purified water/acetonitrile).

DS268_100u: Stable isotope-labeled peptide NLGTLFG (L*)GLA(L*)NSSMYR (Scrum, L*: L-Leucine-$^{13}C_6$, $^{15}N$) was adjusted to 100 µM with 50% cn (purified water/acetonitrile).

IS solution-1: 50 mL of Acetonitrile, 0.5 ml of Trifluoroacetic acid (Nacalai), 20 µl of DS264_100u, 20 µl of DS266_100u, and 0 µl of DS268_100u were suspended.

IS solution-2: 50 mL Acetonitrile, 50 mL purified water, 0.5 mL of Trifluoroacetic acid (Nacalai), 20 µl of DS264_100u. 20 µl of DS266_100u and 20 µl of DS268_100u were suspended.

0.1M Tris-HCl*: 5 mL of 1M Tris-HCl Buffer Solution (pH 8.0) was added to and suspended in 45 mL of purified water.

Urea/EDTA solution: 2.4 g of Urea (Nacalai) and 100 µl of 0.5M EDTA (Sigma-Aldrich) were added to and suspended in 4.9 mL of 0.1M Tris-HCl.

DTT solution (20 mg/ml): 20 mg of DTT (dithiothreitol) (Wako) was added to and suspended in 1 ml of purified water.

IAA solution (50 mg/ml): 50 mg of IAA (iodoacetamide) (Sigma-Aldrich) was added to and suspended in 1 ml of purified water.

Trypsin/LysC Mix solution (200 µg/ml): 20 µg of Trypsin/Lys-C Mix (1 vial) (Promega) was added to and suspended in 100 µl of Resuspension buffer (Promega).

Digestion Treatment

As described below, enzymatic digestion was performed to prepare LC-MS injection samples (per sample).

20 µl of Urea/EDTA solution, 10 µl of protein lysate and 10 µl of DTT solution were suspended and left undisturbed at room temperature for 60 min. To this suspension, 2.5 µl of IAA solution was added and suspended. The suspension was left undisturbed at room temperature for 60 min. Subsequently, 112.5 µl of 0.1M Tris-HCl and 2.5 µl of Trypsin/LysC Mix solution were added and suspended. The resultant suspension was incubated at 37° C. overnight. Then, 150 µl of IS solution-1 and 300 µl of IS solution-2 were added to prepare LC-MS injection sample.

LC-MS Analysis and Measurement of Concentration in Sample

LC-MS analysis of LC-MS injection sample was performed with Ultimate 3000 (Thermo Fisher) and Q Exactive plus (Thermo Fisher). The concentration of the following peptide (DS265) in sample was calculated from mass range 820.0632-820.0782 (m/z) by the internal standard method.

DS265: WCEQPEWVHIDTTPFASLLK (SEQ ID NO: 66)

Measurement of G6PC Enzyme Activity

Individual samples had their microsome fractions extracted as described below and their G6PC activities were then measured.

(1) Preparation of Reagents

Buffer A: 100 mM BIS-TRIS Buffer, pH 6.5, 37° C.

To 180 ml of purified water, 4.2 g of BIS-TRIS (Sigma-Aldrich) was added. Hydrochloric acid and purified water were used for adjustment to pH 6.5, 37° C., 200 ml.

Buffer B: HEPES 20 mM, EDTA 1 mM, Sucrose 250 mM (stored at 4° C.)

To 180 ml of purified water, 4.0 ml of 1.0 M HEPES (Gibco), 0.4 ml 0.5 M EDTA (USB) and 17 g of Sucrose (Wako) were added. The obtained solution was dilution up to 200 ml with purified water and passed through a 0.22 m filter.

Substrate: 200 mM Glucose 6-Phosphate (stored at 4° C.)
To 88.65 ml of purified water, 5 mg of D-Glucose 6-Phosphate Sodium Salt (Sigma-Aldrich) was added.
TCA: 20% Trichloroacetic Acid (stored at room temperature, with light shielded)
To 40 ml of purified water, 10 ml of Trichloroacetic Acid Solution (Sigma-Aldrich) was added.
Standard: Phosphorus Standard Solution, 20 µg/ml (Sigma-Aldrich) (stored at 4° C.)
5M Sulfuric Acid Solution (stored at room temperature, with light shielded)
To 67 ml of purified water, 25 ml of Sulfuric Acid (Aldrich 258105) was added.
TSCR: Taussky-Shorr Color Reagent (prepared just before use)
To 20 ml of 5M Sulfuric Acid Solution, 2.4 mg of Ammonium Molybdate Tetrahydrate (Sigma-Aldrich) was added. The resultant solution was added to 140 ml of purified water. 10 g of Ferrous Sulfate Heptahydrate (Sigma-Aldrich) was further added and stirred until dissolved. The resultant solution was diluted with purified water to a final volume of 200 ml.

(2) Isolation of Microsome Fractions

Microsome fractions were purified and prepared according the following procedures.

The 293A cells co-transfected with Compound of Example and a plasmid vector (in 6-well plates) were washed with ice cold PBS. Ice cold Buffer B was added to each well, and cells were harvested with a cell scraper. Harvested cells were sufficiently homogenized on ice with a Dounce homogenizer and centrifuged at 1000 g for 10 min at 4° C., to thereby collect a supernatant. This supernatant was centrifuged at 13000 g for 60 min at 4° C. The resulting supernatant was removed and the pellet was suspended in Buffer B. This suspension was adjusted with Buffer B so that the protein concentration would lie between 0.3 and 1.0 mg/ml.

(3) Measurement of G6PC Enzyme Activity

The G6PC enzyme activity of the protein concentration-adjusted microsome fraction (sample) was measured by the method described below. For the designations of the respective reagents, see (1).

Briefly, Test and Blank were prepared for each sample. For the Test, 150 µl of Buffer A and 50 µl of substrate were suspended and incubated for 5 min at 37° C. To this suspension, 5 µl of sample was added and suspended. The resultant suspension was incubated for exactly 5 min at 37° C., followed by addition of 45 µl of TCA. After thoroughly suspending the mixture, incubation was conducted for 5 min at 25° C. For the Blank, 150 µl of Buffer A and 50 µl of substrate were suspended and incubated for 5 min at 37° C. A suspension obtained by suspending 5 µl of sample and 45 µl of TCA and incubating at 25° C. was added. The Test and the Blank from each sample were centrifuged at 4000 g for 10 min at room temperature. The resultant supernatant was dispensed into separate tubes. To each supernatant (100 µl), 100 µl of TSCR was added, followed by incubation at room temperature for 5 min. Then, absorbance at 660 nm was measured with a plate reader (Spectra Max M4 Molecular Devices). G6PC enzyme activity (U/mg: the amount of G6P (mol) by which 1 mg of total protein in sample was degraded in 1 min) was calculated from the calibration curve constructed using the dilution series of Standard, absorbances of the Test and Blank for each sample and the protein concentration in sample.

Evaluation of Repair of Abnormal Splicing in G6PC mRNA with Compounds of Examples Using Human G6PC Full-Length Plasmid Vector (pcDNA hG6PC (c.648G>T)+Int4) (1)

Figure 5:
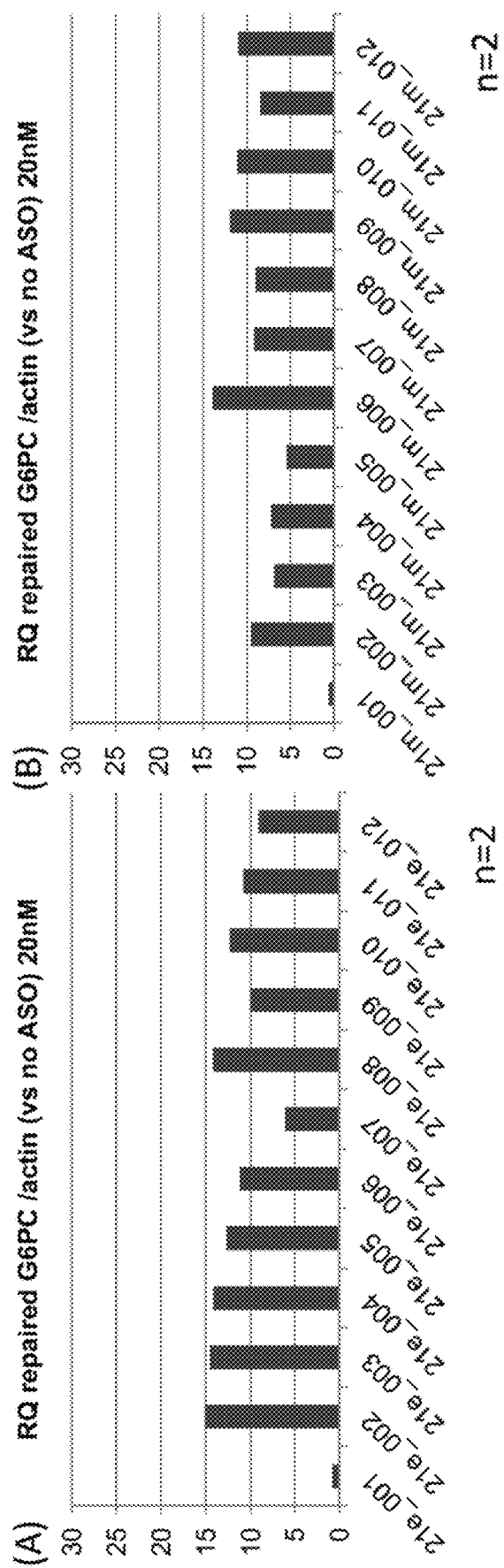
FIG. 5 Effect of correcting the abnormal splicing of G6PC mRNA with ASO is shown by qRT-PCR. (A) ASOs (21e_001 to 21e_012) were used. (B) ASOs (21m_001 to 21m_012) were used. RQ: Relative Quantification FIG. 6 Effect of producing normal human G6PC specific peptide after repairing the abnormal splicing of G6PC mRNA with ASO is shown by LC-MS/MS. (A) ASOs (21e_001 to 21e_012) were used. (B) ASOs (21m_001 to 21m_012) were used.
Figure 6:
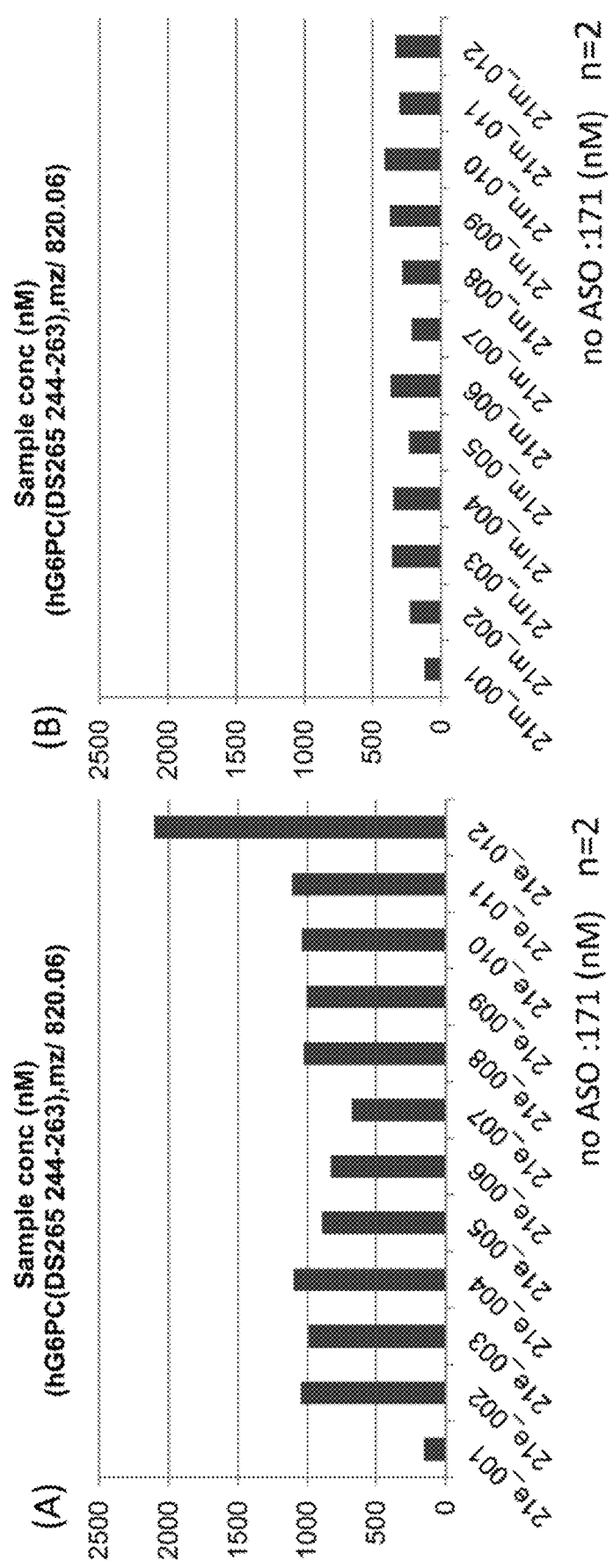
Figure 7:
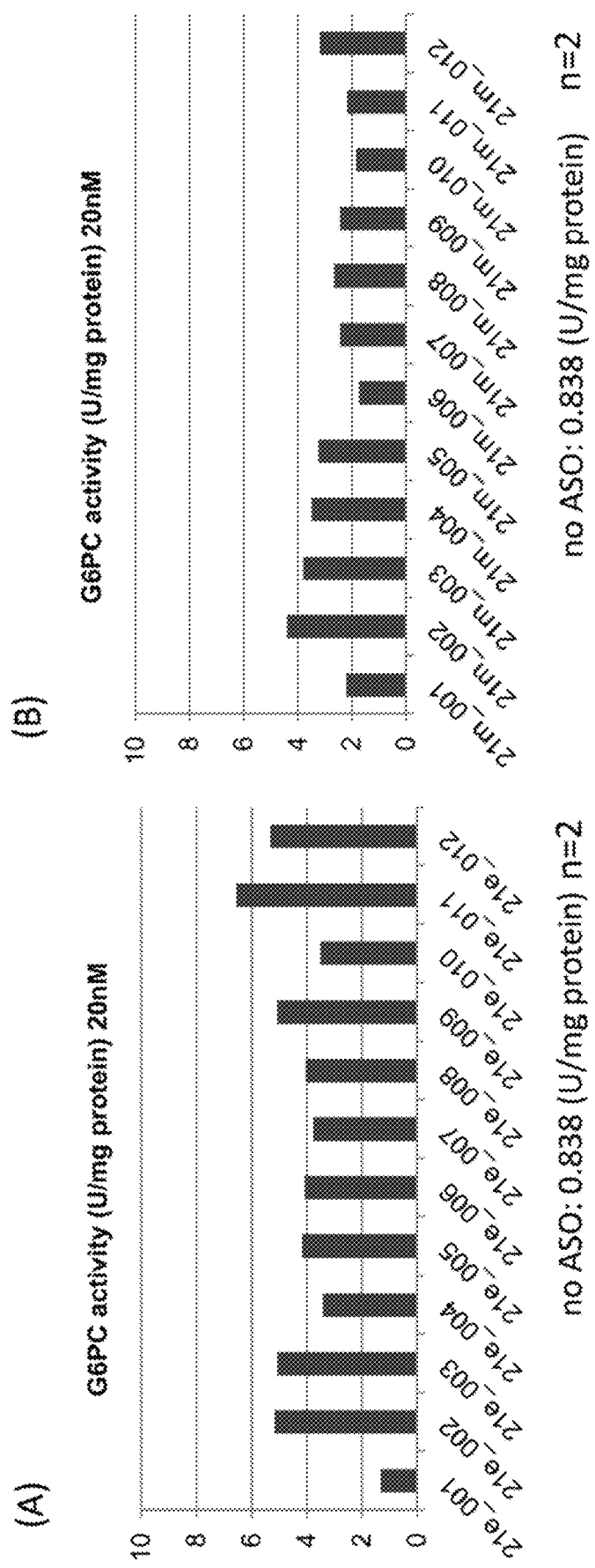
FIG. 7 G6PC enzyme activity after repairing the abnormal splicing of G6PC mRNA with ASO is shown. (A) ASOs (21e_001 to 21e_012) were used. (B) ASOs (21m_001 to 21m_012) were used.

Co-transfection with human G6PC full-length plasmid vector (pcDNA hG6PC (c.648G>T)+Int4) and oligonucleotides (21e_001-012 and 21m_001-012) was performed, and evaluation by qRT-PCR (SYBR Green) was made to see whether the abnormal splicing caused by G6PC (c.648G>T) would be repaired or not. As shown in FIGS. 5A and 5B, normalization of the abnormal splicing of G6PC mRNA was observed in Compounds 21e_002-012 and 21m_002-012. When production of normal human G6PC specific peptide was examined by LC-MS/MS, production of the peptide was observed in Compounds 21e_002-012 and 21m_002-012 as shown in FIGS. 6A and 6B. When G6PC enzyme activity was measured, G6PC enzyme activity was observed in Compounds 21e_002-012 and 21m_002-012 as shown in FIGS. 7A and 7B.

Evaluation of Repair of Abnormal Splicing in G6PC mRNA with Compounds of Examples Using Human G6PC Full-Length Plasmid Vector (pcDNA hG6PC (c.648G>T)+Int4) (2)

Figure 9:
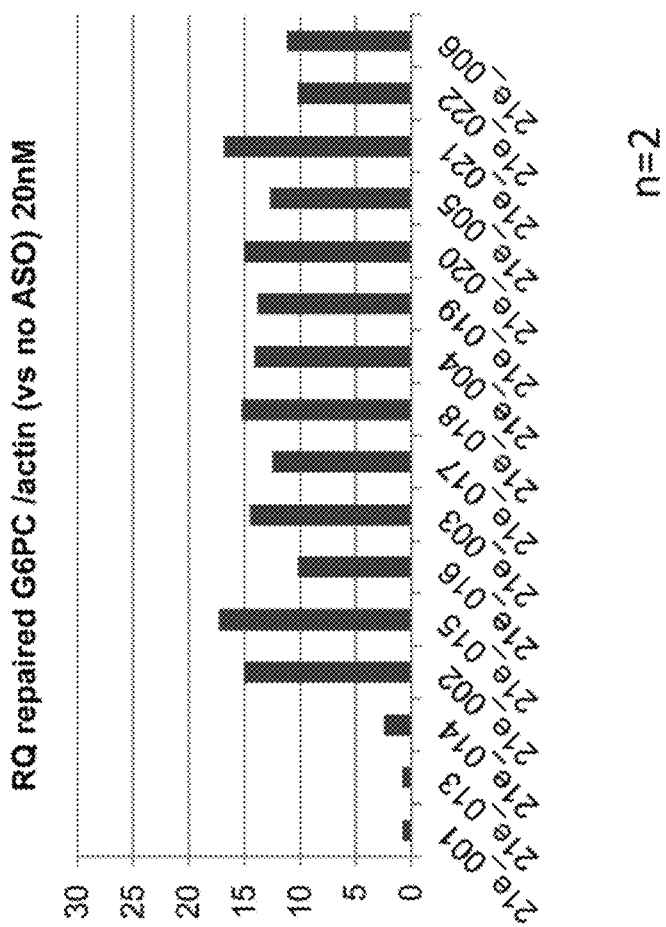
FIG. 9 Effect of correcting the abnormal splicing of G6PC mRNA with ASOs (21e_001 to 21e_006 and 21e_013 to 21e_022) is shown by qRT-PCR. RQ: Relative Quantification FIG. 10 Effect of producing normal human G6PC specific peptide after repairing the abnormal splicing of G6PC mRNA with ASOs (21e_001 to 21e_006 and 21e_013 to 21e_022) is shown by LC-MS/MS.
Figure 10:
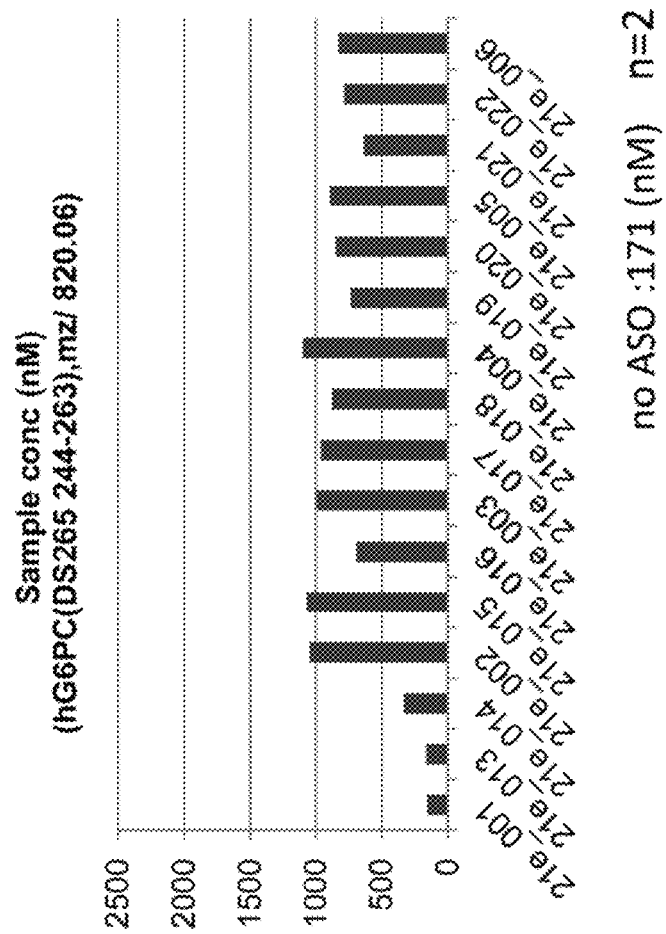
Figure 11:
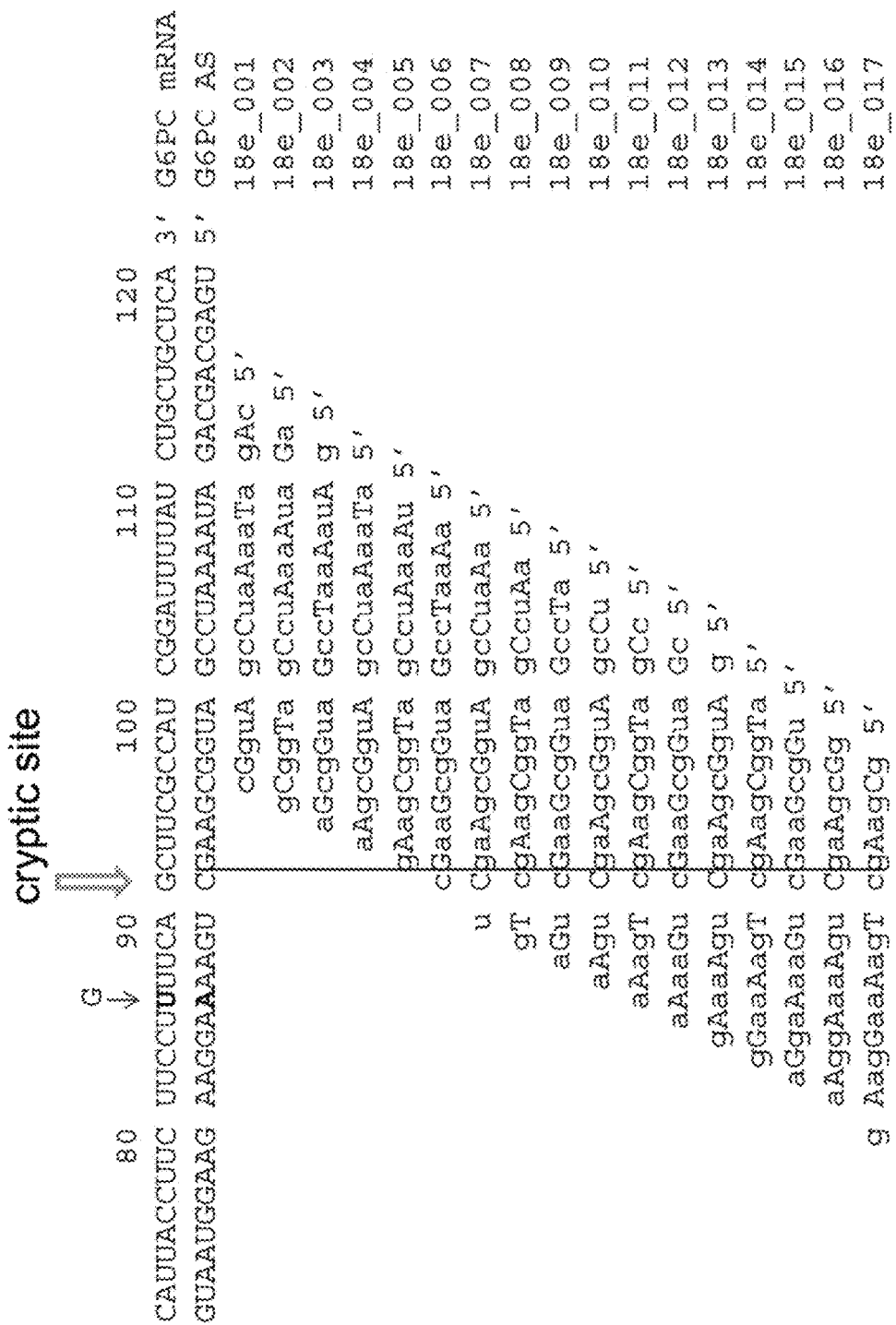
FIG. 11 A diagram showing sequences of ASOs (18e_001 to 18e_017) capable of binding to exon 5 of the mRNA of c.648G>T mutation-harboring G6PC gene.

Co-transfection with human G6PC full-length plasmid vector (pcDNA hG6PC (c.648G>T)+Int4) and oligonucleotides (21e_001-006 and 21e_013-022) was performed, and evaluation by qRT-PCR (SYBR Green) was performed to see whether the abnormal splicing caused by G6PC (c.648G>T) would be repaired or not. As shown in FIG. 9, normalization of the abnormal splicing of G6PC mRNA was observed in Compounds 21e_002-006 and 21e015_022. When production of normal human G6PC specific peptide was examined by LC-MS/MS, production of the peptide was observed in Compounds 21e_002-006 and 21e_015-022 as shown in FIG. 10.

Evaluation of Repair of Abnormal Splicing in G6PC mRNA with Compounds of Examples Using Human G6PC Full-Length Plasmid Vector (pcDNA hG6PC (c.648G>T)+Int4) (3)

Figure 13:
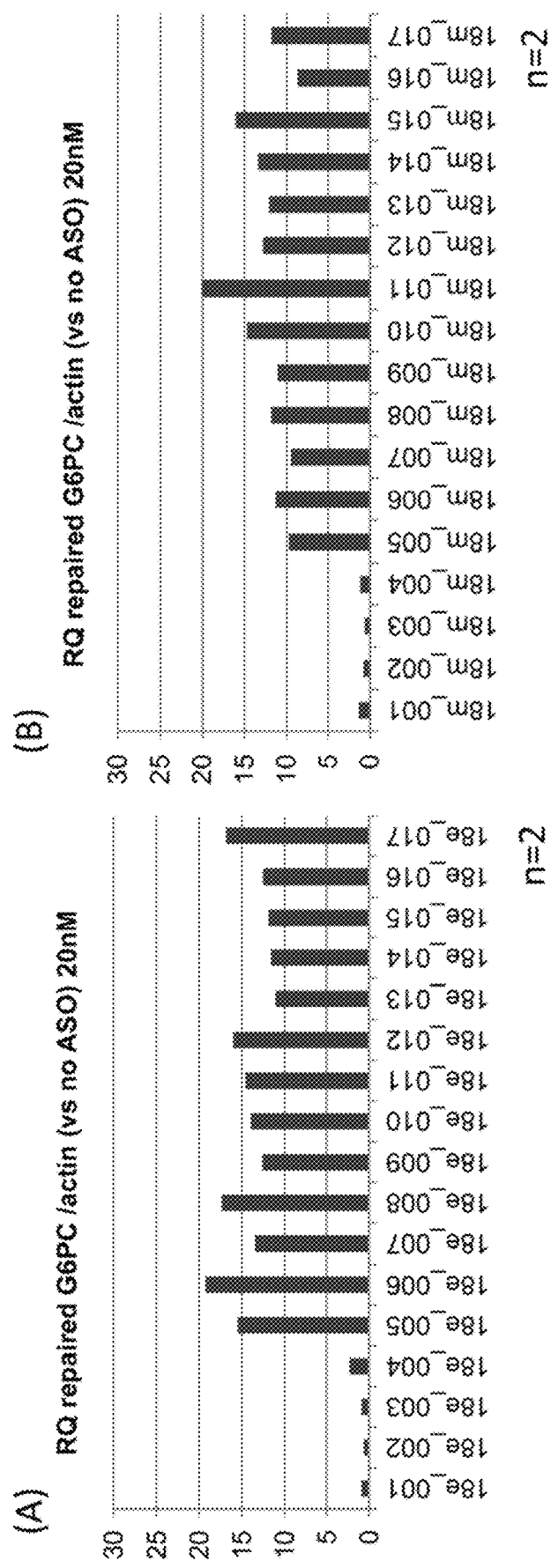
FIG. 13 (A) Effect of correcting the abnormal splicing of G6PC mRNA with ASOs (18e_001 to 18e_017) is shown by qRT-PCR. (B) Effect of correcting the abnormal splicing of G6PC mRNA with ASOs (18m_001 to 18m_017) is shown by qRT-PCR. RQ: Relative Quantification FIG. 14 (A) Effect of producing normal human G6PC specific peptide after repairing the abnormal splicing of G6PC mRNA with ASOs (18e_001 to 18e_017) is shown by LC-MS/MS. (B) Effect of producing normal human G6PC specific peptide after repairing the abnormal splicing of G6PC mRNA with ASOs (18m_001 to 18m_017) is shown by LC-MS/MS.
Figure 14:
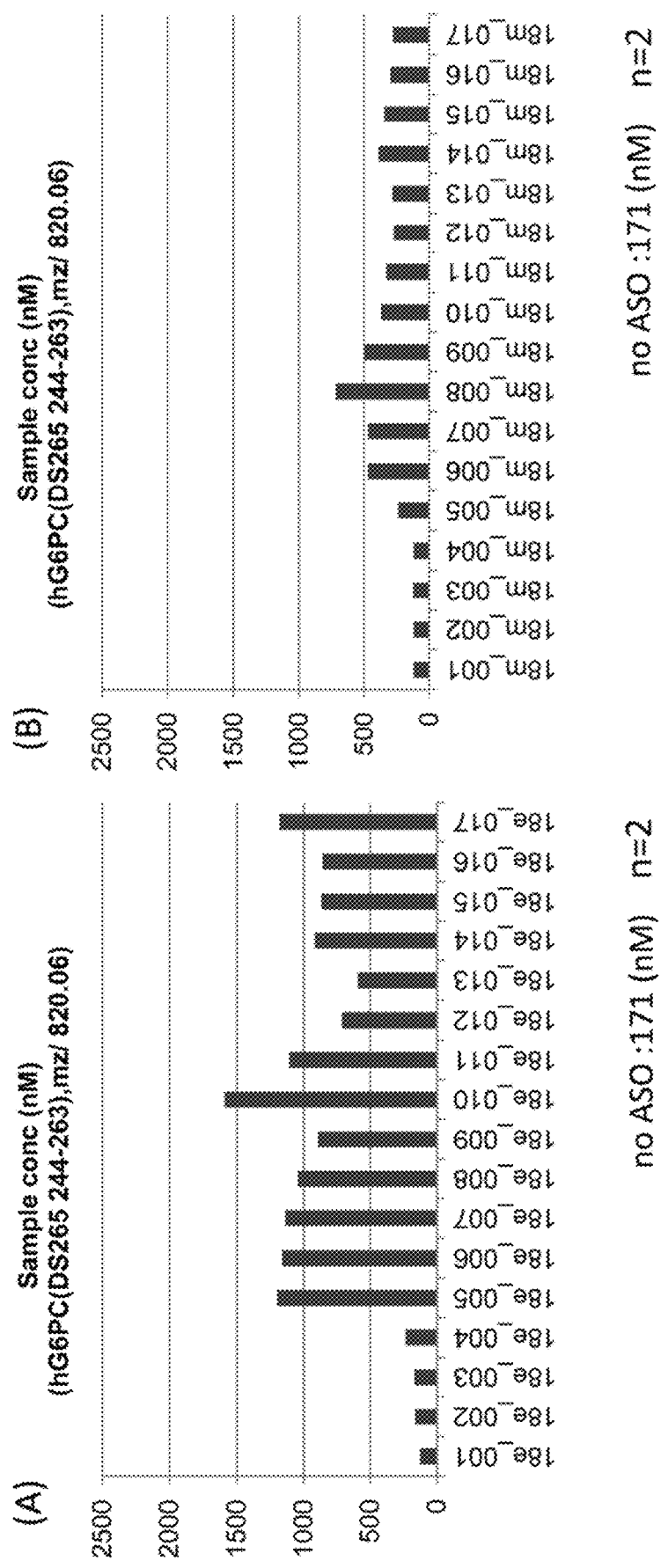

Co-transfection with human G6PC full-length plasmid vector (pcDNA hG6PC (c.648G>T)+Int4) and oligonucleotides (18e_001-017 and 18m_001-017) was performed, and evaluation by qRT-PCR (SYBR Green) was performed to see whether the abnormal splicing caused by G6PC (c.648G>T) would be repaired or not. As shown in FIGS. 13A and 13B, normalization of the abnormal splicing of G6PC mRNA was observed in Compounds 18e_005-017 and 18m_005-017. When production of normal human G6PC specific peptide was examined by LC-MS/MS, production of the peptide was observed in Compounds 18e_005-017 and 18m_005-017 as shown in FIGS. 14A and 14B.

Evaluation of Repair of Abnormal Splicing in G6PC mRNA with Compounds of Examples Using Human G6PC Full-Length Plasmid Vector (pcDNA hG6PC (c.648G>T)+Int4) (4)

Figure 16:
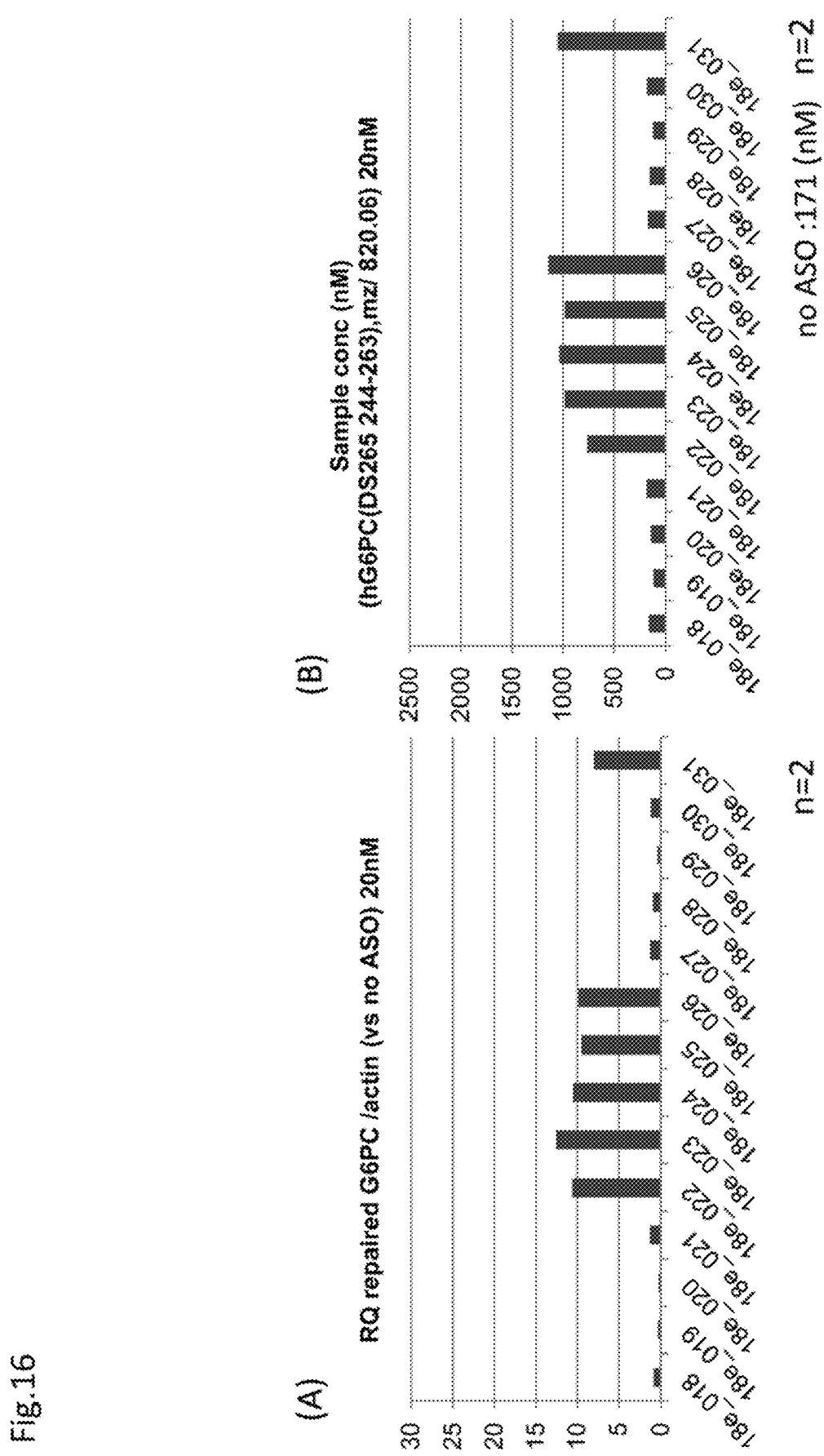
FIG. 16 (A) Effect of correcting the abnormal splicing of G6PC mRNA with ASOs (18e_018 to 18e_031) is shown by qRT-PCR. (B) Effect of producing normal human G6PC specific peptide by repairing the abnormal G6PC mRNA splicing with ASOs (18e_018 to 18e_031) is shown by LC-MS/MS. RQ: Relative Quantification FIG. 17 A diagram showing sequences of ASOs (21e_002, 18e_005, 21m_002, 18e_022, 18m_005, 15e_001, 15ed_001, 18e_008, 18e_025, 18m_008, 15e_002 and 15ed_002) capable of binding to exon 5 of the mRNA of c.648G>T mutation-harboring G6PC gene.
Figure 17:
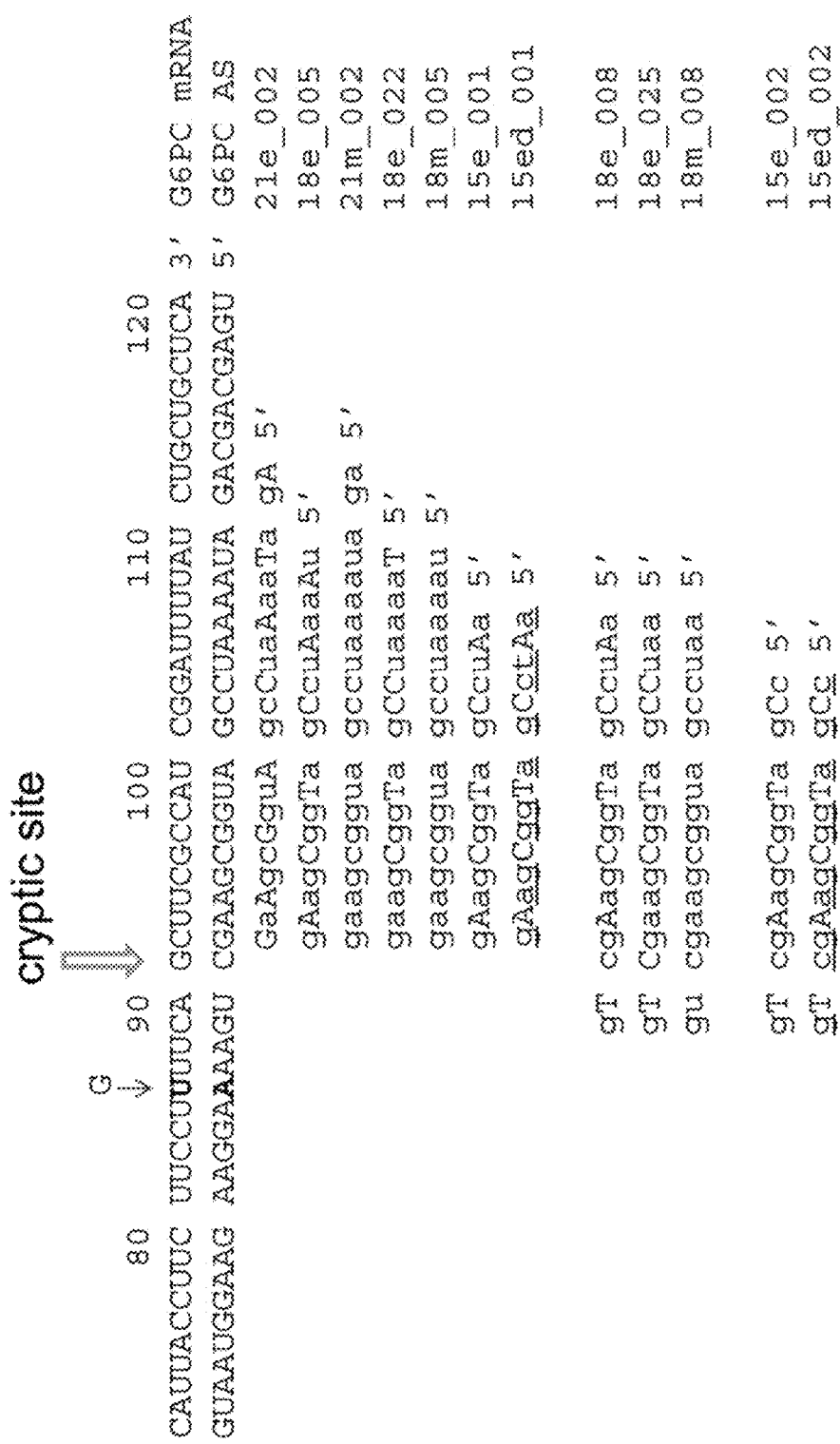
In FIG. 17, G6PC mRNA corresponds to bases 70-120 of SEQ ID NO: 96, G6PC AS corresponds to bases 1-50 of SEQ ID NO: 97, 21e_002 corresponds to SEQ ID NO: 1, 18e_005 corresponds to SEQ ID NO: 20, 21m_002 corresponds to SEQ ID NO: 98, 18e_022 corresponds to SEQ ID NO: 129, 18m_005 corresponds to SEQ ID NO: 135, 15e_001 corresponds to SEQ ID NO: 40, 15ed_001 corresponds to SEQ ID NO: 161, 18e_008 corresponds to SEQ ID NO: 23, 18e_025 corresponds to SEQ ID NO: 132, 18m_008 corresponds to SEQ ID NO: 138, 15e_002 corresponds to SEQ ID NO: 41, and 15ed_002 corresponds to SEQ ID NO: 162.

Co-transfection with human G6PC full-length plasmid vector (pcDNA hG6PC (c.648G>T)+Int4) and oligonucleotides (18e_018-031) was performed, and evaluation by qRT-PCR (SYBR Green) was performed to see whether the abnormal splicing caused by G6PC (c.648G>T) would be repaired or not. As shown in FIG. 16A, normalization of the abnormal splicing of G6PC mRNA was observed in Compounds 18e_022-026 and 18e_031. When production of normal human G6PC specific peptide was examined by LC-MS/MS, production of the peptide was observed in Compounds 18e_022-026 and 18e_031 as shown in FIG. 16B.

Evaluation of Repair of Abnormal Splicing in G6PC mRNA with Compounds of Examples Using Human G6PC Full-Length Plasmid Vector (pcDNA hG6PC (c.648G>T)+Int4) (5)

Figure 18:
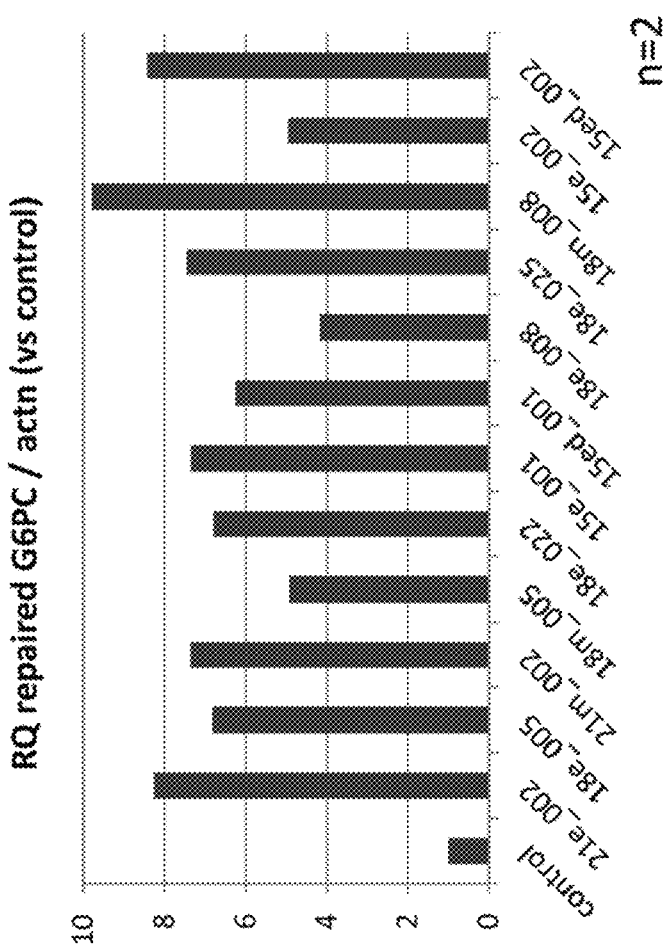
FIG. 18 Effect of correcting the abnormal splicing of G6PC mRNA with ASOs (21e_002, 18e_005, 21m_002, 18m_005, 18e_022, 15e_001, 15ed_001, 18e_008, 18e_025, 18m_008, 15e_002 and 15ed_002) is shown by qRT-PCR. RQ: Relative Quantification; Actn: P-actin.

Co-transfection with human G6PC full-length plasmid vector (pcDNA hG6PC (c.648G>T)+Int4) and oligonucleotides (21e_002, 18e_005, 21m_002, 18e_005, 18m_022, 15e_001, 15ed_001, 18e_008, 18e_025, 18m_008, 15e_002, 15ed_002 and a control, i.e., the compound disclosed in Example 93 of WO 2004/048570) was performed, and evaluation by qRT-PCR (SYBR Green) was performed to see whether the abnormal splicing caused by G6PC (c.648G>T) would be repaired or not. As shown in FIG. 18, normalization of the abnormal splicing of G6PC mRNA was observed in Compounds 21e_002, 18e_005, 21m_002, 18e_005, 18m 022, 15e_001, 15ed_001, 18e_008, 18e_025, 18m_008, 15e_002 and 15ed_002.

Test Example 2

Evaluation of Repair of Abnormal Splicing with Compounds of Examples Using Model Mouse
Creation of Mouse
Preparation of Vectors G6PC KI vector was prepared according to the procedures described below.

Using mouse genomic DNA as a template, G6PC 5' arm region was amplified with the following mG6PC 5' arm amplified primer pair. After further amplification with mG6PC 5' arm IF primer pair, the amplified fragment was inserted into the XhoI site of pBluescriptII(+/−) (G6PC 5' arm vector).

```
mG6PC 5' arm Amplified primer:
Forward primer:
                                   (SEQ ID NO: 67)
5'-GGGAAACATGCATGAAGCCCTGGGC-3'

Reverse primer:
                                   (SEQ ID NO: 68)
5'-TCCCTTGGTACCTCAGGAAGCTGCC-3' mG6PC 5' arm IF primer:
Forward primer:
                                   (SEQ ID NO: 69)
5'-CGGGCCCCCCCTCGAAAACTAGGCCTGAAGAGATGGC-3'

Reverse primer:
                                   (SEQ ID NO: 70)
5'-TACCGTCGACCTCGAGGGTTGGCCTTGATCCCTCTGCTA-3'
```

Subsequently, using Mouse Genomic DNA as a template, G6PC 3' arm region was amplified with the following mG6PC 3' arm Amplified primer pair. After further amplification with mG6PC 3' arm IF primer pair, the amplified fragment was inserted into the NotI site of G6PC 5' arm vector (G6PC 5'+3' arm vector).

```
mG6PC 3' arm Amplified primer:
Forward primer:
                                   (SEQ ID NO: 71)
5'-GGTTGAGTTGATCTTCTACATCTTG-3'

Reverse primer:
                                   (SEQ ID NO: 72)
5'-GCAAGAGAGCCTTCAGGTAGATCCC-3' mG6PC 3' arm IF primer:
Forward primer:
                                   (SEQ ID NO: 73)
5'-AGTTCTAGAGCGGCCGCCCATGCAAAGGACTAGGAACAAC-3'

Reverse primer:
                                   (SEQ ID NO: 74)
5'-ACCGCGGTGGCGGCCAATGTTGCCTGTCTTCCTCAATC-3'
```

Using the above-described pcDNA hG6PC (c.648G>T)+Int4 as a template, hG6PC (c.648G>T)+Intron4 was amplified with the following hG6PC+Int4 IF primer pair. Further, using G6PC 5'+3' arm vector prepared above as a template, amplification was performed with the following Arm vector IF Primer pair. Both fragments were ligated with InFusion System to thereby prepare G6PC KI vector.

```
hG6PC + Int4 IF primer:
Forward primer:
5'-GGCCAACCCTGGAATAACTGCAAGGGCTCTG-  (SEQ ID NO: 75)
3'

Reverse primer:
5'-TTGCATGGTTGTTGACTTTAAACACCGAAGA-  (SEQ ID NO: 76)
3'

Arm vector IF Primer:
Forward primer:
5'-TCAACAACCATGCAAAGGACTAGGAACAAC-3' (SEQ ID NO: 77)

Reverse primer:
5'-ATTCCAGGGTTGGCCTTGATCCCTCTGCTA-3' (SEQ ID NO: 78)
```

The KI 5' gRNA and KI 3' gRNA sequences described below were introduced into the gRNA sequence introduction domain of pSPgRNA (Addgene) to thereby prepare pSPgRNA(KI 5') and pSPgRNA(KI 3').

```
KI 5' gRNA:
5'-GGGATCAAGGCCAACCGGCTGG-3'         (SEQ ID NO: 79)

KI 3' gRNA:
5'-TAAAGTCAACCGCCATGCAAAGG-3'        (SEQ ID NO: 80)
```

Microinjection

Individual vectors were adjusted with sterile distilled water to give the following final concentrations: G6PC KI vetor 10 ng/μl; pSPgRNA(KI 5') 5 ng/μl, pSPgRNA(KI 3') 5 ng/μl and pSPCas9 (Addgene) 5 ng/μl. The resultant vector was passed through MILLEX-GV syringe filter (Millipore) and injected into fertilized eggs of C57BL/6J mouse until the pronucleus was sufficiently swollen (approx. 2 pl/egg). Then, the fertilized egg was transferred into the oviduct of recipient C57BL/6J mouse to thereby obtain F0 mouse.

Genotyping and Establishment of F1 Straine

Genotyping was performed by the following procedures to thereby establish F1 lineage.

Briefly, genomic DNA was extracted from F0 mouse tail tissue with an automatic nucleic acid extractor (PI-200, KURABO) and a dedicated kit. The extracted DNA was amplified using Amplitaq Gold Master mix (Thermo Fisher) and the following KI screening primer pair (95° C. 10 min; 35 cycles of 95° C. 30 sec, 60° C. 30 sec and 72° C. 30 sec; 72° C. 2 min; and 4° C. Hold).

```
KI screening primer:
Forward primer:
5'-TACGTCCTCTTCCCCATCTG-3'      (SEQ ID NO: 81)

Reverse primer:
5'-CTGACAGGACTCCAGCAACA-3'      (SEQ ID NO: 82)
```

The resultant PCR product was subjected to gel electrophoresis and the genomic DNA of individuals that showed a band at around 433 bp was used as a template for amplification using PrimeSTAR GXL (takara) and the following KI genotyping primer pairs (98° C. 2 min; 38 cycles of 95° C. 15 sec and 68° C. 5 min; 68° C. 7 min; and 15° C. Hold)

```
KI genotyping primer (5'):
Forward primer:
5'-TTCCTTCCAAAGCAGGGACTCTCTATGT-3'   (SEQ ID NO: 83)

Reverse primer:
5'-CTTGCAGAAGGACAAGACGTAGAAGACC-3'   (SEQ ID NO: 84)

KI genotyping primer (3'):
Forward primer:
5'-GAGTCTATATTGAGGGCAGGCTGGAGTC-3'   (SEQ ID NO: 85)

Reverse primer:
5'-TAGTCTGCCTGCTCACTCAACCTCTCCT-3'   (SEQ ID NO: 86)
```

The resultant PCR products were subjected to gel electrophoresis to thereby find individuals that show amplification of expected sequence lengths (4705 bp, 4026 bp) with either KI genotyping primer (5') or KI genotyping primer (3'). The PCR product of the genomic DNA of these individuals when KI genotyping primer (5') had been used was subjected to direct sequencing using Genetic analyzer (Life Technology) and the following KI sequence primer. Those individuals in which knock-in of the expected sequence was confirmed were regarded as KI positive F0.

```
KI sequence primer (5'):
                                      (SEQ ID NO: 87)
5'-GAGTCTATATTGAGGGCAGGCTGGAGTC-3'
```

KI positive F0 and C57BL/6J were crossed to obtain F1. Genomic DNA was obtained from an auricle tissue of F1 using DNeasy 96 Blood & Tissue Kit (Qiagen), and amplified with PrimeSTAR GXL (takara) and the above-described KI genotyping primer (5') (98° C. 2 min; 38 cycles of 95° C. 15 sec and 68° C. 5 min; 68° C. 7 min; and 15° C. Hold). The PCR product was subjected to gel electrophoresis. Those individuals showing amplification in the expected sequence length (4705 bp) were regarded as KI positive F1. From KI positive F1 individuals, one line was selected and bred to establish hG6PC (c.648G>T)+Int4 KI strain.

Genotyping of hG6PC (c.648G>T)+Int4 strain

Genomic DNA was extracted from an auricle tissue using DNeasy 96 Blood & Tissue Kit (Qiagen), and multiplex-amplified using KOD FX (TOYOBO) and the following KI genotyping primer and mG6PC WT primer (98° C. 2 min; 21 cycles of 95° C. 15 sec and 68° C. 5.5 min; 68° C. 5 min; and 4° C. Hold).

```
KI genotyping primer (5'):
Forward primer:
5'-TTCCTTCCAAAGCAGGGACTCTCTATGT-3'   (SEQ ID NO: 83)

Reverse primer:
5'-CTTGCAGAAGGACAAGACGTAGAAGACC-3'   (SEQ ID NO: 84)
```

```
mG6PC WT primer:
Forward primer:
5'-TAAATTTGACCAATGAGCACTGGAGGTC-3'   (SEQ ID NO: 88)

Reserve primer:
5'-AAAATCATGTGTATGCGTGCCTTTCCTA-3'   (SEQ ID NO: 89)
```

The PCR product was subjected to gel electrophoresis. The offspring was genotyped (WT, Ht or Homo) with a KI allele that was amplified around 4705 bp and a mG6PC WT allele amplified around 2536 bp.

Sample Collection from Mouse

Sample collection from mouse was performed as follows.

In the evening of the day before sample collection, a net floor was placed to avoid coprophagy and fasting was then started. On the next day, mice received laparotomy under anesthetization. After sufficient blood removal, the liver and the kidney were removed. Each organ was washed with ice cold PBS, trimmed to an appropriate size, and stored in tubes loaded with homogenizing beads. Each organ was cooled instantaneously with liquid nitrogen and then stored at −80° C.

RNA Extraction (In Vivo)

RNA was extracted as described below.

Briefly, 600 μl of cell lysis solution of RNeasy mini kit or Qiacube system (Qiagen) was added to each tissue storage tube. The tissue was homogenized with tissue lyser II (Qiagen) at 25 kHz for 2 min. After incubation for 10 min under ice cooling, the homogenized tissue was centrifuged at 8000G for 10 min at room temperature. The supernatant was collected and subjected to RNA purification according to the protocols of the respective kits including DAase treatment. RNase-Free DNase set (Qiagen) was used for DAase treatment. Purified/eluted RNA was reverse-transcribed as described earlier, and repaired G6PC mRNA was quantified according to the above-described qRT-PCR (Tagman assay).

Evaluation of Repair of Abnormal Splicing with Compounds of Examples Using hG6PC (c.648G>T)+Int4 Ht KI Mouse (1)

Compounds prepared in Examples 116 to 127 may be dissolved in PBS and injected into the tail vein of hG6PC (c.648G>T)+Int4 Ht KI mice at a dose of 3 mg/kg body weight. Seven days after the administration, mouse liver tissue may be collected under overnight fasting conditions and evaluated by qRT-PCR (Tagman) to see whether or not the abnormal splicing caused by G6PC (c.648G>T) is repaired.

Evaluation of Repair of Abnormal Splicing with Compounds of Examples Using hG6PC (c.648G>T)+Int4 Ht KI Mouse (2)

Figure 19:
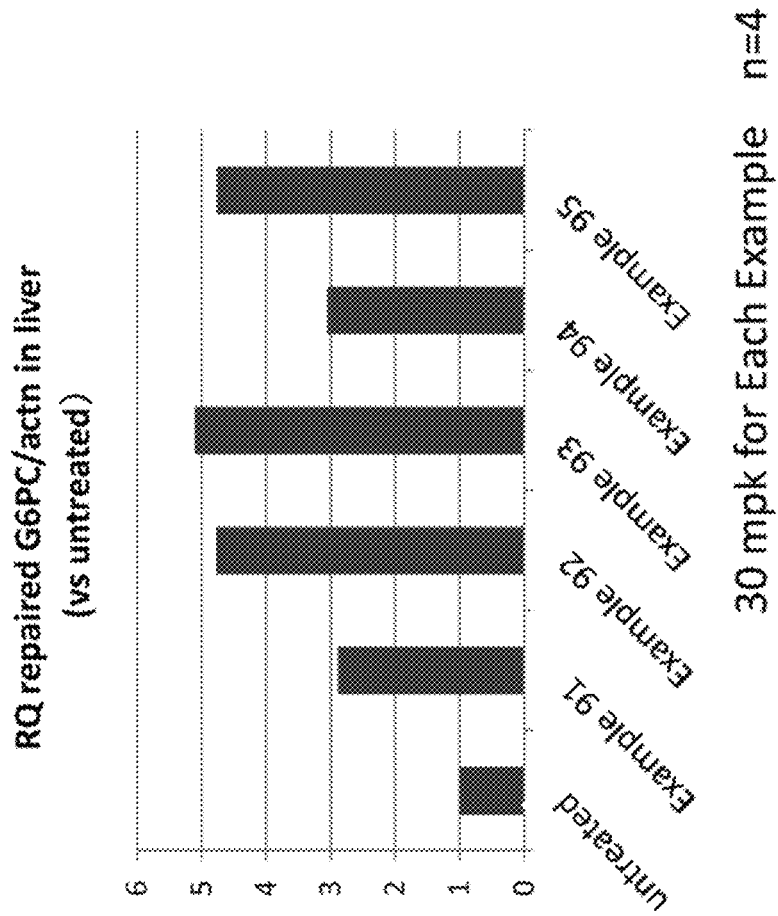
FIG. 19 Effect of correcting the abnormal splicing of G6PC mRNA in the liver of hetero-knock-in mice administered with Compounds of Examples 91 to 95 is shown by qRT-PCR. RQ: Relative Quantification; Actn: P-actin; mpk: mg/kg.

Compounds prepared in Examples 91 to 95 were dissolved in Otsuka Normal Saline and administered subcutaneously to hG6PC (c.648G>T)+Int4 Ht KI mice at a dose of 25 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 19, normalization of mRNA abnormal splicing was observed in the liver of hG6PC (c.648G>T)+Int4 Ht KI mice when Compounds of Examples 91 to 95 were used.

Evaluation of Repair of Abnormal Splicing with Compounds of Examples Using hG6PC (c.648G>T)+Int4 Ht KI Mouse (3)

Figure 20:
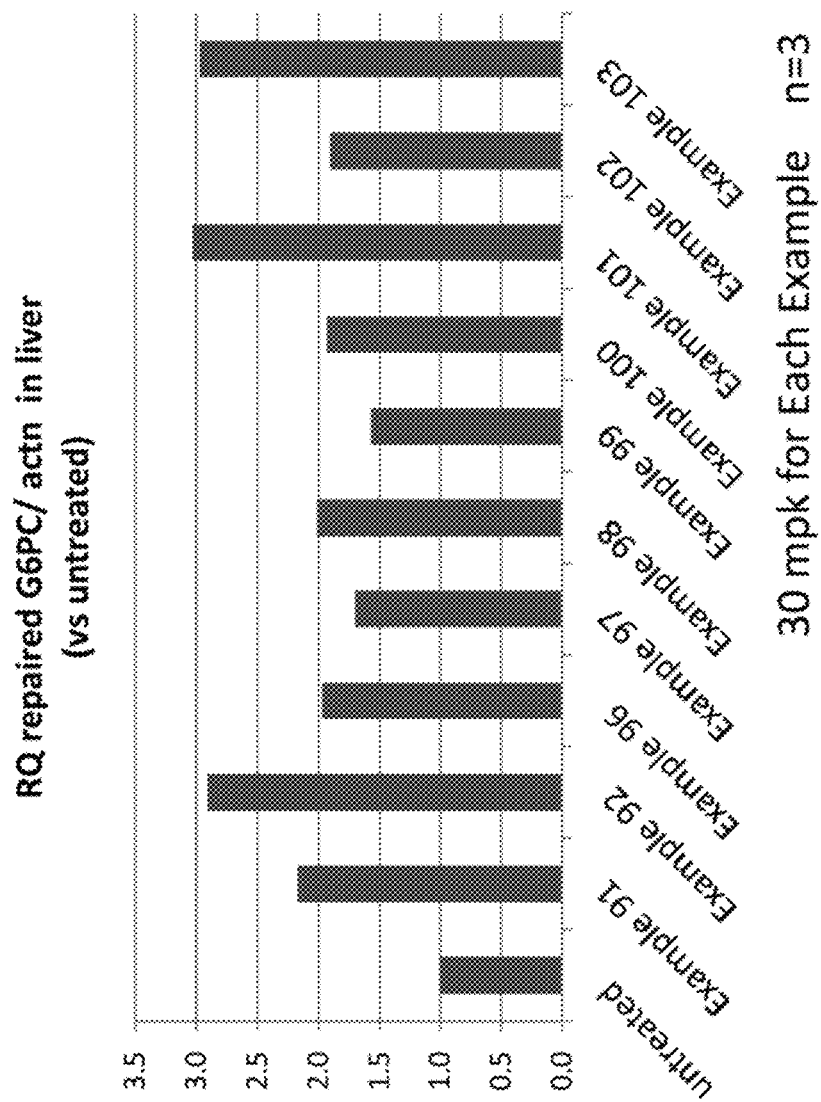
FIG. 20 Effect of correcting the abnormal splicing of G6PC mRNA in the liver of hetero-knock-in mice administered with Compounds of Examples 91 and 96 to 103 is shown by qRT-PCR. RQ: Relative Quantification; Actn: P-actin; mpk: mg/kg.

Compounds prepared in Examples 91, 92 and 96 to 103 were dissolved in Otsuka Normal Saline and administered subcutaneously to hG6PC (c.648G>T)+Int4 Ht KI mice at a dose of 25 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 20, normalization of mRNA abnormal splicing was observed in the liver of hG6PC (c.648G>T)+Int4 Ht KI mice when Compounds of Examples 91, 92 and 96 to 103 were used.

Evaluation of Repair of Abnormal Splicing with Compounds of Examples Using hG6PC (c.648G>T)+Int4 Ht KI Mouse (4)

Figure 21:
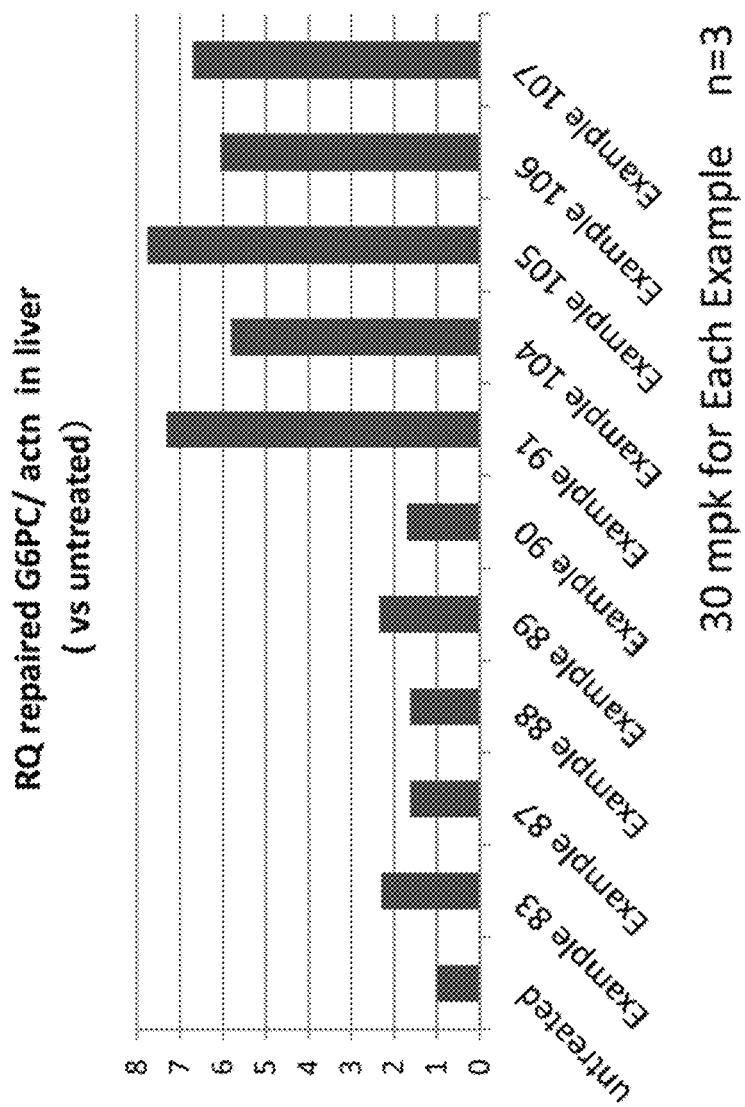
FIG. 21 Effect of correcting the abnormal splicing of G6PC mRNA in the liver of hetero-knock-in mice administered with Compounds of Examples 83, 87 to 91 and 104 to 107 is shown by qRT-PCR. RQ: Relative Quantification; Actn: P-actin; mpk: mg/kg.

Compounds prepared in Examples 83 to 91 and 104 to 107 were dissolved in Otsuka Normal Saline and administered subcutaneously to hG6PC (c.648G>T)+Int4 Ht KI mice at a dose of 30 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 21, normalization of mRNA abnormal splicing was observed in the liver of hG6PC (c.648G>T)+Int4 Ht KI mice when Compounds of Examples 83 to 91 and 104 to 107 were used.

Evaluation of Repair of Abnormal Splicing with Compounds of Examples Using hG6PC (c.648G>T)+Int4 Ht KI Mouse (5)

Figure 22:
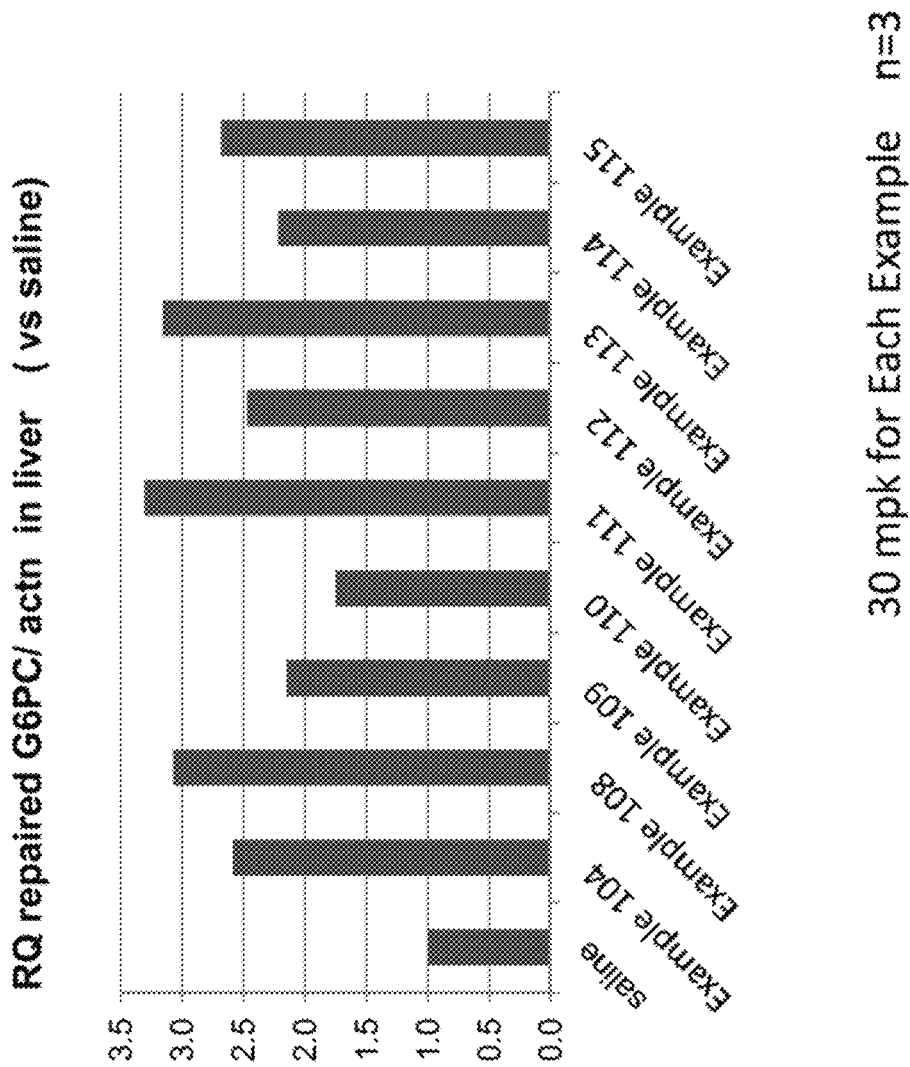
FIG. 22 Effect of correcting the abnormal splicing of G6PC mRNA in the liver of hetero-knock-in mice administered with Compounds of Examples 104 and 108 to 115 is shown by qRT-PCR. RQ: Relative Quantification; Actn: P-actin; mpk: mg/kg.

Compounds prepared in Examples 104 and 108 to 115 were dissolved in Otsuka Normal Saline and administered subcutaneously to hG6PC (c.648G>T)+Int4 Ht KI mice at a dose of 30 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 22, normalization of mRNA abnormal splicing was observed in the liver of hG6PC (c.648G>T)+Int4 Ht KI mice when Compounds of Examples 83 to 91 and 104 to 107 were used.

Evaluation of Repair of Abnormal Splicing with Compounds of Examples Using hG6PC (c.648G>T)+Int4 Ht KI Mouse (6)

Figure 23:
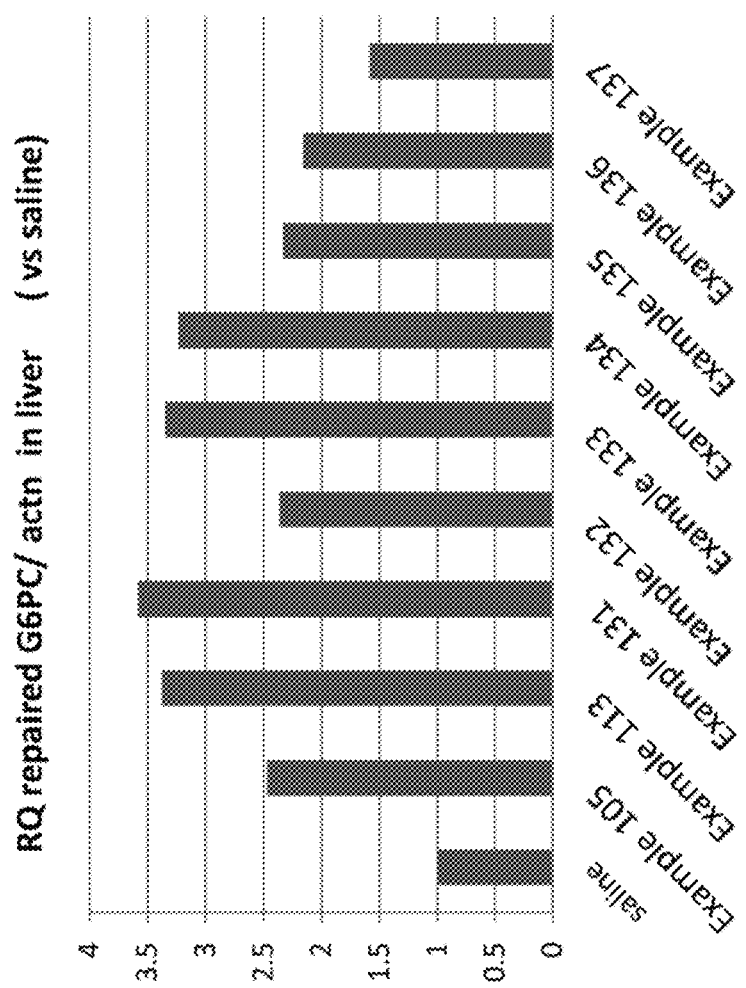
FIG. 23 Effect of correcting the abnormal splicing of G6PC mRNA in the liver of hetero-knock-in mice administered with Compounds of Examples 105, 113 and 131 to 137 is shown by qRT-PCR. RQ: Relative Quantification; Actn: P-actin; mpk: mg/kg.

Compounds prepared in Examples 105, 113 and 131 to 137 were dissolved in Otsuka Normal Saline and administered subcutaneously to hG6PC (c.648G>T)+Int4 Ht KI mice at a dose of 30 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 23, normalization of mRNA abnormal splicing was recognized in the liver of hG6PC (c.648G>T)+Int4 Ht KI mice when Compounds of Examples 105, 113 and 131 to 137 were used.

(Test Example 3) Fragment Analysis of Abnormal Splicing-Repaired Sequence

PCR Reaction and Fragment Sequence Analysis

PCR reactions and fragment sequence analyses were performed as described below.

Briefly, hG6PC splicing validation primer pair was designed as follows:

```
hG6PC splicing validation primer:
Forward primer:
5'-TTGTGGTTGGGATTCTGGGC-3'     (SEQ ID NO: 90)

Reverse primer:
5'-TCCAGAGTCCACAGGAGGTC-3'     (SEQ ID NO: 91)
```

PCR reaction solutions were prepared as follows and PCR reactions were performed. 23 μl of Platinum™ PCR SuperMix High Fidelity (Thermo Fisher), 2 μl of Primer mix (10 μM) and 1 μl of cDNA (5-fold dilution) were suspended and subjected to PCR reaction (95° C. 5 min; 36 cycles of 95° C. 30 sec, 62° C. 30 sec, and 68° C. 30 sec; 68° C. 4 min; 4° C. Hold).

Figure 24:
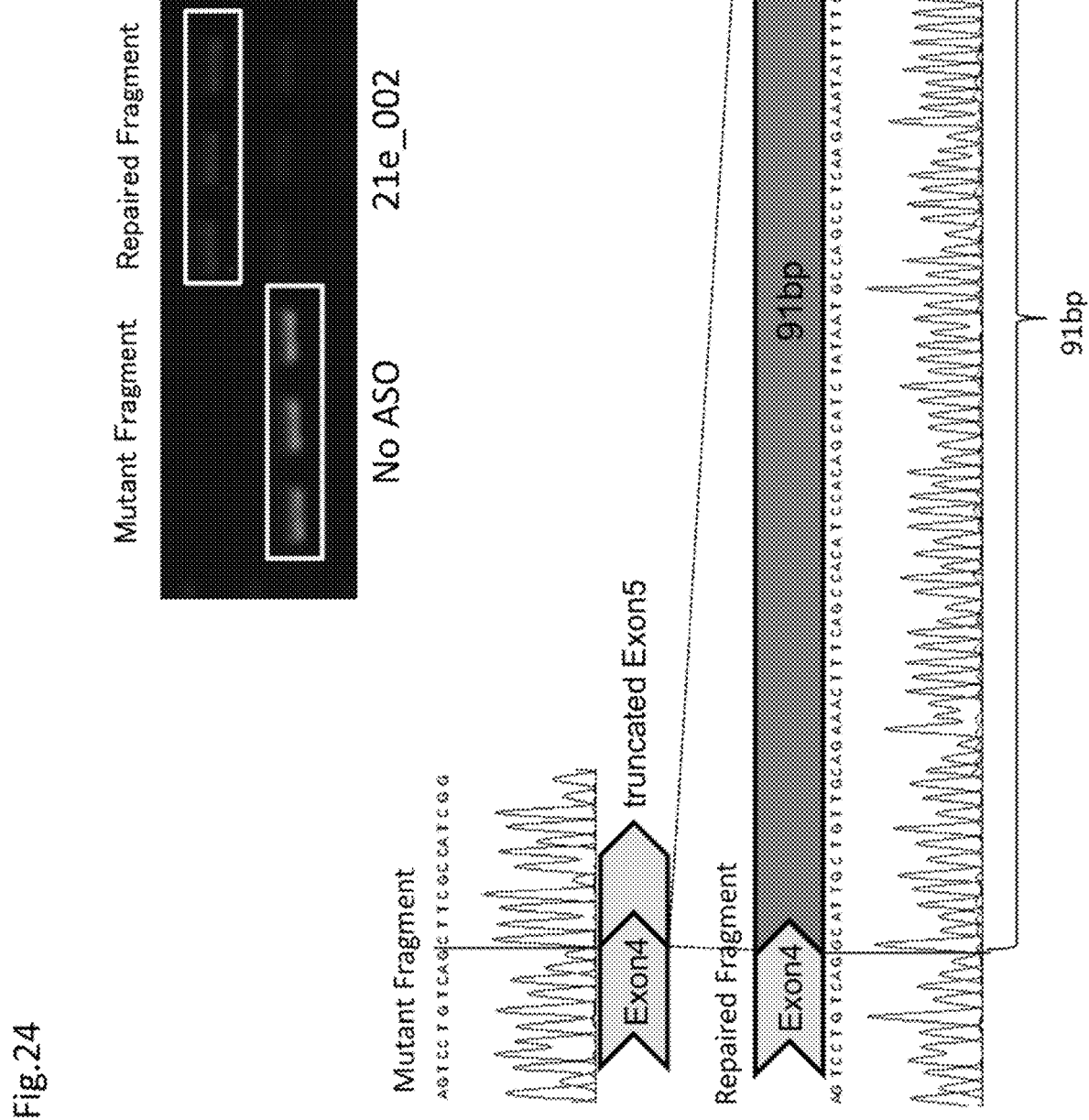
FIG. 24 A diagram showing fragment analysis of abnormal splicing-repaired sequence in cultured cells using Compound of Example 1.

PCR products were electrophoresed on E-gel Ex 2% agarose (Invitrogen) using E-Gel™ agarose gel electrophoresis system and analyzed. Each fragment was extracted from the gel using NucleoSpin™ Gel and PCR Clean-up (MACHEREY-NAGEL). After addition of G6PC sequence primer, sequencing was performed using BigDye v3.1. Nucleotide sequences were confirmed with Applied Biosystems 3730×1 DNA Analyzer (Life Technologies) (FIG. 24).

```
G6PC sequence primer:
5'-GCTGTGCAGCTGAATGTCTG-3'     (SEQ ID NO: 92)
```

Fragment Analysis of Abnormal Splicing-Repaired Sequence in Cultured Cells Using Compound of Example 1 (21e_002)

cDNAs were prepared from (a) a sample transfected with human G6PC full length plasmid vector (pcDNA hG6PC (c.648G>T)+Int4) alone and (b) a sample co-transfected with human G6PC full length plasmid vector (pcDNA hG6PC (c.648G>T)+Int4) and oligonucleotide (21e_002) (both samples had been prepared in "Evaluation of Repair of Abnormal Splicing in G6PC mRNA with Compounds of Examples Using Human G6PC Full-Length Plasmid Vector (pcDNA hG6PC (c.648G>T)+Int4) (1)" described earlier). PCR was performed using the resultant cDNA as a template, and fragment sequence analysis was conducted. As shown in FIG. 24, abnormal splicing causing deletion of 91 nucleotides was normalized by means of Compound (21e_002) of Example 1.

(Test Example 4) Evaluation of Repair of Abnormal Splicing with Compounds of Examples Using Model Mouse Evaluation of Compounds of Examples was performed using the model mouse in the same manner as described in Test Example 2.

Evaluation of Repair of Abnormal Splicing with Compounds of Examples Using hG6PC (c.648G>T)+Int4 Ht KI Mouse (7)

Figure 25:
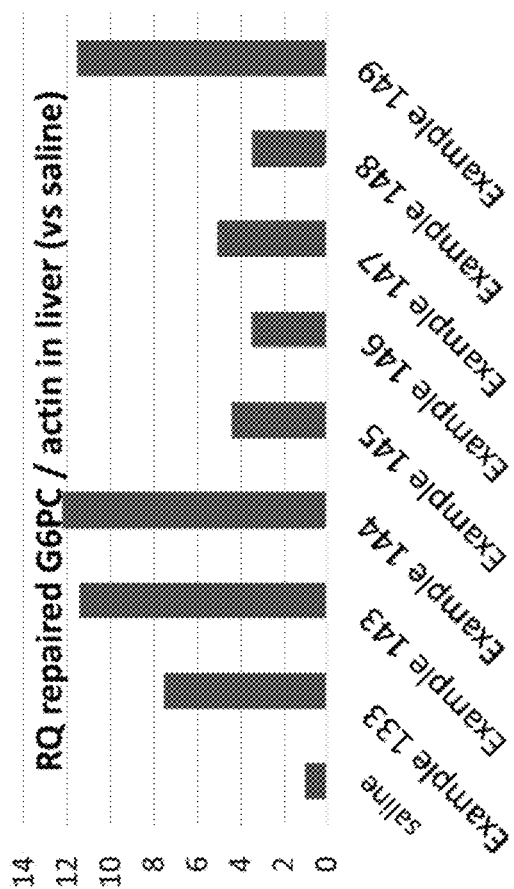
FIG. 25 Effect of correcting the abnormal splicing of G6PC mRNA in the liver of hetero-knock-in mice administered with Compounds of Examples 133 and 143 to 149 is shown by qRT-PCR. RQ: Relative Quantification; mpk: mg/kg.

Compounds prepared in Examples 133 and 143 to 149 were dissolved in Otsuka Normal Saline and administered subcutaneously to hG6PC (c.648G>T)+Int4 Ht KI mice at a dose of 30 mg/kg body weight. Seven days after the administration, mouse liver tissue was collected under overnight fasting conditions and evaluated by qRT-PCR (Tagman) to see whether or not the abnormal splicing caused by G6PC (c.648G>T) would be repaired. As a result, as shown in FIG. 25, normalization of mRNA abnormal splicing was observed in the liver of hG6PC (c.648G>T)+Int4 Ht KI mice when Compounds of Examples 133 and 143 to 149 were used.

Evaluation of Repair of Abnormal Splicing with Compounds of Examples Using hG6PC (c.648G>T)+Int4 Ht KI Mouse (8)

Figure 26:
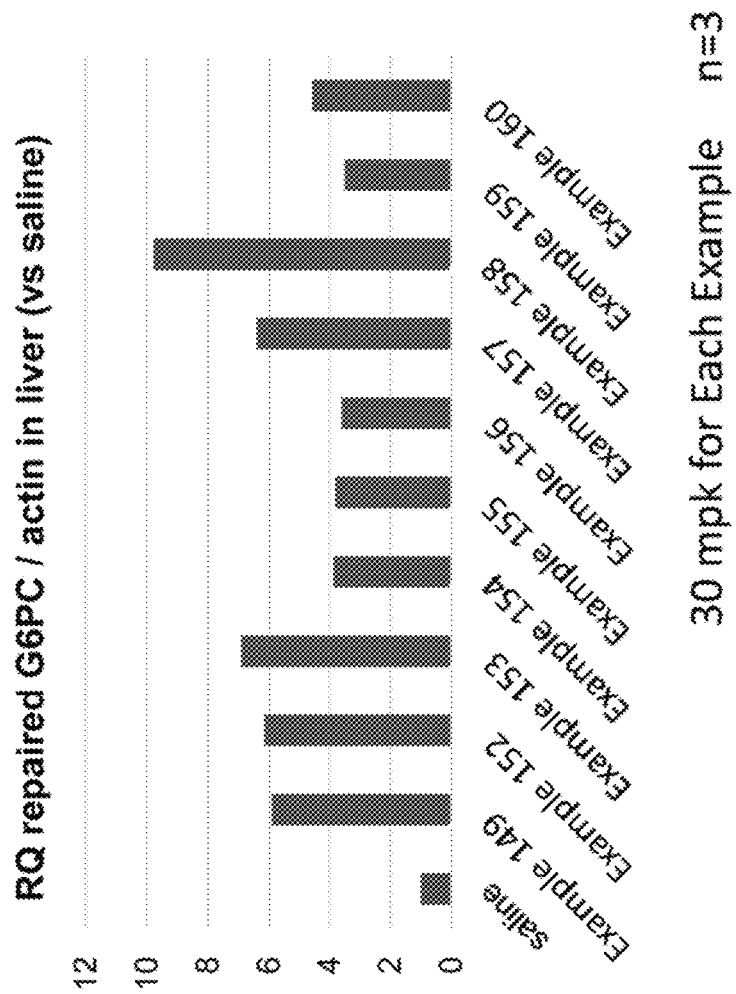
FIG. 26 Effect of correcting the abnormal splicing of G6PC mRNA in the liver of hetero-knock-in mice administered with Compounds of Examples 149 and 152 to 160 is shown by qRT-PCR. RQ: Relative Quantification; mpk: mg/kg.

Compounds prepared in Examples 149 and 152 to 160 were dissolved in Otsuka Normal Saline and administered subcutaneously to hG6PC (c.648G>T)+Int4 Ht KI mice at a dose of 30 mg/kg body weight. Seven days after the administration, mouse liver tissue was collected under overnight fasting conditions and evaluated by qRT-PCR (Taqman) to see whether or not the abnormal splicing caused by G6PC (c.648G>T) would be repaired. As a result, as shown in FIG. 26, normalization of mRNA abnormal splicing was observed in the liver of hG6PC (c.648G>T)+Int4 Ht KI mice when Compounds of Examples 149 and 152 to 160 were used.

Example 161

$X^{20}$-$A^{m1s}$-$A^{m1s}$-$T^{e2s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{m1s}$-$G^{m1t}$-H (SEQ ID NO: 93)

Synthesis was performed in the same manner as described in Example 133, except that the above-described sequence (designation: 15e_001.6) was substituted for the sequence used in Example 133 and that $X^{18}$ was replaced by $X^{20}$.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6278.03).

Example 162

$X^{20}$-$A^{m1s}$-$T^{e2s}$-$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{m1s}$-$G^{m1s}$-$C^{e2t}$—H (SEQ ID NO: 94)

Synthesis was performed in the same manner as described in Example 133, except that the above-described sequence (designation: 15e_005.6) was substituted for the sequence used in Example 133 and that $X^{18}$ was replaced by $X^{20}$.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6280.03).

Example 163

$X^{20}$-$A^{m1s}$-$A^{m1s}$-$T^{e2s}$-$C^{e2s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{m1s}$-$G^{m1t}$-H (SEQ ID NO: 180)

Synthesis was performed in the same manner as described in Example 133, except that the above-described sequence (designation: 15e_001.7) was substituted for the sequence used in Example 133 and that $X^{18}$ was replaced by $X^{20}$.

The nucleotide sequence of the subject compound is complementary to a sequence from the $92^{nd}$ to the $106^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6304.04).

Example 164

$X^{20}$-$A^{m1s}$-$T^{e2s}$-$C^{e2s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{m1s}$-$G^{m1s}$-$C^{e2t}$—H (SEQ ID NO: 181)

Synthesis was performed in the same manner as described in Example 133, except that the above-described sequence (designation: 15e_005.7) was substituted for the sequence used in Example 133 and that $X^{18}$ was replaced by $X^{20}$.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6306.03).

Example 165

$X^{20}$-$A^{m1s}$-$U^{m1s}$—$C^{m1s}$-$C^{m1s}$-$G^{m1s}$-$A^{m1s}$-$U^{m1s}$-$G^{m1s}$-$G^{m1s}$-$C^{m1s}$-$G^{m1s}$-$A^{m1s}$-$A^{m1s}$-$G^{m1s}$-$C^{m1t}$—H (SEQ ID NO: 95)

Synthesis was performed in the same manner as described in Example 133, except that the above-described sequence (designation: 15e_005.8) was substituted for the sequence used in Example 133 and that $X^{18}$ was replaced by $X^{20}$.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6149.93).

Example 166

$X^{20}$-$A^{e2s}$-$U^{m1p}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 182)

Synthesis was performed in the same manner as described in Example 153, except that the above-described sequence (designation: 15e_005.5.01) was substituted for the sequence used in Example 153. However, among reagents used in the automated nucleic acid synthesizer, Oxidizer 0.05 M (Sigma-Aldrich; product No. L560250-04) or iodine (Kanto Chemical Co., Inc.; product No. 20035-00) dissolved in mixed solution of tetrahydrofuran (dehydrated; Kanto Chemical Co., Inc.; product No. 40993-05), pyridine (dehydrated; Kanto Chemical Co., Inc.; product No. 11339-05) and distilled water (78:20:2; v/v/v) to give a concentration of 0.02 M was used appropriately as an oxidizer necessary for the synthesis of the above-described sequence.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 167

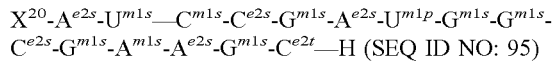
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.02) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 168

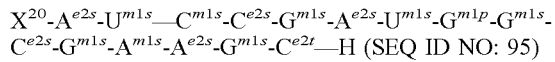
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.03) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6247.99).

Example 169

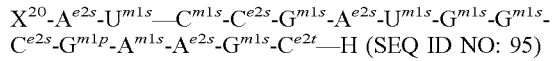
$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.04) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 170

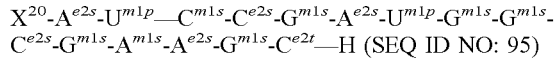
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.05) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 171

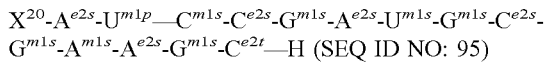
$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.06) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 172

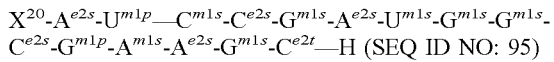
$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.07) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 173

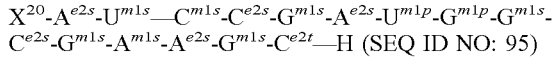
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.08) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 174

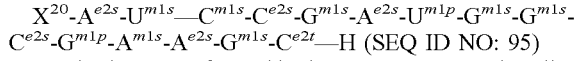
$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.09) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.01).

Example 175

$X^{20}$-$A^{e2s}$-$U^{m1s}$—$C^{m1s}$-$C^{e2s}$-$G^{m1s}$-$A^{e2s}$-$U^{m1s}$-$G^{m1p}$-$G^{m1s}$-$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.10) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.01).

Example 176

$X^{20}$-$A^{e2s}$-$U^{m1p}$—$C^{m1s}$-$C^{e2s}$-$G^{m1s}$-$A^{e2s}$-$U^{m1p}$-$G^{m1p}$-$G^{m1s}$-$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.11) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.00).

Example 177

$X^{20}$-$A^{e2s}$-$U^{m1p}$—$C^{m1s}$-$C^{e2s}$-$G^{m1s}$-$A^{e2s}$-$U^{m1p}$-$G^{m1s}$-$G^{m1s}$-$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.12) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.03).

Example 178

$X^{20}$-$A^{e2s}$-$U^{m1p}$—$C^{m1s}$-$C^{e2s}$-$G^{m1s}$-$A^{e2s}$-$U^{m1s}$-$G^{m1p}$-$G^{m1s}$-$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.13) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.02).

Example 179

$X^{20}$-$A^{e2s}$-$U^{m1s}$—$C^{m1s}$-$C^{e2s}$-$G^{m1s}$-$A^{e2s}$-$U^{m1p}$-$G^{m1p}$-$G^{m1s}$-$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.14) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.03).

Example 180

$X^{20}$-$A^{e2s}$-$U^{m1p}$—$C^{m1s}$-$C^{e2s}$-$G^{m1s}$-$A^{e2s}$-$U^{m1p}$-$G^{m1p}$-$G^{m1s}$-$C^{e2s}$-$G^{m1p}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.15) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6200.06).

Example 181

$X^{20}$-$A^{e2p}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.16) was substituted for the sequence used therein.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6247.99).

Example 182

$C^{e2s}$-$G^{m1s}$-$G^{m1s}$-$C^{e2t}$—H (SEQ ID NO: 95)

Synthesis was performed in the same manner as described in Example 166, except that the above-described sequence (designation: 15e_005.5.17) was substituted for the sequence used therein.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.01).

Example 183

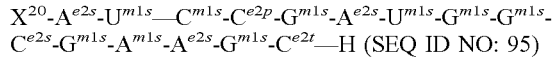
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.18) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 184

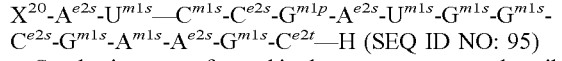
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.19) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.01).

Example 185

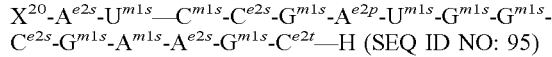
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.20) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 186

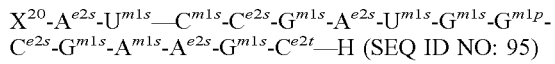
$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.21) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.01).

Example 187

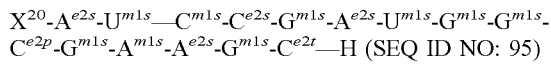
$C^{e2p}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.22) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 188

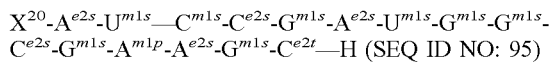
$C^{e2s}$-$G^{m1s}$-$A^{m1p}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.23) was substituted for the sequence used in Example 166.

The nucleotide sequence of the subject compound is complementary to a sequence from the 91$^{st}$ to the 105$^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 189

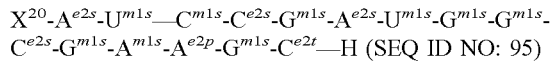
$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.24) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 190

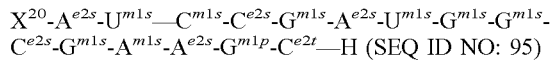
$C^{e2s}$-$G^{m1s}$-$A^{m1s}$-$A^{e2s}$-$G^{m1p}$-$C^{e2t}$—H (SEQ ID NO: 95)

Synthesis was performed in the same manner as described in Example 166, except that the above-described sequence (designation: 15e_005.5.25) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6248.00).

Example 191

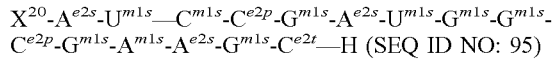
$C^{e2p}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.26) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.01).

Example 192

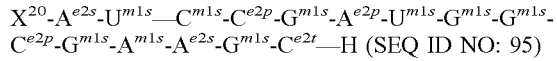
$C^{e2p}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.27) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.03).

Example 193

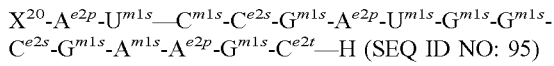
$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.28) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.03).

Example 194

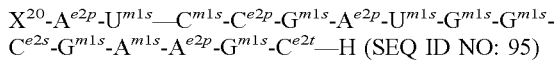
$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.29) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6200.06).

Example 195

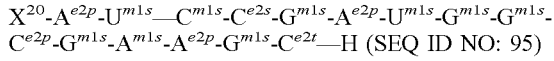
$C^{e2p}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.30) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6200.06).

Example 196

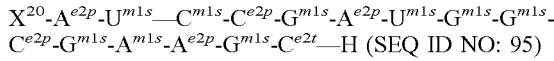
$C^{e2p}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.31) was substituted for the sequence used in Example 166.

Example 197

$X^{20}$-$A^{e2p}$-$U^{m1p}$—$C^{e2p}$-$C^{e2p}$-$G^{m1p}$-$A^{e2p}$-$U^{m1p}$-$G^{m1p}$-$G^{m1p}$-$C^{e2p}$-$G^{m1p}$-$A^{m1p}$-$A^{e2p}$-$G^{m1p}$-$C^{e2t}$—H (SEQ ID NO: 95)

Synthesis was performed in the same manner as described in Example 166, except that the above-described sequence (designation: 15e_005.5.32) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6040.30).

Example 198

$X^{20}$-$A^{e2p}$-$U^{m1s}$—$C^{m1s}$-$C^{e2p}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.33) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 199

$X^{20}$-$A^{e2p}$-$U^{m1s}$—$C^{m1s}$-$C^{e2s}$-$G^{m1s}$-$A^{e2p}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.34) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.01).

Example 200

$X^{20}$-$A^{e2p}$-$U^{m1s}$—$C^{m1s}$-$C^{e2s}$-$G^{m1s}$-$A^{e2s}$-$U^{m1s}$-$G^{m1s}$-$G^{m1s}$-$C^{e2p}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.35) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.04).

Example 201

$X^{20}$-$A^{e2p}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.36) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.03).

Example 202

$X^{20}$-$A^{e2s}$-$U^{m1s}$—$C^{m1s}$-$C^{e2p}$-$G^{m1s}$-$A^{e2p}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.37) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 203

$X^{20}$-$A^{e2s}$-$U^{m1s}$—$C^{m1s}$-$C^{e2p}$-$G^{m1s}$-$A^{e2s}$-$U^{m1s}$-$G^{m1s}$-$G^{m1s}$-$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.38) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.01).

Example 204

$X^{20}$-$A^{e2s}$-$U^{m1s}$—$C^{m1s}$-$C^{e2s}$-$G^{m1s}$-$A^{e2p}$-$U^{m1s}$-$G^{m1s}$-$G^{m1s}$-$C^{e2p}$-$G^{m1s}$-$A^{m1s}$-$A^{e2s}$-$G^{m1s}$-$C^{e2t}$—H (SEQ ID NO: 95)

Synthesis was performed in the same manner as described in Example 166, except that the above-described sequence (designation: 15e_005.5.39) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 205

$X^{20}$-$A^{e2s}$-$U^{m1s}$—$C^{m1s}$-$C^{e2s}$-$G^{m1s}$-$A^{e2p}$-$U^{m1s}$-$G^{m1s}$-$G^{m1s}$-$C^{e2s}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.40) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 206

$X^{20}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2p}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.41) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6232.02).

Example 207

$X^{20}$-$A^{e2s}$-$U^{m1s}$—$C^{m1s}$-$C^{e2p}$-$G^{m1s}$-$A^{e2s}$-$U^{m1s}$-$G^{m1s}$-$G^{m1s}$-$C^{e2p}$-$G^{m1s}$-$A^{m1s}$-$A^{e2p}$-$G^{m1s}$-$C^{e2t}$—H (SEQ ID NO: 95)

Synthesis was performed in the same manner as described in Example 166, except that the above-described sequence (designation: 15e_005.5.42) was substituted for the sequence used in Example 166.

The nucleotide sequence of the subject compound is complementary to a sequence from the $91^{st}$ to the $105^{th}$ nucleotide from the 5' end of exon 5 in c.648G>T-mutated G6PC gene in which nucleotide No. 728 of *Homo sapiens* glucose-6-phosphatase catalytic subunit (G6PC), transcript variant 1, mRNA (NCBI-GenBank accession No. NM_000151.3) is mutated from G to T. The compound was identified by negative-ion ESI mass spectrometry (measured molecular weight: 6216.00).

As used herein, $A^t$, $G^t$, 5meC$^t$, $C^t$, $T^t$, $U^t$, $A^p$, $G^p$, 5meC$^p$, $C^p$, $T^p$, $U^p$, $A^s$, $G^s$, 5meC$^s$, $C^s$, $T^s$, $U^s$, $A^{m1t}$, $G^{m1t}$, $C^{m1t}$, 5meC$^{m1t}$, $U^{m1t}$, $A^{m1p}$, $G^{m1p}$, $C^{m1p}$, 5meC$^{m1p}$, $U^{m1p}$, $A^{m1s}$, $G^{m1s}$ $C^{m1s}$, 5meC$^{m1s}$, $U^{m1s}$, $A^{e2t}$, $G^{e2t}$, $C^{e2t}$, $T^{e2t}$, $A^{e2p}$, $G^{e2p}$, $C^{e2p}$, $T^{e2p}$, $A^{e2s}$, $G^{e2s}$ $C^{e2s}$, $T^{e2s}$, $A^{1t}$, $G^{1t}$, $C^{1t}$, $T^{1t}$, $A^{e1p}$, $G^{e1p}$, $C^{e1p}$, $T^{e1p}$, $A^{e1s}$, $G^{e1s}$, $C^{e1s}$, $T^{e1s}$, $A^{m2t}$, $G^{m2t}$, 5meC$^{m2t}$, $T^{m2t}$, $A^{m2p}$, $G^{m2p}$, 5meC$^{m2p}$, $T^{m2p}$, $A^{m2s}$, $G^{m2s}$, 5meC$^{m2s}$, $T^{m2s}$, X, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$ and $X^{22}$ represent groups with the following structures, respectively.

[Formula 195]

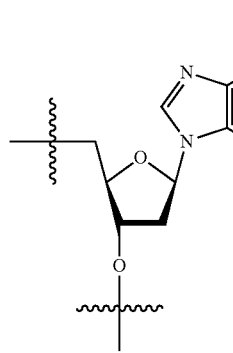
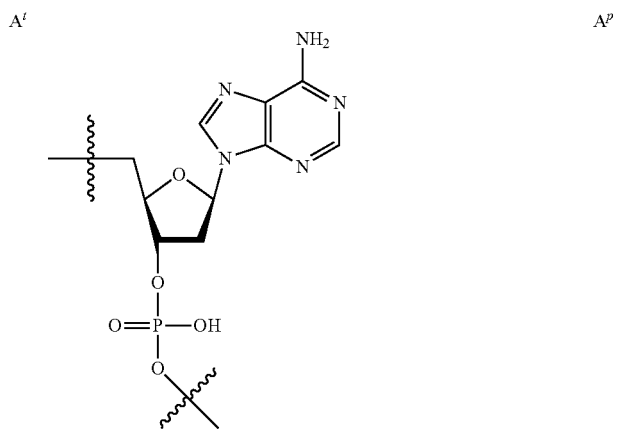

233
-continued
A<sup>s</sup>
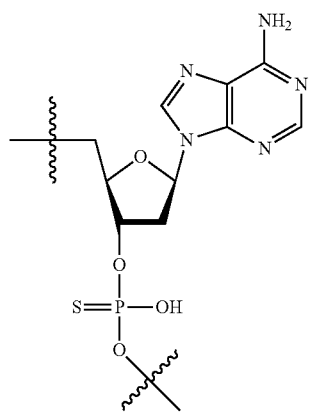
234
G<sup>t</sup>
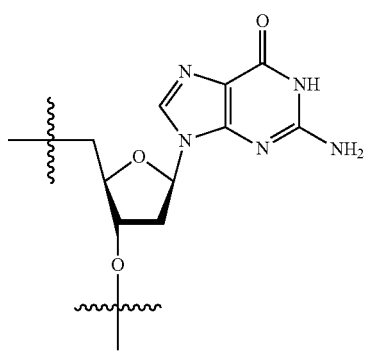
G<sup>p</sup>
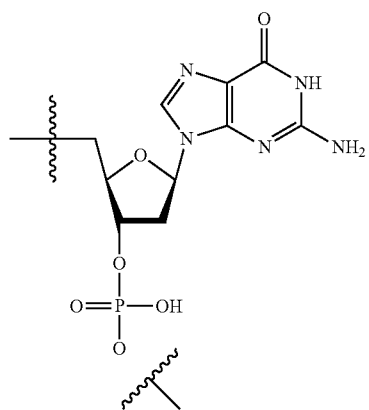
G<sup>s</sup>
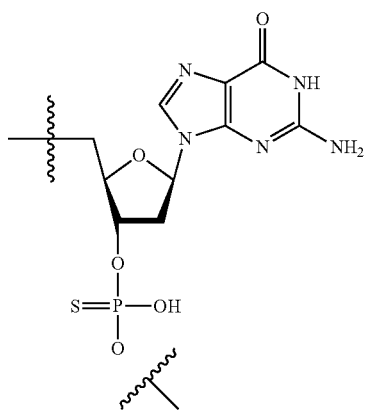
5meC<sup>t</sup>
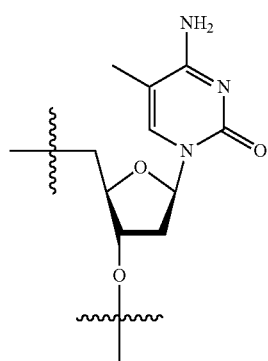
5meC<sup>p</sup>
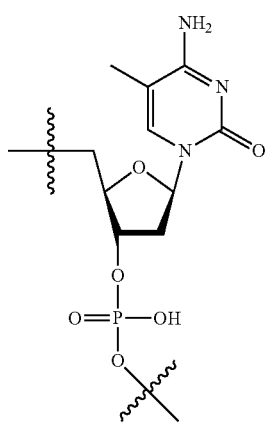

5MeC$^s$
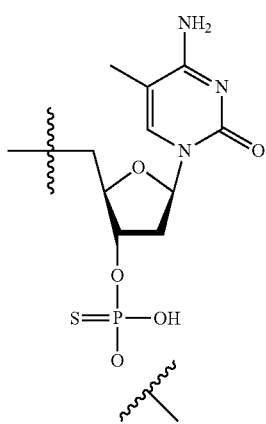
C$^t$
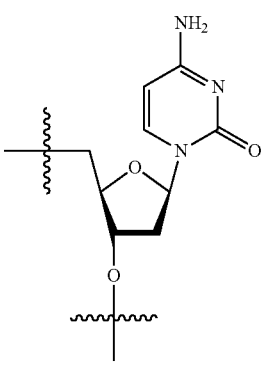
C$^p$
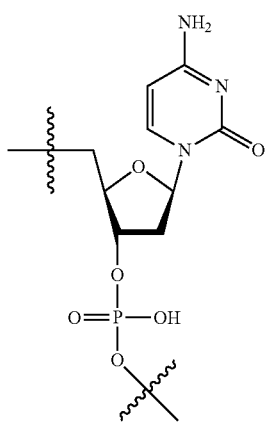
C$^s$
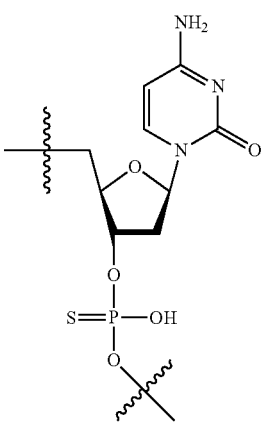
T$^t$
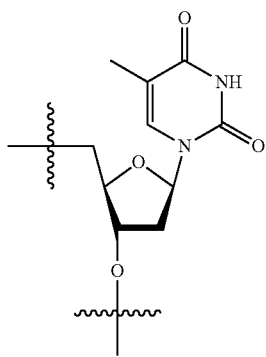
T$^p$
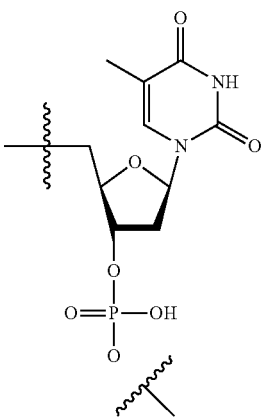

-continued
T<sup>s</sup>
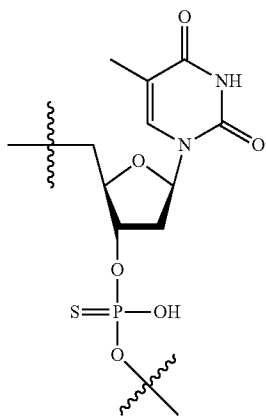
U<sup>t</sup>
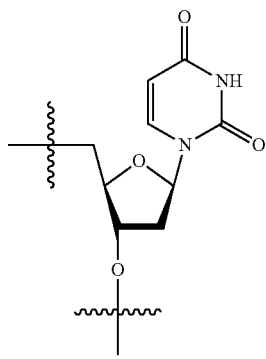
U<sup>p</sup>
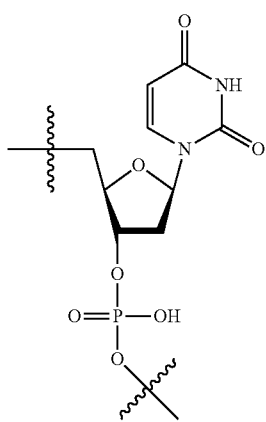
U<sup>s</sup>
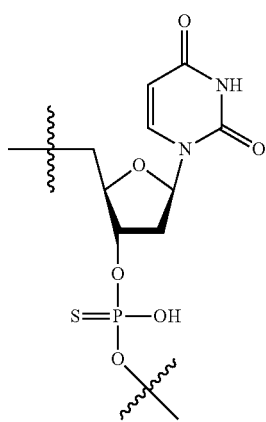
[Formula 196]
A<sup>m1t</sup>
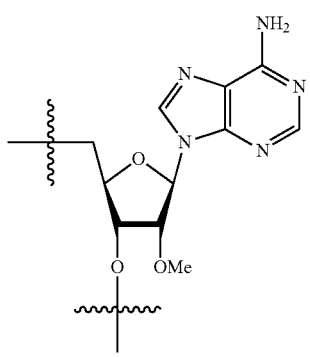
A<sup>m1p</sup>
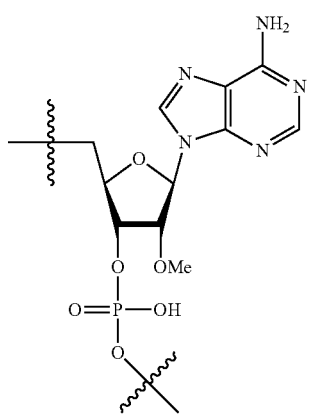

-continued
A^{m1s}
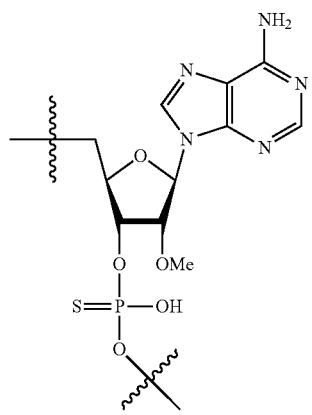
G^{m1t}
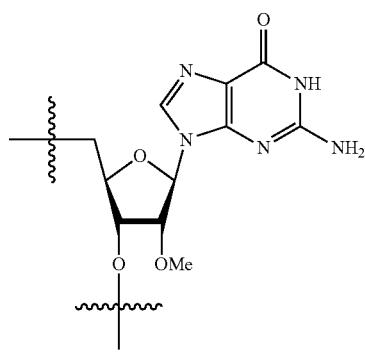
G^{m1p}
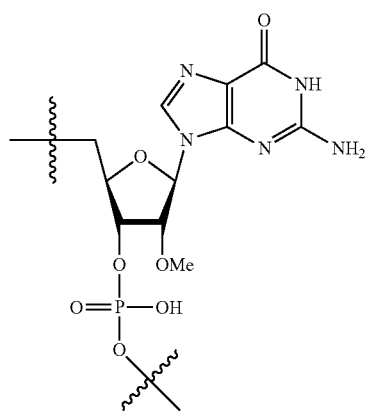
G^{m1s}
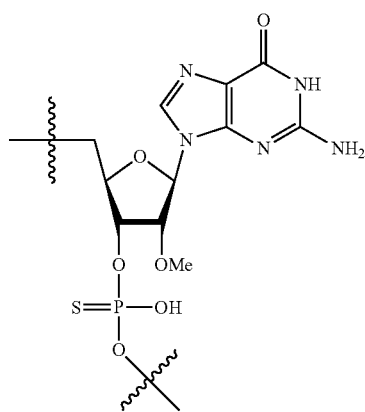
C^{m1t}
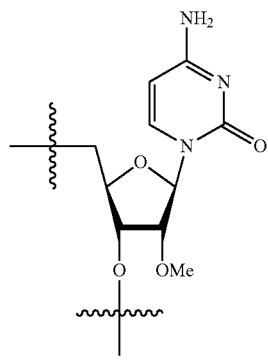
C^{m1p}
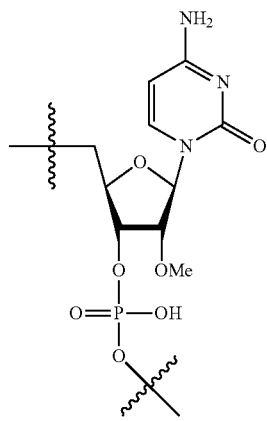

-continued
C<sup>m1s</sup>
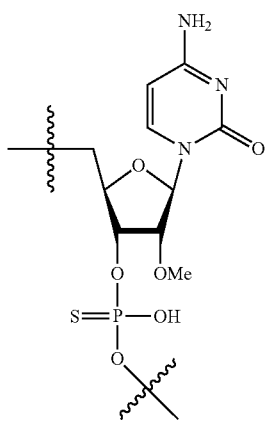
5meC<sup>m1t</sup>
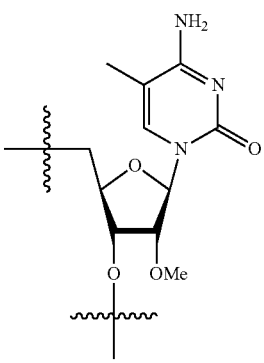
5meC<sup>m1p</sup>
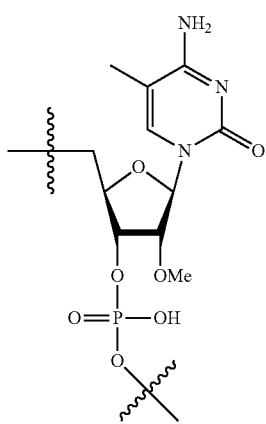
5meC<sup>m1s</sup>
U<sup>m1t</sup>
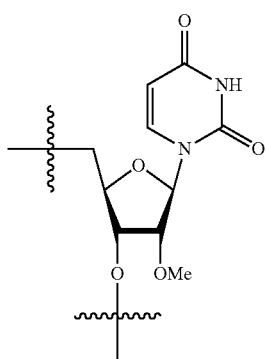
U<sup>m1p</sup>
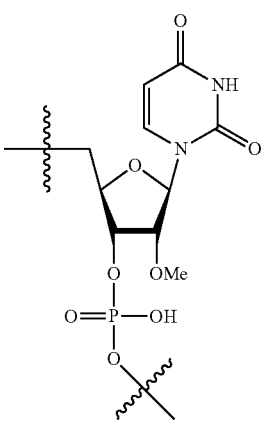

-continued
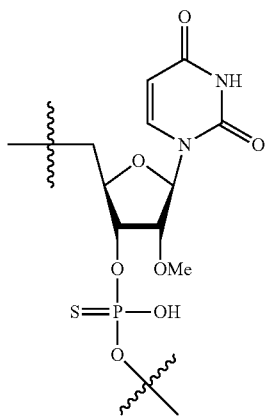
[Formula 197]
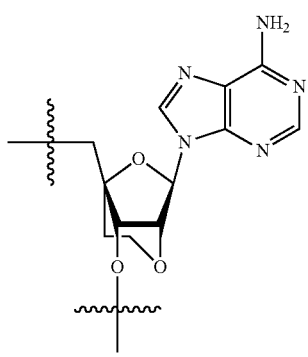 A$^{e2t}$
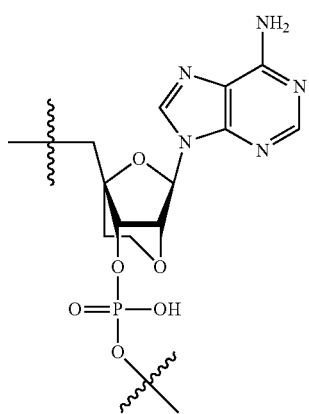 A$^{e2p}$
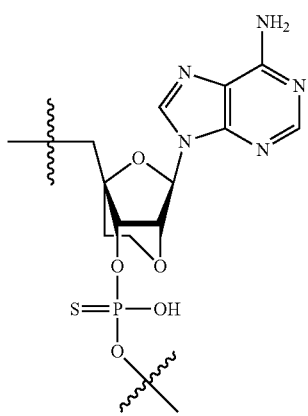 A$^{e2s}$
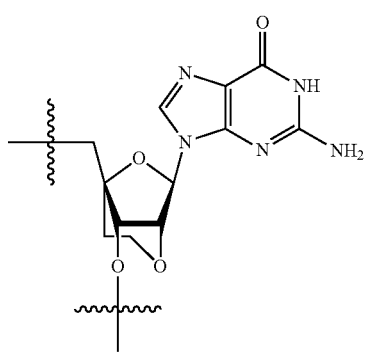 G$^{e2t}$
U$^{m1s}$ -continued
$G^{e2p}$
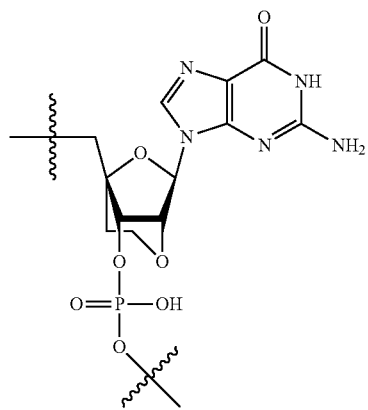
$G^{e2s}$
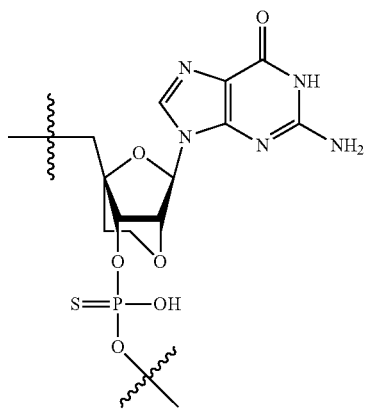
$C^{e2t}$
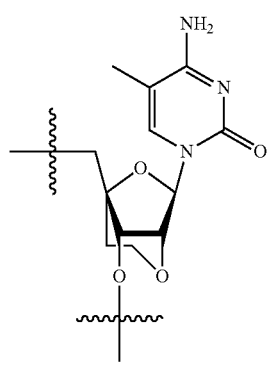
$C^{e2p}$
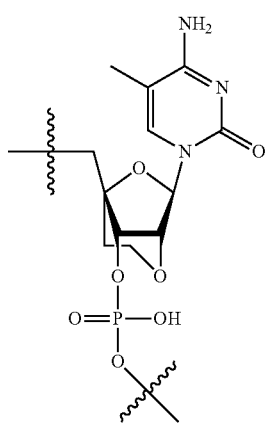
$C^{e2s}$
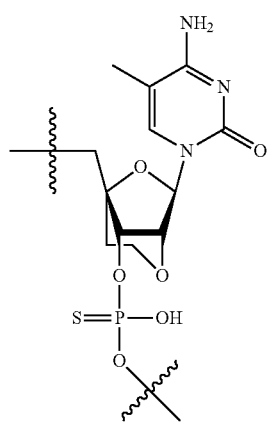
$T^{e2t}$
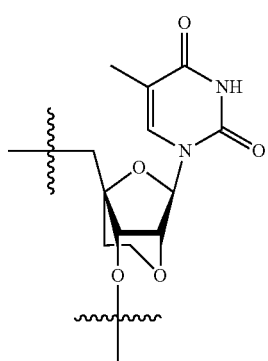

247 248
-continued
T$^{e2p}$ 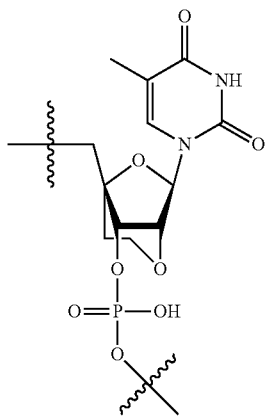 T$^{e2s}$ 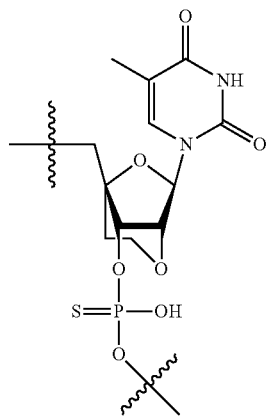
[Formula 198]
A$^{lt}$ 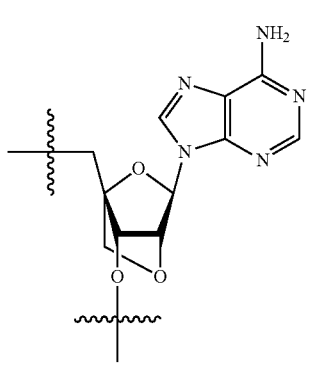 A$^{e1p}$ 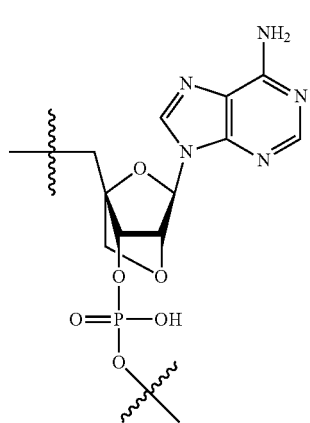
A$^{e1s}$ 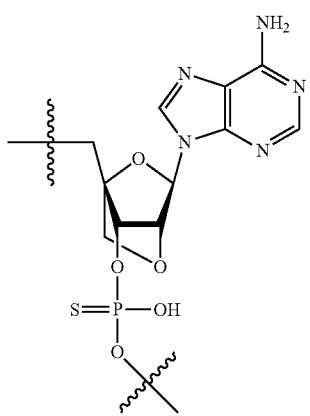 G$^{lt}$ 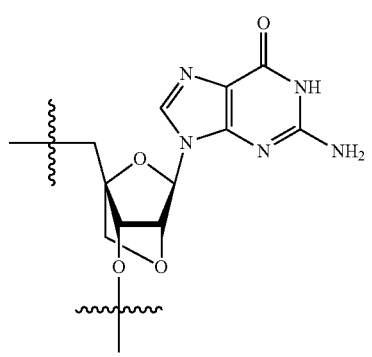

249 250
-continued
G<sup>elp</sup>
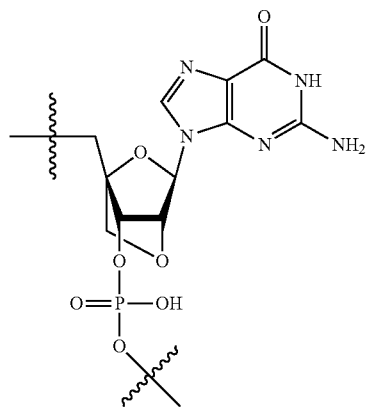
G<sup>els</sup>
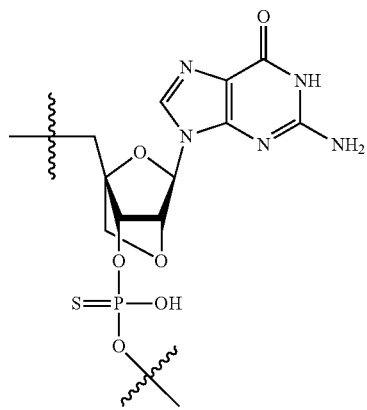
C<sup>lt</sup>
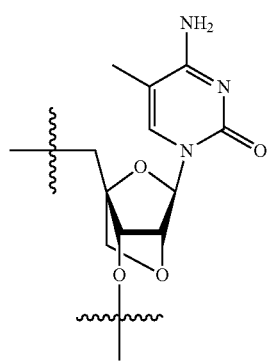
C<sup>elp</sup>
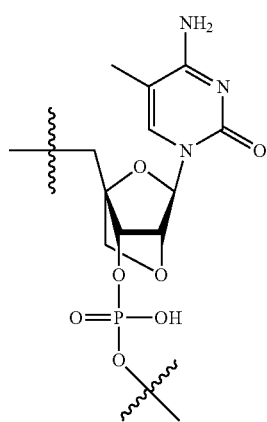
C<sup>els</sup>
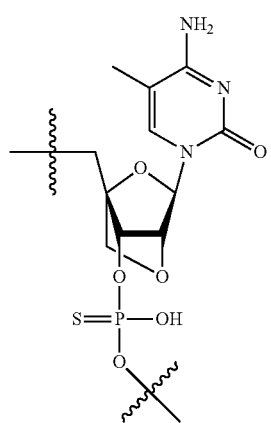
T<sup>lt</sup>
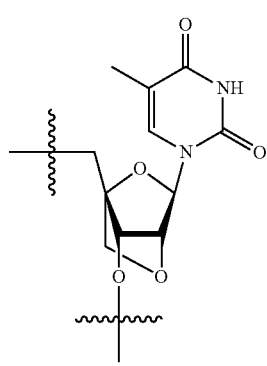

-continued
T<sup>elp</sup>
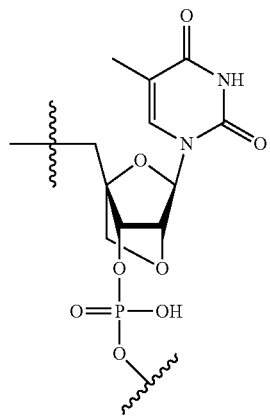
T<sup>els</sup>
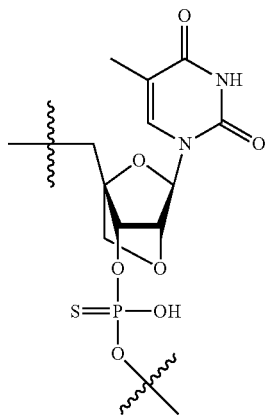
[Formula 199]
A<sup>m2t</sup>
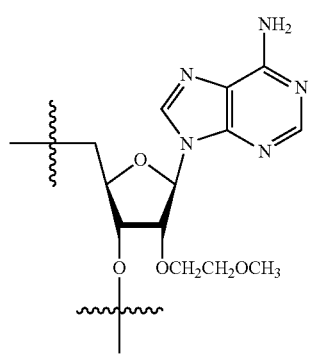
A<sup>m2p</sup>
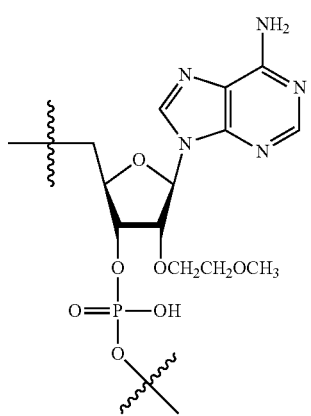
A<sup>m2s</sup>
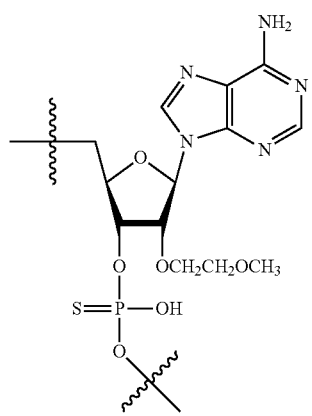
G<sup>m2t</sup>
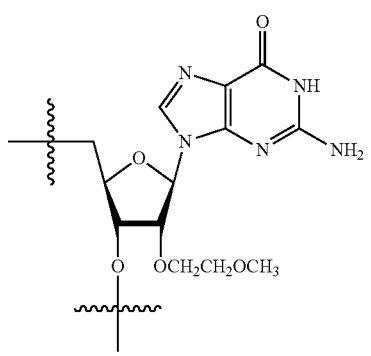

-continued
G<sup>m2p</sup>
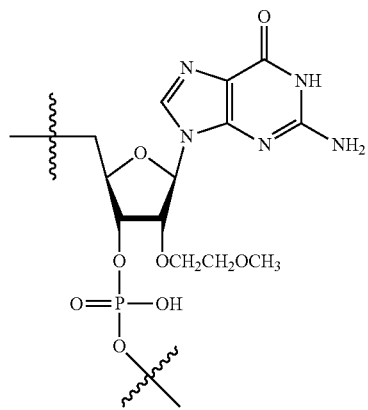
G<sup>m2s</sup>
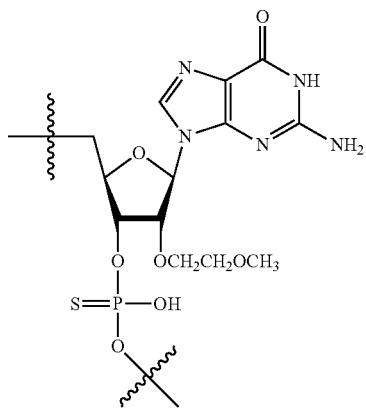
5meC<sup>m2t</sup>
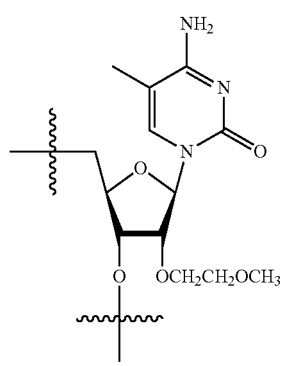
5meC<sup>m2p</sup>
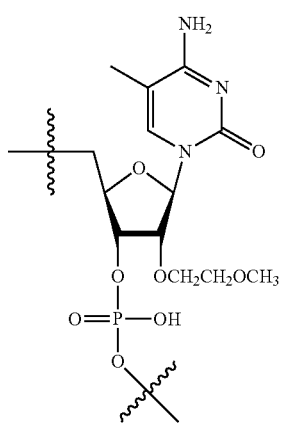
5meC<sup>m2s</sup>
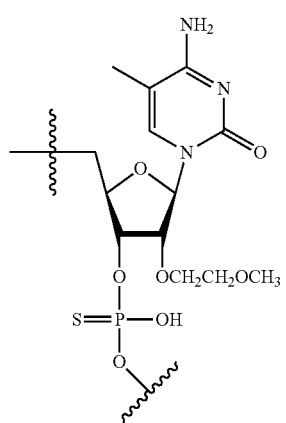
T<sup>m2t</sup>
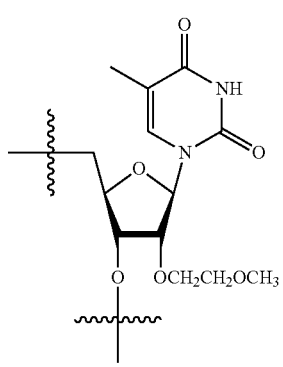

-continued
255 T$^{m2p}$
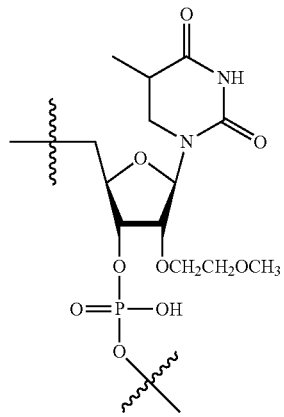
256 T$^{m2s}$
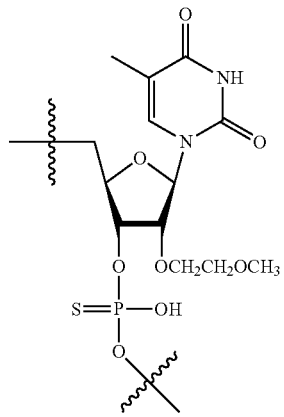
[Formula 200]
X$^1$
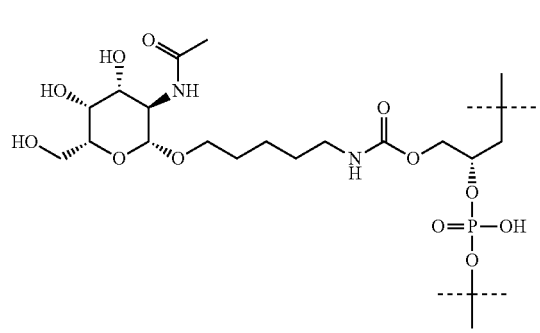
X$^2$
X$^3$
X$^4$
X$^5$ -continued
X⁶
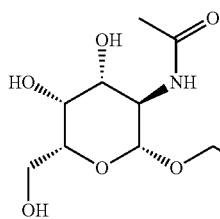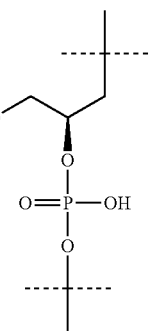
X⁷
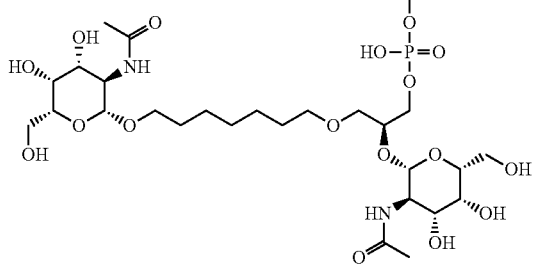
X⁸
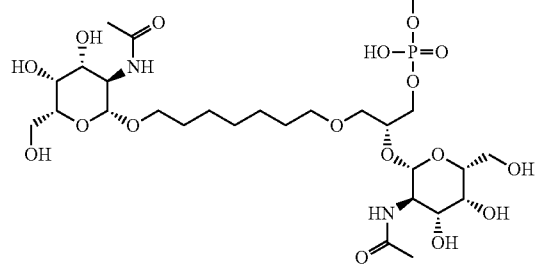
[Formula 201]
X⁹
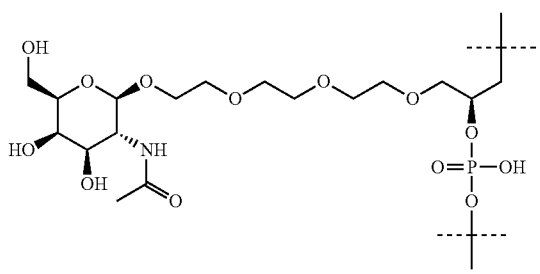
X¹⁰
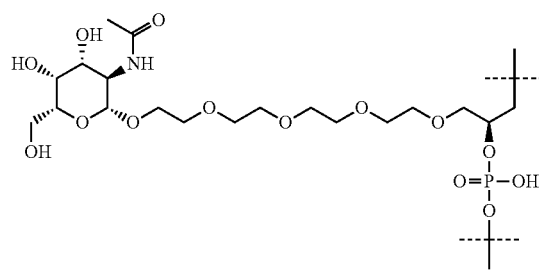
X¹¹
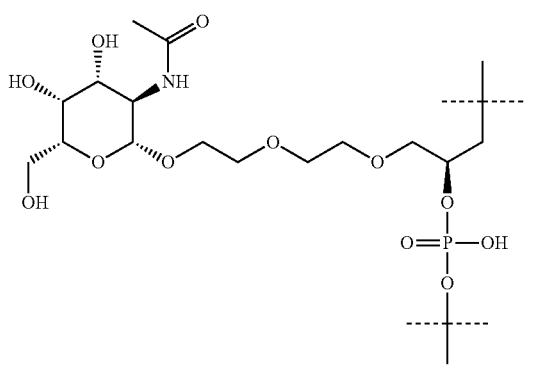
X¹²
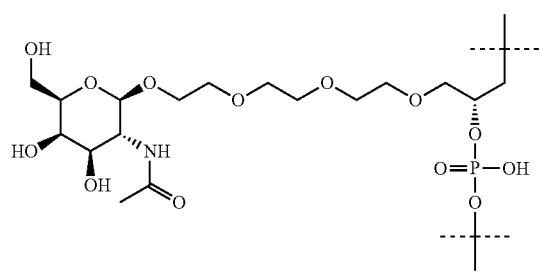

-continued
[Formula 202]
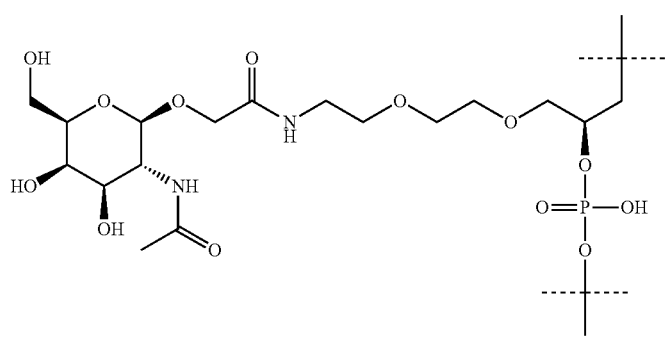
X¹³
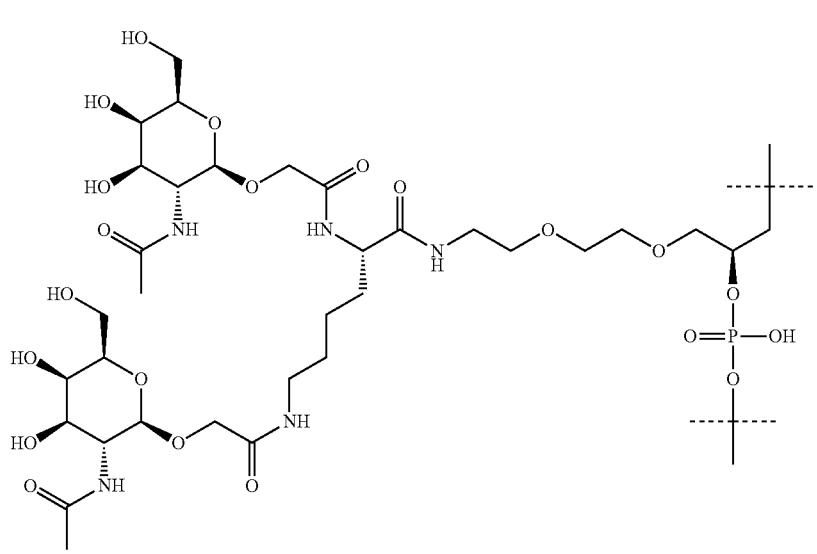
X¹⁴
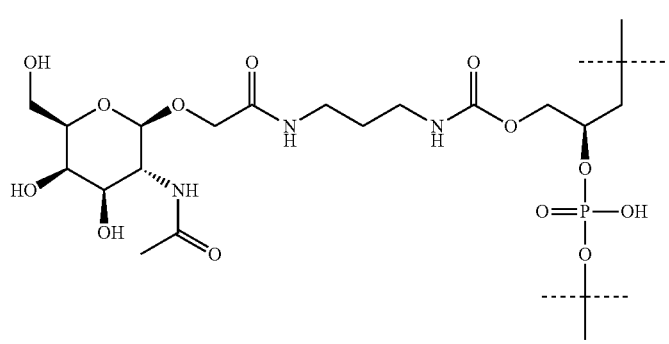
X¹⁵

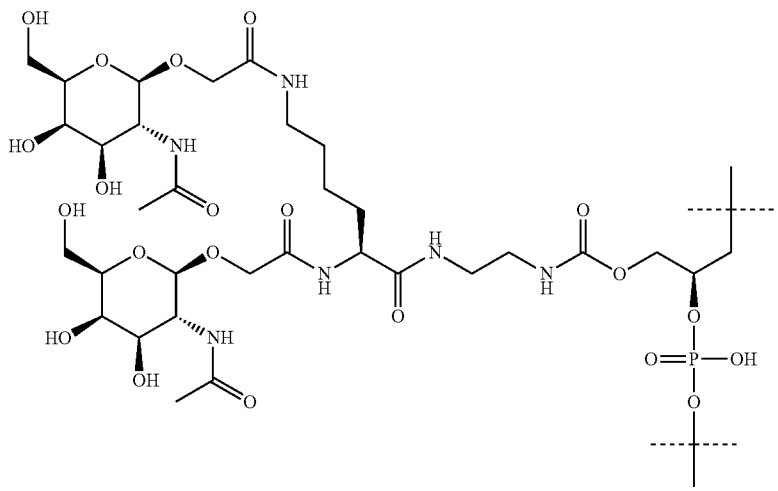
X[16]
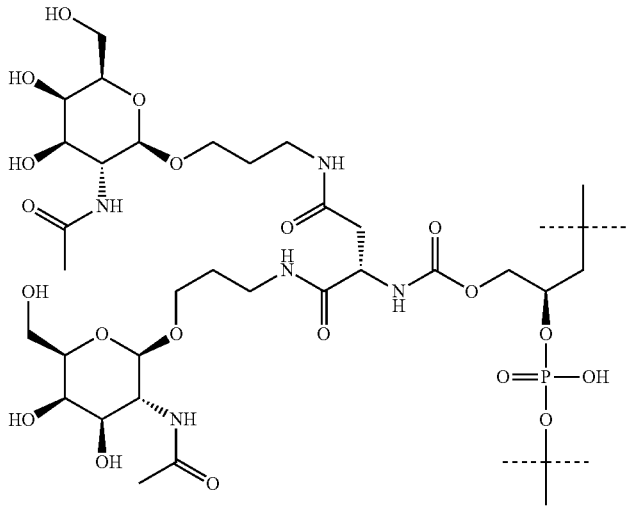
X[17]
[Formula 203]
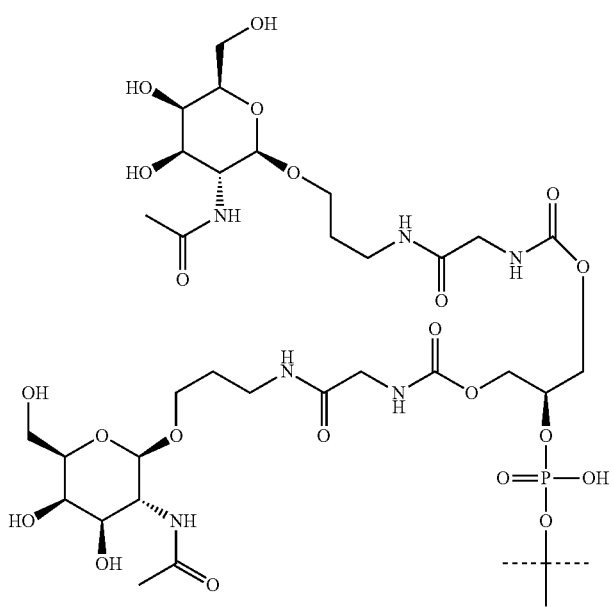
X[18]

-continued
[Formula 204]
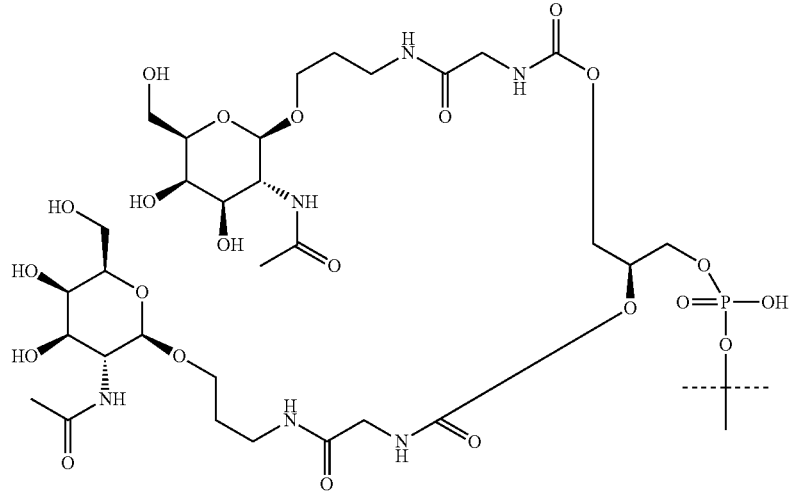
X19
[Formula 205]
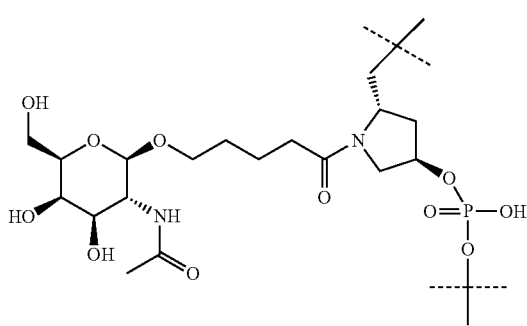
X
[Formula 206]
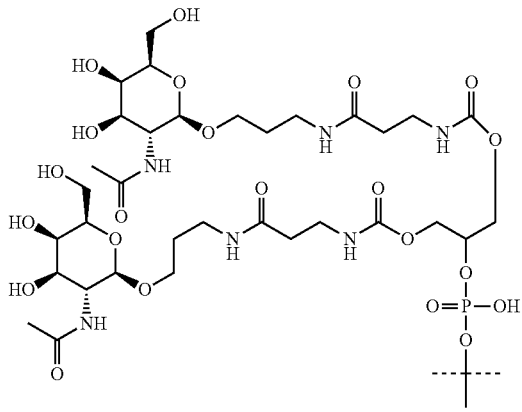
X20
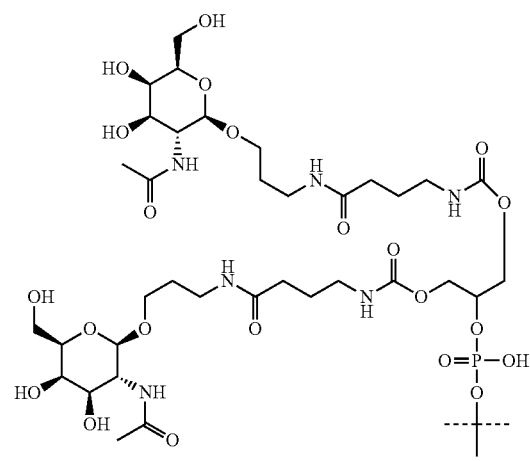
X21

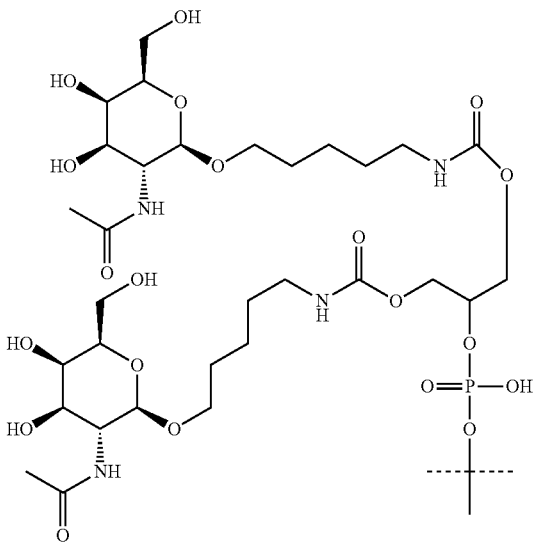

All publication, patents and patent applications cited herein are incorporated herein by reference in their entirety.

INDUSTRIAL APPLICABILITY

The present invention is applicable to treatment of glycogen storage disease type Ia.

SEQUENCE LISTING FREE TEXT

<SEQ ID NOS: 1 to 48, 93 to 95, and 98 to 182>
These sequences show the sequences of antisense oligonucleotides. Nucleotides constituting the antisense oligonucleotide may be either natural DNA, natural RNA, chimera DNA/RNA, or modified DNA, RNA or DNA/RNA. Preferably, at least one of the nucleotides is a modified nucleotide.

<SEQ ID NOS: 49 to 65 and 67 to 92>
These sequences show primer sequences.

<SEQ ID NO: 66>
This sequence shows a peptide sequence.

<SEQ ID NOs: 96 and 97>
These sequences show G6PC mRNA and G6PC antisense, respectively.

The invention claimed is:

1. A conjugate of an oligonucleotide and a GalNAc unit or a pharmacologically acceptable salt or solvate thereof, wherein the conjugate is selected from:

5'-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H-3' (SEQ ID NO: 40) and $X^{18}$, wherein the $X^{18}$ is a GalNAc unit attached to the 5' end of SEQ ID NO: 40, 5'-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H-3' (SEQ ID NO: 171) and $X^{18}$, wherein the $X^{18}$ is a GalNAc unit attached to the 5' end of SEQ ID NO: 171, 5'-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H-3' (SEQ ID NO: 172) and $X^{18}$, wherein the $X^{18}$ is a GalNAc unit attached to the 5' end of SEQ ID NO: 172, 5'-$A^{m1s}$-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1t}$-H-3' (SEQ ID NO: 42) and $X^{18}$, wherein the $X^{18}$ is a GalNAc unit attached to the 5' end of SEQ ID NO: 42, 5'-$A^{m1s}$-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2t}$—H-3' (SEQ ID NO: 47) and $X^{18}$, wherein the $X^{18}$ is a GalNAc unit attached to the 5' end of SEQ ID NO: 47, 5'-$A^{e2s}$-$U^{m1s}$—$C^{m1s}$-$C^{e2s}$-$G^{m1s}$-$A^{m1s}$-$T^{e2s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H-3' (SEQ ID NO: 48) and $X^{18}$, wherein the $X^{18}$ is a GalNAc unit attached to the 5' end of SEQ ID NO: 48, 5'-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H-3' (SEQ ID NO: 173) and $X^{18}$, wherein the $X^{18}$ is a GalNAc unit attached to the 5' end of SEQ ID NO: 173, 5'-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H-3' (SEQ ID NO: 174) and $X^{18}$, wherein the $X^{18}$ is a GalNAc unit attached to the 5' end of SEQ ID NO: 174, 5'-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H-3' (SEQ ID NO: 175) and $X^{18}$, wherein the $X^{18}$ is a GalNAc unit attached to the 5' end of SEQ ID NO: 175, 5'-$A^{m1s}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H-3' (SEQ ID NO: 176) and $X^{18}$, wherein the $X^{18}$ is a GalNAc unit attached to the 5' end of SEQ ID NO: 176, 5'-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H-3' (SEQ ID NO: 177) and $X^{18}$, wherein the $X^{18}$ is a GalNAc unit attached to the 5' end of SEQ ID NO: 177, 5'-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2s}$—$U^{m1t}$—H-3' (SEQ ID NO: 178) and $X^{18}$, wherein the $X^{18}$ is a GalNAc unit attached to the 5' end of SEQ ID NO: 178, 5'-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H-3' (SEQ ID NO: 173) and $X^{20}$, wherein the $X^{20}$ is a GalNAc unit attached to the 5' end of SEQ ID NO: 173, 5'-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$-$C^{e2t}$—H-3' (SEQ ID NO: 174) and $X^{20}$, wherein the $X^{20}$ is a GalNAc unit attached to the 5' end of SEQ ID NO: 174, 5'-$A^{m1s}$-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1t}$-H-3' (SEQ ID NO: 176) and $X^{20}$, wherein the $X^{20}$ is a GalNAc unit attached to the 5' end of SEQ ID NO: 176, and 5'-$A^{m1s}$-$A^{e2s}$-$U^{m1s}$—$C^{m1s}$-$C^{e2s}$-$G^{m1s}$-$A^{e2s}$-$U^{m1s}$-$G^{m1s}$-$G^{m1s}$-$C^{e2s}$-$G^{m1s}$-$A^{m1s}$-$A^{e2s}$-$G^{m1s}$$C^{e2t}$—H-3' (SEQ ID NO: 177) and $X^{20}$, wherein the $X^{20}$ is a GalNAc unit attached to the 5' end of SEQ ID NO: 177, wherein $G^{m1t}$, $U^{m1t}$, $A^{m1s}$, $G^{m1s}$, $C^{m1s}$, $U^{m1s}$, $C^{e2t}$, $A^{e2s}$, $C^{e2s}$, $T^{e2s}$, $X^{18}$ and $X^{20}$ are defined as follows:

493
G$^{m1t}$
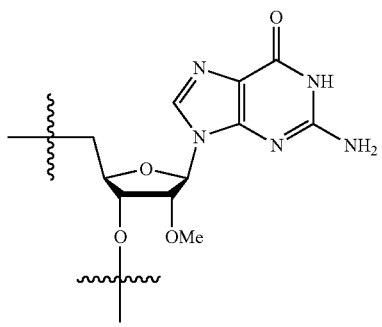
U$^{m1t}$
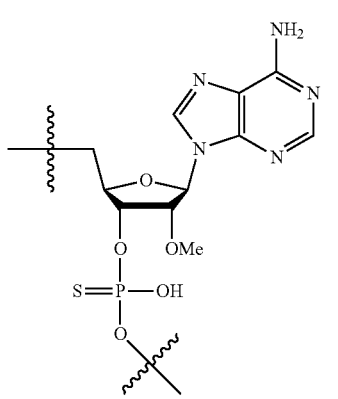
A$^{m1s}$
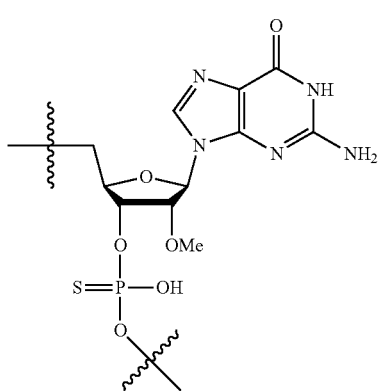
G$^{m1s}$
494
-continued
C$^{m1s}$
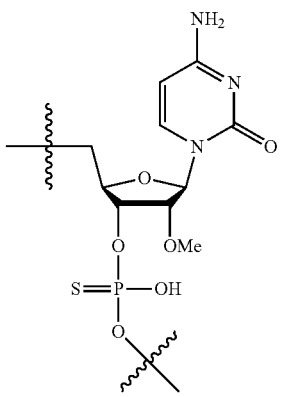
U$^{m1s}$
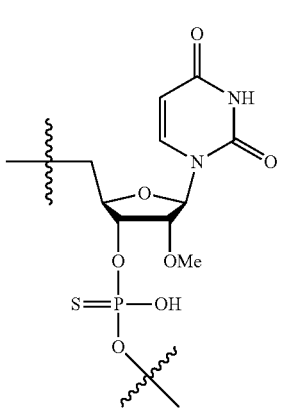
C$^{e2t}$
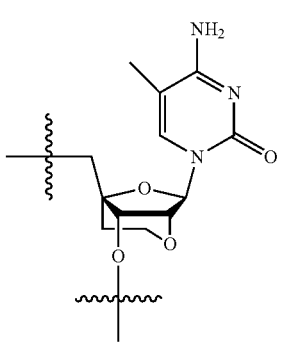
A$^{e2s}$
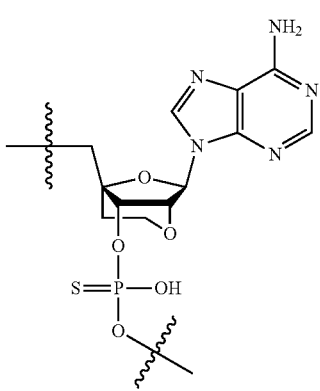

$C^{e2s}$

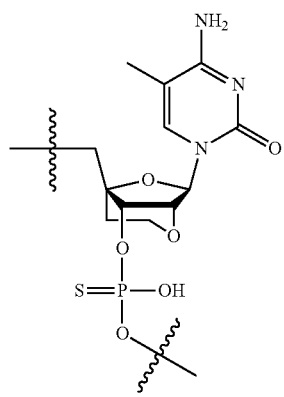

$T^{e2s}$

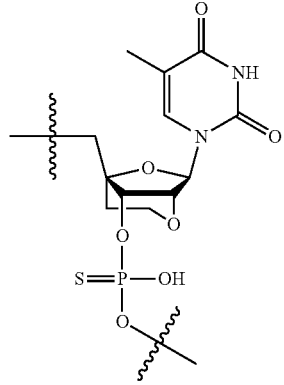

$X^{18}$

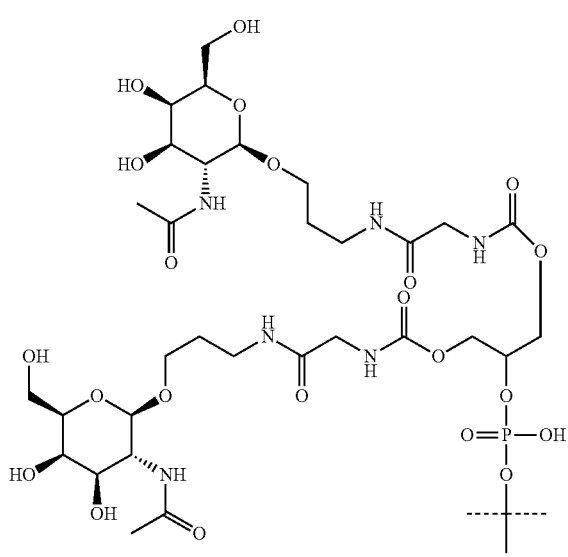

$X^{20}$

[structure continued]

wherein the atomic bonding to phosphate group in $X^{18}$ and $X^{20}$ comprises formation of a phosphodiester bond by binding to the carbon atom at the 5' end of the oligonucleotide.

2. A pharmaceutical drug comprising the conjugate or a pharmaceutically acceptable salt or solvate thereof of claim 1.

3. A therapeutic drug for glycogen storage disease type Ia, comprising the conjugate or a pharmaceutically acceptable salt or solvate thereof of claim 1.

4. A formulation for oral or parenteral administration, comprising the conjugate or a pharmaceutically acceptable salt or solvate thereof of claim 3.

5. A method of treating glycogen storage disease type Ia, comprising administering to a subject in need thereof a pharmaceutically effective amount of the conjugate or a pharmacologically acceptable salt or solvate thereof of claim 1.

6. The method of claim 5, wherein the subject has a G6PC c.648G>T mutation.

\* \* \* \* \*

```
                        SEQUENCE LISTING

<160> NUMBER OF SEQ ID NOS: 182

<210> SEQ ID NO 1
<211> LENGTH: 21
<212> TYPE: DNA
<213> ORGANISM: Artificial Sequence
<220> FEATURE:
<223> OTHER INFORMATION: antisense oligonucleotide 21e_002
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
```

-continued

```
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 1
agataaaauc cgauggcgaa g                                             21

<210> SEQ ID NO 2
<211> LENGTH: 21
<212> TYPE: DNA
<213> ORGANISM: Artificial Sequence
<220> FEATURE:
<223> OTHER INFORMATION: antisense oligonucleotide 21e_003
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
```

```
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: modified_base
<222> LOCATION: (7)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: modified_base
<222> LOCATION: (19)..(19)
<223> OTHER INFORMATION: m5c
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 2
taaaauccga uggcgaagcu g                                          21

<210> SEQ ID NO 3
<211> LENGTH: 21
<212> TYPE: DNA
<213> ORGANISM: Artificial Sequence
<220> FEATURE:
<223> OTHER INFORMATION: antisense oligonuleotide 21e_004
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
```

```
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: modified_base
<222> LOCATION: (16)..(16)
<223> OTHER INFORMATION: m5c
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 3
aauccgaugg cgaagcugaa a                                           21

<210> SEQ ID NO 4
<211> LENGTH: 21
<212> TYPE: DNA
<213> ORGANISM: Artificial Sequence
<220> FEATURE:
<223> OTHER INFORMATION: antisense oligonucleotide 21e_005
```

-continued

```
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 4
```
ccgauggcga agcugaaaag g                                         21

```
<210> SEQ ID NO 5
<211> LENGTH: 21
<212> TYPE: DNA
<213> ORGANISM: Artificial Sequence
<220> FEATURE:
<223> OTHER INFORMATION: antisense oligonucleotide 21e_006
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
```

<222> LOCATION: (21)..(21)
<223> OTHER INFORMATION: 3'-position is hydroxyl group

<400> SEQUENCE: 5
auggcgaagc ugaaaaggaa g                                              21

<210> SEQ ID NO 6
<211> LENGTH: 21
<212> TYPE: DNA
<213> ORGANISM: Artificial Sequence
<220> FEATURE:
<223> OTHER INFORMATION: antisense oligonucleotide 21e_007
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: modified_base
<222> LOCATION: (7)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:

<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 6
gcgaagcuga aaaggaagaa g                                              21

<210> SEQ ID NO 7
<211> LENGTH: 21
<212> TYPE: DNA
<213> ORGANISM: Artificial Sequence
<220> FEATURE:
<223> OTHER INFORMATION: antisense oligonucleotide 21e_008
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA -continued

```
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 7
aagcugaaaa ggaagaaggu a                                              21

<210> SEQ ID NO 8
<211> LENGTH: 21
<212> TYPE: DNA
<213> ORGANISM: Artificial Sequence
<220> FEATURE:
<223> OTHER INFORMATION: antisense oligonucleotide 21e_009
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
```

```
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 8
cugaaaagga agaagguaau g                                                   21

<210> SEQ ID NO 9
<211> LENGTH: 21
<212> TYPE: DNA
<213> ORGANISM: Artificial Sequence
<220> FEATURE:
<223> OTHER INFORMATION: antisense oligonucleotide 21e_010
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
```

```
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 9
aaaaggaaga agguaaugag a                                         21

<210> SEQ ID NO 10
<211> LENGTH: 21
<212> TYPE: DNA
<213> ORGANISM: Artificial Sequence
<220> FEATURE:
<223> OTHER INFORMATION: antisense oligonucleotide 21e_011
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
```

```
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 10
aggaagaagg uaaugagaaa a                                              21

<210> SEQ ID NO 11
<211> LENGTH: 21
<212> TYPE: DNA
<213> ORGANISM: Artificial Sequence
<220> FEATURE:
<223> OTHER INFORMATION: antisense oligonucleotide 21e_012
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
```

```
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 11
aagaagguaa ugagaaaata t                                              21

<210> SEQ ID NO 12
<211> LENGTH: 21
<212> TYPE: DNA
<213> ORGANISM: Artificial Sequence
<220> FEATURE:
<223> OTHER INFORMATION: antisense oligonucleotide 21e_015
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
```

```
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: modified_base
<222> LOCATION: (16)..(16)
<223> OTHER INFORMATION: m5c
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: modified_base
<222> LOCATION: (21)..(21)
<223> OTHER INFORMATION: m5c
<220> FEATURE:
<221> NAME/KEY: misc_feature
<222> LOCATION: (21)..(21)
<223> OTHER INFORMATION: 3'-position is hydroxyl group

<400> SEQUENCE: 12
gauaaaaucc gatggcgaag c                                              21

<210> SEQ ID NO 13
<211> LENGTH: 21
<212> TYPE: DNA
<213> ORGANISM: Artificial Sequence
<220> FEATURE:
<223> OTHER INFORMATION: antisense oligonucleotide 21e_016
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
```

-continued

```
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 13
auaaaatccg auggcgaagc t                                          21

<210> SEQ ID NO 14
<211> LENGTH: 21
<212> TYPE: DNA
<213> ORGANISM: Artificial Sequence
<220> FEATURE:
<223> OTHER INFORMATION: antisense oligonucleotide 21e_017
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: modified_base
<222> LOCATION: (7)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
```

```
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 14
aaaauccgat ggcgaagctg a                                              21

<210> SEQ ID NO 15
<211> LENGTH: 21
<212> TYPE: DNA
<213> ORGANISM: Artificial Sequence
<220> FEATURE:
<223> OTHER INFORMATION: antisense oligonucleotide  21e_018
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
```

```
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 15
aaatccgaug gcgaagcuga a                                         21

<210> SEQ ID NO 16
<211> LENGTH: 21
<212> TYPE: DNA
<213> ORGANISM: Artificial Sequence
<220> FEATURE:
<223> OTHER INFORMATION: antisense oligonucleotide 21e_019
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
```

```
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 16
auccgatggc gaagctgaaa a                                              21

<210> SEQ ID NO 17
<211> LENGTH: 21
<212> TYPE: DNA
<213> ORGANISM: Artificial Sequence
<220> FEATURE:
<223> OTHER INFORMATION: antisense oligonucleotide 21e_020
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
```

```
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 17
tccgauggcg aagcugaaaa g                                      21

<210> SEQ ID NO 18
<211> LENGTH: 21
<212> TYPE: DNA
<213> ORGANISM: Artificial Sequence
<220> FEATURE:
<223> OTHER INFORMATION: antisense oligonucleotide 21e_021
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(20)
<223> OTHER INFORMATION: phosphorothioate bond
<220> FEATURE:
```

```
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: modified_base
<222> LOCATION: (7)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 18
cgatggcgaa gctgaaaagg a                                          21

<210> SEQ ID NO 19
<211> LENGTH: 21
<212> TYPE: DNA
<213> ORGANISM: Artificial Sequence
<220> FEATURE:
<223> OTHER INFORMATION: antisense oligonucleotide 21e_022
<220> FEATURE:
<221> NAME/KEY: misc_feature
<222> LOCATION: (1)..(1)
<223> OTHER INFORMATION: ENA
```

```
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 19
gauggcgaag cugaaaagga a                                               21

<210> SEQ ID NO 20
<211> LENGTH: 18
<212> TYPE: DNA
<213> ORGANISM: Artificial Sequence
<220> FEATURE:
<223> OTHER INFORMATION: antisense oligonucleotide 18e_005
<220> FEATURE:
<221> NAME/KEY: misc_feature
<222> LOCATION: (1)..(1)
```

```
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 20
uaaaauccga tggcgaag                                                   18

<210> SEQ ID NO 21
<211> LENGTH: 18
<212> TYPE: DNA
<213> ORGANISM: Artificial Sequence
<220> FEATURE:
<223> OTHER INFORMATION: antisense oligonucleotide 18e_006
<220> FEATURE:
<221> NAME/KEY: misc_feature
```

```
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 21
aaaatccgau ggcgaagc                                                 18

<210> SEQ ID NO 22
<211> LENGTH: 18
<212> TYPE: DNA
<213> ORGANISM: Artificial Sequence
<220> FEATURE:
<223> OTHER INFORMATION: antisense oligonucleotide 18e_007
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
```

```
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: modified_base
<222> LOCATION: (17)..(17)
<223> OTHER INFORMATION: m5c
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 22
aaauccgaug gcgaagcu                                              18

<210> SEQ ID NO 23
<211> LENGTH: 18
<212> TYPE: DNA
<213> ORGANISM: Artificial Sequence
<220> FEATURE:
<223> OTHER INFORMATION: antisense oligonucleotide 18e_008
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
```

```
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 23
aauccgatgg cgaagctg                                                 18

<210> SEQ ID NO 24
<211> LENGTH: 18
<212> TYPE: DNA
<213> ORGANISM: Artificial Sequence
<220> FEATURE:
<223> OTHER INFORMATION: antisense oligonucleotide 18e_009
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
```

```
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 24
atccgauggc gaagcuga                                                 18

<210> SEQ ID NO 25
<211> LENGTH: 18
<212> TYPE: DNA
<213> ORGANISM: Artificial Sequence
<220> FEATURE:
<223> OTHER INFORMATION: antisense oligonucleotide 18e_010
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: modified_base
```

```
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 25
uccgauggcg aagcugaa                                                   18

<210> SEQ ID NO 26
<211> LENGTH: 18
<212> TYPE: DNA
<213> ORGANISM: Artificial Sequence
<220> FEATURE:
<223> OTHER INFORMATION: antisense oligonucleotide 18e_011
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
```

```
<221> NAME/KEY: modified_base
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 26
ccgatggcga agctgaaa                                                 18

<210> SEQ ID NO 27
<211> LENGTH: 18
<212> TYPE: DNA
<213> ORGANISM: Artificial Sequence
<220> FEATURE:
<223> OTHER INFORMATION: antisense oligonucleotide 18e_012
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
```

```
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 27
cgauggcgaa gcugaaaa                                                 18

<210> SEQ ID NO 28
<211> LENGTH: 18
<212> TYPE: DNA
<213> ORGANISM: Artificial Sequence
<220> FEATURE:
<223> OTHER INFORMATION: antisense oligonucleotide 18e_013
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
```

```
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 28
gauggcgaag cugaaaag                                                   18

<210> SEQ ID NO 29
<211> LENGTH: 18
<212> TYPE: DNA
<213> ORGANISM: Artificial Sequence
<220> FEATURE:
<223> OTHER INFORMATION: antisense oligonucleotide 18e_014
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
```

```
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 29
atggcgaagc tgaaaagg                                                       18

<210> SEQ ID NO 30
<211> LENGTH: 18
<212> TYPE: DNA
<213> ORGANISM: Artificial Sequence
<220> FEATURE:
<223> OTHER INFORMATION: antisense oligonucleotide 18e_015
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
```

```
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 30
uggcgaagcu gaaaagga                                                   18

<210> SEQ ID NO 31
<211> LENGTH: 18
<212> TYPE: DNA
<213> ORGANISM: Artificial Sequence
<220> FEATURE:
<223> OTHER INFORMATION: antisense oligonucleotide 18e_016
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
```

```
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 31
ggcgaagcug aaaaggaa                                                 18

<210> SEQ ID NO 32
<211> LENGTH: 18
<212> TYPE: DNA
<213> ORGANISM: Artificial Sequence
<220> FEATURE:
<223> OTHER INFORMATION: antisense oligonucleotide 18e_017
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
```

-continued

```
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 32
gcgaagctga aaaggaag                                                 18

<210> SEQ ID NO 33
<211> LENGTH: 21
<212> TYPE: DNA
<213> ORGANISM: Artificial Sequence
<220> FEATURE:
<223> OTHER INFORMATION: antisense oligonucleotide 21e_001
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
```

-continued

```
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 33
agataaaauc cgauggcgaa g                                          21

<210> SEQ ID NO 34
<211> LENGTH: 21
<212> TYPE: DNA
<213> ORGANISM: Artificial Sequence
<220> FEATURE:
<223> OTHER INFORMATION: antisense oligonucleotide 21e_013
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
```

```
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: modified_base
<222> LOCATION: (19)..(19)
<223> OTHER INFORMATION: m5c
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 34
gcagauaaaa uccgatggcg a                                              21

<210> SEQ ID NO 35
<211> LENGTH: 21
<212> TYPE: DNA
<213> ORGANISM: Artificial Sequence
<220> FEATURE:
<223> OTHER INFORMATION: antisense oligonucleotide 21e_014
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
```

```
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 35
cagauaaaat ccgauggcga a                                            21

<210> SEQ ID NO 36
<211> LENGTH: 18
<212> TYPE: DNA
<213> ORGANISM: Artificial Sequence
<220> FEATURE:
<223> OTHER INFORMATION: antisense oligonucleotide 18e_001
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
```

```
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 36
cagataaaau ccgauggc                                                 18

<210> SEQ ID NO 37
<211> LENGTH: 18
<212> TYPE: DNA
<213> ORGANISM: Artificial Sequence
<220> FEATURE:
<223> OTHER INFORMATION: antisense oligonucleotide 18e_002
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
```

```
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: modified_base
<222> LOCATION: (17)..(17)
<223> OTHER INFORMATION: m5c
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 37
agauaaaauc cgatggcg                                                 18

<210> SEQ ID NO 38
<211> LENGTH: 18
<212> TYPE: DNA
<213> ORGANISM: Artificial Sequence
<220> FEATURE:
<223> OTHER INFORMATION: antisense oligonucleotide 18e_003
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
```

```
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 38
gauaaaatcc gauggcga                                              18

<210> SEQ ID NO 39
<211> LENGTH: 18
<212> TYPE: DNA
<213> ORGANISM: Artificial Sequence
<220> FEATURE:
<223> OTHER INFORMATION: antisense oligonucleotide 18e_004
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
```

```
<220> FEATURE:
<221> NAME/KEY: modified_base
<222> LOCATION: (8)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 39
ataaaauccg auggcgaa                                                       18

<210> SEQ ID NO 40
<211> LENGTH: 15
<212> TYPE: DNA
<213> ORGANISM: Artificial Sequence
<220> FEATURE:
<223> OTHER INFORMATION: antisense oligonucleotide 15e_001
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
```

```
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 40
aauccgatgg cgaag                                               15

<210> SEQ ID NO 41
<211> LENGTH: 15
<212> TYPE: DNA
<213> ORGANISM: Artificial Sequence
<220> FEATURE:
<223> OTHER INFORMATION: antisense oligonucleotide 15e_002
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
<220> FEATURE:
<221> NAME/KEY: misc_feature
```

```
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 41
ccgatggcga agctg                                                         15

<210> SEQ ID NO 42
<211> LENGTH: 16
<212> TYPE: DNA
<213> ORGANISM: Artificial Sequence
<220> FEATURE:
<223> OTHER INFORMATION: antisense oligonucleotide 16e_001
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (2)..(15)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (7)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: modified_base
<222> LOCATION: (12)..(12)
<223> OTHER INFORMATION: m5c
<220> FEATURE:
```

```
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (16)..(16)
<223> OTHER INFORMATION: 3'-position is hydroxyl group

<400> SEQUENCE: 42
aaauccgatg gcgaag                                                         16

<210> SEQ ID NO 43
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (4)..(4)
<223> OTHER INFORMATION: 2'-OMe-RNA
<220> FEATURE:
<221> NAME/KEY: misc_feature
<222> LOCATION: (4)..(17)
<223> OTHER INFORMATION: phosphorothioate bond
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
```

```
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 43
tcaaauccga tggcgaag                                                 18

<210> SEQ ID NO 44
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 44
atccgauggc gaagc                                                    15

<210> SEQ ID NO 45
```

```
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 45
uccgauggcg aagcu                                                  15

<210> SEQ ID NO 46
<211> LENGTH: 17
<212> TYPE: DNA
<213> ORGANISM: Artificial Sequence
<220> FEATURE:
<223> OTHER INFORMATION: antisense oligonucleotide 17e_001
<220> FEATURE:
<221> NAME/KEY: misc_feature
```

<222> LOCATION: (1)..(3)
<223> OTHER INFORMATION: 2'-OMe-RNA
<220> FEATURE:
<221> NAME/KEY: misc_feature
<222> LOCATION: (1)..(16)
<223> OTHER INFORMATION: phosphorothioate bond
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: modified_base
<222> LOCATION: (7)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(17)
<223> OTHER INFORMATION: 2'-OMe-RNA
<220> FEATURE:
<221> NAME/KEY: misc_feature
<222> LOCATION: (17)..(17)
<223> OTHER INFORMATION: 3'-position is hydroxyl group

<400> SEQUENCE: 46
aaaauccgat ggcgaag                                                17

<210> SEQ ID NO 47
<211> LENGTH: 16
<212> TYPE: DNA
<213> ORGANISM: Artificial Sequence
<220> FEATURE:
<223> OTHER INFORMATION: antisense oligonucleotide 16e_002
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(15)
<223> OTHER INFORMATION: phosphorothioate bond
<220> FEATURE:

```
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: modified_base
<222> LOCATION: (16)..(16)
<223> OTHER INFORMATION: m5c
<220> FEATURE:
<221> NAME/KEY: misc_feature
<222> LOCATION: (16)..(16)
<223> OTHER INFORMATION: 3'-position is hydroxyl group

<400> SEQUENCE: 47
aauccgatgg cgaagc                                              16

<210> SEQ ID NO 48
<211> LENGTH: 16
<212> TYPE: DNA
<213> ORGANISM: Artificial Sequence
<220> FEATURE:
<223> OTHER INFORMATION: antisense oligonucleotide 16e_003
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(15)
<223> OTHER INFORMATION: phosphorothioate bond
```

```
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (16)..(16)
<223> OTHER INFORMATION: 3'-position is hydroxyl group

<400> SEQUENCE: 48
auccgatggc gaagcu                                                    16

<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
atagcagagc aatcaccacc aagcc                                          25

<210> SEQ ID NO 50
```

```
<211> LENGTH: 25
<212> TYPE: DNA
<213> ORGANISM: Artificial Sequence
<220> FEATURE:
<223> OTHER INFORMATION: primer

<400> SEQUENCE: 50
attccacgac ggcagaatgg atggc                                          25

<210> SEQ ID NO 51
<211> LENGTH: 39
<212> TYPE: DNA
<213> ORGANISM: Artificial Sequence
<220> FEATURE:
<223> OTHER INFORMATION: primer

<400> SEQUENCE: 51
taccgagctc ggatccacca ccaagcctgg aataactgc                           39

<210> SEQ ID NO 52
<211> LENGTH: 39
<212> TYPE: DNA
<213> ORGANISM: Artificial Sequence
<220> FEATURE:
<223> OTHER INFORMATION: primer

<400> SEQUENCE: 52
ctggactagt ggatcctggc atggttgttg actttaaac                           39

<210> SEQ ID NO 53
<211> LENGTH: 25
<212> TYPE: DNA
<213> ORGANISM: Artificial Sequence
<220> FEATURE:
<223> OTHER INFORMATION: primer

<400> SEQUENCE: 53
tctgggctgt gcagctgaat gtctg                                          25

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54 gtagggatg acactgacgg atgcc                                           25

<210> SEQ ID NO 55
<211> LENGTH: 23
<212> TYPE: DNA
<213> ORGANISM: Artificial Sequence
<220> FEATURE:
<223> OTHER INFORMATION: primer

<400> SEQUENCE: 55
ctggagtcct gtcaggtatg ggc                                            23

<210> SEQ ID NO 56
<211> LENGTH: 25
<212> TYPE: DNA
<213> ORGANISM: Artificial Sequence
<220> FEATURE:
<223> OTHER INFORMATION: primer

<400> SEQUENCE: 56
```

```
agctgaaaag gaagaaggta atgag                                              25

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcttcctttt cagcttcgcc atcgg                                              25

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
ctgacaggac tccagcaaca ac                                                 22

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
ttgtggttgg gattctgggc                                                    20

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
atgctgtgga tgtggctgaa                                                    20

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
tggcacccag cacaatgaa                                                     19

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ctaagtcata gtccgcctag aagca                                              25

<210> SEQ ID NO 63
<211> LENGTH: 24
<212> TYPE: DNA
```

```
<213> ORGANISM: Artificial Sequence
<220> FEATURE:
<223> OTHER INFORMATION: primer

<400> SEQUENCE: 63
gctgctcatt ttcctcatca agtt                                            24

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
tggatgtggc tgaaagtttc tgta                                            24

<210> SEQ ID NO 65
<211> LENGTH: 16
<212> TYPE: DNA
<213> ORGANISM: Artificial Sequence
<220> FEATURE:
<223> OTHER INFORMATION: primer

<400> SEQUENCE: 65
tcctgtcagg cattgc                                                     16

<210> SEQ ID NO 66
<211> LENGTH: 20
<212> TYPE: PRT
<213> ORGANISM: Artificial Sequence
<220> FEATURE:
<223> OTHER INFORMATION: peptide

<400> SEQUENCE: 66

Trp Cys Glu Gln Pro Glu Trp Val His Ile Asp Thr Thr Pro Phe Ala
1               5                   10                  15

Ser Leu Leu Lys
            20

<210> SEQ ID NO 67
<211> LENGTH: 25
<212> TYPE: DNA
<213> ORGANISM: Artificial Sequence
<220> FEATURE:
<223> OTHER INFORMATION: primer

<400> SEQUENCE: 67
gggaaacatg catgaagccc tgggc                                           25

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
tcccttggta cctcaggaag ctgcc                                           25

<210> SEQ ID NO 69
<211> LENGTH: 37
<212> TYPE: DNA
<213> ORGANISM: Artificial Sequence
<220> FEATURE:
<223> OTHER INFORMATION: primer
```

<400> SEQUENCE: 69
cgggcccccc ctcgaaaact aggcctgaag agatggc                              37

<210> SEQ ID NO 70
<211> LENGTH: 39
<212> TYPE: DNA
<213> ORGANISM: Artificial Sequence
<220> FEATURE:
<223> OTHER INFORMATION: primer

<400> SEQUENCE: 70
taccgtcgac ctcgagggtt ggccttgatc cctctgcta                            39

<210> SEQ ID NO 71
<211> LENGTH: 25
<212> TYPE: DNA
<213> ORGANISM: Artificial Sequence
<220> FEATURE:
<223> OTHER INFORMATION: primer

<400> SEQUENCE: 71
ggttgagttg atcttctaca tcttg                                           25

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
gcaagagagc cttcaggtag atccc                                           25

<210> SEQ ID NO 73
<211> LENGTH: 40
<212> TYPE: DNA
<213> ORGANISM: Artificial Sequence
<220> FEATURE:
<223> OTHER INFORMATION: primer

<400> SEQUENCE: 73
agttctagag cggccgccca tgcaaaggac taggaacaac                           40

<210> SEQ ID NO 74
<211> LENGTH: 38
<212> TYPE: DNA
<213> ORGANISM: Artificial Sequence
<220> FEATURE:
<223> OTHER INFORMATION: primer

<400> SEQUENCE: 74
accgcggtgg cggccaatgt tgcctgtctt cctcaatc                             38

<210> SEQ ID NO 75
<211> LENGTH: 31
<212> TYPE: DNA
<213> ORGANISM: Artificial Sequence
<220> FEATURE:
<223> OTHER INFORMATION: primer

<400> SEQUENCE: 75
ggccaaccct ggataactg caagggctct g                                     31

<210> SEQ ID NO 76

-continued

```
<211> LENGTH: 31
<212> TYPE: DNA
<213> ORGANISM: Artificial Sequence
<220> FEATURE:
<223> OTHER INFORMATION: primer

<400> SEQUENCE: 76
ttgcatggtt gttgacttta aacaccgaag a                              31

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
tcaacaacca tgcaaaggac taggaacaac                                30

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
attccagggt tggccttgat ccctctgcta                                30

<210> SEQ ID NO 79
<211> LENGTH: 22
<212> TYPE: DNA
<213> ORGANISM: Artificial Sequence
<220> FEATURE:
<223> OTHER INFORMATION: primer

<400> SEQUENCE: 79
gggatcaagg ccaaccggct gg                                        22

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
taaagtcaac cgccatgcaa agg                                       23

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
tacgtcctct tccccatctg                                           20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
```
ctgacaggac tccagcaaca                                                        20

<210> SEQ ID NO 83
<211> LENGTH: 28
<212> TYPE: DNA
<213> ORGANISM: Artificial Sequence
<220> FEATURE:
<223> OTHER INFORMATION: primer

<400> SEQUENCE: 83
ttccttccaa agcagggact ctctatgt                                               28

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
cttgcagaag gacaagacgt agaagacc                                               28

<210> SEQ ID NO 85
<211> LENGTH: 28
<212> TYPE: DNA
<213> ORGANISM: Artificial Sequence
<220> FEATURE:
<223> OTHER INFORMATION: primer

<400> SEQUENCE: 85
gagtctatat tgagggcagg ctggagtc                                               28

<210> SEQ ID NO 86
<211> LENGTH: 28
<212> TYPE: DNA
<213> ORGANISM: Artificial Sequence
<220> FEATURE:
<223> OTHER INFORMATION: primer

<400> SEQUENCE: 86
tagtctgcct gctcactcaa cctctcct                                               28

<210> SEQ ID NO 87
<211> LENGTH: 28
<212> TYPE: DNA
<213> ORGANISM: Artificial Sequence
<220> FEATURE:
<223> OTHER INFORMATION: primer

<400> SEQUENCE: 87
gagtctatat tgagggcagg ctggagtc                                               28

<210> SEQ ID NO 88
<211> LENGTH: 28
<212> TYPE: DNA
<213> ORGANISM: Artificial Sequence
<220> FEATURE:
<223> OTHER INFORMATION: primer

<400> SEQUENCE: 88
taaatttgac caatgagcac tggaggtc                                               28

<210> SEQ ID NO 89
<211> LENGTH: 28
<212> TYPE: DNA

```
<213> ORGANISM: Artificial Sequence
<220> FEATURE:
<223> OTHER INFORMATION: primer

<400> SEQUENCE: 89
aaaatcatgt gtatgcgtgc ctttccta                                              28

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
ttgtggttgg gattctgggc                                                       20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
tccagagtcc acaggaggtc                                                       20

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
gctgtgcagc tgaatgtctg                                                       20

<210> SEQ ID NO 93
<211> LENGTH: 15
<212> TYPE: DNA
<213> ORGANISM: Artificial Sequence
<220> FEATURE:
<223> OTHER INFORMATION: antisense oligonucleotide 15e_001.6
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
```

```
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 93
aatccgatgg cgaag                                                    15

<210> SEQ ID NO 94
<211> LENGTH: 15
<212> TYPE: DNA
<213> ORGANISM: Artificial Sequence
<220> FEATURE:
<223> OTHER INFORMATION: antisense oligonucleotide 15e_005.6
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
```

```
<223> OTHER INFORMATION: m5c
<220> FEATURE:
<221> NAME/KEY: misc_feature
<222> LOCATION: (11)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: 3'-position is hydroxyl group

<400> SEQUENCE: 94
atccgatggc gaagc                                                15

<210> SEQ ID NO 95
<211> LENGTH: 15
<212> TYPE: DNA
<213> ORGANISM: Artificial Sequence
<220> FEATURE:
<223> OTHER INFORMATION: antisense oligonucleotide 15e_005.8
<220> FEATURE:
<221> NAME/KEY: misc_feature
<222> LOCATION: (1)..(15)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (15)..(15)
<223> OTHER INFORMATION: 3'-position is hydroxyl group

<400> SEQUENCE: 95
auccgauggc gaagc                                                15

<210> SEQ ID NO 96
<211> LENGTH: 120
<212> TYPE: RNA
<213> ORGANISM: homo sapiens
<220> FEATURE:
<221> NAME/KEY: misc_feature
<222> LOCATION: (1)..(120)
<223> OTHER INFORMATION: G6PC mRNA

<400> SEQUENCE: 96
gcauugcugu uacagaaacu uucagccaca uccacagcau cuauaaugcc agccucaaga     60
aauauuuucu cauuaccuuc uuccuuuuca gcuucgccau cggauuuuau cugcugcuca    120

<210> SEQ ID NO 97
<211> LENGTH: 120
<212> TYPE: RNA
<213> ORGANISM: homo sapiens
<220> FEATURE:
<221> NAME/KEY: misc_feature
<222> LOCATION: (1)..(120)
<223> OTHER INFORMATION: G6PC antisense

<400> SEQUENCE: 97
ugagcagcag auaaaauccg auggcgaagc ugaaaaggaa gaagguaaug agaaaauauu     60
ucuugaggcu ggcauuauag augcugugga uguggcugaa aguucugua acagcaaugc    120
```

```
<210> SEQ ID NO 98
<211> LENGTH: 21
<212> TYPE: DNA
<213> ORGANISM: Artificial Sequence
<220> FEATURE:
<223> OTHER INFORMATION: antisense oligonucleotide 21m_002
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 98
agauaaaauc cgauggcgaa g                                              21

<210> SEQ ID NO 99
<211> LENGTH: 21
<212> TYPE: DNA
<213> ORGANISM: Artificial Sequence
<220> FEATURE:
<223> OTHER INFORMATION: antisense oligonucleotide 21m_003
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(21)
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 99
uaaaauccga uggcgaagcu g                                              21

<210> SEQ ID NO 100
<211> LENGTH: 21
<212> TYPE: DNA
<213> ORGANISM: Artificial Sequence
<220> FEATURE:
<223> OTHER INFORMATION: antisense oligonuleotide 21m_004
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 100
aauccgaugg cgaagcugaa a                                              21

<210> SEQ ID NO 101
<211> LENGTH: 21
<212> TYPE: DNA
<213> ORGANISM: Artificial Sequence
```

<220> FEATURE:
<223> OTHER INFORMATION: antisense oligonucleotide 21m_005
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 101
ccgauggcga agcugaaaag g                                        21

<210> SEQ ID NO 102
<211> LENGTH: 21
<212> TYPE: DNA
<213> ORGANISM: Artificial Sequence
<220> FEATURE:
<223> OTHER INFORMATION: antisense oligonucleotide 21m_006
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 102
auggcgaagc ugaaaaggaa g                                        21

<210> SEQ ID NO 103
<211> LENGTH: 21
<212> TYPE: DNA
<213> ORGANISM: Artificial Sequence
<220> FEATURE:
<223> OTHER INFORMATION: antisense oligonucleotide 21m_007
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 103
gcgaagcuga aaggaagaa g                                         21

<210> SEQ ID NO 104
<211> LENGTH: 21
<212> TYPE: DNA
<213> ORGANISM: Artificial Sequence
<220> FEATURE:
<223> OTHER INFORMATION: antisense oligonucleotide 21m_008
<220> FEATURE:
<221> NAME/KEY: misc_feature
<222> LOCATION: (1)..(21)
<223> OTHER INFORMATION: 2'-OMe-RNA
<220> FEATURE:

<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 104
aagcugaaaa ggaagaaggu a                                              21

<210> SEQ ID NO 105
<211> LENGTH: 21
<212> TYPE: DNA
<213> ORGANISM: Artificial Sequence
<220> FEATURE:
<223> OTHER INFORMATION: antisense oligonucleotide 21m_009
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 105
cugaaaagga agaagguaau g                                              21

<210> SEQ ID NO 106
<211> LENGTH: 21
<212> TYPE: DNA
<213> ORGANISM: Artificial Sequence
<220> FEATURE:
<223> OTHER INFORMATION: antisense oligonucleotide 21m_010
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 106
aaaaggaaga agguaaugag a                                              21

<210> SEQ ID NO 107
<211> LENGTH: 21
<212> TYPE: DNA
<213> ORGANISM: Artificial Sequence
<220> FEATURE:
<223> OTHER INFORMATION: antisense oligonucleotide 21m_011
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 107
aggaagaagg uaaugagaaa a                                        21

<210> SEQ ID NO 108
<211> LENGTH: 21
<212> TYPE: DNA
<213> ORGANISM: Artificial Sequence
<220> FEATURE:
<223> OTHER INFORMATION: antisense oligonucleotide 21m_012
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 108
aagaagguaa ugagaaaaua u                                        21

<210> SEQ ID NO 109
<211> LENGTH: 21
<212> TYPE: DNA
<213> ORGANISM: Artificial Sequence
<220> FEATURE:
<223> OTHER INFORMATION: antisense oligonucleotide 21e_002m01
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(21)
<223> OTHER INFORMATION: 2'-OMe-RNA
<220> FEATURE:
<221> NAME/KEY: misc_feature
<222> LOCATION: (21)..(21)
<223> OTHER INFORMATION: 3'-position is hydroxyl group

<400> SEQUENCE: 109
agauaaaauc cgauggcgaa g                                        21

<210> SEQ ID NO 110
<211> LENGTH: 21
<212> TYPE: DNA
<213> ORGANISM: Artificial Sequence
<220> FEATURE:
<223> OTHER INFORMATION: antisense oligonucleotide 21e_002m02
<220> FEATURE:
<221> NAME/KEY: misc_feature
<222> LOCATION: (1)..(20)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)

-continued

<223> OTHER INFORMATION: 3'-position is hydroxyl group

<400> SEQUENCE: 110
agauaaaauc cgauggcgaa g    21

<210> SEQ ID NO 111
<211> LENGTH: 21
<212> TYPE: DNA
<213> ORGANISM: Artificial Sequence
<220> FEATURE:
<223> OTHER INFORMATION: antisense oligonucleotide 21e_002m03
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 111
agauaaaauc cgauggcgaa g    21

<210> SEQ ID NO 112
<211> LENGTH: 21
<212> TYPE: DNA
<213> ORGANISM: Artificial Sequence
<220> FEATURE:
<223> OTHER INFORMATION: antisense oligonucleotide 21e_002m04
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 112
agauaaaauc cgauggcgaa g    21

```
<210> SEQ ID NO 113
<211> LENGTH: 21
<212> TYPE: DNA
<213> ORGANISM: Artificial Sequence
<220> FEATURE:
<223> OTHER INFORMATION: antisense oligonucleotide 21e_002m05
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 113
agauaaaauc cgauggcgaa g                                             21

<210> SEQ ID NO 114
<211> LENGTH: 21
<212> TYPE: DNA
<213> ORGANISM: Artificial Sequence
<220> FEATURE:
<223> OTHER INFORMATION: antisense oligonucleotide 21e_002m06
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
```

```
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 114
agataaaauc cgauggcgaa g                                              21

<210> SEQ ID NO 115
<211> LENGTH: 21
<212> TYPE: DNA
<213> ORGANISM: Artificial Sequence
<220> FEATURE:
<223> OTHER INFORMATION: antisense oligonucleotide 21e_002m07
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 115
agauaaaauc cgauggcgaa g                                              21

<210> SEQ ID NO 116
<211> LENGTH: 21
<212> TYPE: DNA
<213> ORGANISM: Artificial Sequence
<220> FEATURE:
<223> OTHER INFORMATION: antisense oligonucleotide 21e_002m08
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
```

```
<220> FEATURE:
<221> NAME/KEY: misc_feature
<222> LOCATION: (2)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 116
agauaaaauc cgauggcgaa g                                       21

<210> SEQ ID NO 117
<211> LENGTH: 21
<212> TYPE: DNA
<213> ORGANISM: Artificial Sequence
<220> FEATURE:
<223> OTHER INFORMATION: antisense oligonucleotide 21e_002m09
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(20)
```

```
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 117
agataaaauc cgauggcgaa g                                              21

<210> SEQ ID NO 118
<211> LENGTH: 21
<212> TYPE: DNA
<213> ORGANISM: Artificial Sequence
<220> FEATURE:
<223> OTHER INFORMATION: antisense oligonucleotide 21e_002m10
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 118
agauaaaauc cgauggcgaa g                                              21

<210> SEQ ID NO 119
<211> LENGTH: 21
<212> TYPE: DNA
<213> ORGANISM: Artificial Sequence
<220> FEATURE:
<223> OTHER INFORMATION: antisense oligonucleotide 21e_002m11
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
```

```
<222> LOCATION: (2)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 119
agauaaaauc cgauggcgaa g                                              21

<210> SEQ ID NO 120
<211> LENGTH: 21
<212> TYPE: DNA
<213> ORGANISM: Artificial Sequence
<220> FEATURE:
<223> OTHER INFORMATION: antisense oligonucleotide 21e_002m12
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(15)
<223> OTHER INFORMATION: 2'-OMe-RNA
<220> FEATURE:
```

<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 120
agauaaaauc cgauggcgaa g         21

<210> SEQ ID NO 121
<211> LENGTH: 21
<212> TYPE: DNA
<213> ORGANISM: Artificial Sequence
<220> FEATURE:
<223> OTHER INFORMATION: antisense oligonucleotide 21e_002m13
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 121
agataaaauc cgauggcgaa g                                              21

<210> SEQ ID NO 122
<211> LENGTH: 21
<212> TYPE: DNA
<213> ORGANISM: Artificial Sequence
<220> FEATURE:
<223> OTHER INFORMATION: antisense oligonucleotide 21e_002m14
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 122
agataaaauc cgauggcgaa g                                              21

<210> SEQ ID NO 123
<211> LENGTH: 21
<212> TYPE: DNA
<213> ORGANISM: Artificial Sequence
<220> FEATURE:

-continued

```
<223> OTHER INFORMATION: antisense oligonucleotide 21e_002m15
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 123
agauaaaauc cgauggcgaa g                                              21

<210> SEQ ID NO 124
<211> LENGTH: 21
<212> TYPE: DNA
<213> ORGANISM: Artificial Sequence
<220> FEATURE:
<223> OTHER INFORMATION: antisense oligonucleotide 21e_002m16
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
```

```
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 124
agataaaauc cgauggcgaa g                                              21

<210> SEQ ID NO 125
<211> LENGTH: 21
<212> TYPE: DNA
<213> ORGANISM: Artificial Sequence
<220> FEATURE:
<223> OTHER INFORMATION: antisense oligonucleotide 21e_002m17
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
```

```
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 125
agataaaauc cgauggcgaa g                                              21

<210> SEQ ID NO 126
<211> LENGTH: 21
<212> TYPE: DNA
<213> ORGANISM: Artificial Sequence
<220> FEATURE:
<223> OTHER INFORMATION: antisense oligonucleotide 21e_002m18
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
```

```
<220> FEATURE:
<221> NAME/KEY: misc_feature
<222> LOCATION: (5)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: misc_feature
<222> LOCATION: (10)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 126
agataaaatc cgatggcgaa g                                          21

<210> SEQ ID NO 127
<211> LENGTH: 21
<212> TYPE: DNA
<213> ORGANISM: Artificial Sequence
<220> FEATURE:
<223> OTHER INFORMATION: antisense oligonucleotide 21e_002m19
<220> FEATURE:
<221> NAME/KEY: misc_feature
<222> LOCATION: (1)..(1)
```

-continued

```
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
```

<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 127
agauaaaauc cgatggcgaa g    21

<210> SEQ ID NO 128
<211> LENGTH: 21
<212> TYPE: DNA
<213> ORGANISM: Artificial Sequence
<220> FEATURE:
<223> OTHER INFORMATION: antisense oligonucleotide 21e_002m20
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: misc_feature
<222> LOCATION: (10)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:

<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (19)..(19)
<223> OTHER INFORMATION: ENA
<220> FEATURE:
<221> NAME/KEY: misc_feature
<222> LOCATION: (20)..(20)
<223> OTHER INFORMATION: 2'-OMe-RNA
<220> FEATURE:
<221> NAME/KEY: misc_feature
<222> LOCATION: (21)..(21)
<223> OTHER INFORMATION: ENA
<220> FEATURE:
<221> NAME/KEY: misc_feature
<222> LOCATION: (21)..(21)
<223> OTHER INFORMATION: 3'-position is hydroxyl group

<400> SEQUENCE: 128
agauaaaatc cgauggcgaa g                                             21

<210> SEQ ID NO 129
<211> LENGTH: 18
<212> TYPE: DNA
<213> ORGANISM: Artificial Sequence
<220> FEATURE:
<223> OTHER INFORMATION: antisense oligonucleotide 18e_022
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(6)
<223> OTHER INFORMATION: 2'-OMe-RNA
<220> FEATURE:
<221> NAME/KEY: misc_feature
<222> LOCATION: (7)..(8)
<223> OTHER INFORMATION: ENA
<220> FEATURE:
<221> NAME/KEY: modified_base
<222> LOCATION: (7)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-RNA

```
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 129
taaaauccga tggcgaag                                                 18

<210> SEQ ID NO 130
<211> LENGTH: 18
<212> TYPE: DNA
<213> ORGANISM: Artificial Sequence
<220> FEATURE:
<223> OTHER INFORMATION: antisense oligonucleotide 18e_023
<220> FEATURE:
<221> NAME/KEY: misc_feature
<222> LOCATION: (1)..(5)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (6)..(7)
<223> OTHER INFORMATION: ENA
<220> FEATURE:
<221> NAME/KEY: modified_base
<222> LOCATION: (6)..(7)
<223> OTHER INFORMATION: m5c
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: modified_base
<222> LOCATION: (13)..(13)
<223> OTHER INFORMATION: m5c
<220> FEATURE:
<221> NAME/KEY: misc_feature
<222> LOCATION: (14)..(17)
<223> OTHER INFORMATION: 2'-OMe-RNA
<220> FEATURE:
<221> NAME/KEY: misc_feature
<222> LOCATION: (18)..(18)
<223> OTHER INFORMATION: ENA
<220> FEATURE:
<221> NAME/KEY: modified_base
<222> LOCATION: (18)..(18)
<223> OTHER INFORMATION: m5c
<220> FEATURE:
<221> NAME/KEY: misc_feature
<222> LOCATION: (18)..(18)
```

<223> OTHER INFORMATION: 3'-position is hydroxyl group

<400> SEQUENCE: 130
aaaauccgat ggcgaagc                                           18

<210> SEQ ID NO 131
<211> LENGTH: 18
<212> TYPE: DNA
<213> ORGANISM: Artificial Sequence
<220> FEATURE:
<223> OTHER INFORMATION: antisense oligonucleotide 18e_024
<220> FEATURE:
<221> NAME/KEY: misc_feature
<222> LOCATION: (1)..(4)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (5)..(6)
<223> OTHER INFORMATION: ENA
<220> FEATURE:
<221> NAME/KEY: modified_base
<222> LOCATION: (5)..(6)
<223> OTHER INFORMATION: m5c
<220> FEATURE:
<221> NAME/KEY: misc_feature
<222> LOCATION: (7)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: modified_base
<222> LOCATION: (12)..(12)
<223> OTHER INFORMATION: m5c
<220> FEATURE:
<221> NAME/KEY: misc_feature
<222> LOCATION: (13)..(16)
<223> OTHER INFORMATION: 2'-OMe-RNA
<220> FEATURE:
<221> NAME/KEY: misc_feature
<222> LOCATION: (17)..(18)
<223> OTHER INFORMATION: ENA
<220> FEATURE:
<221> NAME/KEY: modified_base
<222> LOCATION: (17)..(17)
<223> OTHER INFORMATION: m5c
<220> FEATURE:
<221> NAME/KEY: misc_feature
<222> LOCATION: (18)..(18)
<223> OTHER INFORMATION: 3'-position is hydroxyl group

<400> SEQUENCE: 131
aaauccgatg gcgaagct                                           18

<210> SEQ ID NO 132
<211> LENGTH: 18
<212> TYPE: DNA
<213> ORGANISM: Artificial Sequence
<220> FEATURE:
<223> OTHER INFORMATION: antisense oligonucleotide 18e_025
<220> FEATURE:
<221> NAME/KEY: misc_feature

```
<222> LOCATION: (1)..(3)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (4)..(5)
<223> OTHER INFORMATION: ENA
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(15)
<223> OTHER INFORMATION: 2'-OMe-RNA
<220> FEATURE:
<221> NAME/KEY: misc_feature
<222> LOCATION: (16)..(17)
<223> OTHER INFORMATION: ENA
<220> FEATURE:
<221> NAME/KEY: modified_base
<222> LOCATION: (16)..(16)
<223> OTHER INFORMATION: m5c
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 132
aauccgatgg cgaagctg                                                       18

<210> SEQ ID NO 133
<211> LENGTH: 18
<212> TYPE: DNA
<213> ORGANISM: Artificial Sequence
<220> FEATURE:
<223> OTHER INFORMATION: antisense oligonucleotide 18e_026
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (3)..(4)
<223> OTHER INFORMATION: ENA
<220> FEATURE:
```

<221> NAME/KEY: modified_base
<222> LOCATION: (3)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(14)
<223> OTHER INFORMATION: 2'-OMe-RNA
<220> FEATURE:
<221> NAME/KEY: misc_feature
<222> LOCATION: (15)..(16)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 133
auccgatggc gaagctga                                                   18

<210> SEQ ID NO 134
<211> LENGTH: 18
<212> TYPE: DNA
<213> ORGANISM: Artificial Sequence
<220> FEATURE:
<223> OTHER INFORMATION: antisense oligonucleotide 18e_031
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA

```
<220> FEATURE:
<221> NAME/KEY: misc_feature
<222> LOCATION: (7)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 134
taaaatccga uggcgaag                                                 18

<210> SEQ ID NO 135
<211> LENGTH: 18
<212> TYPE: DNA
<213> ORGANISM: Artificial Sequence
<220> FEATURE:
<223> OTHER INFORMATION: antisense oligonucleotide 18m_005
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 135
uaaaauccga uggcgaag                                                 18

<210> SEQ ID NO 136
<211> LENGTH: 18
<212> TYPE: DNA
<213> ORGANISM: Artificial Sequence
<220> FEATURE:
<223> OTHER INFORMATION: antisense oligonucleotide 18m_006
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 136
aaaauccgau ggcgaagc                                                 18

<210> SEQ ID NO 137
```

```
<211> LENGTH: 18
<212> TYPE: DNA
<213> ORGANISM: Artificial Sequence
<220> FEATURE:
<223> OTHER INFORMATION: antisense oligonucleotide 18m_007
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 137
aaauccgaug gcgaagcu                                                 18

<210> SEQ ID NO 138
<211> LENGTH: 18
<212> TYPE: DNA
<213> ORGANISM: Artificial Sequence
<220> FEATURE:
<223> OTHER INFORMATION: antisense oligonucleotide 18m_008
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 138
aauccgaugg cgaagcug                                                 18

<210> SEQ ID NO 139
<211> LENGTH: 18
<212> TYPE: DNA
<213> ORGANISM: Artificial Sequence
<220> FEATURE:
<223> OTHER INFORMATION: antisense oligonucleotide 18m_009
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 139
auccgauggc gaagcuga                                                 18

<210> SEQ ID NO 140
<211> LENGTH: 18
<212> TYPE: DNA
<213> ORGANISM: Artificial Sequence
<220> FEATURE:
<223> OTHER INFORMATION: antisense oligonucleotide 18m_010
<220> FEATURE:
<221> NAME/KEY: misc_feature
```

<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 140
uccgauggcg aagcugaa                                                       18

<210> SEQ ID NO 141
<211> LENGTH: 18
<212> TYPE: DNA
<213> ORGANISM: Artificial Sequence
<220> FEATURE:
<223> OTHER INFORMATION: antisense oligonucleotide 18m_011
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 141
ccgauggcga agctgaaa                                                       18

<210> SEQ ID NO 142
<211> LENGTH: 18
<212> TYPE: DNA
<213> ORGANISM: Artificial Sequence
<220> FEATURE:
<223> OTHER INFORMATION: antisense oligonucleotide 18m_012
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 142
cgauggcgaa gcugaaaa                                                       18

<210> SEQ ID NO 143
<211> LENGTH: 18
<212> TYPE: DNA
<213> ORGANISM: Artificial Sequence
<220> FEATURE:
<223> OTHER INFORMATION: antisense oligonucleotide 18m_013
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:

<221> NAME/KEY: misc_feature
<222> LOCATION: (18)..(18)
<223> OTHER INFORMATION: 3'-position is hydroxyl group

<400> SEQUENCE: 143
gauggcgaag cugaaaag                                              18

<210> SEQ ID NO 144
<211> LENGTH: 18
<212> TYPE: DNA
<213> ORGANISM: Artificial Sequence
<220> FEATURE:
<223> OTHER INFORMATION: antisense oligonucleotide 18m_014
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 144
auggcgaagc ugaaaagg                                              18

<210> SEQ ID NO 145
<211> LENGTH: 18
<212> TYPE: DNA
<213> ORGANISM: Artificial Sequence
<220> FEATURE:
<223> OTHER INFORMATION: antisense oligonucleotide 18m_015
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 145
uggcgaagcu gaaaagga                                              18

<210> SEQ ID NO 146
<211> LENGTH: 18
<212> TYPE: DNA
<213> ORGANISM: Artificial Sequence
<220> FEATURE:
<223> OTHER INFORMATION: antisense oligonucleotide 18m_016
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 146
ggcgaagcug aaaaggaa                                              18

<210> SEQ ID NO 147
<211> LENGTH: 18
<212> TYPE: DNA
<213> ORGANISM: Artificial Sequence
<220> FEATURE:
<223> OTHER INFORMATION: antisense oligonucleotide 18m_017
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 147
gcgaagcuga aaaggaag                                          18

<210> SEQ ID NO 148
<211> LENGTH: 18
<212> TYPE: DNA
<213> ORGANISM: Artificial Sequence
<220> FEATURE:
<223> OTHER INFORMATION: antisense oligonucleotide 18e_018
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(10)
<223> OTHER INFORMATION: 2'-OMe-RNA
<220> FEATURE:
<221> NAME/KEY: misc_feature
<222> LOCATION: (11)..(12)
<223> OTHER INFORMATION: ENA
<220> FEATURE:
<221> NAME/KEY: modified_base
<222> LOCATION: (11)..(12)
<223> OTHER INFORMATION: m5c
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(17)
<223> OTHER INFORMATION: 2'-OMe-RNA
<220> FEATURE:
<221> NAME/KEY: misc_feature
<222> LOCATION: (18)..(18)

```
<223> OTHER INFORMATION: ENA
<220> FEATURE:
<221> NAME/KEY: modified_base
<222> LOCATION: (18)..(18)
<223> OTHER INFORMATION: m5c
<220> FEATURE:
<221> NAME/KEY: misc_feature
<222> LOCATION: (18)..(18)
<223> OTHER INFORMATION: 3'-position is hydroxyl group

<400> SEQUENCE: 148
cagataaaau ccgatggc                                                 18

<210> SEQ ID NO 149
<211> LENGTH: 18
<212> TYPE: DNA
<213> ORGANISM: Artificial Sequence
<220> FEATURE:
<223> OTHER INFORMATION: antisense oligonucleotide 18e_019
<220> FEATURE:
<221> NAME/KEY: misc_feature
<222> LOCATION: (1)..(3)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(9)
<223> OTHER INFORMATION: 2'-OMe-RNA
<220> FEATURE:
<221> NAME/KEY: misc_feature
<222> LOCATION: (10)..(11)
<223> OTHER INFORMATION: ENA
<220> FEATURE:
<221> NAME/KEY: modified_base
<222> LOCATION: (10)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(16)
<223> OTHER INFORMATION: 2'-OMe-RNA
<220> FEATURE:
<221> NAME/KEY: misc_feature
<222> LOCATION: (17)..(17)
<223> OTHER INFORMATION: ENA
<220> FEATURE:
<221> NAME/KEY: modified_base
<222> LOCATION: (17)..(17)
<223> OTHER INFORMATION: m5c
<220> FEATURE:
<221> NAME/KEY: misc_feature
<222> LOCATION: (18)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 149
agataaaauc cgatggcg                                                 18
```

```
<210> SEQ ID NO 150
<211> LENGTH: 18
<212> TYPE: DNA
<213> ORGANISM: Artificial Sequence
<220> FEATURE:
<223> OTHER INFORMATION: antisense oligonucleotide 18e_020
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(8)
<223> OTHER INFORMATION: 2'-OMe-RNA
<220> FEATURE:
<221> NAME/KEY: misc_feature
<222> LOCATION: (9)..(10)
<223> OTHER INFORMATION: ENA
<220> FEATURE:
<221> NAME/KEY: modified_base
<222> LOCATION: (9)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: modified_base
<222> LOCATION: (16)..(16)
<223> OTHER INFORMATION: m5c
<220> FEATURE:
<221> NAME/KEY: misc_feature
<222> LOCATION: (17)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 150
gataaaatcc gatggcga                                                 18

<210> SEQ ID NO 151
<211> LENGTH: 18
<212> TYPE: DNA
<213> ORGANISM: Artificial Sequence
<220> FEATURE:
<223> OTHER INFORMATION: antisense oligonucleotide 18e_021
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
```

```
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(7)
<223> OTHER INFORMATION: 2'-OMe-RNA
<220> FEATURE:
<221> NAME/KEY: misc_feature
<222> LOCATION: (8)..(9)
<223> OTHER INFORMATION: ENA
<220> FEATURE:
<221> NAME/KEY: modified_base
<222> LOCATION: (8)..(9)
<223> OTHER INFORMATION: m5c
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 151
ataaaauccg atggcgaa                                          18

<210> SEQ ID NO 152
<211> LENGTH: 18
<212> TYPE: DNA
<213> ORGANISM: Artificial Sequence
<220> FEATURE:
<223> OTHER INFORMATION: antisense oligonucleotide 18e_027
<220> FEATURE:
<221> NAME/KEY: misc_feature
<222> LOCATION: (1)..(1)
<223> OTHER INFORMATION: ENA
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
```

```
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: modified_base
<222> LOCATION: (12)..(12)
<223> OTHER INFORMATION: m5c
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 152
cagauaaaau ccgatggc                                             18

<210> SEQ ID NO 153
<211> LENGTH: 18
<212> TYPE: DNA
<213> ORGANISM: Artificial Sequence
<220> FEATURE:
<223> OTHER INFORMATION: antisense oligonucleotide 18e_028
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(14)
```

<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 153
agauaaaauc cgauggcg                                                       18

<210> SEQ ID NO 154
<211> LENGTH: 18
<212> TYPE: DNA
<213> ORGANISM: Artificial Sequence
<220> FEATURE:
<223> OTHER INFORMATION: antisense oligonucleotide 18e_029
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 154
gataaaaucc gauggcga                                                       18

-continued

```
<210> SEQ ID NO 155
<211> LENGTH: 18
<212> TYPE: DNA
<213> ORGANISM: Artificial Sequence
<220> FEATURE:
<223> OTHER INFORMATION: antisense oligonucleotide 18e_030
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (16)..(18)
<223> OTHER INFORMATION: 2'-OMe-RNA
<220> FEATURE:
<221> NAME/KEY: misc_feature
<222> LOCATION: (18)..(18)
<223> OTHER INFORMATION: 3'-position is hydroxyl group

<400> SEQUENCE: 155
auaaaauccg atggcgaa                                                 18

<210> SEQ ID NO 156
<211> LENGTH: 18
<212> TYPE: DNA
<213> ORGANISM: Artificial Sequence
<220> FEATURE:
<223> OTHER INFORMATION: antisense oligonucleotide 18m_001
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
```

<221> NAME/KEY: misc_feature
<222> LOCATION: (18)..(18)
<223> OTHER INFORMATION: 3'-position is hydroxyl group

<400> SEQUENCE: 156
cagauaaaau ccgauggc                                                  18

<210> SEQ ID NO 157
<211> LENGTH: 18
<212> TYPE: DNA
<213> ORGANISM: Artificial Sequence
<220> FEATURE:
<223> OTHER INFORMATION: antisense oligonucleotide 18m_002
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 157
agauaaaauc cgauggcg                                                  18

<210> SEQ ID NO 158
<211> LENGTH: 18
<212> TYPE: DNA
<213> ORGANISM: Artificial Sequence
<220> FEATURE:
<223> OTHER INFORMATION: antisense oligonucleotide 18m_003
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 158
gauaaaaucc gauggcga                                                  18

<210> SEQ ID NO 159
<211> LENGTH: 18
<212> TYPE: DNA
<213> ORGANISM: Artificial Sequence
<220> FEATURE:
<223> OTHER INFORMATION: antisense oligonucleotide 18m_004
<220> FEATURE:
<221> NAME/KEY: misc_feature
<222> LOCATION: (1)..(18)
<223> OTHER INFORMATION: 2'-OMe-RNA
<220> FEATURE:
<221> NAME/KEY: misc_feature
<222> LOCATION: (1)..(17)
<223> OTHER INFORMATION: phosphorothioate bond
<220> FEATURE:
<221> NAME/KEY: misc_feature
<222> LOCATION: (18)..(18)
<223> OTHER INFORMATION: 3'-position is hydroxyl group

<400> SEQUENCE: 159
auaaaauccg auggcgaa                                                  18

```
<210> SEQ ID NO 160
<211> LENGTH: 21
<212> TYPE: DNA
<213> ORGANISM: Artificial Sequence
<220> FEATURE:
<223> OTHER INFORMATION: antisense oligonucleotide 21m_001
<220> FEATURE:
<221> NAME/KEY: misc_feature
<222> LOCATION: (1)..(21)
<223> OTHER INFORMATION: 2'-OMe-RNA
<220> FEATURE:
<221> NAME/KEY: misc_feature
<222> LOCATION: (1)..(20)
<223> OTHER INFORMATION: phosphorothioate bond
<220> FEATURE:
<221> NAME/KEY: misc_feature
<222> LOCATION: (21)..(21)
<223> OTHER INFORMATION: 3'-position is hydroxyl group

<400> SEQUENCE: 160
agcagauaaa auccgauggc g                                          21

<210> SEQ ID NO 161
<211> LENGTH: 15
<212> TYPE: DNA
<213> ORGANISM: Artificial Sequence
<220> FEATURE:
<223> OTHER INFORMATION: antisense oligonucleotide 15ed_001
<220> FEATURE:
<221> NAME/KEY: misc_feature
<222> LOCATION: (1)..(1)
<223> OTHER INFORMATION: 2'-OMe-DNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-DNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-DNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-DNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
```

<223> OTHER INFORMATION: 2'-OMe-DNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-DNA
<220> FEATURE:
<221> NAME/KEY: misc_feature
<222> LOCATION: (15)..(15)
<223> OTHER INFORMATION: 3'-position is hydroxyl group

<400> SEQUENCE: 161
aatccgatgg cgaag                                                          15

<210> SEQ ID NO 162
<211> LENGTH: 15
<212> TYPE: DNA
<213> ORGANISM: Artificial Sequence
<220> FEATURE:
<223> OTHER INFORMATION: antisense oligonucleotide 15ed_002
<220> FEATURE:
<221> NAME/KEY: misc_feature
<222> LOCATION: (1)..(1)
<223> OTHER INFORMATION: 2'-OMe-DNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (3)..(4)
<223> OTHER INFORMATION: 2'-OMe-DNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(7)
<223> OTHER INFORMATION: 2'-OMe-DNA
<220> FEATURE:
<221> NAME/KEY: misc_feature
<222> LOCATION: (8)..(8)
<223> OTHER INFORMATION: ENA
<220> FEATURE:
<221> NAME/KEY: modified_base
<222> LOCATION: (8)..(8)
<223> OTHER INFORMATION: m5c
<220> FEATURE:
<221> NAME/KEY: misc_feature
<222> LOCATION: (9)..(10)
<223> OTHER INFORMATION: 2'-OMe-DNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(13)
<223> OTHER INFORMATION: 2'-OMe-DNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature

```
<222> LOCATION: (15)..(15)
<223> OTHER INFORMATION: 2'-OMe-DNA
<220> FEATURE:
<221> NAME/KEY: misc_feature
<222> LOCATION: (15)..(15)
<223> OTHER INFORMATION: 3'-position is hydroxyl group

<400> SEQUENCE: 162
ccgatggcga agctg                                                    15

<210> SEQ ID NO 163
<211> LENGTH: 15
<212> TYPE: DNA
<213> ORGANISM: Artificial Sequence
<220> FEATURE:
<223> OTHER INFORMATION: antisense oligonucleotide 15e_001.1
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (4)..(5)
<223> OTHER INFORMATION: ENA
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group
```

-continued

<400> SEQUENCE: 163
aauccgatgg cgaag                                                    15

<210> SEQ ID NO 164
<211> LENGTH: 15
<212> TYPE: DNA
<213> ORGANISM: Artificial Sequence
<220> FEATURE:
<223> OTHER INFORMATION: antisense oligonucleotide 15e_001.2
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(12)
<223> OTHER INFORMATION: 2'-OMe-RNA
<220> FEATURE:
<221> NAME/KEY: misc_feature
<222> LOCATION: (13)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 164
aauccgatgg cgaag                                                    15

<210> SEQ ID NO 165
<211> LENGTH: 15

```
<212> TYPE: DNA
<213> ORGANISM: Artificial Sequence
<220> FEATURE:
<223> OTHER INFORMATION: antisense oligonucleotide 15e_001.3
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (4)..(5)
<223> OTHER INFORMATION: ENA
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(12)
<223> OTHER INFORMATION: 2'-OMe-RNA
<220> FEATURE:
<221> NAME/KEY: misc_feature
<222> LOCATION: (13)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 165
aauccgatgg cgaag                                                15

<210> SEQ ID NO 166
<211> LENGTH: 15
<212> TYPE: DNA
<213> ORGANISM: Artificial Sequence
<220> FEATURE:
<223> OTHER INFORMATION: antisense oligonucleotide 15e_001.4
<220> FEATURE:
<221> NAME/KEY: misc_feature
<222> LOCATION: (1)..(1)
```

```
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (4)..(5)
<223> OTHER INFORMATION: ENA
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(12)
<223> OTHER INFORMATION: 2'-OMe-RNA
<220> FEATURE:
<221> NAME/KEY: misc_feature
<222> LOCATION: (13)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 166
aauccgatgg cgaag                                                    15

<210> SEQ ID NO 167
<211> LENGTH: 16
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (2)..(15)
<223> OTHER INFORMATION: phosphorothioate bond
<220> FEATURE:
<221> NAME/KEY: misc_feature
```

```
<222> LOCATION: (3)..(3)
<223> OTHER INFORMATION: ENA
<220> FEATURE:
<221> NAME/KEY: misc_feature
<222> LOCATION: (4)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: misc_feature
<222> LOCATION: (10)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: misc_feature
<222> LOCATION: (12)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (16)..(16)
<223> OTHER INFORMATION: 3'-position is hydroxyl group

<400> SEQUENCE: 167
aaauccgatg gcgaag                                                    16

<210> SEQ ID NO 168
<211> LENGTH: 16
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (2)..(2)
<223> OTHER INFORMATION: ENA
<220> FEATURE:
```

```
<221> NAME/KEY: misc_feature
<222> LOCATION: (2)..(15)
<223> OTHER INFORMATION: phosphorothioate bond
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: misc_feature
<222> LOCATION: (5)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (7)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: misc_feature
<222> LOCATION: (11)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: modified_base
<222> LOCATION: (12)..(12)
<223> OTHER INFORMATION: m5c
<220> FEATURE:
<221> NAME/KEY: misc_feature
<222> LOCATION: (13)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (16)..(16)
<223> OTHER INFORMATION: 3'-position is hydroxyl group

<400> SEQUENCE: 168
aaatccgaug gcgaag                                                     16

<210> SEQ ID NO 169
<211> LENGTH: 15
```

```
<212> TYPE: DNA
<213> ORGANISM: Artificial Sequence
<220> FEATURE:
<223> OTHER INFORMATION: antisense oligonucleotide 15e_005.1
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: 3'-position is hydroxyl group

<400> SEQUENCE: 169
auccgatggc gaagc                                                      15

<210> SEQ ID NO 170
<211> LENGTH: 15
<212> TYPE: DNA
<213> ORGANISM: Artificial Sequence
<220> FEATURE:
```

```
<223> OTHER INFORMATION: antisense oligonucleotide 15e_006.1
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: modified_base
<222> LOCATION: (3)..(3)
<223> OTHER INFORMATION: m5c
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 170
uccgatggcg aagcu                                              15

<210> SEQ ID NO 171
<211> LENGTH: 15
<212> TYPE: DNA
<213> ORGANISM: Artificial Sequence
<220> FEATURE:
<223> OTHER INFORMATION: antisense oligonucleotide 15e_005.1
<220> FEATURE:
<221> NAME/KEY: misc_feature
```

```
<222> LOCATION: (1)..(1)
<223> OTHER INFORMATION: ENA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: 3'-position is hydroxyl group

<400> SEQUENCE: 171
auccgatggc gaagc                                              15

<210> SEQ ID NO 172
<211> LENGTH: 15
<212> TYPE: DNA
<213> ORGANISM: Artificial Sequence
<220> FEATURE:
<223> OTHER INFORMATION: antisense oligonucleotide 15e_006.1
<220> FEATURE:
<221> NAME/KEY: misc_feature
<222> LOCATION: (1)..(2)
<223> OTHER INFORMATION: 2'-OMe-RNA
<220> FEATURE:
```

```
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: modified_base
<222> LOCATION: (3)..(3)
<223> OTHER INFORMATION: m5c
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 172
uccgatggcg aagcu                                                    15

<210> SEQ ID NO 173
<211> LENGTH: 15
<212> TYPE: DNA
<213> ORGANISM: Artificial Sequence
<220> FEATURE:
<223> OTHER INFORMATION: antisense oligonucleotide 15e_001.5
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
```

```
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 173
aauccgaugg cgaag                                                    15

<210> SEQ ID NO 174
<211> LENGTH: 15
<212> TYPE: DNA
<213> ORGANISM: Artificial Sequence
<220> FEATURE:
<223> OTHER INFORMATION: antisense oligonucleotide 15e_005.5
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
```

```
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (15)..(15)
<223> OTHER INFORMATION: 3'-position is hydroxyl group
<220> FEATURE:
<221> NAME/KEY: modified_base
<222> LOCATION: (15)..(15)
<223> OTHER INFORMATION: m5c

<400> SEQUENCE: 174
auccgauggc gaagc                                                    15

<210> SEQ ID NO 175
<211> LENGTH: 15
<212> TYPE: DNA
<213> ORGANISM: Artificial Sequence
<220> FEATURE:
<223> OTHER INFORMATION: antisense oligonucleotide 15e_006.5
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: modified_base
<222> LOCATION: (3)..(3)
<223> OTHER INFORMATION: m5c
<220> FEATURE:
<221> NAME/KEY: misc_feature
```

-continued

```
<222> LOCATION: (4)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: misc_feature
<222> LOCATION: (6)..(8)
<223> OTHER INFORMATION: 2'-OMe-RNA
<220> FEATURE:
<221> NAME/KEY: misc_feature
<222> LOCATION: (9)..(9)
<223> OTHER INFORMATION: ENA
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: misc_feature
<222> LOCATION: (13)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: modified_base
<222> LOCATION: (14)..(14)
<223> OTHER INFORMATION: m5c
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 175
uccgauggcg aagcu                                                15

<210> SEQ ID NO 176
<211> LENGTH: 16
<212> TYPE: DNA
<213> ORGANISM: Artificial Sequence
<220> FEATURE:
<223> OTHER INFORMATION: antisense oligonucleotide 16e_001.5
<220> FEATURE:
<221> NAME/KEY: misc_feature
<222> LOCATION: (1)..(2)
<223> OTHER INFORMATION: 2'-OMe-RNA
<220> FEATURE:
<221> NAME/KEY: misc_feature
<222> LOCATION: (1)..(15)
<223> OTHER INFORMATION: phosphorothioate bond
<220> FEATURE:
<221> NAME/KEY: misc_feature
<222> LOCATION: (3)..(3)
<223> OTHER INFORMATION: ENA
<220> FEATURE:
<221> NAME/KEY: misc_feature
<222> LOCATION: (4)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
```

```
<221> NAME/KEY: modified_base
<222> LOCATION: (6)..(6)
<223> OTHER INFORMATION: m5c
<220> FEATURE:
<221> NAME/KEY: misc_feature
<222> LOCATION: (7)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(11)
<223> OTHER INFORMATION: 2'-OMe-RNA
<220> FEATURE:
<221> NAME/KEY: misc_feature
<222> LOCATION: (12)..(12)
<223> OTHER INFORMATION: ENA
<220> FEATURE:
<221> NAME/KEY: modified_base
<222> LOCATION: (12)..(12)
<223> OTHER INFORMATION: m5c
<220> FEATURE:
<221> NAME/KEY: misc_feature
<222> LOCATION: (13)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (16)..(16)
<223> OTHER INFORMATION: 3'-position is hydroxyl group

<400> SEQUENCE: 176
aaauccgaug gcgaag                                                   16

<210> SEQ ID NO 177
<211> LENGTH: 16
<212> TYPE: DNA
<213> ORGANISM: Artificial Sequence
<220> FEATURE:
<223> OTHER INFORMATION: antisense oligonucleotide 16e_002.5
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(15)
<223> OTHER INFORMATION: phosphorothioate bond
<220> FEATURE:
<221> NAME/KEY: misc_feature
<222> LOCATION: (2)..(2)
<223> OTHER INFORMATION: ENA
<220> FEATURE:
<221> NAME/KEY: misc_feature
<222> LOCATION: (3)..(4)
<223> OTHER INFORMATION: 2'-OMe-RNA
<220> FEATURE:
<221> NAME/KEY: misc_feature
<222> LOCATION: (5)..(5)
<223> OTHER INFORMATION: ENA
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(6)
<223> OTHER INFORMATION: 2'-OMe-RNA
```

```
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(13)
<223> OTHER INFORMATION: 2'-OMe-RNA
<220> FEATURE:
<221> NAME/KEY: misc_feature
<222> LOCATION: (14)..(14)
<223> OTHER INFORMATION: ENA
<220> FEATURE:
<221> NAME/KEY: misc_feature
<222> LOCATION: (15)..(15)
<223> OTHER INFORMATION: 2'-OMe-RNA
<220> FEATURE:
<221> NAME/KEY: misc_feature
<222> LOCATION: (16)..(16)
<223> OTHER INFORMATION: ENA
<220> FEATURE:
<221> NAME/KEY: misc_feature
<222> LOCATION: (16)..(16)
<223> OTHER INFORMATION: 3'-position is hydroxyl group
<220> FEATURE:
<221> NAME/KEY: modified_base
<222> LOCATION: (16)..(16)
<223> OTHER INFORMATION: m5c

<400> SEQUENCE: 177
aauccgaugg cgaagc                                                 16

<210> SEQ ID NO 178
<211> LENGTH: 16
<212> TYPE: DNA
<213> ORGANISM: Artificial Sequence
<220> FEATURE:
<223> OTHER INFORMATION: antisense oligonucleotide 16e_003.5
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(15)
<223> OTHER INFORMATION: phosphorothioate bond
<220> FEATURE:
<221> NAME/KEY: misc_feature
<222> LOCATION: (2)..(3)
<223> OTHER INFORMATION: 2'-OMe-RNA
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(5)
<223> OTHER INFORMATION: 2'-OMe-RNA
<220> FEATURE:
<221> NAME/KEY: misc_feature
<222> LOCATION: (6)..(6)
```

```
<223> OTHER INFORMATION: ENA
<220> FEATURE:
<221> NAME/KEY: misc_feature
<222> LOCATION: (7)..(9)
<223> OTHER INFORMATION: 2'-OMe-RNA
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (16)..(16)
<223> OTHER INFORMATION: 2'-OMe-RNA
<220> FEATURE:
<221> NAME/KEY: misc_feature
<222> LOCATION: (16)..(16)
<223> OTHER INFORMATION: 3'-position is hydroxyl group

<400> SEQUENCE: 178
auccgauggc gaagcu                                                    16

<210> SEQ ID NO 179
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(3)
<223> OTHER INFORMATION: 2'-OMe-RNA
<220> FEATURE:
<221> NAME/KEY: modified_base
<222> LOCATION: (2)..(5)
<223> OTHER INFORMATION: 2'O,4'-5-methylcytosine-ethylene bridged
      nucleic acid

<400> SEQUENCE: 179
aauccgatgg cgaag                                                     15

<210> SEQ ID NO 180
<211> LENGTH: 15
<212> TYPE: DNA
<213> ORGANISM: Artificial Sequence
<220> FEATURE:
<223> OTHER INFORMATION: antisense oligonucleotide  15e_001.7
<220> FEATURE:
<221> NAME/KEY: misc_feature
<222> LOCATION: (1)..(2)
<223> OTHER INFORMATION: 2'-OMe-RNA
<220> FEATURE:
```

```
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (3)..(5)
<223> OTHER INFORMATION: ENA
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (6)..(7)
<223> OTHER INFORMATION: 2'-OMe-RNA
<220> FEATURE:
<221> NAME/KEY: misc_feature
<222> LOCATION: (8)..(8)
<223> OTHER INFORMATION: ENA
<220> FEATURE:
<221> NAME/KEY: misc_feature
<222> LOCATION: (9)..(10)
<223> OTHER INFORMATION: 2'-OMe-RNA
<220> FEATURE:
<221> NAME/KEY: misc_feature
<222> LOCATION: (11)..(11)
<223> OTHER INFORMATION: ENA
<220> FEATURE:
<221> NAME/KEY: modified_base
<222> LOCATION: (11)..(11)
<223> OTHER INFORMATION: m5c
<220> FEATURE:
<221> NAME/KEY: misc_feature
<222> LOCATION: (12)..(15)
<223> OTHER INFORMATION: 2'-OMe-RNA
<220> FEATURE:
<221> NAME/KEY: misc_feature
<222> LOCATION: (15)..(15)
<223> OTHER INFORMATION: 3'-position is hydroxyl group

<400> SEQUENCE: 180
aatccgatgg cgaag                                             15

<210> SEQ ID NO 181
<211> LENGTH: 15
<212> TYPE: DNA
<213> ORGANISM: Artificial Sequence
<220> FEATURE:
<223> OTHER INFORMATION: antisense oligonucleotide 15e_005.7
<220> FEATURE:
<221> NAME/KEY: misc_feature
<222> LOCATION: (1)..(1)
<223> OTHER INFORMATION: 2'-OMe-RNA
<220> FEATURE:
<221> NAME/KEY: misc_feature
<222> LOCATION: (1)..(14)
<223> OTHER INFORMATION: phosphorothioate bond
<220> FEATURE:
<221> NAME/KEY: misc_feature
<222> LOCATION: (2)..(4)
<223> OTHER INFORMATION: ENA
<220> FEATURE:
<221> NAME/KEY: modified_base
<222> LOCATION: (3)..(4)
<223> OTHER INFORMATION: m5c
<220> FEATURE:
<221> NAME/KEY: misc_feature
<222> LOCATION: (5)..(6)
<223> OTHER INFORMATION: 2'-OMe-RNA
<220> FEATURE:
<221> NAME/KEY: misc_feature
<222> LOCATION: (7)..(7)
<223> OTHER INFORMATION: ENA
<220> FEATURE:
<221> NAME/KEY: misc_feature
<222> LOCATION: (8)..(9)
<223> OTHER INFORMATION: 2'-OMe-RNA
```

-continued

```
<220> FEATURE:
<221> NAME/KEY: misc_feature
<222> LOCATION: (10)..(10)
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: 3'-position is hydroxyl group

<400> SEQUENCE: 181
atccgatggc gaagc                                             15

<210> SEQ ID NO 182
<211> LENGTH: 15
<212> TYPE: DNA
<213> ORGANISM: Artificial Sequence
<220> FEATURE:
<223> OTHER INFORMATION: antisense oligonucleotide 15e_005.501
<220> FEATURE:
<221> NAME/KEY: misc_feature
<222> LOCATION: (1)..(1)
<223> OTHER INFORMATION: ENA
<220> FEATURE:
<221> NAME/KEY: misc_feature
<222> LOCATION: (1)..(1)
<223> OTHER INFORMATION: phosphorothioate bond
<220> FEATURE:
<221> NAME/KEY: misc_feature
<222> LOCATION: (2)..(2)
<223> OTHER INFORMATION: 2'-OMe-RNA
<220> FEATURE:
<221> NAME/KEY: misc_feature
<222> LOCATION: (3)..(3)
<223> OTHER INFORMATION: 2'-OMe-RNA
<220> FEATURE:
<221> NAME/KEY: misc_feature
<222> LOCATION: (3)..(14)
<223> OTHER INFORMATION: phosphorothioate bond
<220> FEATURE:
<221> NAME/KEY: misc_feature
<222> LOCATION: (4)..(4)
<223> OTHER INFORMATION: ENA
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(5)
<223> OTHER INFORMATION: 2'-OMe-RNA
<220> FEATURE:
<221> NAME/KEY: misc_feature
<222> LOCATION: (6)..(6)
<223> OTHER INFORMATION: ENA
<220> FEATURE:
<221> NAME/KEY: misc_feature
<222> LOCATION: (7)..(9)
<223> OTHER INFORMATION: 2'-OMe-RNA
<220> FEATURE:
<221> NAME/KEY: misc_feature
<222> LOCATION: (10)..(10)
```

```
<223> OTHER INFORMATION: ENA
<220> FEATURE:
<221> NAME/KEY: modified_base
<222> LOCATION: (10)..(10)
<223> OTHER INFORMATION: m5c
<220> FEATURE:
<221> NAME/KEY: misc_feature
<222> LOCATION: (11)..(12)
<223> OTHER INFORMATION: 2'-OMe-RNA
<220> FEATURE:
<221> NAME/KEY: misc_feature
<222> LOCATION: (13)..(13)
<223> OTHER INFORMATION: ENA
<220> FEATURE:
<221> NAME/KEY: misc_feature
<222> LOCATION: (14)..(14)
<223> OTHER INFORMATION: 2'-OMe-RNA
<220> FEATURE:
<221> NAME/KEY: misc_feature
<222> LOCATION: (15)..(15)
<223> OTHER INFORMATION: ENA
<220> FEATURE:
<221> NAME/KEY: modified_base
<222> LOCATION: (15)..(15)
<223> OTHER INFORMATION: m5c
<220> FEATURE:
<221> NAME/KEY: misc_feature
<222> LOCATION: (15)..(15)
<223> OTHER INFORMATION: 3'-position is hydroxyl group

<400> SEQUENCE: 182
auccgauggc gaagc                                            15
```